US009698348B2

(12) United States Patent
Hayoz et al.

(10) Patent No.: US 9,698,348 B2
(45) Date of Patent: *Jul. 4, 2017

(54) POLYMERS BASED ON FUSED DIKETOPYRROLOPYRROLES

(71) Applicant: BASF SE, Ludwigshafen (DE)

(72) Inventors: Pascal Hayoz, Hofstetten (CH); Marek Grzybowski, Szczecin (PL); Daniel T. Gryko, Warsaw (PL); Artur Jezewski, Warsaw (PL)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/899,757

(22) PCT Filed: Jun. 19, 2014

(86) PCT No.: PCT/EP2014/062970
§ 371 (c)(1),
(2) Date: Dec. 18, 2015

(87) PCT Pub. No.: WO2014/206863
PCT Pub. Date: Dec. 31, 2014

(65) Prior Publication Data
US 2016/0181534 A1    Jun. 23, 2016

(30) Foreign Application Priority Data

Jun. 24, 2013  (EP) .................................... 13173387
Oct. 7, 2013   (EP) .................................... 13187562

(51) Int. Cl.
*H01L 51/40*    (2006.01)
*H01L 51/00*    (2006.01)
(Continued)

(52) U.S. Cl.
CPC ........ *H01L 51/0035* (2013.01); *C07D 401/14* (2013.01); *C07D 409/14* (2013.01); *C08G 61/124* (2013.01); *C08G 61/126* (2013.01); *C09B 57/004* (2013.01); *C09B 69/008* (2013.01); *C09B 69/109* (2013.01); *H01L 51/0036* (2013.01); *H01L 51/0039* (2013.01); *H01L 51/0043* (2013.01); *C08G 2261/12* (2013.01); *C08G 2261/1412* (2013.01); *C08G 2261/1424* (2013.01); *C08G 2261/3142* (2013.01); *C08G 2261/3223* (2013.01); *C08G 2261/3241* (2013.01); *C08G 2261/3243* (2013.01); *C08G 2261/3327* (2013.01);
(Continued)

(58) Field of Classification Search
USPC ............ 136/263; 526/256; 257/40, E51.005, 257/E51.018
See application file for complete search history.

(56) References Cited

U.S. PATENT DOCUMENTS 6,690,029 B1    2/2004  Anthony et al.
2003/0021913 A1  1/2003  O'Neill et al.
(Continued)

FOREIGN PATENT DOCUMENTS

EP     13157961.7      3/2013
WO     WO-03/052841 A1  6/2003
(Continued)

OTHER PUBLICATIONS

U.S. Appl. No. 61/773,166.
(Continued)

*Primary Examiner* — Shane Fang
(74) *Attorney, Agent, or Firm* — Drinker Biddle & Reath LLP

(57) ABSTRACT

The present invention relates to polymers comprising one or more (repeating) unit(s) of the formula (I), wherein Y is a group of formula (II); and their use as IR absorber, organic semiconductor in organic devices, especially in organic photovoltaics and photodiodes, or in a device containing a diode and/or an organic field effect transistor. The polymers according to the invention can have excellent solubility in organic solvents 10 and excellent film-forming properties. In addition, high efficiency of energy conversion, excellent field-effect mobility, good on/off current ratios and/or excellent stability can be observed, when the polymers according to the invention are used in organic field effect transistors, organic photovoltaics and photodiodes.

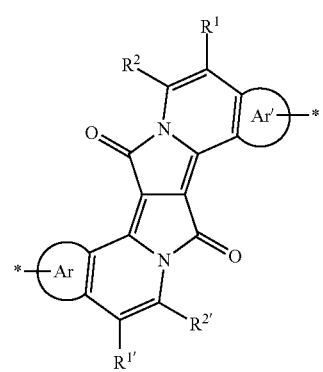

20 Claims, No Drawings

(51) Int. Cl.

| | |
|---|---|
| *C08G 61/12* | (2006.01) |
| *C07D 401/14* | (2006.01) |
| *C07D 409/14* | (2006.01) |
| *C09B 57/00* | (2006.01) |
| *C09B 69/00* | (2006.01) |
| *C09B 69/10* | (2006.01) |
| *H01L 51/05* | (2006.01) |
| *H01L 51/50* | (2006.01) |
| *H01L 51/42* | (2006.01) |

(52) U.S. Cl.
CPC .. *C08G 2261/344* (2013.01); *C08G 2261/411* (2013.01); *C08G 2261/414* (2013.01); *C08G 2261/91* (2013.01); *C08G 2261/92* (2013.01); *C08G 2261/95* (2013.01); *H01L 51/0541* (2013.01); *H01L 51/0558* (2013.01); *H01L 51/42* (2013.01); *H01L 51/50* (2013.01); *Y02E 10/549* (2013.01)

(56) References Cited

U.S. PATENT DOCUMENTS

| | | | |
|---|---|---|---|
| 2006/0013549 | A1 | 1/2006 | Shtein et al. |
| 2007/0079867 | A1 | 4/2007 | Chittibabu et al. |
| 2007/0272296 | A1 | 11/2007 | Brabec et al. |
| 2008/0241492 | A1 | 10/2008 | Demartin Maeder et al. |
| 2011/0004004 | A1 | 1/2011 | Hao et al. |
| 2011/0028644 | A1 | 2/2011 | Brown et al. |
| 2014/0353628 | A1* | 12/2014 | Facchetti ............ H01L 51/0035 257/40 |
| 2014/0357869 | A1 | 12/2014 | Grzybowski et al. |

FOREIGN PATENT DOCUMENTS

| | | |
|---|---|---|
| WO | WO-2004101581 A2 | 11/2004 |
| WO | WO-2004/112161 A2 | 12/2004 |
| WO | WO-2006061343 A1 | 6/2006 |
| WO | WO-2007082584 A1 | 7/2007 |
| WO | WO-2007113107 A1 | 10/2007 |
| WO | WO-2008/001123 A1 | 1/2008 |
| WO | WO-2008107089 A1 | 9/2008 |
| WO | WO-2009/047104 A2 | 4/2009 |
| WO | WO-2010/108873 A1 | 9/2010 |
| WO | WO-2010/136352 A1 | 12/2010 |
| WO | WO-2011144566 A2 | 11/2011 |
| WO | WO-2013/092474 A1 | 6/2013 |
| WO | WO-2014135491 A1 | 9/2014 |

OTHER PUBLICATIONS

International Search Report for PCT/EP2014/062970 mailed Dec. 3, 2014.

International Search Report issued Apr. 23, 2012 in PCT/EP2012/075762.

Chandran, D., et al., Macromol. Res. 2013, 21 pp. 272-283.

Deng, Ling, "Synthesis and Application of Sulfydryl fluorescent probes based on diketopyrrolopyrrole (DPP)", Masteral Thesis of Dalian University of Technology, Engineering Technology I, pp. 23 and 24 (Jun. 2012).

Fischer, George M., et al., "Selective NIR chromophores: Bis(Pyrrolopyrrole) Cyanines" Angewandte Chemie International Edition, vol. 50, No. 6, XP55057949, Feb. 7, 2011, pp. 1406-1409.

Fischer, George Michael, et al., "Asymmetric PPCys: Strongly fluorescing NIR labels" Chemical Communications, vol. 46, No. 29, XP55057947, Jan. 1, 2010, pp. 5289-5291.

Grzybowski, M. et al., "Bright, Color-Tunable Fluorescent Dyes Based on ?-Expanded Diketopyrrolopyrroles" Organic Letters, vol. 14, No. 11, XP55057863, Jun. 1, 2012, pp. 2670-2673.

Nowak-Krol, A., et al., "Strong two-photon absorption enhancement in a unique bis-porphyrin bearing a diketopyrrolopyrrole unit", Chem. Communic. 2013, 49, pp. 8368-8370.

\* cited by examiner

POLYMERS BASED ON FUSED DIKETOPYRROLOPYRROLES

CROSS-REFERENCE TO RELATED APPLICATIONS

This application is a national stage application (under 35 U.S.C. §371) of PCT/EP2014/062970, filed Jun. 19, 2014, which claims benefit of European Application Nos. 13173387.5, filed Jun. 24, 2013, and 13187562.7, filed Oct. 7, 2013, each application of which is incorporated herein by reference in their entirety.

The present invention relates to polymers comprising one or more (repeating) unit(s) of the formula (I) and their use as IR absorber, organic semiconductor in organic devices, especially in organic photovoltaics and photodiodes, or in a device containing a diode and/or an organic field effect transistor. The polymers according to the invention can have excellent solubility in organic solvents and excellent film-forming properties. In addition, high efficiency of energy conversion, excellent field-effect mobility, good on/off current ratios and/or excellent stability can be observed, when the polymers according to the invention are used in organic field effect transistors, organic photovoltaics and photodiodes.

BACKGROUND OF THE INVENTION

In recent years, diketopyrrolopyrroles (DPPs) have become one of the Extensively studied organic building blocks of oligomers and polymers having promising optoelectronic properties, especially in solar cells. Reference is made to D. Chandran and Kwang-Sup Lee, Macromolecular Research 21 (2013) 272.

US2011/0004004 relates to compounds of the formula

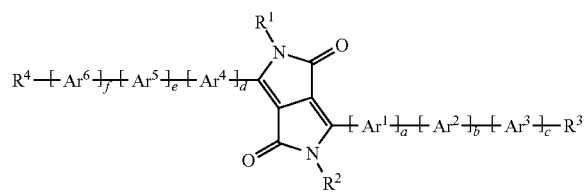

(I)

and their use as organic semiconductor in organic devices, like diodes, organic field effect transistors and/or a solar cells.

WO2011/144566 relates to polymers comprising one or more (repeating) unit(s) of the formula

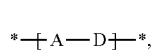

(I)

or a polymer of formula

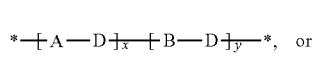

(II)

or

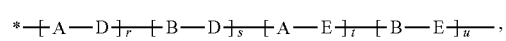

(III)

wherein A is a group of formula

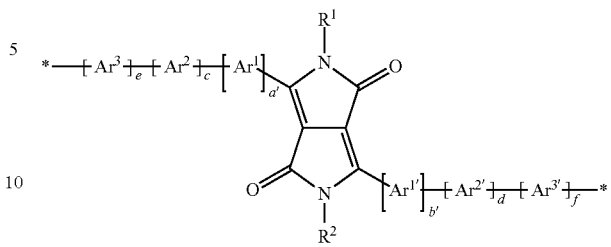

and their use as organic semiconductor in organic devices, especially in organic photovoltaics (solar cells) and photodiodes, or in a device containing a diode and/or an organic field effect transistor.

Daniel T. Gryko et al. Organic Letters 14 (2012) 2670 disclose a synthetic approach to π-expanded diketopyrrolopyrroles. A three-step strategy appears to be very general and starts with the preparation of diketopyrrolopyrroles followed by N-alkylation with bromoacetaldehyde diethyl acetal and electrophilic aromatic substitution. The final reaction regioselectively furnishes fluorescent dyes.

WO2013/092474 (PCT/EP2012/075762), which enjoys an earlier priority date than the present invention, but has been published after the priority date of the present invention, relates to compounds of formula (III):

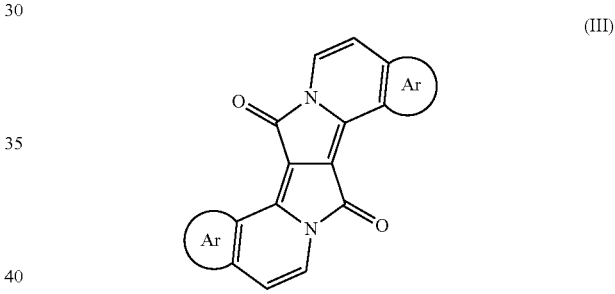

(III)

where Ar denotes a homo- or heteroaromatic system.

PCT/EP2014/054060, which enjoys an earlier priority date than the present invention, but has been published after the priority date of the present invention, relates to novel compounds of formula

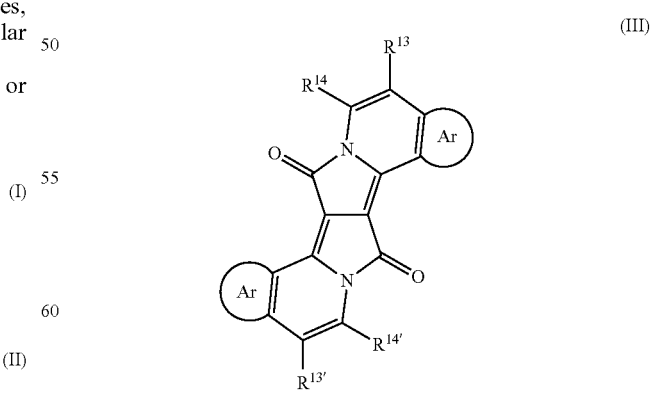

(III)

that can be used as heterocyclic dyes of unique structure and properties. These compounds can be obtained in a three-step synthesis from simple substrates.

DETAILED DESCRIPTION OF THE INVENTION

It is one object of the present invention to provide polymers, which show high efficiency of energy conversion, excellent field-effect mobility, good on/off current ratios and/or excellent stability, when used in organic field effect transistors, organic photovoltaics (solar cells) and photodiodes. Another object of the invention is to provide polymers with very low band gap, which can also be used as infrared (IR) absorbers.

Said object has been solved by (conjugated) polymers, comprising one or more (repeating) unit(s) of the formula

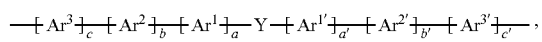
(I)

wherein
Y is a group of formula

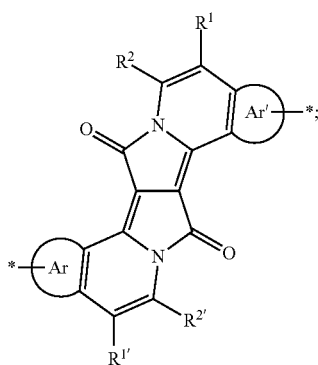

a is 0, 1, 2, or 3; a' is 0, 1, 2, or 3; b is 0, 1, 2, or 3; b' is 0, 1, 2, or 3; c is 0, 1, 2, or 3; c' is 0, 1, 2, or 3;

Ar and Ar' denote a homo- or heteroaromatic system, which may be substituted, or unsubstituted.

$R^1$, $R^{1'}$, $R^2$ and $R^{2'}$ may be the same or different and are selected from hydrogen, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —NR$^{39}$—, CONR$^{39}$—, NR$^{39}$CO—, —COO—, —CO— or —OCO—, a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —NR$^{39}$—, CONR$^{39}$—, NR$^{39}$CO—, —COO—, —CO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —NR$^{39}$—, CONR$^{39}$—, NR$^{39}$CO—, —COO—, —CO— or —OCO—, a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —NR$^{39}$—, CONR$^{39}$—, NR$^{39}$CO—, —COO—, —CO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group;

a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group;

a —CO—$C_1$-$C_{18}$alkyl group, a —CO—$C_5$-$C_{12}$cycloalkyl group, or —COO—$C_1$-$C_{18}$alkyl group;

$R^{39}$ is hydrogen, $C_1$-$C_{18}$alkyl, $C_1$-$C_{18}$haloalkyl, $C_7$-$C_{25}$arylalkyl, or $C_1$-$C_{18}$alkanoyl, $Ar^1$, $Ar^{1'}$, $Ar^2$, $Ar^{2'}$, $Ar^3$ and $Ar^{3'}$ are independently of each other

(XIa)

(XIb)

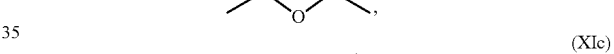
(XIc)

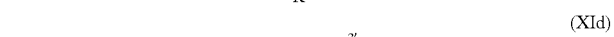
(XId)

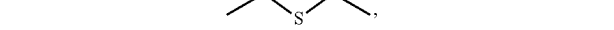
(XIe)

(XIf)

(XIg)

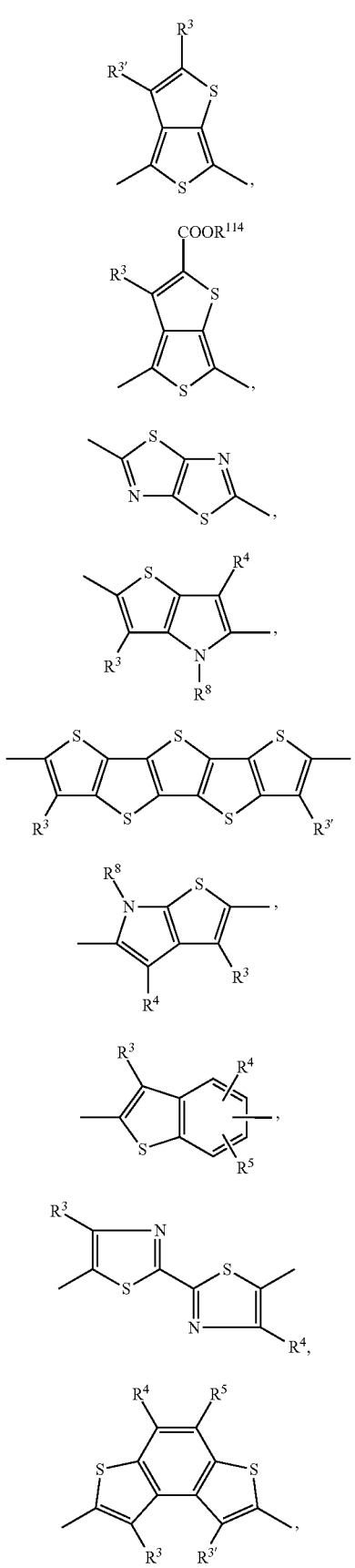
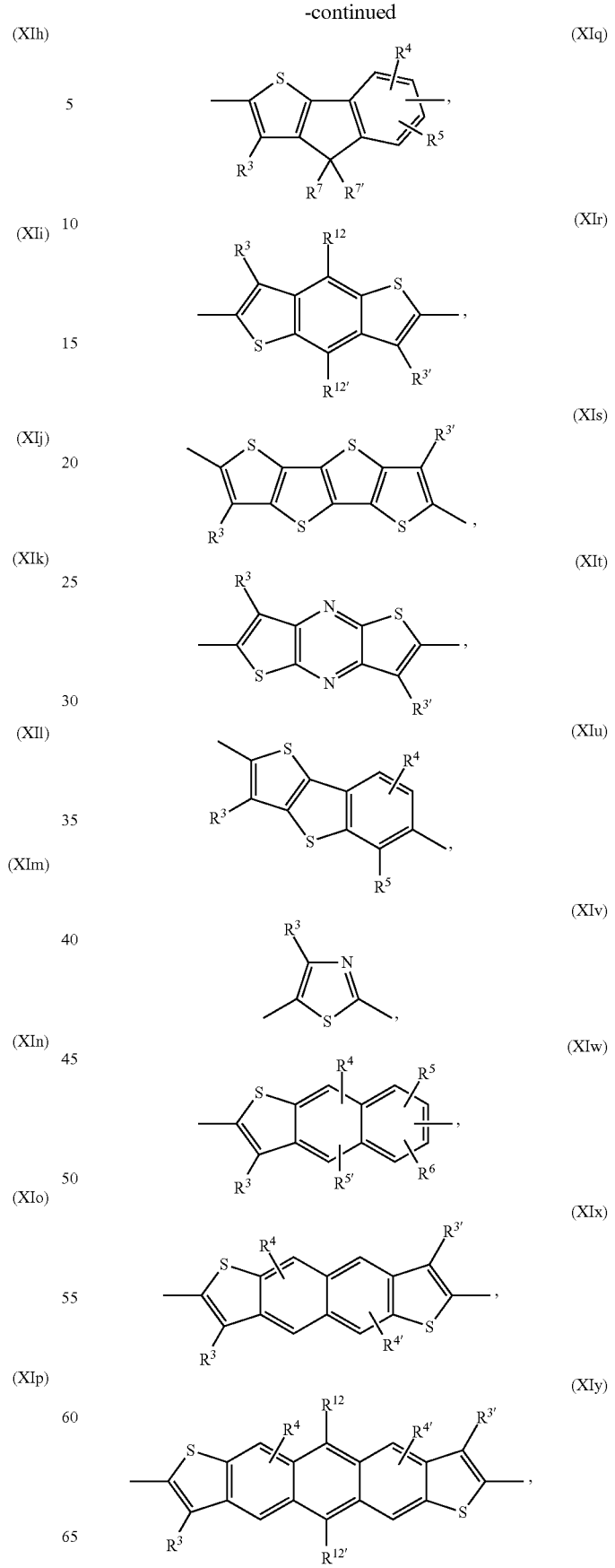

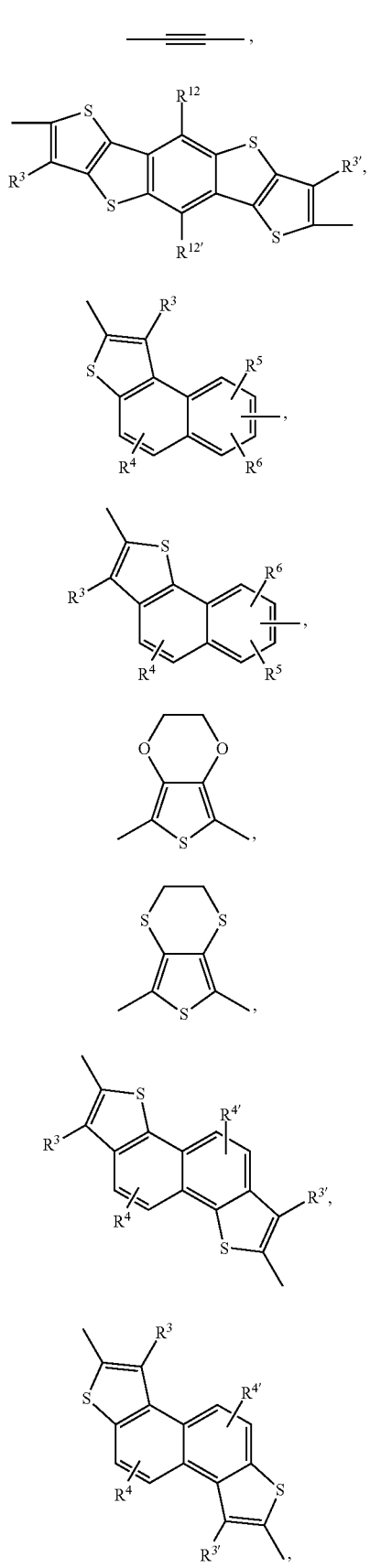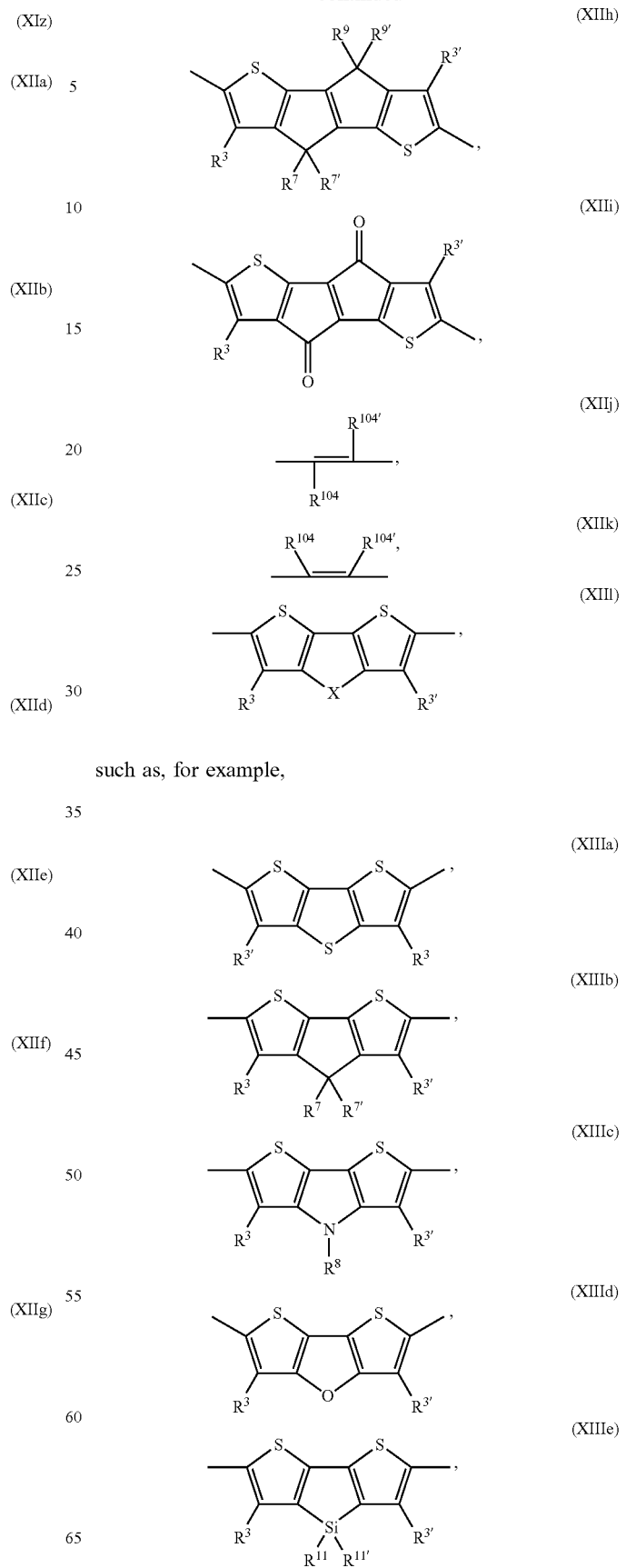
such as, for example,

-continued
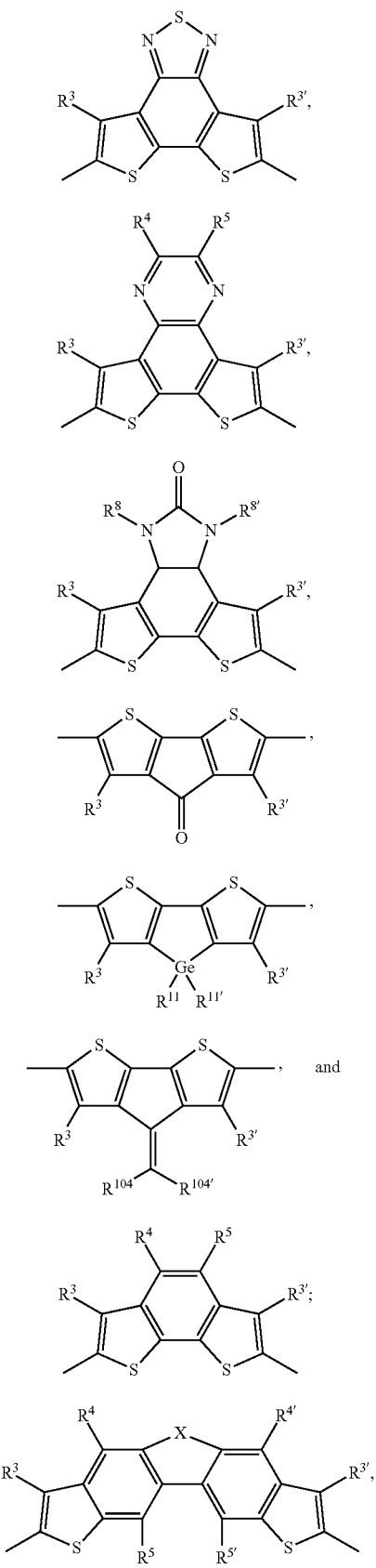
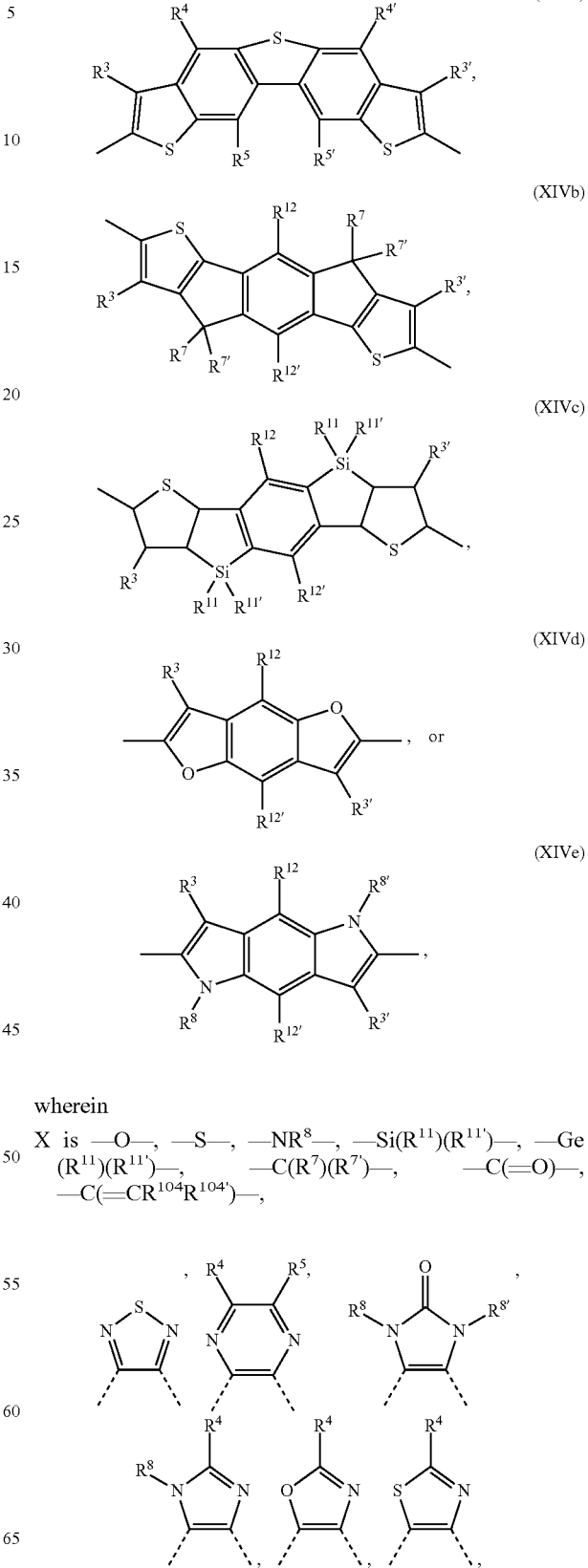
such as, for example,
wherein
X is —O—, —S—, —NR⁸—, —Si(R¹¹)(R¹¹')—, —Ge(R¹¹)(R¹¹')—, —C(R⁷)(R⁷')—, —C(=O)—, —C(=CR¹⁰⁴R¹⁰⁴')—,
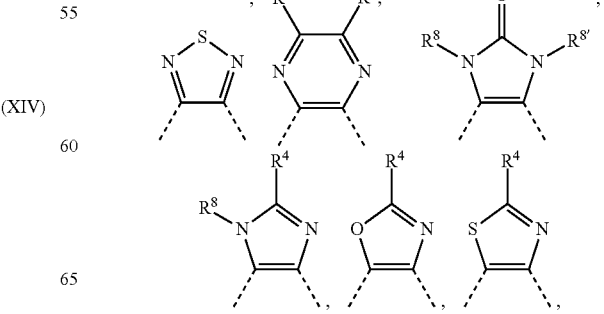

-continued
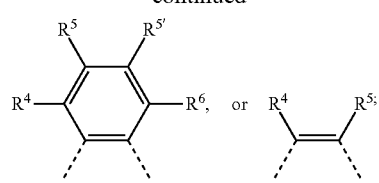
especially
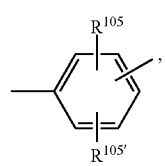 (XVa)
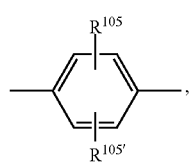 (XVa')
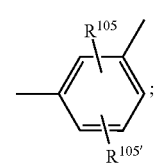 (XVa")
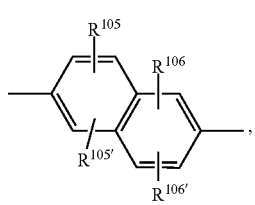 (XVb)
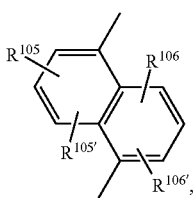 (XVc)
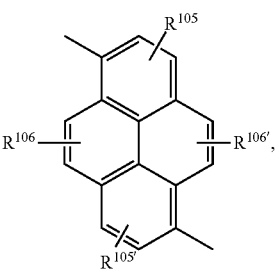 (XVd)
-continued
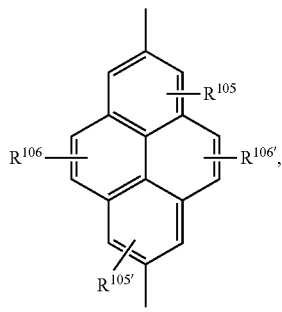 (XVe)
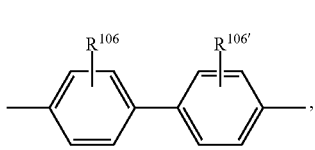 (XVf)
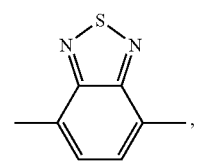 (XVg)
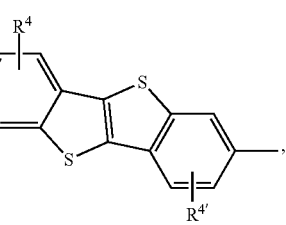 (XVh)
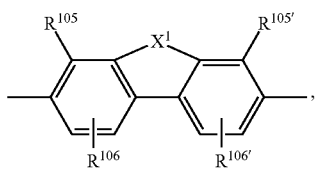 (XVI)
such as, for example,
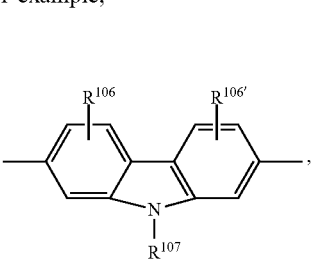 (XVIa)
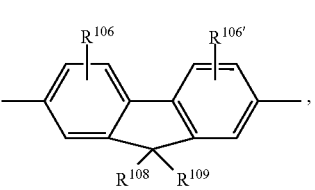 (XVIb)

-continued

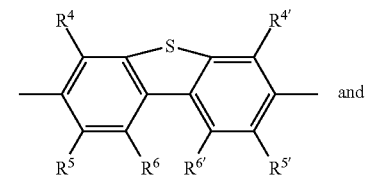
and

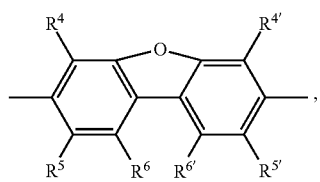,

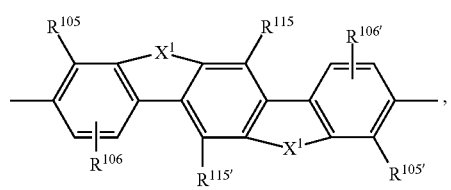

such as, for example,

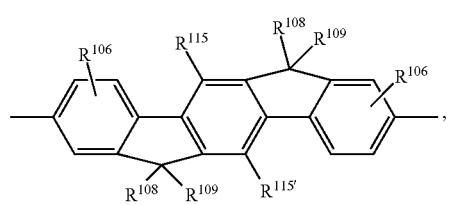,

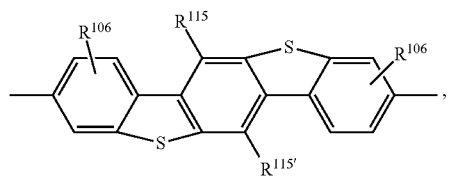,

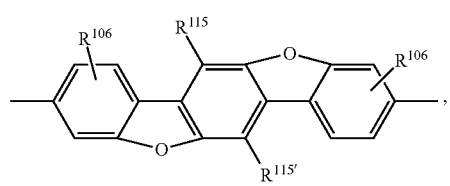

and
wherein
$X^1$ is S, O, $NR^{107}$—, —$Si(R^{117})(R^{117'})$—, —$Ge(R^{117})(R^{117'})$—, —$C(R^{108})(R^{109})$—, —$C(=O)$—, —$C(=CR^{104}R^{104'})$—,

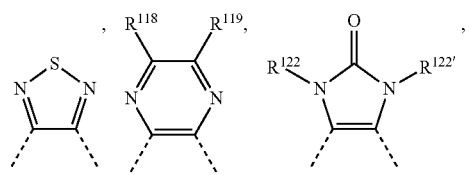

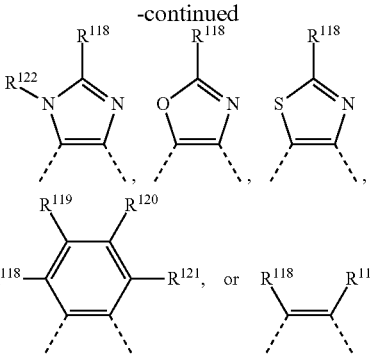

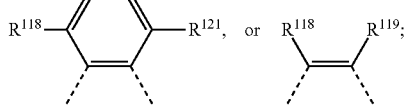

$R^3$ and $R^{3'}$ are independently of each other hydrogen, halogen, halogenated $C_1$-$C_{25}$alkyl, especially $CF_3$, cyano, $C_1$-$C_{25}$alkyl, especially $C_3$-$C_{25}$alkyl, which may optionally be interrupted by one or more oxygen or sulphur atoms; $C_7$-$C_{25}$arylalkyl, or $C_1$-$C_{25}$alkoxy;

$R^4$, $R^{4'}$, $R^5$, $R^{5'}$, $R^6$, and $R^{6'}$ are independently of each other hydrogen, halogen, halogenated $C_1$-$C_{25}$alkyl, especially $CF_3$, cyano, $C_1$-$C_{25}$alkyl, especially $C_3$-$C_{25}$alkyl, which may optionally be interrupted by one or more oxygen or sulphur atoms; $C_7$-$C_{25}$arylalkyl, or $C_1$-$C_{25}$alkoxy;

$R^7$, $R^{7'}$, $R^9$ and $R^{9'}$ are independently of each other hydrogen, $C_1$-$C_{25}$alkyl, especially $C_3$-$C_{25}$alkyl, which may optionally be interrupted by one, or more oxygen, or sulphur atoms; or $C_7$-$C_{25}$arylalkyl, $R^8$ and $R^{8'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_3$-$C_{25}$alkyl, which may optionally be interrupted by one or more oxygen or sulphur atoms; or $C_7$-$C_{25}$arylalkyl, $R^{11}$ and $R^{11'}$ are independently of each other $C_1$-$C_{25}$alkyl group, especially a $C_1$-$C_8$alkyl group, $C_7$-$C_{25}$arylalkyl, or a phenyl group, which can be substituted one to three times with $C_1$-$C_8$alkyl and/or $C_1$-$C_8$alkoxy;

$R^{12}$ and $R^{12'}$ are independently of each other hydrogen, halogen, cyano, $C_1$-$C_{25}$alkyl, especially $C_3$-$C_{25}$alkyl, which may optionally be interrupted by one, or more oxygen, or sulphur atoms, $C_1$-$C_{25}$alkoxy, $C_7$-$C_{25}$arylalkyl, or —≡—$R^{13}$, wherein $R^{13}$ is a $C_1$-$C_{18}$alkyl group, or a tri($C_1$-$C_8$alkyl)silyl group;

$R^{104}$ and $R^{104'}$ are independently of each other hydrogen, $C_1$-$C_{18}$alkyl, cyano, $COOR^{103}$, $C_6$-$C_{10}$aryl, which may optionally be substituted by G, or $C_2$-$C_8$heteroaryl, which may optionally be substituted by G, $R^{103}$ and $R^{103'}$ are independently of each other $C_1$-$C_{100}$alkyl, especially $C_3$-$C_{25}$alkyl, $C_1$-$C_{25}$alkyl substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, $R^{105}$, $R^{105'}$, $R^{106}$ and $R^{106'}$ are independently of each other hydrogen, halogen, cyano, $C_1$-$C_{25}$alkyl, which may optionally be interrupted by one or more oxygen or sulphur atoms; $C_7$-$C_{25}$arylalkyl, or $C_1$-$C_{18}$alkoxy, $R^{107}$ is hydrogen, $C_7$-$C_{25}$arylalkyl, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$perfluoroalkyl; $C_1$-$C_{25}$alkyl; especially $C_3$-$C_{25}$alkyl, which may be interrupted by —O—, or —S—; or —$COOR^{103}$; $R^{103}$ is as defined above;

$R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, or R$^{108}$ and R$^{109}$ together form a group of formula =CR$^{110}$R$^{111}$ wherein R$^{110}$ and R$^{111}$ are independently of each other H, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, or C$_2$-C$_{20}$heteroaryl, or C$_2$-C$_{20}$heteroaryl which is substituted by G, or R$^{108}$ and R$^{109}$ together form a five or six membered ring, which optionally can be substituted by C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, D is —CO—, —COO—, —S—, —O—, or —NR$^{112}$—, E is C$_1$-C$_8$thioalkoxy, C$_1$-C$_8$alkoxy, CN, —NR$^{112}$R$^{113}$, —CONR$^{112}$R$^{113}$, or halogen, G is E, or C$_1$-C$_{18}$alkyl, and R$^{112}$ and R$^{113}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{114}$ is C$_1$-C$_{25}$alkyl, especially C$_3$-C$_{25}$alkyl, which may optionally be interrupted by one, or more oxygen, or sulphur atoms, R$^{115}$ and R$^{115'}$ are independently of each other hydrogen, halogen, cyano, C$_1$-C$_{25}$alkyl, especially C$_3$-C$_{25}$alkyl, which may optionally be interrupted by one, or more oxygen, or sulphur atoms, C$_1$-C$_{25}$alkoxy, C$_7$-C$_{25}$arylalkyl, or —≡—R$^{116}$, wherein R$^{116}$ is a C$_1$-C$_{10}$alkyl group, or a tri(C$_1$-C$_8$alkyl)silyl group;

R$^{117}$ and R$^{117'}$ are independently of each other C$_1$-C$_{25}$alkyl group, especially a C$_1$-C$_8$alkyl group, C$_7$-C$_{25}$arylalkyl, or a phenyl group, which can be substituted one to three times with C$_1$-C$_8$alkyl and/or C$_1$-C$_8$alkoxy;

R$^{118}$, R$^{119}$, R$^{120}$ and R$^{121}$ are independently of each other hydrogen, halogen, halogenated C$_1$-C$_{25}$alkyl, especially CF$_3$, cyano, C$_1$-C$_{25}$alkyl, especially C$_3$-C$_{25}$alkyl, which may optionally be interrupted by one or more oxygen or sulphur atoms; C$_7$-C$_{25}$arylalkyl, or C$_1$-C$_{25}$alkoxy;

R$^{122}$ and R$^{122'}$ are independently of each other hydrogen, C$_6$-C$_{18}$aryl; C$_6$-C$_{18}$aryl which is substituted by C$_1$-C$_{18}$alkyl, or C$_1$-C$_{18}$alkoxy; or C$_1$-C$_{25}$alkyl, especially C$_3$-C$_{25}$alkyl, which may optionally be interrupted by one or more oxygen or sulphur atoms; or C$_7$-C$_{25}$arylalkyl.

The polymers of the present invention are preferably conjugated. Polymers, comprising a repeating unit of the formula (I) are preferred.

In a preferred embodiment the present invention is directed to polymers comprising a repeating unit of formula

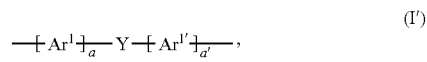
(I)

wherein Y is a group of formula

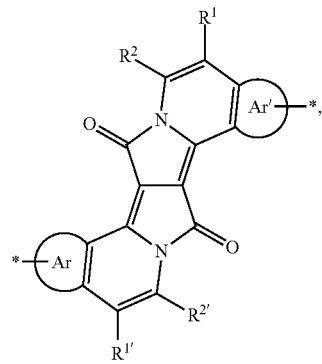

a is 0 or 1, a' is 0 or 1, b is 0, b' is 0, c is 0 and c' is 0; and Ar$^1$ and Ar$^{1'}$ are as defined above.

In said embodiment the polymer comprises preferably one or more (repeating) unit(s) of the formula $$\mathrm{\{Ar^1\}_a\!-\!Y\!-\!\{Ar^{1'}\}_{a'}},\qquad (I')$$

wherein Y is a group of formula

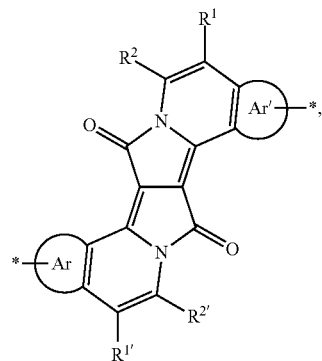

wherein a is 0, 1, 2, or 3, especially 0, or 1; a' is 0, 1, 2, or 3, especially 0, or 1; wherein Ar$^1$, Ar$^{1'}$, Ar and Ar' and R$^1$, R$^{1'}$, R$^2$ and R$^{2'}$ are as defined in claim 1.

More preferred a is 0, a' is 0, b is 0, b' is 0, c is 0 and c' is 0.

In a preferred embodiment Ar$^1$ and Ar$^{1'}$ are independently of each other a group of formula (XIa), (XIb), (XIc), (XIe), (XIf), (XIk), (XIm), (XIn), (XIq), (XIr), (XIu), (XIw), (XIx), (XIII), such as, for example, (XIIIa) and (XIIIb); or (XIV), such as, for example, (XIVb). Preferably, Ar$^1$ and Ar$^{1'}$ are independently of each other a group of formula XIa, XIb, XIe, XIf, XIr, or XIIIa. More preferably, Ar$^1$ and Ar$^{1'}$ are independently of each other a group of formula XIa, XIb, or XIf, most preferred a group of formula XIa.

R$^1$, R$^{1'}$, R$^2$ and R$^{2'}$ are preferably selected from hydrogen, a C$_1$-C$_{100}$alkyl group which can optionally be substituted one or more times with C$_1$-C$_{12}$alkyl, C$_1$-C$_{12}$alkoxy, halogen, C$_5$-C$_{12}$cycloalkyl, nitro, cyano, vinyl, allyl, C$_6$-C$_{24}$aryl, or C$_2$-C$_{20}$heteroaryl; and/or can optionally be interrupted by —O—, —S—, —NR$^{39}$—, —COO—, —CO— or —OCO—, a C$_2$-C$_{100}$alkenyl group which can optionally be substituted one or more times with C$_1$-C$_{12}$alkyl, C$_1$-C$_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl; and/or can optionally be interrupted by —O—, —S—, —NR$^{39}$—, —COO—, —CO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl; and/or can optionally be interrupted by —O—, —S—, —NR$^{39}$—, —COO—, —CO— or —OCO—, a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl; and/or can optionally be interrupted by —O—, —S—, —NR$^{39}$—, —COO—, —CO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl;

a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl;

a —CO—$C_1$-$C_{18}$alkyl group, a —CO—$C_5$-$C_{12}$cycloalkyl group, or —COO—$C_1$-$C_{18}$alkyl group, wherein R$^{39}$ is $C_1$-$C_{18}$alkyl.

Advantageously, the polymer of the present invention, or an organic semiconductor material, layer or component, comprising the polymer of the present invention can be used in organic photovoltaics (solar cells), photodiodes, in an organic field effect transistor (OFET), as IR absorber, in thin film transistors (TFT), intergrated circuits (IC), radio frequency identification (RFID) tags, devices or components, organic light emitting diodes (OLED), organic light emitting transistors (OLET), flat panel displays, backlights of displays, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

The term polymer comprises oligomers as well as polymers. The oligomers of this invention have a weight average molecular weight of <4,000 Daltons. The polymers of this invention preferably have a weight average molecular weight of 4,000 Daltons or greater, especially 4,000 to 2,000,000 Daltons, very especially 10,000 to 1,000,000 Daltons, more preferably 10,000 to 100,000 Daltons and most preferred 20,000 to 60,000 Daltons. Molecular weights are determined according to high-temperature gel permeation chromatography (HT-GPC) using polystyrene standards. The polymers of this invention preferably have a polydispersity of 1.01 to 10, more preferably 1.1 to 3.0, most preferred 1.5 to 2.5. The polymers of the present invention are preferably conjugated.

Oligomers of the present invention preferably have a weight average molecular weight below 4,000 Daltons.

In an embodiment of the present invention the polymer is a polymer of formula

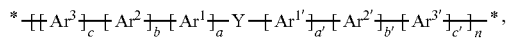

wherein n is usually in the range of 4 to 1000, especially 4 to 200, very especially 5 to 150.

In the definition of R$^1$, R$^{1'}$, R$^2$ and R$^{2'}$ a silyl group or a siloxanyl group means —SiR$^{161}$R$^{162}$R$^{163}$, or —O—SiR$^{161}$R$^{162}$R$^{163}$.

R$^{161}$, R$^{162}$ and R$^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—SiR$^{164}$R$^{165}$R$^{166}$, —(O—SiR$^{164}$R$^{165}$)$_d$—R$^{166}$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl, which is substituted 1 to 3 times by $C_1$-$C_{25}$ alkyl, halogen, cyano or $C_1$-$C_{25}$alkoxy; preferably hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—SiR$^{164}$R$^{165}$R$^{166}$, —O—(SiR$^{164}$R$^{165}$)$_d$—R$^{166}$ or phenyl; more preferably $C_1$-$C_8$alkyl, $C_5$-$C_6$cycloalkyl, which might optionally be substituted with $C_1$-$C_4$alkyl; $C_1$-$C_8$haloalkyl, $C_2$-$C_8$alkenyl, —O—SiR$^{164}$R$^{165}$R$^{166}$, —(O—SiR$^{164}$R$^{165}$)$_d$—R$^{166}$ or phenyl; most preferably $C_1$-$C_8$alkyl, $C_1$-$C_8$haloalkyl, especially $C_1$-$C_8$alkyl which is substituted one, or more times with fluorine atoms; —O—SiR$^{164}$R$^{165}$R$^{166}$ or —(O—SiR$^{164}$R$^{165}$)$_d$—R$^{166}$.

R$^{164}$, R$^{165}$ and R$^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—SiR$^{169}$R$^{170}$R$^{171}$, —(O—SiR$^{169}$R$^{170}$)$_d$—R$^{171}$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl, which is substituted 1 to 3 times by $C_1$-$C_{25}$alkyl, halogen, cyano or $C_1$-$C_{25}$alkoxy; preferably hydrogen, $C_1$-$C_{25}$alkyl, $C_1$-$C_{25}$haloalkyl, $C_2$-$C_{25}$alkenyl, —O—SiR$^{169}$R$^{170}$R$^{171}$, —(O—SiR$^{169}$R$^{170}$)$_d$—R$^{171}$, or phenyl; more preferably $C_1$-$C_8$alkyl, $C_1$-$C_8$haloalkyl, $C_2$-$C_8$alkenyl, —O—SiR$^{169}$R$^{170}$R$^{171}$, —(O—SiR$^{169}$R$^{170}$)$_d$—R$^{171}$, or phenyl; most preferably $C_1$-$C_8$alkyl, $C_1$-$C_8$haloalkyl, especially $C_1$-$C_8$alkyl which is substituted one or more times with fluorine atoms; —O—SiR$^{169}$R$^{170}$R$^{171}$ or —(O—SiR$^{169}$R$^{170}$)$_d$—R$^{171}$.

R$^{169}$, R$^{178}$ and R$^{171}$ are independently of each other hydrogen, $C_1$-$C_{25}$alkyl, $C_3$-$C_{12}$cycloalkyl, which might optionally be substituted with $C_1$-$C_4$alkyl, $C_1$-$C_{25}$haloalkyl, $C_2$-$C_{25}$alkenyl, —O—Si(CH$_3$)$_3$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl, which is substituted 1 to 3 times by $C_1$-$C_{25}$alkyl, halogen, cyano, or $C_1$-$C_{25}$alkoxy; preferably hydrogen, $C_1$-$C_{25}$alkyl, $C_1$-$C_{25}$haloalkyl, $C_2$-$C_{25}$alkenyl, —O—Si(CH$_3$)$_3$, or phenyl; more preferably $C_1$-$C_8$alkyl, $C_1$-$C_8$haloalkyl, $C_2$-$C_8$alkenyl, Si(CH$_3$)$_3$, or phenyl; most preferably $C_1$-$C_8$alkyl, $C_1$-$C_8$haloalkyl, especially $C_1$-$C_8$alkyl which is substituted one or more times with fluorine atoms; or —O—Si(CH$_3$)$_3$.

d is an integer from 1 to 50, preferably 1 to 40, even more preferably 1 to 30, still more preferably 1 to 20, more preferably 1 to 15, still more preferably 1 to 10 and even more preferably 1 to 5 and most preferably 1 to 3.

R$^{167}$ and R$^{168}$ are independently of each other hydrogen, $C_1$-$C_{25}$alkyl, $C_1$-$C_{25}$haloalkyl, $C_3$-$C_{25}$alkenyl, or phenyl; preferably $C_1$-$C_{25}$alkyl, $C_1$-$C_{25}$haloalkyl, or phenyl; most preferably $C_1$-$C_{25}$alkyl.

In a particularly preferred embodiment R$^{161}$, R$^{162}$ and R$^{163}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; $C_3$-$C_{12}$cycloalkyl, especially $C_5$-$C_6$cycloalkyl, which might optionally be substituted with $C_1$-$C_4$alkyl; phenyl, —O—$SiR^{164}R^{165}R^{166}$, or —(O—$SiR^{164}R^{165})_d$—$R^{166}$. In case of a group —O—$SiR^{164}R^{165}R^{166}$ $R^{164}$, $R^{165}$ and $R^{166}$ are independently of each other $C_8$alkyl, $C_1$-$C_8$haloalkyl, $C_2$-$C_8$alkenyl, or phenyl. In case of a group —(O—$SiR^{164}R^{165})_d$—$R^{166}$ $R^{164}$ and $R^{165}$ are independently of each other $C_1$-$C_8$alkyl, $R^{166}$ is $C_1$-$C_8$alkyl, or phenyl and d is an integer of 2 to 5.

Examples of groups of formula —$SiR^{161}R^{162}R^{163}$ or —O—$SiR^{161}R^{162}R^{163}$ are shown below:

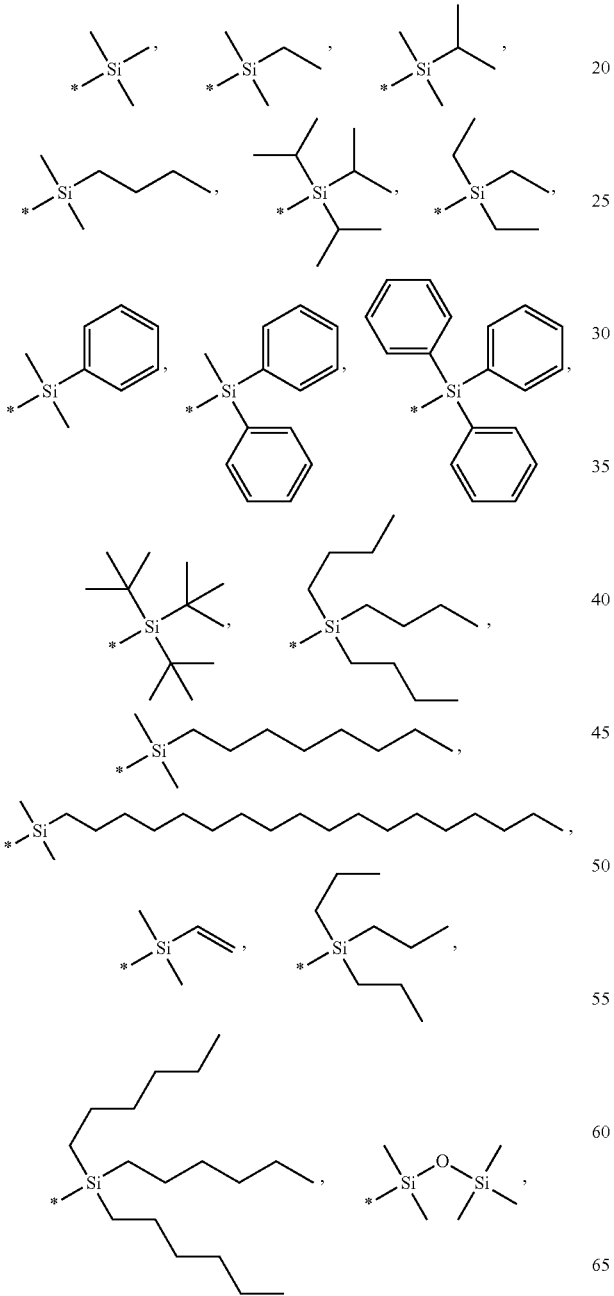

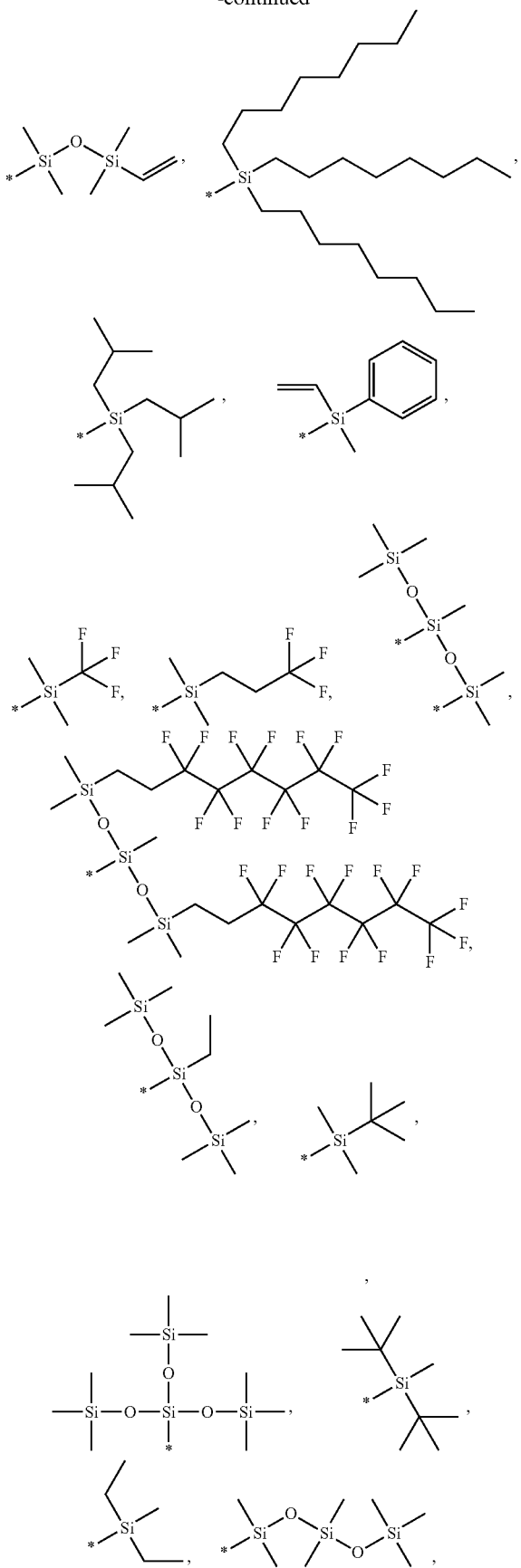

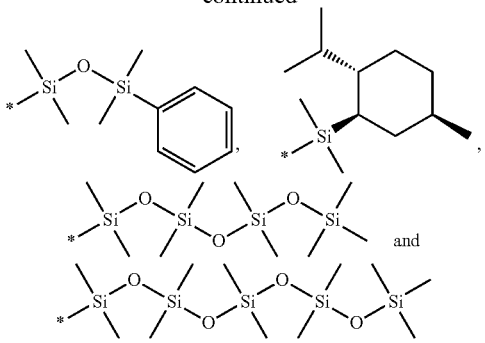

(*—indicates the bond to the carbon atom, to which the silyl group or siloxanyl group is connected).

$R^2$ and $R^{2'}$ may be the same or different and are preferably selected from hydrogen, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_4$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl, a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl, —CO—$C_1$-$C_{18}$alkyl, —CO—$C_5$-$C_{12}$cycloalkyl, and —COO—$C_1$-$C_{18}$alkyl.

More preferably $R^1$, $R^{1'}$, $R^2$ and $R^{2'}$ are selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl, or naphthyl which can optionally be substituted one or more times with $C_1$-$C_{12}$alkyl or $C_1$-$C_{12}$alkoxy, —CO—$C_1$-$C_{18}$alkyl, —CO—$C_5$-$C_{12}$cycloalkyl and —COO—$C_1$-$C_{18}$alkyl. Even more preferably $R^1$, $R^{1'}$, $R^2$ and $R^{2'}$ are a $C_1$-$C_{50}$alkyl group. Still more preferably $R^1$, $R^{1'}$, $R^2$ and $R^{2'}$ are a $C_1$-$C_{36}$alkyl group, such as, for example, methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, especially n-dodecyl, tridecyl, tetradecyl, pentadecyl, hexadecyl, 2-ethyl-hexyl, 2-butyl-hexyl, 2-butyl-octyl, 2-hexyldecyl, 2-decyl-tetradecyl, heptadecyl, octadecyl, eicosyl, heneicosyl, docosyl, or tetracosyl. Preferably $R^1$ and $R^{1'}$ have the same meaning and independently $R^2$ and $R^{2'}$ have the same meaning.

More preferably if $R^1$ and $R^{1'}$ are hydrogen, $R^2$ and $R^{2'}$ are different from hydrogen, or if $R^1$ and $R^{1'}$ are different from hydrogen $R^2$ and $R^{2'}$ are hydrogen.

Most preferably $R^2$ and $R^{2'}$ are hydrogen and $R^1$ and $R^{1'}$ are different from hydrogen.

Advantageously, the groups $R^1$, $R^2$, $R^{1'}$ and $R^{2'}$ can be represented by formula

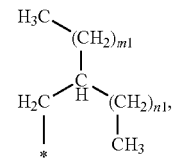

wherein m1=n1+2 and m1+n1≤24. Chiral side chains, such as $R^1$, $R^2$, $R^{1'}$ and $R^{2'}$ can either be homochiral, or racemic, which can influence the morphology of the compounds.

Preferably, $R^{103}$ is independently of each other $C_1$-$C_{25}$alkyl, $C_1$-$C_{25}$alkyl substituted by halogen, $C_7$-$C_{25}$arylalkyl, or phenyl; more preferably $C_1$-$C_{25}$alkyl.

In a preferred embodiment $Ar^1$ and $Ar^{1'}$ are independently of each other a group of formula (XIa), (XIb), (XIc), (XIe), (XIf), (XIk), (XIm), (XIn), (XIq), (XIr), (XIu), (XIw), (XIx), (XIII), such as, for example, (XIIIa) and (XIIIb); or (XIV), such as, for example, (XIVb). Preferably, $Ar^1$ and $Ar^{1'}$ are independently of each other a group of formula XIa, XIb, XIe, XIf, XIr, or XIIIa. More preferably, $Ar^1$ and $Ar^{1'}$ are independently of each other a group of formula XIa, XIb, or XIf, most preferred a group of formula XIa.

Preferably, $R^3$ and $R^{3'}$ are independently of each other hydrogen, halogen, $CF_3$, cyano, $C_1$-$C_{25}$alkyl or $C_1$-$C_{25}$alkoxy; more preferably $CF_3$, cyano or $C_1$-$C_{25}$alkyl; most preferred hydrogen, or $C_1$-$C_{25}$alkyl.

Preferably, $R^{104}$ and $R^{104'}$ are independently of each other hydrogen, cyano or a $C_1$-$C_{25}$alkyl group, more preferably hydrogen, or a $C_1$-$C_{25}$alkyl group, most preferred hydrogen.

Preferably, $R^4$, $R^{4'}$, $R^5$, $R^{5'}$, $R^6$ and $R^{6'}$ are independently of each other hydrogen, halogen, $CF_3$, cyano, $C_1$-$C_{25}$alkyl or $C_1$-$C_{25}$alkoxy, more preferably hydrogen, $CF_3$, cyano or $C_1$-$C_{25}$alkyl; most preferred hydrogen, or $C_1$-$C_{25}$alkyl.

Preferably $R^7$, $R^{7'}$, $R^9$ and $R^{9'}$ are independently of each other hydrogen, $C_1$-$C_{25}$alkyl, more preferably $C_4$-$C_{25}$alkyl.

Preferably, $R^8$ and $R^{8'}$ are independently of each other hydrogen, $C_1$-$C_{25}$alkyl, $C_1$-$C_{25}$alkyl, which may optionally be interrupted by one or more oxygen or sulphur atoms; or $C_7$-$C_{25}$arylalkyl, more preferably hydrogen, or $C_1$-$C_{25}$alkyl.

Preferably, $R^{11}$ and $R^{11'}$ are independently of each other a $C_1$-$C_{25}$alkyl group, especially a $C_1$-$C_8$alkyl group, or phenyl; more preferably a $C_1$-$C_8$alkyl group.

Preferably, $R^{12}$ and $R^{12'}$ are independently of each other hydrogen, $C_1$-$C_{25}$alkyl, $C_1$-$C_{25}$alkoxy, or ═$R^{13}$, wherein $R^{13}$ is a $C_1$-$C_{18}$alkyl group, or a tri($C_1$-$C_8$alkyl)silyl group, more preferably hydrogen, $C_1$-$C_{25}$alkyl, or $C_1$-$C_{25}$alkoxy.

Preferably, $Ar^2$, $Ar^{2'}$, $Ar^3$, $Ar^{3'}$, $Ar^4$ and $Ar^{4'}$ have independently of each other the meaning of $Ar^1$.

In a preferred embodiment $Ar^2$, $Ar^{2'}$, $Ar^3$, $Ar^{3'}$, $Ar^4$ and $Ar^{4'}$ are independently of each other a group of formula (XIa), (XIb), (XIc), (XIe), (XIf), (XIk), (XIm), (XIn), (XIr), (XIx), (XIz), (XIIj), (XIII), such as, for example, (XIIIa), or (XIIIb); or (XIV), such as, for example, (XIVb). Preferably, $Ar^2$, $Ar^{2'}$, $Ar^3$, $Ar^{3'}$, $Ar^4$ and $Ar^{4'}$ are independently of each other a group of formula XIa, XIb, XIf, XIr, XIIj, or XIIIa. More preferably, Ar², Ar²', Ar³, Ar³', Ar⁴ and Ar⁴' are independently of each other a group of formula XIa, XIb, XIf, or XIIj, Most preferred a group of formula XIa.

Preferably, $R^{105}$, $R^{105'}$, $R^{106}$ and $R^{106'}$ are independently of each other hydrogen, halogen, cyano, $C_1$-$C_{25}$alkyl or $C_1$-$C_{18}$alkoxy, more preferably $C_1$-$C_{25}$alkyl or $C_1$-$C_{18}$alkoxy, most preferred hydrogen, or $C_1$-$C_{25}$alkyl.

$R^{107}$ is preferably hydrogen, $C_1$-$C_{25}$alkyl, $C_1$-$C_{25}$alkyl, which may optionally be interrupted by one or more oxygen or sulphur atoms; or $C_7$-$C_{25}$arylalkyl, more preferably hydrogen, or $C_1$-$C_{25}$alkyl, most preferred $C_4$-$C_{25}$alkyl.

Preferably, $R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_2$-$C_{18}$alkenyl, or $C_7$-$C_{25}$aralkyl, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, D is —CO—, —COO—, —S— or —O—, E is $C_1$-$C_8$thioalkoxy, $C_1$-$C_8$alkoxy, CN or halogen, G is E, or $C_1$-$C_{18}$alkyl. More preferably, $R^{108}$ and $R^{109}$ are independently of each other H, $C_1$-$C_{25}$alkyl or $C_7$-$C_{25}$arylalkyl. Most preferred $R^{108}$ and $R^{109}$ are independently of each other H, or $C_1$-$C_{25}$alkyl.

D is preferably —CO—, —COO—, —S— or —O—, more preferably —COO—, —S— or —O—, most preferred —S— or —O—.

Preferably, E is $C_1$-$C_8$thioalkoxy, $C_1$-$C_8$alkoxy, CN, or halogen, more preferably $C_1$-$C_8$alkoxy, CN, or halogen, most preferred halogen, especially F.

Preferably, $R^{112}$ and $R^{113}$ are independently of each other H; $C_1$-$C_{18}$alkyl; or $C_1$-$C_{18}$alkyl which is interrupted by —O—, more preferably H, or $C_1$-$C_{18}$alkyl; most preferred $C_1$-$C_{18}$alkyl.

In a preferred embodiment the present invention is directed to polymers comprising one or more (repeating) unit(s) of the formula

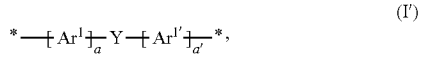

(I')

wherein Y is a group of formula

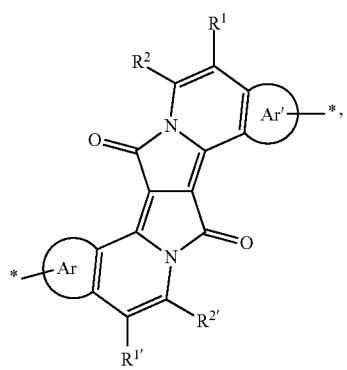

wherein
$R^1$, $R^{1'}$, $R^2$ and $R^{2'}$ may be different, but are preferably the same are preferably selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl and naphthyl, which can optionally be substituted one or more times with $C_1$-$C_{12}$alkyl or $C_1$-$C_{12}$alkoxy, —CO—$C_5$-$C_{12}$cycloalkyl and —COO—$C_1$-$C_{18}$alkyl; more preferably $C_1$-$C_{50}$alkyl; most preferred $C_1$-$C_{38}$alkyl group;
a is 0, 1, 2, or 3, a' is 0, 1, 2, or 3; wherein $Ar^1$ and $Ar^{1'}$ are as defined above; and $R^{103}$, $R^{103'}$, D and E are as defined above.

Preferably a is 0, 1, or 2, a' is 0, 1, or 2.

a and a' may be different, but are preferably the same. a and a' are preferably 0 or 1, more preferably 0.

In formula

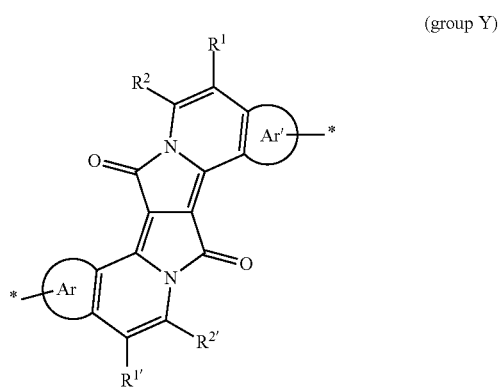

(group Y)

Ar and Ar' are selected independently of each other a homo- or heteroaromatic system, which may be substituted, or unsubstituted. The homo- or heteroaromatic systems, Ar and Ar', may be different, but are preferably the same.

The homo- or heteroaromatic system (Ar and Ar', respectively) is preferably selected from the group consisting of benzene, furan, thiopene, pyrrole, selenophene, benzofuran, benzothiophene, indole, benzoselenophene, thieno[2,3-b]thiophene, thieno[3,2-b]thiophene and 9H-fluorene, which may optionally be substituted. Ar and Ar' are selected independently of each other preferably from

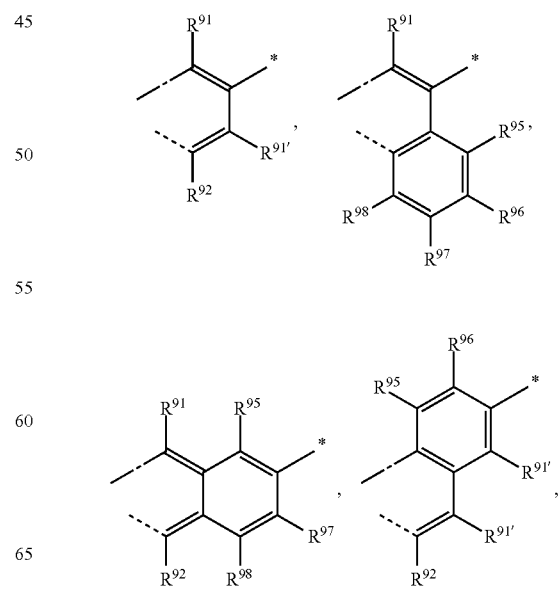

-continued

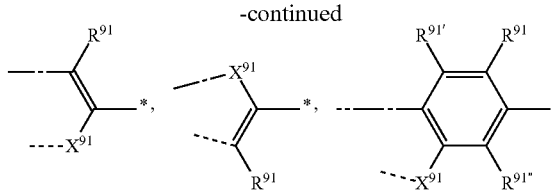

especially

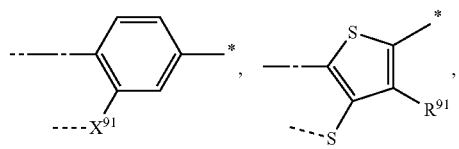

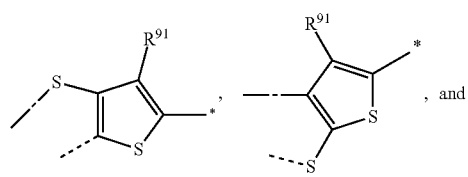

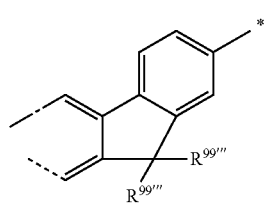

wherein the dotted lines denotes the bonds to the 6-membered ring (the dotted line —·— indicates the bond to the carbon atom in para-position to the nitrogen atom, the dotted line ····· indicates the bond to the carbon atom in meta-position to the nitrogen atom).

$R^1$, $R^{1'}$, $R^2$ and $R^{2'}$ may be the same or different and are selected from hydrogen or a $C_1$-$C_{38}$alkyl group, especially where in the pair $R^1$, $R^2$ one is a hydrogen and the other is a $C_8$-$C_{36}$alkyl group and in the pair $R^{1'}$, $R^{2'}$ one is a hydrogen and the other is a $C_8$-$C_{36}$alkyl group.

$R^{99'''}$ is hydrogen, $C_1$-$C_{25}$alkyl, or $C_1$-$C_{25}$alkyl substituted with one or more halogen atoms and/or interrupted by one or more oxygen atoms, or two moieties $R^{99}$ can form a 5 or 6 membered alkyl ring.

In another preferred embodiment Ar and Ar' are selected independently of each other from

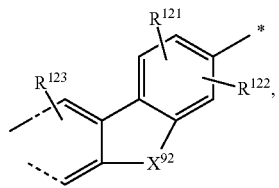

such as, for example,

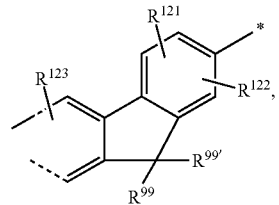

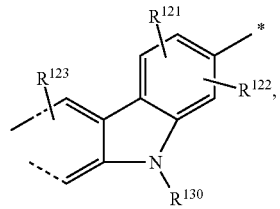

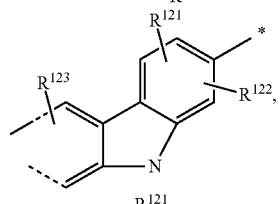

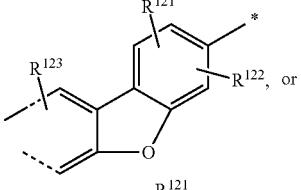

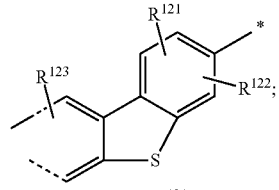

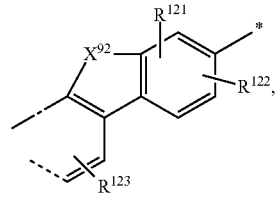

such as, for example,

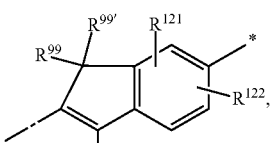 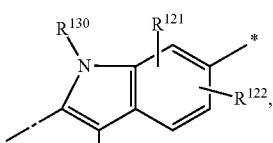

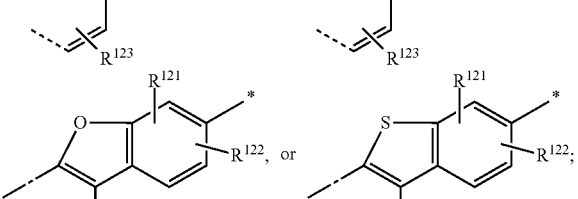

-continued
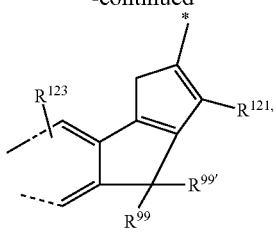
such as, for example,
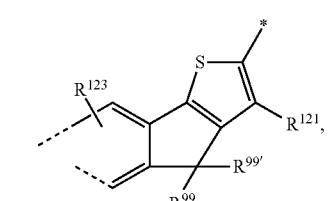
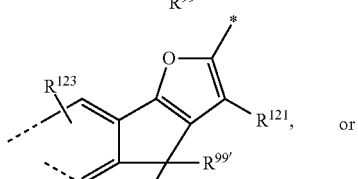
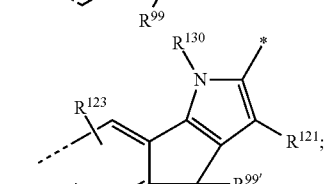
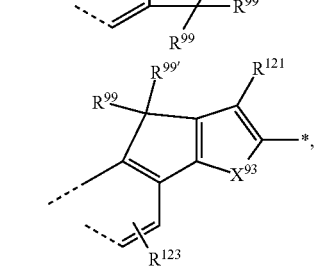
such as, for example,
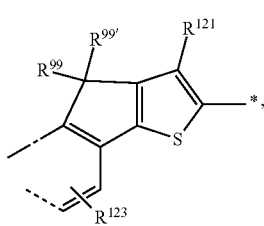 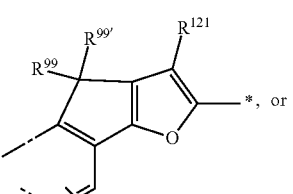
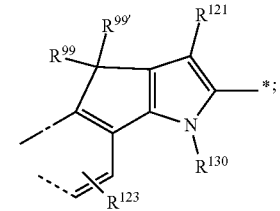 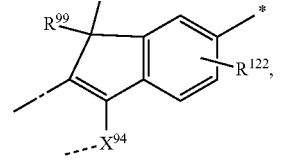
such as, for example,
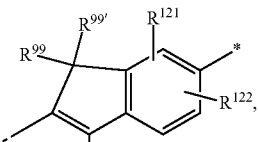
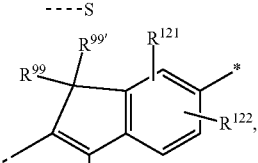
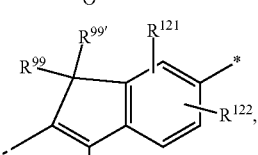
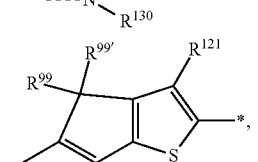
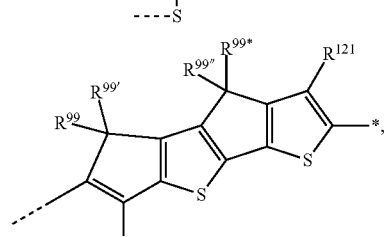
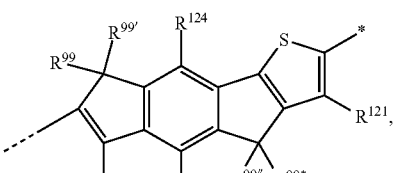
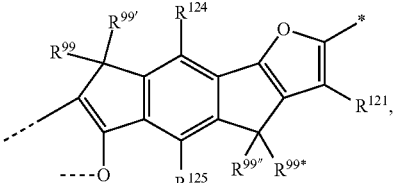
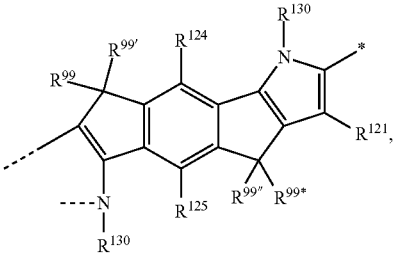

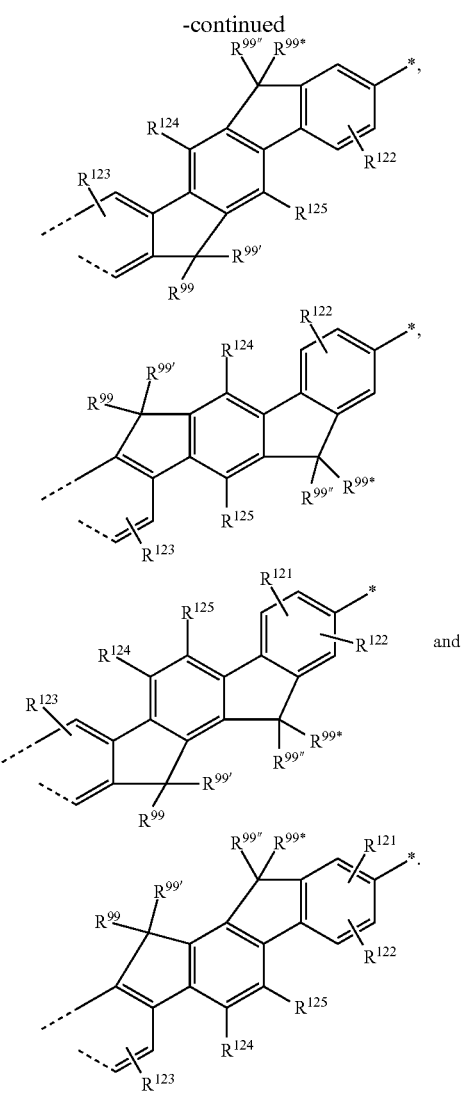

$R^{91}$, $R^{91'}$ and $R^{91''}$ are independently of each other H, halogen, especially F; cyano, $C_1$-$C_{25}$alkoxy, $C_1$-$C_{25}$alkyl substituted with one or more halogen atoms, especially F; or $C_1$-$C_{25}$alkyl, $R^{92}$ is H, halogen, especially F; cyano, $C_1$-$C_{25}$alkoxy, or $C_1$-$C_{25}$alkyl, $R^{95}$, $R^{96}$, $R^{97}$ and $R^{98}$ are independently of each other hydrogen, halogen, especially F; cyano, $C_1$-$C_{25}$alkyl, $C_1$-$C_{25}$alkoxy, or $C_1$-$C_{25}$alkyl substituted with one or more halogen atoms, especially F;

$X^{91}$ is O, S, Se, or $NR^{94}$, $X^{92}$ is O, S, $CR^{99}R^{99'}$, or $NR^{130}$, $X^{93}$ is O, S, or $NR^{130}$, $X^{94}$ is O, S, or $NR^{130}$, $R^{94}$ and $R^{130}$ are independently of each other hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl, and $R^{99}$, $R^{99'}$, $R^{99''}$ and $R^{99*}$ are independently of each other hydrogen, $C_1$-$C_{25}$alkyl, or $C_1$-$C_{25}$alkyl substituted with one or more halogen atoms and/or interrupted by one or more oxygen atoms, or two moieties $R^{99}$ and $R^{99'}$ or $R^{99''}$ and $R^{99*}$ can form a 5 or 6 membered alkyl ring, which optionally can be substituted with one or more halogen atoms and/or interrupted by one or more oxygen atoms. Preferably $R^{99}$, $R^{99'}$, $R^{99''}$ and $R^{99*}$ are independently of each other hydrogen, $C_1$-$C_{25}$alkyl, or $C_1$-$C_{25}$alkyl substituted with one or more halogen atoms and/or interrupted by one or more oxygen atoms. More preferably $R^{99}$, $R^{99'}$, $R^{99''}$ and $R^{99*}$ are independently of each other hydrogen, $C_1$-$C_{25}$alkyl, or $C_1$-$C_{25}$alkyl interrupted by one or more oxygen atoms. Most preferably $R^{99}$, $R^{99'}$, $R^{99''}$ and $R^{99*}$ are independently of each other $C_3$-$C_{25}$alkyl, or $C_3$-$C_{25}$alkyl interrupted by one or more oxygen atoms.

$R^{121}$, $R^{122}$, $R^{123}$, $R^{124}$ and $R^{125}$ are independently of each other hydrogen, halogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl; preferably hydrogen, halogen, $C_1$-$C_{18}$alkoxy or $C_1$-$C_{25}$alkyl; most preferably hydrogen.

Preferably, $X^{91}$ is O, S, or Se, more preferably $X^{91}$ is O, or S, most preferred, $X^{91}$ is S.

Preferably, $X^{92}$, $X^{93}$ and $X^{94}$ are O, or S, more preferably S.

Preferably, $R^{94}$ is hydrogen, or $C_1$-$C_{25}$alkyl, which may optionally be interrupted by one or more oxygen or sulphur atoms. More preferably, $R^{94}$ is $C_1$-$C_{25}$alkyl.

$R^{95}$, $R^{96}$, $R^{97}$ and $R^{98}$ are preferably hydrogen, halogen, especially F; $C_1$-$C_{25}$alkyl, or $C_1$-$C_{25}$alkyl substituted with one or more halogen atoms, especially F; more preferred hydrogen or $C_1$-$C_{25}$alkyl, most preferred H.

In a preferred embodiment the present invention is directed to polymers comprising one or more (repeating) unit(s) of the formula

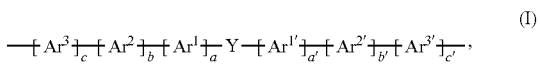

wherein a, b, c, a', b', c', $Ar^1$, $Ar^{1'}$, $Ar^2$, $Ar^{2'}$, $Ar^3$ and $Ar^{3'}$ are as defined above, Y is a group of formula

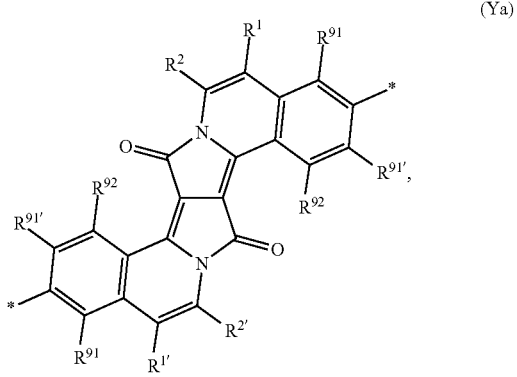

-continued
(Yb)
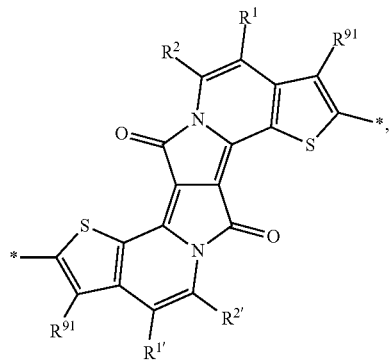
(Yc)
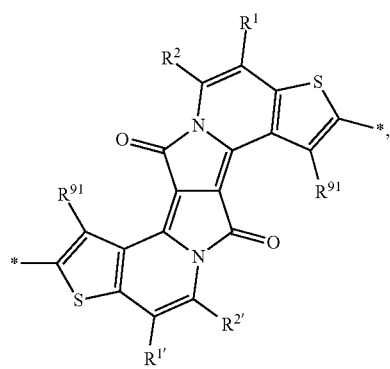
(Yd)
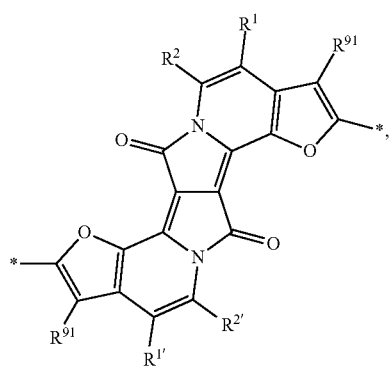
(Ye)
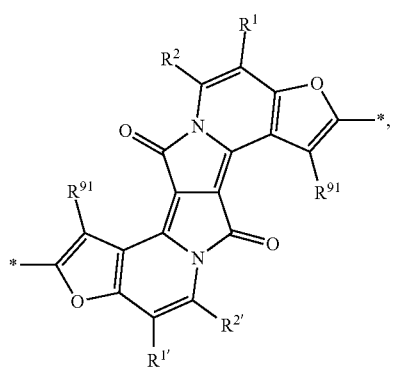
(Yf)
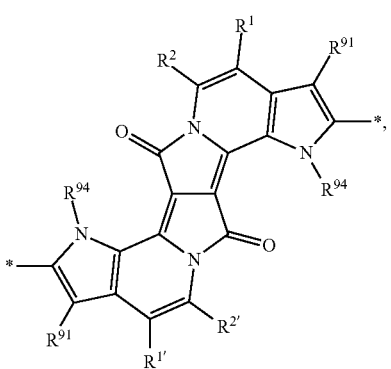
(Yg)
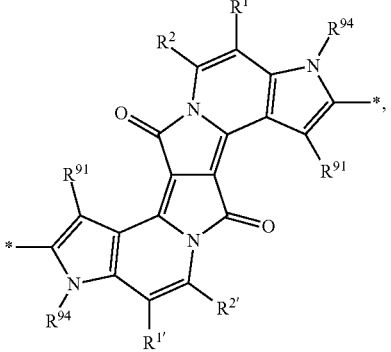
(Yh)
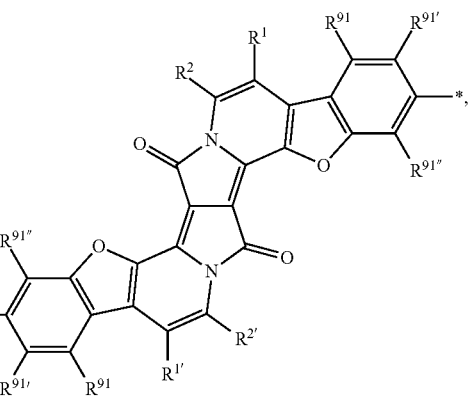
(Yi)
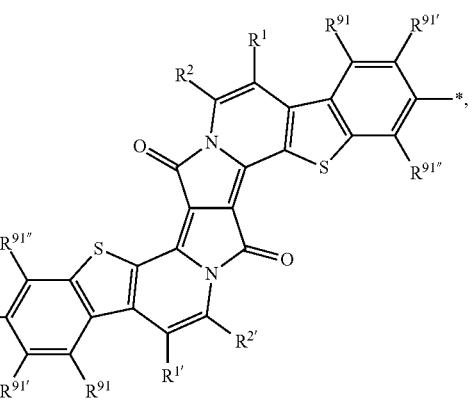

(Yj) 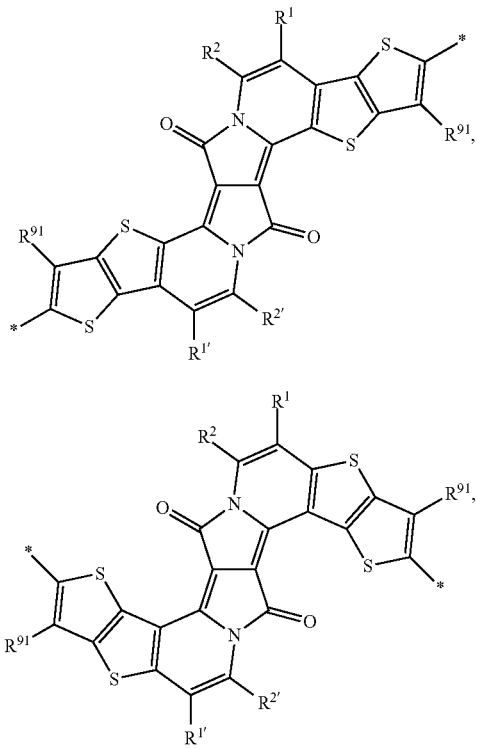

(Yk)

(Yl)

(Ym) 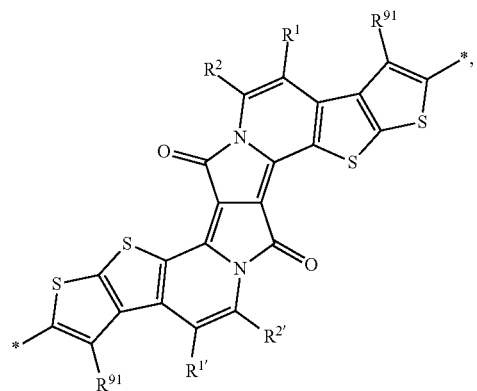 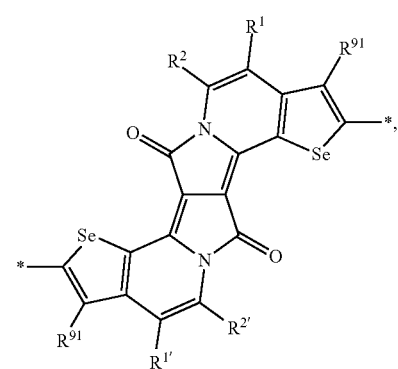

(Yn) 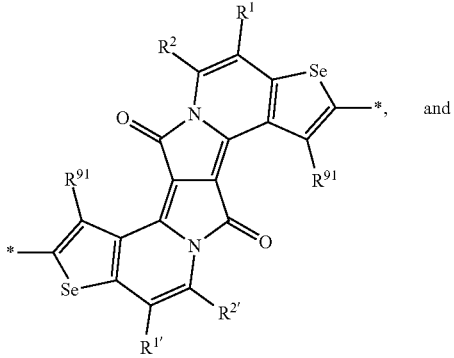

(Yo) 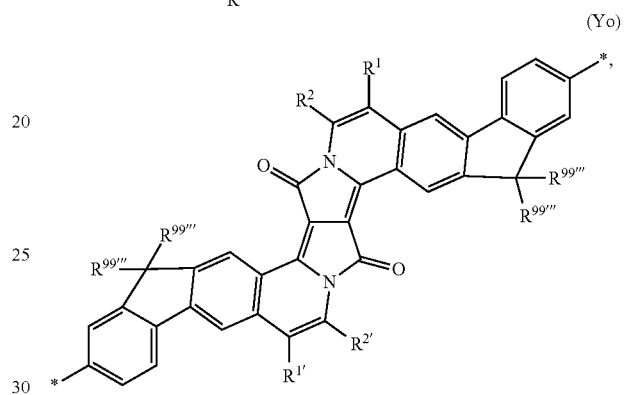

wherein
$R^1$, $R^{1'}$, $R^2$ and $R^{2'}$ may be the same or different and are selected from hydrogen or a $C_1$-$C_{38}$alkyl group;

$R^{91}$, $R^{91'}$ and $R^{91''}$ are independently of each other H, halogen, especially F; cyano, $C_1$-$C_{25}$alkoxy, $C_1$-$C_{25}$alkyl substituted with one or more halogen atoms, especially F; or $C_1$-$C_{25}$alkyl, $R^{92}$ is H, halogen, especially F; cyano, $C_1$-$C_{25}$alkoxy, or $C_1$-$C_{25}$alkyl, $R^{94}$ is hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl; and $R^{99'''}$ is hydrogen, $C_1$-$C_{25}$alkyl, or $C_1$-$C_{25}$alkyl substituted with one or more halogen atoms and/or interrupted by one or more oxygen atoms, or two groups $R^{99}$ can form a 5 or 6 membered alkyl ring.

Polymers, comprising a repeating unit (I) with Y of the formula (Ya), (Yb), (Yc), (Yd), (Ye), (Yf), (Yg), (Yh), (Yi), (Yj), (Yk), (Yl), (Ym), (Yn) and (Yo) are preferred. Polymers, comprising a repeating unit (I) with Y of the formula (Ya), (Yb), (Yd), (Yf), (Yh), (Yi), (Yj), (Ym) and (Yo) are more preferred. Polymers, comprising a repeating unit (I) with Y of the formula (Yb), (Yd), (Yj) and (Yo) are most preferred.

$R^{91}$ is preferably H, $C_1$-$C_{25}$alkoxy, or $C_1$-$C_{25}$alkyl; more preferred hydrogen, or $C_1$-$C_{25}$alkyl, most preferred hydrogen.

$R^{91'}$ is preferably H, $C_1$-$C_{25}$alkoxy, or $C_1$-$C_{25}$alkyl; more preferred hydrogen, or $C_1$-$C_{25}$alkyl, most preferred hydrogen.

$R^{91''}$ is preferably H, $C_1$-$C_{25}$alkoxy, or $C_1$-$C_{25}$alkyl; more preferred hydrogen, or $C_1$-$C_{25}$alkyl, most preferred hydrogen.

$R^{92}$ is preferably H, $C_1$-$C_{25}$alkoxy, or $C_1$-$C_{25}$alkyl; more preferred hydrogen, or $C_1$-$C_{25}$alkyl, most preferred hydrogen.

Among repeating units of formula Ya to Yo repeating units are more preferred, wherein $R^2$ and $R^{2'}$ are hydrogen. $R^1$ and $R^{1'}$ may be different, but are preferably the same and are selected from $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $E^{Si}$ or one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, $R^1$ is $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. Most preferred $R^1$ is $C_1$-$C_{25}$alkyl.

In another preferred embodiment the present invention is directed to polymers comprising one or more (repeating) unit(s) of the formula

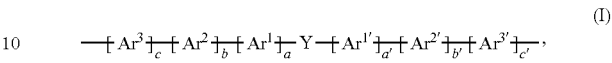

(I)

wherein
a, b, c, a', b', c', $Ar^1$, $Ar^{1'}$, $Ar^2$, $Ar^{2'}$, $Ar^3$ and $Ar^{3'}$ are as defined above,
Y is a group of formula

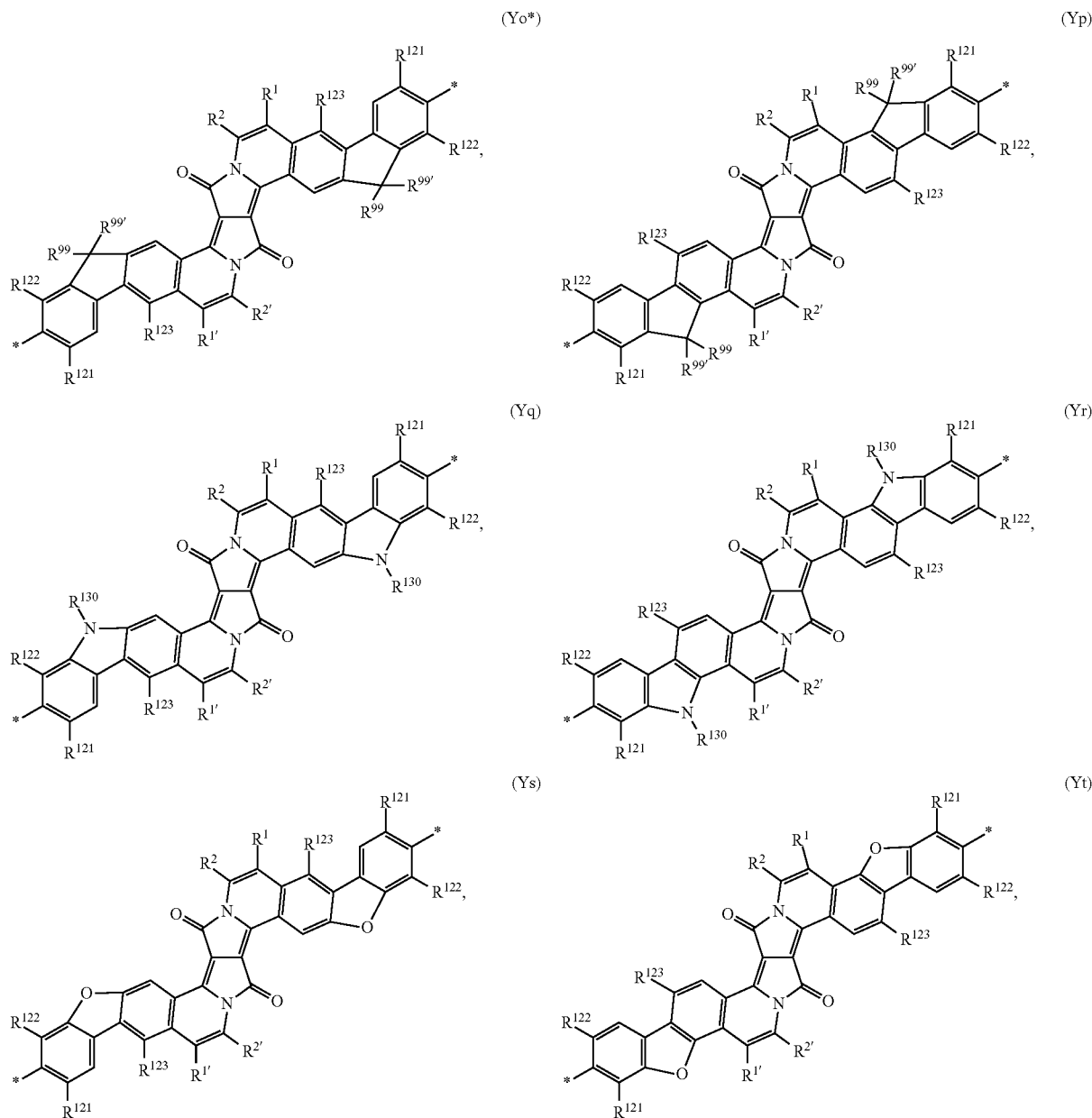

-continued
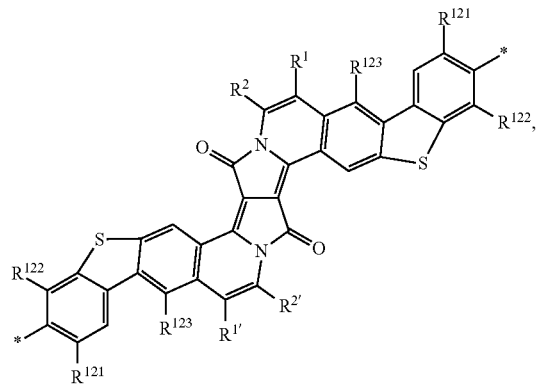
(Yu)
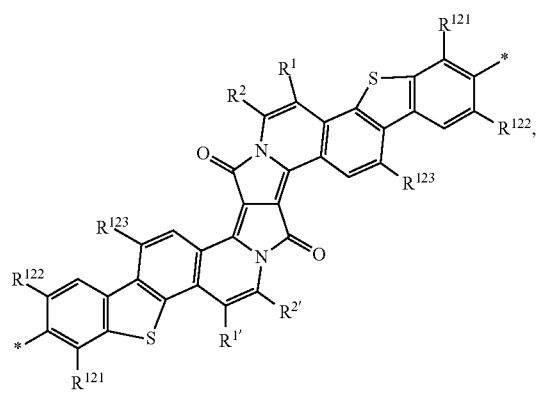
(Yv)
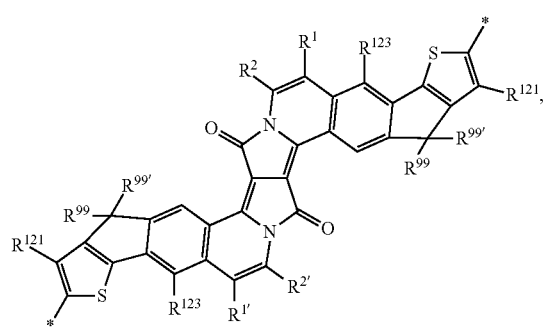
(Yw)
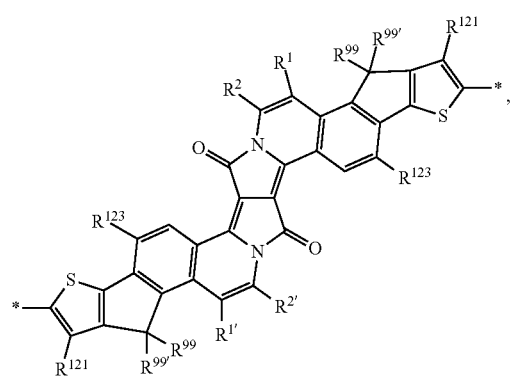
(Yx)
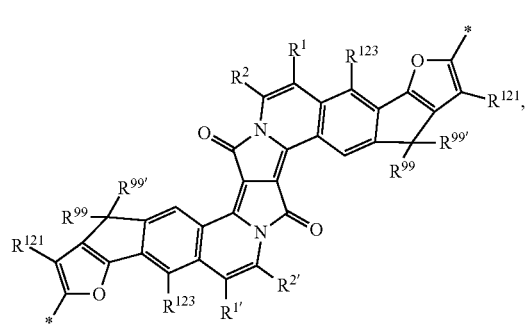
(Yy)
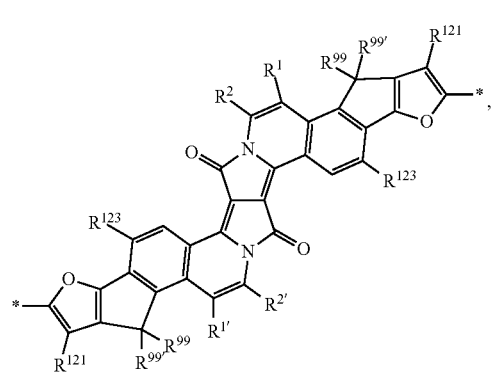
(Yz)
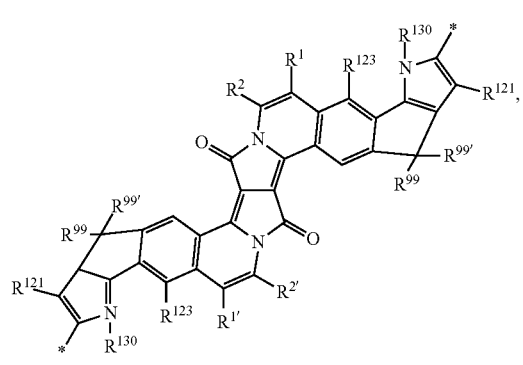
(Yaa)
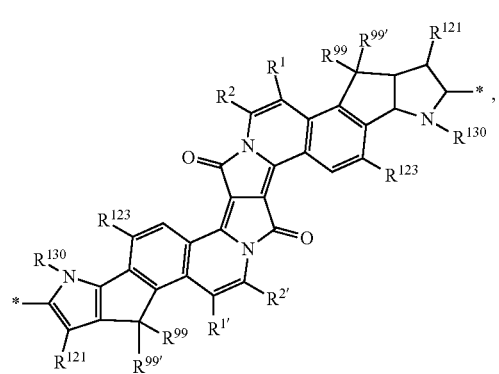
(Yab)

-continued
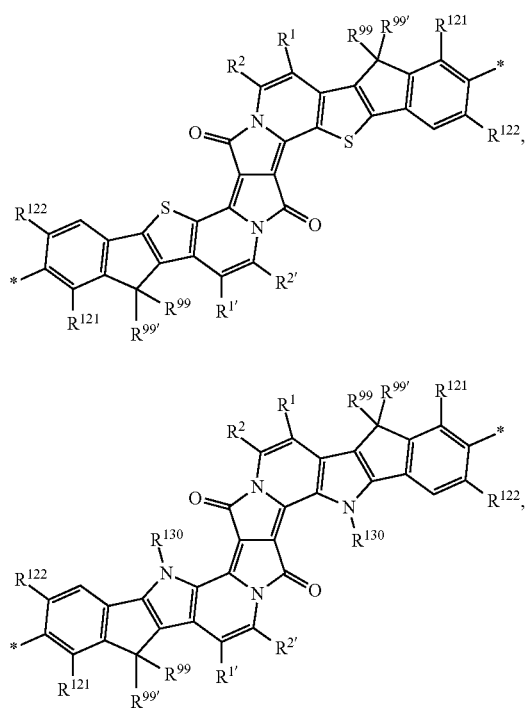
(Yac)
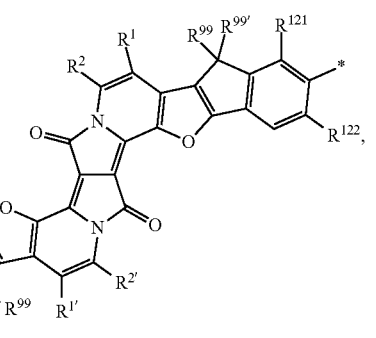
(Yad)
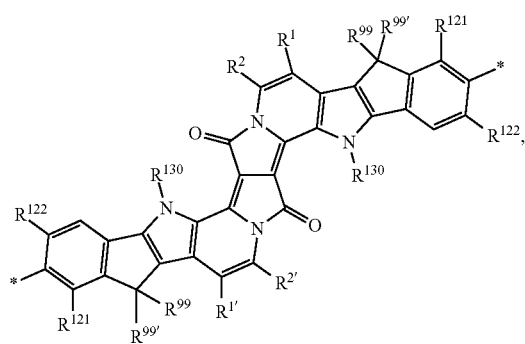
(Yae)
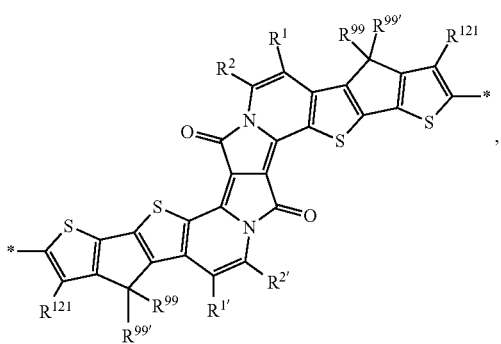
(Yaf)
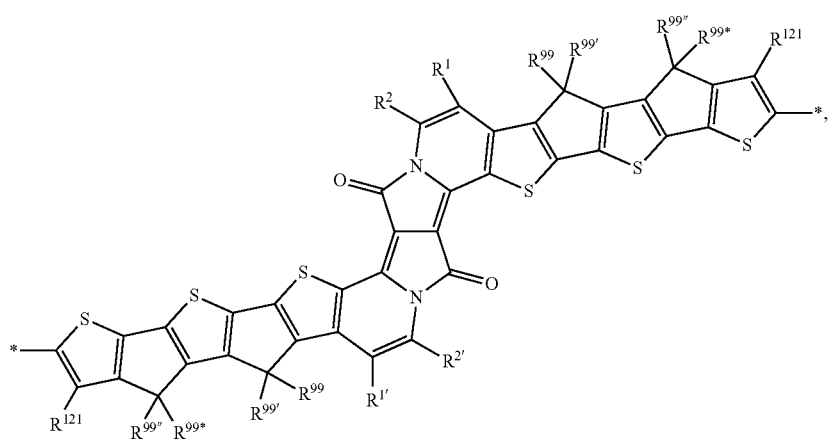
(Yag)
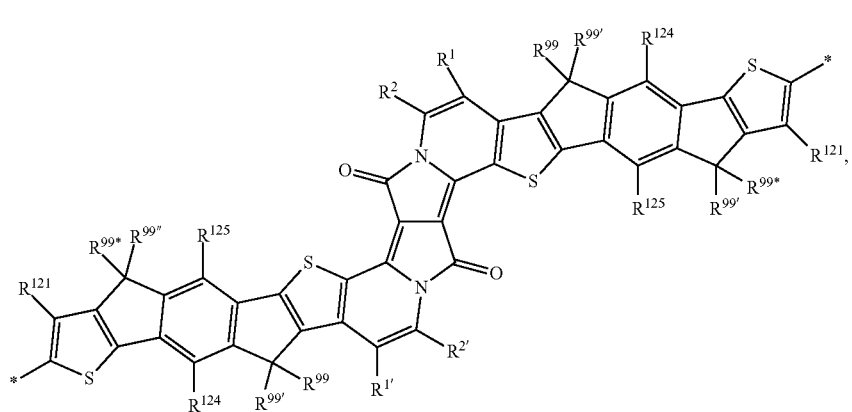
(Yah)

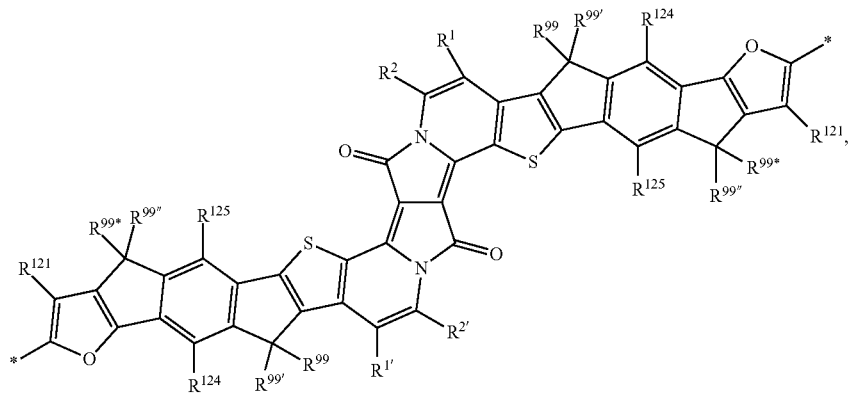
(Yai)
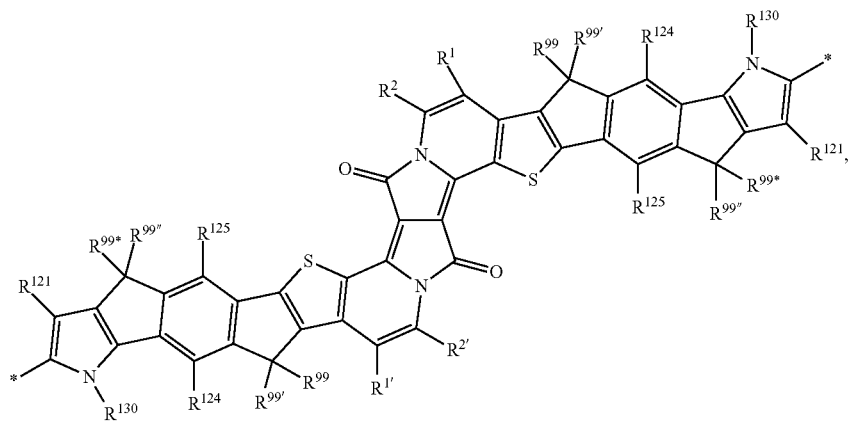
(Yaj)
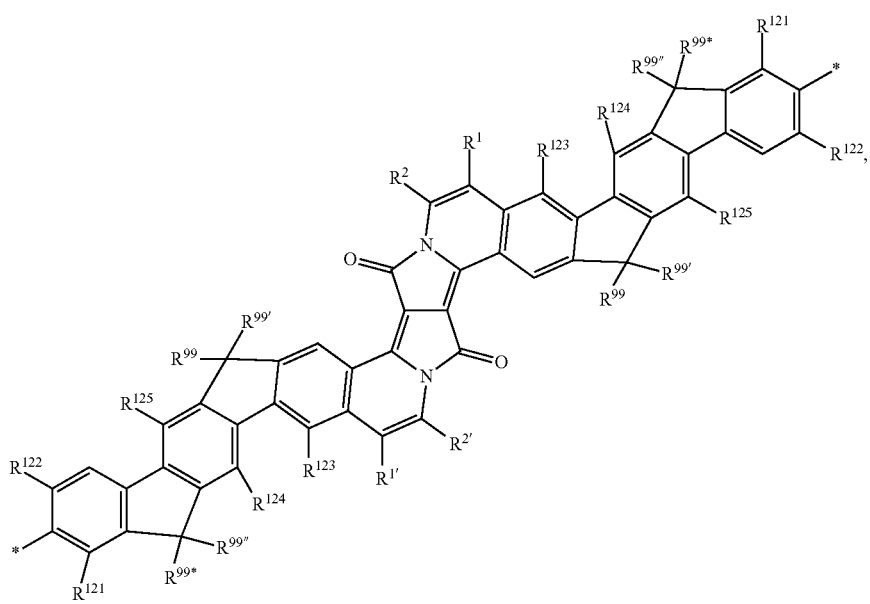
(Yak)

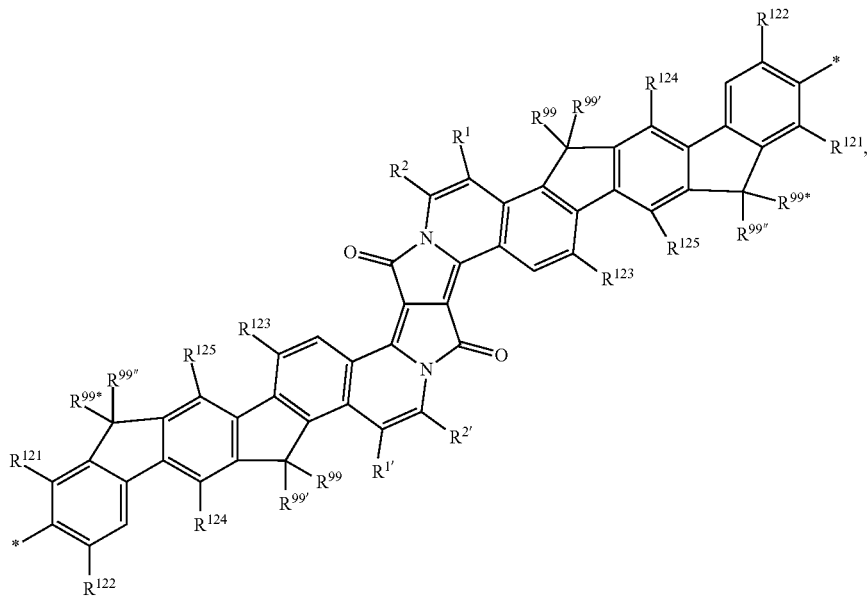
(Yal)
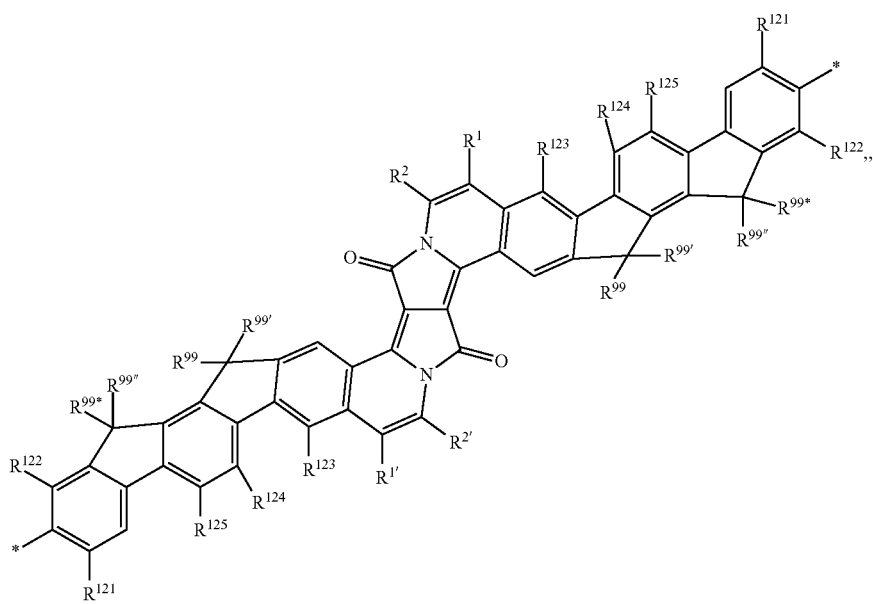
(Yam)

-continued

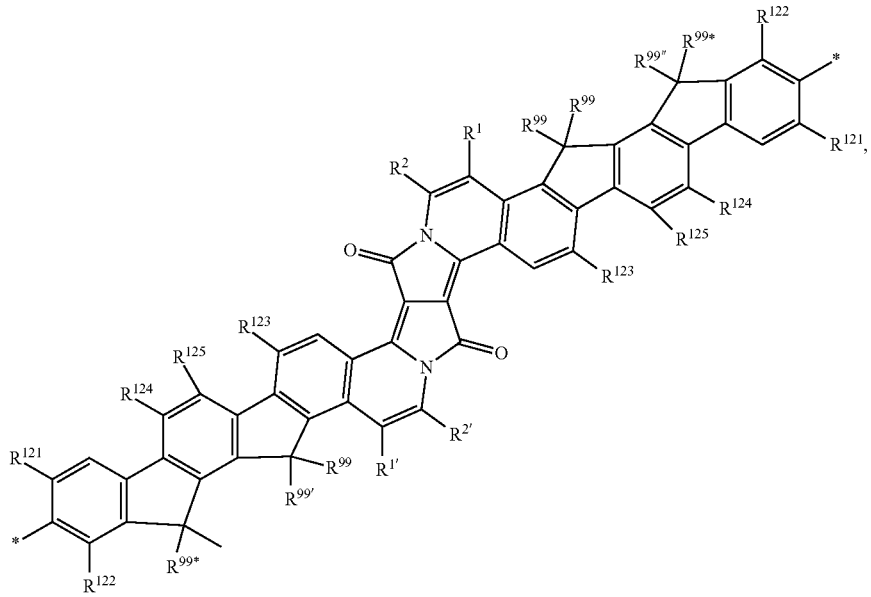
(Yan)

wherein
$R^1$, $R^{1'}$, $R^2$ and $R^{2'}$ may be the same or different and are selected from hydrogen or a $C_1$-$C_{38}$alkyl group;
$R^{99}$, $R^{99'}$, $R^{99''}$ and $R^{99*}$ are independently of each other hydrogen, $C_1$-$C_{25}$alkyl, or $C_1$-$C_{25}$alkyl interrupted by one or more oxygen atoms; preferably $C_3$-$C_{25}$alkyl, or $C_3$-$C_{25}$alkyl which is interrupted by one or more oxygen atoms;
$R^{121}$, $R^{122}$, $R^{123}$, $R^{124}$ and $R^{125}$ are independently of each other hydrogen, halogen, $C_1$-$C_{18}$alkoxy or $C_1$-$C_{25}$alkyl; preferably hydrogen; and
$R^{130}$ is hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl.

In said embodiment polymers, comprising a repeating unit (I) with Y of the formula (Yo*), (Yp), (Yw), (Yx), (Yy), (Yz), (Yaa), (Yab), (Yac), (Yad), (Yae), (Yaf), (Yag), (Yah), (Yai), (Yaj), (Yak), (Yal), (Yam) and (Yan) are preferred. Polymers, comprising a repeating unit (I) with Y of the formula (Yo*), (Yw), (Yx), (Yy), (Yz), (Yac), (Yad), (Yaf), (Yag), (Yah), (Yai), (Yak), (Yal), (Yam) and (Yan) are more preferred. Polymers, comprising a repeating unit (I) with Y of the formula (Yo*), (Yw), (Yac), (Yaf), (Yag), (Yah), (Yak) and (Yam) are even more preferred. Polymers, comprising a repeating unit (I) with Y of the formula (Yo*), (Yaf) and (Yah), especially a repeating unit (I) with Y of the formula (Yo*), are most preferred.

Among repeating units of formula Yo* to Yan repeating units are more preferred, wherein $R^2$ and $R^{2'}$ are hydrogen. $R^1$ and $R^{1'}$ may be different, but are preferably the same and are selected from hydrogen, $C_1$-$C_{25}$alkyl, $C_2$-$C_{25}$alkenyl, $C_2$-$C_{25}$alkenyl, which may optionally be interrupted by one or more oxygen atoms and/or is optionally substituted by a group $E^{Si}$ or one or more halogen atoms, especially F; $C_3$-$C_{10}$heteroaryl; $C_3$-$C_{10}$heteroaryl, which is substituted by halogen, $C_1$-$C_{18}$alkyl, or $C_1$-$C_{18}$alkoxy; or $C_1$-$C_{25}$alkyl, which may optionally be interrupted by one or more oxygen atoms and/or is optionally substituted by a group $E^{Si}$ or one or more halogen atoms, especially F. More preferred, $R^1$ is hydrogen, $C_1$-$C_{25}$alkyl, or $C_1$-$C_{25}$alkyl, which may optionally be interrupted by one or more oxygen atoms and/or is optionally substituted by a group $E^{Si}$ or one or more fluorine atoms. Most preferred $R^1$ is hydrogen or $C_1$-$C_{25}$alkyl. In another preferred embodiment $R^1$, $R^{1'}$, $R^2$ and $R^{2'}$ in the repeating units of formula Yo* to Yan are hydrogen.

In another embodiment the present invention is directed to polymers, comprising (repeating) unit(s) of the formula

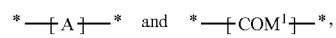

wherein
A is a repeating unit of formula (I), and
-COM$^1$- is a repeating unit, which has the meaning of Ar$^1$, wherein Ar$^1$ is as defined above, or is a group of formula

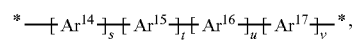

s is 1, t is 1, u is 0, or 1, v is 0, or 1, and
Ar$^{14}$, Ar$^{15}$, Ar$^{16}$ and Ar$^{17}$ are independently of each other a group of formula

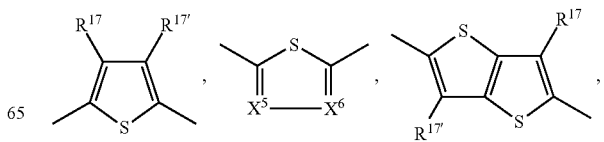

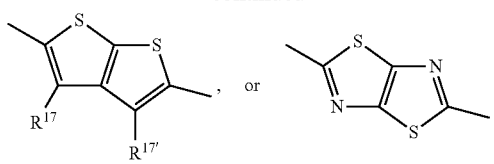

wherein one of $X^5$ and $X^6$ is N and the other is $CR^{14}$, and $R^{17}$ and $R^{17'}$ are independently of each other H, or a $C_1$-$C_{25}$alkyl group.

Preferably $Ar^{14}$, $Ar^{15}$, $Ar^{16}$ and $Ar^{17}$ are independently of each other a group of formula

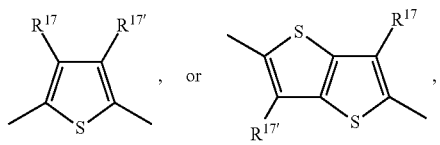

most preferably

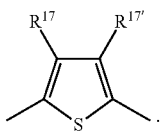

In a preferred embodiment -COM$^1$- is a group of formula (XIa), (XIb), (XIc), (XIe), (XIf), (XIk), (XIm), (XIn), (XIr), (XIx), (XIz), (XIIj), (XIII), such as, for example, (XIIIa), or (XIIIb); or (XIV), such as, for example, (XIVb). Preferably -COM$^1$- is a group of formula XIa, XIb, XIf, XIr, XIIj, or XIIIa. More preferably, -COM$^1$- is a group of formula XIa, XIb, XIf, or XIIj; most preferred XIa.

Examples of a group of formula

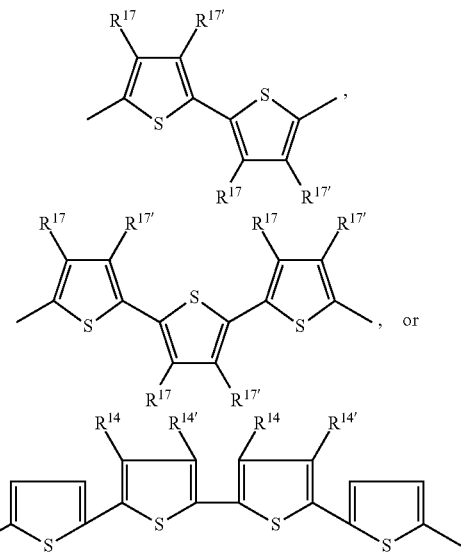

are

In a particularly preferred embodiment the repeating unit -COM$^1$- is a group of formula

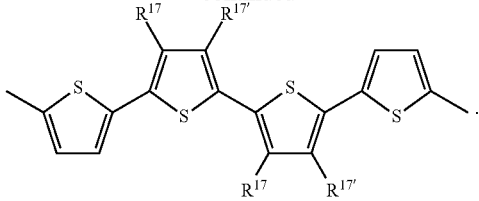

(Xa)

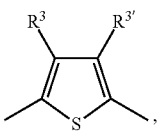

(Xf)

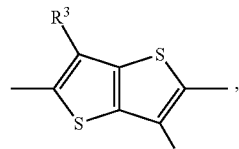

(XIIj)

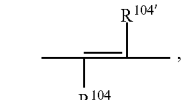

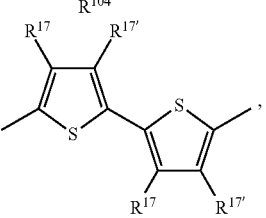

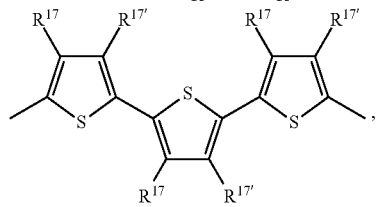

where $R^3$ and $R^{3'}$ are independently of each other hydrogen, or $C_1$-$C_{25}$alky, $R^{104}$ and $R^{104'}$ preferably are independently of each other hydrogen, cyano or a $C_1$-$C_{25}$alkyl group, and $R^{17}$ and $R^{17'}$ are independently of each other H, or a $C_1$-$C_{25}$alkyl group, especially a $C_6$-$C_{25}$alkyl, which may optionally be interrupted by one or more oxygen atoms.

In another preferred embodiment the repeating unit -COM$^1$- is a group of formula (XVa)

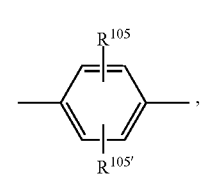

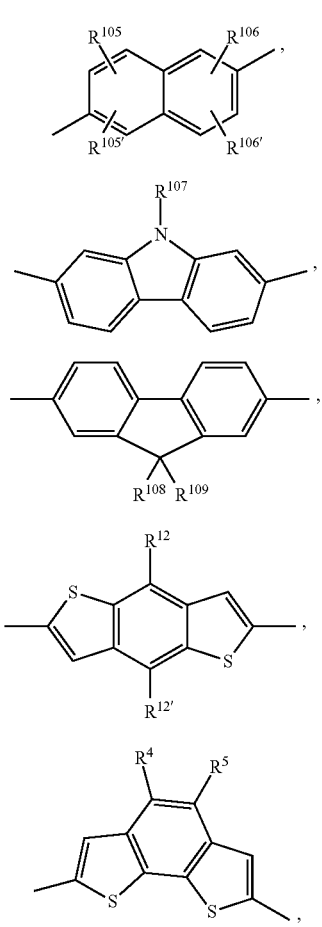

wherein
R⁴ and R⁵ are independently of each other hydrogen, or $C_1$-$C_{25}$alkyl;
R¹² and R¹²' are H, or a $C_1$-$C_{25}$alkyl group;
R¹⁰⁵, R¹⁰⁵', R¹⁰⁶ and R¹⁰⁶' are independently of each other hydrogen, halogen, cyano, $C_1$-$C_{25}$alkyl or $C_1$-$C_{25}$alkoxy, especially hydrogen or $C_1$-$C_{25}$alkyl;
R¹⁰⁷ is $C_1$-$C_{25}$alkyl, and
R¹⁰⁸ and R¹⁰⁹ are independently of each other a $C_1$-$C_{25}$alkyl, which may be interrupted by one or more oxygen atoms.

In a preferred embodiment of the present invention the polymer is a copolymer, comprising repeating units of formula $$*\!-\!\!+\!\!A\!\!-\!\!+\!\!COM^1\!\!+\!\!-\!*,\quad(VII)$$

especially a copolymer of formula $$*\!-\!\!+\!\![A]\!-\![COM^1]\!\!+\!\!_n\!-\!*,\quad(VII')$$

wherein A and COM¹ are as defined above; n is number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150.

In a preferred embodiment the present invention is directed to polymers, wherein A is a repeating unit of formula (Ya), (Yb), (Yc), (Yd), (Ye), (Yf), (Yg), (Yh), (Yi), (Yj), (Yk), (Yl), (Ym), (Yn), or (Yo), especially of formula (Ya), (Yb), (Yd), (Yf), (Yh), (Yi), (Yj), (Ym), or (Yo), and very especially of formula (Yb), (Yd), (Yj), or (Yo), and

is a group of formula

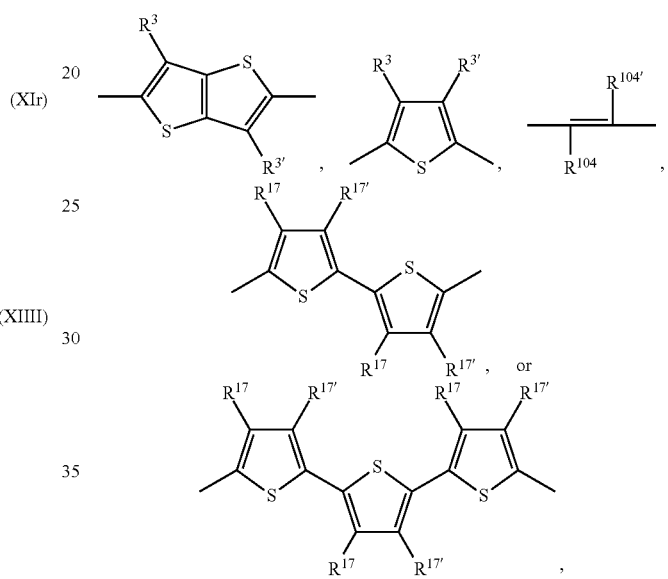

where R³, R³', R¹⁷ and R¹⁷' are independently of each other hydrogen, or $C_1$-$C_{25}$alkyl, and R¹⁰⁴ and R¹⁰⁴' preferably are independently of each other hydrogen, cyano or a $C_1$-$C_{25}$alkyl group.

In another preferred embodiment the present invention is directed to polymers, wherein A is a repeating unit of formula (Yo*), (Yw), (Yx), (Yy), (Yz), (Yac), (Yad), (Yaf), (Yag), (Yah), (Yai), (Yak), (Yal), (Yam), or (Yan), especially of formula (Yo*), (Yw), (Yac), (Yaf), (Yag), (Yah), (Yak), or (Yam), very especially of the formula (Yo*), (Yaf), or (Yah), and

is a group of formula

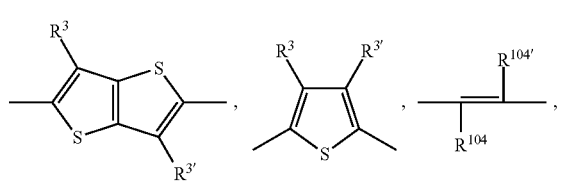

-continued

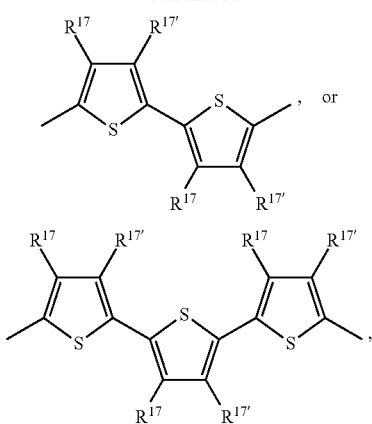

where $R^3$, $R^{3'}$, $R^{17}$ and $R^{17'}$ are independently of each other hydrogen, or $C_1$-$C_{25}$alkyl, and $R^{104}$ and $R^{104'}$ preferably are independently of each other hydrogen, cyano or a $C_1$-$C_{25}$alkyl group. Among the repeating units (Yo*), (Yaf), or (Yah) (Yo*) is more preferred.

In another preferred embodiment the present invention is directed to polymers, wherein A is a repeating unit of formula (Ya), (Yb), (Yc), (Yd), (Ye), (Yf), (Yg), (Yh), (Yi), (Yj), (Yk), (Yl), (Ym), (Yn) and (Yo), especially of formula (Ya), (Yb), (Yd), (Yf), (Yh), (Yi), (Yj), (Ym) and (Yo), and very especially of formula (Yb), (Yd), (Yj) and (Yo), and

is a group of formula

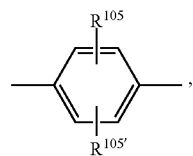
(XVa)

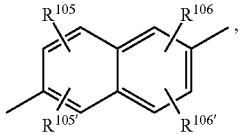
(XVb)

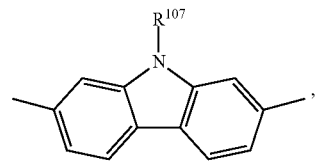
(XVIa)

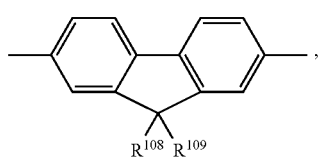
(XVIb)

-continued

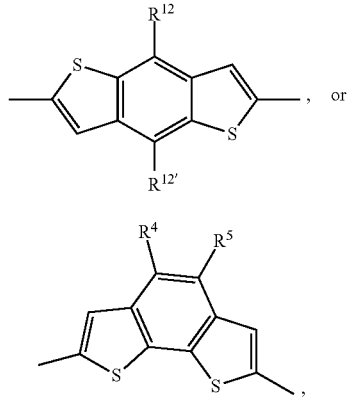

wherein $R^4$ and $R^5$ are independently of each other hydrogen, or $C_1$-$C_{25}$alkyl;

$R^{12}$ and $R^{12'}$ are H, or a $C_1$-$C_{25}$alkyl group;

$R^{105}$, $R^{105'}$, $R^{106}$ and $R^{106'}$ are independently of each other hydrogen, halogen, cyano, $C_1$-$C_{25}$alkyl or $C_1$-$C_{25}$alkoxy, especially hydrogen or $C_1$-$C_{25}$alkyl;

$R^{107}$ is $C_1$-$C_{25}$alkyl, $R^{108}$ and $R^{109}$ are independently of each other a $C_1$-$C_{25}$alkyl, which may be interrupted by one or more oxygen atoms.

In another preferred embodiment the present invention is directed to polymers, wherein A is a repeating unit of formula (Yo*), (Yw), (Yx), (Yy), (Yz), (Yac), (Yad), (Yaf), (Yag), (Yah), (Yai), (Yak), (Yal), (Yam), or (Yan), especially of formula (Yo*), (Yw), (Yac), (Yaf), (Yag), (Yah), (Yak), or (Yam), very especially of the formula (Yo*), (Yaf), or (Yah), and

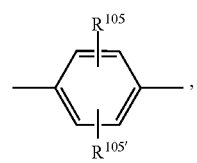

is a group of formula

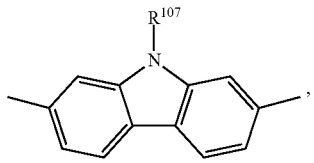
(XVa)

(XVb)

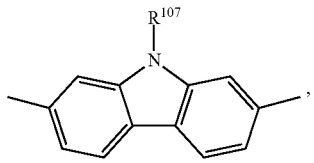
(XVIa)

(XVIb)

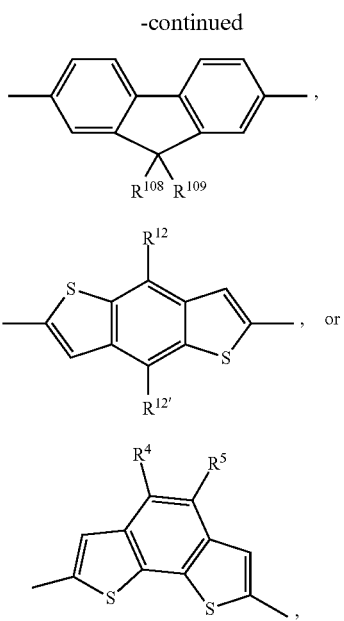

(XIII)

wherein
R⁴ and R⁵ are independently of each other hydrogen, or $C_1$-$C_{25}$alkyl;
$R^{12}$ and $R^{12'}$ are H, or a $C_1$-$C_{25}$alkyl group;
$R^{105}$, $R^{105'}$, $R^{106}$ and $R^{106'}$ are independently of each other hydrogen, halogen, cyano, $C_1$-$C_{25}$alkyl or $C_1$-$C_{25}$alkoxy, especially hydrogen or $C_1$-$C_{25}$alkyl;
$R^{107}$ is $C_1$-$C_{25}$alkyl,
$R^{108}$ and $R^{109}$ are independently of each other a $C_1$-$C_{25}$alkyl, which may be interrupted by one or more oxygen atoms. Among the repeating units (Yo*), (Yaf), or (Yah) (Yo*) is more preferred.

Among the polymers of formula VII' the polymers of formula (Ia-1), (Ia-2), (Ia-3), (Ia-4), (Ia-5), (Ia-6), (Ia-7), (Ia-8), (Ia-9), (Ia-10), (Ia-11), (Ia-12), (Ia-13), (Ia-14), (Ia-15), (Ia-16), (Ia-17), (Ia-18), (Ia-19), (Ia-20), (Ia-21), (Ia-22), (Ia-23), (Ia-24), (Ia-25), (Ia-26), (Ia-27), (Ia-28), (Ia-29) and (Ia-30), as defined in claim 9, are preferred.
n is preferably 4 to 1000, especially 4 to 200, very especially 5 to 100,
$R^1$ is preferably a $C_1$-$C_{38}$alkyl group, especially $C_8$-$C_{36}$alkyl group,
$R^2$ is hydrogen;
$R^3$ and $R^{3'}$ are preferably hydrogen, halogen, cyano, $C_1$-$C_{25}$alkyl or $C_1$-$C_{25}$alkoxy, especially hydrogen or $C_1$-$C_{25}$alkyl;
$R^{17}$ and $R^{17'}$ are preferably H, or a $C_1$-$C_{25}$alkyl group;
$R^{91}$, $R^{91'}$ and $R^{91''}$ are preferably H, or $C_1$-$C_{25}$alkyl,
$R^{92}$ is H, or $C_1$-$C_{25}$alkyl, and
$R^{99}$ is $C_1$-$C_{25}$alkyl, or $C_1$-$C_{25}$alkyl.

According to one embodiment of the present invention polymers of formula (Ia-1), (Ia-3), (Ia-4), (Ia-6), (Ia-7), (Ia-8), (Ia-9), (Ia-10), (Ia-11), (Ia-13), (Ia-15) and (Ia-17) are more preferred.

Examples of polymers are polymers P-1 to P-25 shown in claim 10. Polymer P-15 is less preferred than polymers P-1 to P-14 and P-16 to P-25.

The polymers of the present invention can comprise more than 2 different repeating units, such as, for example, repeating units A, B and D, which are different from each other. If the polymers comprise repeating units of the formula ―(A―D*)― and ―(B―D*)―, they are preferably (random) copolymers of formula

*―(A―D*)ₓ―(B―D*)ᵧ―*,   (XIr)

wherein x=0.995 to 0.005, y=0.005 to 0.995, especially x=0.2 to 0.8, y=0.8 to 0.2, and wherein x+y=1. A is a repeating unit of formula (I), D* is a repeating unit -COM¹- and B is a repeating unit -COM¹-, or a repeating unit of formula (I); with the proviso that A, B and D* are different from each other. For A and -COM¹- the same preferences apply as above.

Copolymers of formula VII can be obtained, for example, by the Suzuki reaction. The condensation reaction of an aromatic boronate and a halogenide, especially a bromide, commonly referred to as the "Suzuki reaction", is tolerant of the presence of a variety of organic functional groups as reported by N. Miyaura and A. Suzuki in Chemical Reviews, Vol. 95, pp. 457-2483 (1995). Preferred catalysts are 2-dicyclohexylphosphino-2',6'-di-alkoxybiphenyl/palladium(II) acetates, tri-alykl-phosphonium salts/palladium (0) derivatives and tri-alkylphosphine/palladium (0) derivatives. Especially preferred catalysts are 2-dicyclohexylphosphino-2',6'-di-methoxybiphenyl (sPhos)/palladium(II)acetate and, tri-tert-butylphosphonium tetrafluoroborate ((t-Bu)₃P* HBF4)/tris(dibenzylideneacetone) dipalladium (0) (Pd₂ (dba)₃) and tri-tert-butylphosphine (t-Bu)₃P/tris(dibenzylideneacetone) dipalladium (0) (Pd₂(dba)₃). This reaction can be applied to preparing high molecular weight polymers and copolymers.

To prepare polymers corresponding to formula VII a dihalogenide of formula $X^{10}$-A-$X^{10}$ is reacted with an (equimolar) amount of a diboronic acid or diboronate corresponding to formula $X^{11}$-COM¹-$X^{11}$; or a dihalogenide of formula $X^{10}$-COM¹-$X^{10}$ is reacted with an (equimolar) amount of a diboronic acid or diboronate corresponding to formula $X^{11}$-A-$X^{11}$, wherein $X^{10}$ is halogen, especially Br, or I; and $X^{11}$ is independently in each occurrence —B(OH)₂, —B(OY¹)₂,

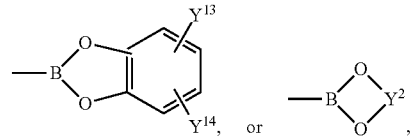

wherein $Y^1$ is independently in each occurrence a $C_1$-$C_{10}$alkyl group and $Y^2$ is independently in each occurrence a $C_2$-$C_{10}$alkylene group, such as —CY³Y⁴—CY⁵Y⁶—, or —CY⁷Y⁸—CY⁹Y¹⁰—CY¹¹Y¹²—, wherein Y³, Y⁴, Y⁵, Y⁶, Y⁷, Y⁸, Y⁹, Y¹⁰, Y¹¹ and Y¹² are independently of each other hydrogen, or a $C_1$-$C_{10}$alkyl group, especially —C(CH₃)₂C(CH₃)₂—, —CH₂C(CH₃)₂CH₂—, or —C(CH₃)₂CH₂C(CH₃)₂—, and Y¹³ and Y¹⁴ are independently of each other hydrogen, or a $C_1$-$C_{10}$alkyl group, under the catalytic action of Pd and triphenylphosphine. The reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A polymerization reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252. Control of molecular weight is possible by using either an excess of dibromide, diboronic acid, or diboronate, or a chain terminator.

According to the process described in WO2010/136352 the polymerisation is carried out in presence of
a) a catalyst/ligand system comprising a palladium catalyst and an organic phosphine or phosphonium compound,
b) a base,
c) a solvent or a mixture of solvents, characterized in that the organic phosphine is a trisubstituted phosphine of formula

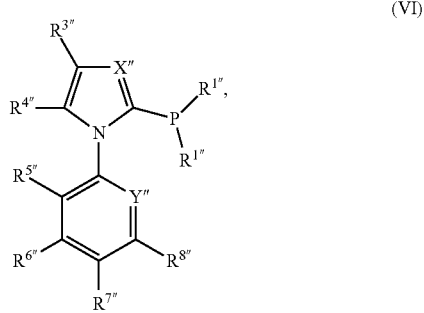

(VI)

or phosphonium salt thereof, wherein X" independently of Y" represents a nitrogen atom or a C—$R^{2'''}$ group and Y" independently of X" represents a nitrogen atom or a C—$R^{9'''}$ group, $R^{1'''}$ for each of the two $R^{1'''}$ groups independently of the other represents a radical selected from the group $C_1$-$C_{25}$-alkyl, $C_3$-$C_{20}$-cycloalkyl, which includes especially both monocyclic and also bi- and tri-cyclic cycloalkyl radicals, $C_5$-$C_{14}$-aryl, which includes especially the phenyl, naphthyl, fluorenyl radical, $C_2$-$C_{13}$-heteroaryl, wherein the number of hetero atoms, selected from the group N, O, S, may be from 1 to 2, wherein the two radicals $R^{1'''}$ may also be linked to one another,
and wherein the above-mentioned radicals $R^{1'''}$ may themselves each be mono- or poly-substituted independently of one another by substituents selected from the group hydrogen, $C_1$-$C_{20}$-alkyl, $C_2$-$C_{20}$-alkenyl, $C_3$-$C_8$-cycloalkyl, $C_2$-$C_9$-hetero-alkyl, $C_5$-$C_{10}$-aryl, $C_2$-$C_9$-heteroaryl, wherein the number of hetero atoms from the group N, O, S may be from 1 to 4, $C_1$-$C_{20}$-alkoxy, $C_1$-$C_{10}$-haloalkyl, hydroxy, amino of the forms NH—($C_1$-$C_{20}$-alkyl), NH—($C_5$-$C_{10}$-aryl), N($C_1$-$C_{20}$-alkyl)$_2$, N($C_1$-$C_{20}$-alkyl) ($C_5$-$C_{10}$-aryl), N($C_5$-$C_{10}$-aryl)$_2$, N($C_1$-$C_{20}$-alkyl/$C_5$-$C_{10}$-aryl)$_3^+$, NH—CO—$C_1$-$C_{20}$-alkyl, NH—CO—$C_5$-$C_{10}$-aryl, carboxylato of the forms COOH and COOQ (wherein Q represents either a monovalent cation or $C_1$-$C_8$-alkyl), $C_1$-$C_6$-acyloxy, sulfinato, sulfonato of the forms $SO_3H$ and $SO_3Q'$ (wherein Q' represents either a monovalent cation, $C_1$-$C_{20}$-alkyl, or $C_5$-$C_{10}$-aryl), tri-$C_1$-$C_6$-alkylsilyl, wherein two of the mentioned substituents may also be bridged with one another, $R^{2'''}$-$R^{9'''}$ represent a hydrogen, alkyl, alkenyl, cycloalkyl, aromatic or heteroaromatic aryl, O-alkyl, NH-alkyl, N-(alkyl)$_2$, O-(aryl), NH-(aryl), N-(alkyl)(aryl), O—CO-alkyl, O—CO-aryl, F, Si(alkyl)$_3$, $CF_3$, CN, $CO_2H$, COH, $SO_3H$, $CONH_2$, CONH(alkyl), CON(alkyl)$_2$, $SO_2$(alkyl), SO(alkyl), SO(aryl), $SO_2$(aryl), $SO_3$(alkyl), $SO_3$(aryl), S-alkyl, S-aryl, NH—CO (alkyl), $CO_2$(alkyl), $CONH_2$, CO(alkyl), NHCOH, $NHCO_2$(alkyl), CO(aryl), $CO_2$(aryl) radical, wherein two or more adjacent radicals, each independently of the other (s), may also be linked to one another so that a condensed ring system is present and wherein in $R^{2'''}$ to $R^{9'''}$ alkyl represents a hydrocarbon radical having from 1 to 20 carbon atoms which may in each case be linear or branched, alkenyl represents a mono- or poly-unsaturated hydrocarbon radical having from 2 to 20 carbon atoms which may in each case be linear or branched, cycloalkyl represents a hydrocarbon having from 3 to 20 carbon atoms, aryl represents a 5- to 14-membered aromatic radical, wherein from one to four carbon atoms in the aryl radical may also be replaced by hetero atoms from the group nitrogen, oxygen and sulfur so that a 5- to 14-membered heteroaromatic radical is present, wherein the radicals $R^{2'''}$ to $R^{9'''}$ may also carry further substituents as defined for $R^{1'''}$.

The organic phosphines and their synthesis are described in WO2004101581.

Preferred organic phosphines are selected from trisubstituted phosphines of formula

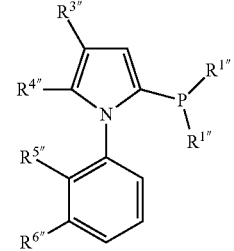

| Cpd. | $R^{1'''}$ | $R^{5'''}$ | $R^{6'''}$ | $R^{3'''}$ | $R^{4'''}$ |
|---|---|---|---|---|---|
| A-1 | H₃C—C(CH₃)(CH₃) | H | H | H | H |
| A-2 | cyclohexyl | H | H | H | H |
| A-3 | phenyl | H | H | H | H |
| A-4 | adamantyl | H | H | H | H |
| A-5 | cyclohexyl | —OCH₃ | H | H | H |
| A-6 | cyclohexyl | 1) | 1) | H | H |
| A-7 | H₃C—C(CH₃)(CH₃) | 1) | 1) | H | H |
| A-8 | phenyl | 1) | 1) | H | H |
| A-9 | adamantyl | 1) | 1) | H | H |
| A-10 | cyclohexyl | H | H | 2) | 2) |
| A-11 | H₃C—C(CH₃)(CH₃) | H | H | 2) | 2) |

| Cpd. | R¹" | R⁵" | R⁶" | R³" | R⁴" |
|---|---|---|---|---|---|
| A-12 | phenyl | H | H | 2) | 2) |
| A-13 | adamantyl | H | H | 2) | 2) |

1) R⁵" and R⁶" together form a ring 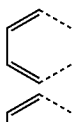.

2) R³" and R⁴" together form a ring .

Examples of preferred catalysts include the following compounds:
palladium(II) acetylacetonate, palladium(0) dibenzylideneacetone complexes, palladium(II) propionate,
Pd₂(dba)₃: [tris(dibenzylideneacetone) dipalladium(0)],
Pd(dba)₂: [bis(dibenzylideneacetone) palladium(0)],
Pd(PR₃)₂, wherein PR₃ is a trisubstituted phosphine of formula VI,
Pd(OAc)₂: [palladium(II) acetate], palladium(II) chloride, palladium(II) bromide, lithium tetrachloropalladate(II),
PdCl₂(PR₃)₂; wherein PR₃ is a trisubstituted phosphine of formula VI; palladium(0) diallyl ether complexes, palladium(II) nitrate,
PdCl₂(PhCN)₂: [dichlorobis(benzonitrile) palladium(II)],
PdCl₂(CH₃CN): [dichlorobis(acetonitrile) palladium(II)], and
PdCl₂(COD): [dichloro(1,5-cyclooctadiene) palladium(II)].

Especially preferred are PdCl₂, Pd₂(dba)₃, Pd(dba)₂, Pd(OAc)₂, or Pd(PR₃)₂. Most preferred are Pd₂(dba)₃ and Pd(OAc)₂.

The palladium catalyst is present in the reaction mixture in catalytic amounts. The term "catalytic amount" refers to an amount that is clearly below one equivalent of the (hetero)aromatic compound(s), preferably 0.001 to 5 mol-%, most preferably 0.001 to 1 mol-%, based on the equivalents of the (hetero)aromatic compound(s) used.

The amount of phosphines or phosphonium salts in the reaction mixture is preferably from 0.001 to 10 mol-%, most preferably 0.01 to 5 mol-%, based on the equivalents of the (hetero)aromatic compound(s) used. The preferred ratio of Pd:phosphine is 1:4.

The base can be selected from all aqueous and nonaqueous bases and can be inorganic, or organic. It is preferable that at least 1.5 equivalents of said base per functional boron group is present in the reaction mixture. Suitable bases are, for example, alkali and alkaline earth metal hydroxides, carboxylates, carbonates, fluorides and phosphates such as sodium and potassium hydroxide, acetate, carbonate, fluoride and phosphate or also metal alcoholates. It is also possible to use a mixture of bases. The base is preferably a lithium salt, such as, for example, lithium alkoxides (such as, for example, lithium methoxide and lithium ethoxide), lithium hydroxide, carboxylate, carbonate, fluoride and/or phosphate.

The at present most preferred base is aqueous LiOHxH₂O (monohydrate of LiOH) and (waterfree) LiOH.

The reaction is typically conducted at about 0° C. to 180° C., preferably from 20 to 160° C., more preferably from 40 to 140° C. and most preferably from 40° C. to 120° C. A polymerization reaction may take 0.1, especially 0.2 to 100 hours.

In a preferred embodiment of the present invention the solvent is THF, the base is LiOH*H₂O and the reaction is conducted at reflux temperature of THF (about 65° C.).

The solvent is for example selected from toluene, xylenes, anisole, THF, 2-methyltetrahydrofuran, dioxane, chlorobenzene, fluorobenzene or solvent mixtures comprising one or more solvents like e.g. THF/toluene and optionally water. Most preferred is THF, or THF/water.

Advantageously, the polymerisation is carried out in presence of a) palladium(II) acetate, or Pd₂(dba)₃, (tris(dibenzylideneacetone)dipalladium(0)) and an organic phosphine A-1 to A-13,
b) LiOH, or LiOHxH₂O; and
c) THF, and optionally water. If the monohydrate of LiOH is used, no water needs to be added.

Most preferred the polymerisation is carried out in presence of a) palladium(II) acetate, or Pd₂(dba)₃ (tris(dibenzylideneacetone)dipalladium(0)) and

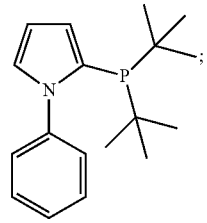 [SMILES: CC(C)(C)P(c1cccn1-c1ccccc1)C(C)(C)C]

b) LiOHxH₂O; and
c) THF. The palladium catalyst is present in an amount of preferably about 0.5 mol-%, based on the equivalents of the (hetero)aromatic compound(s) used. The amount of phosphines or phosphonium salts in the reaction mixture is preferably about 2 mol-%, based on the equivalents of the (hetero)aromatic compound(s) used. The preferred ratio of Pd:phosphine is about 1:4.

Preferably the polymerization reaction is conducted under inert conditions in the absence of oxygen. Nitrogen and more preferably argon are used as inert gases.

The process described in WO2010/136352 is suitable for large-scale applications, is readily accessible and convert starting materials to the respective polymers in high yield, with high purity and high selectivity. The process can provide polymers having weight average molecular weights of at least 10,000, more preferably at least 20,000, most preferably at least 30,000. The at present most preferred polymers have a weight average molecular weight of 30,000 to 80,000 Daltons. Molecular weights are determined according to high-temperature gel permeation chromatography (HT-GPC) using polystyrene standards. The polymers preferably have a polydispersibility of 1.01 to 10, more preferably 1.1 to 3.0, most preferred 1.5 to 2.5.

If desired, a monofunctional aryl halide or aryl boronate, such as, for example,

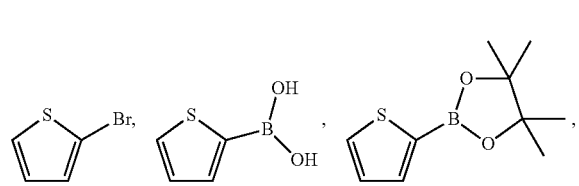

-continued

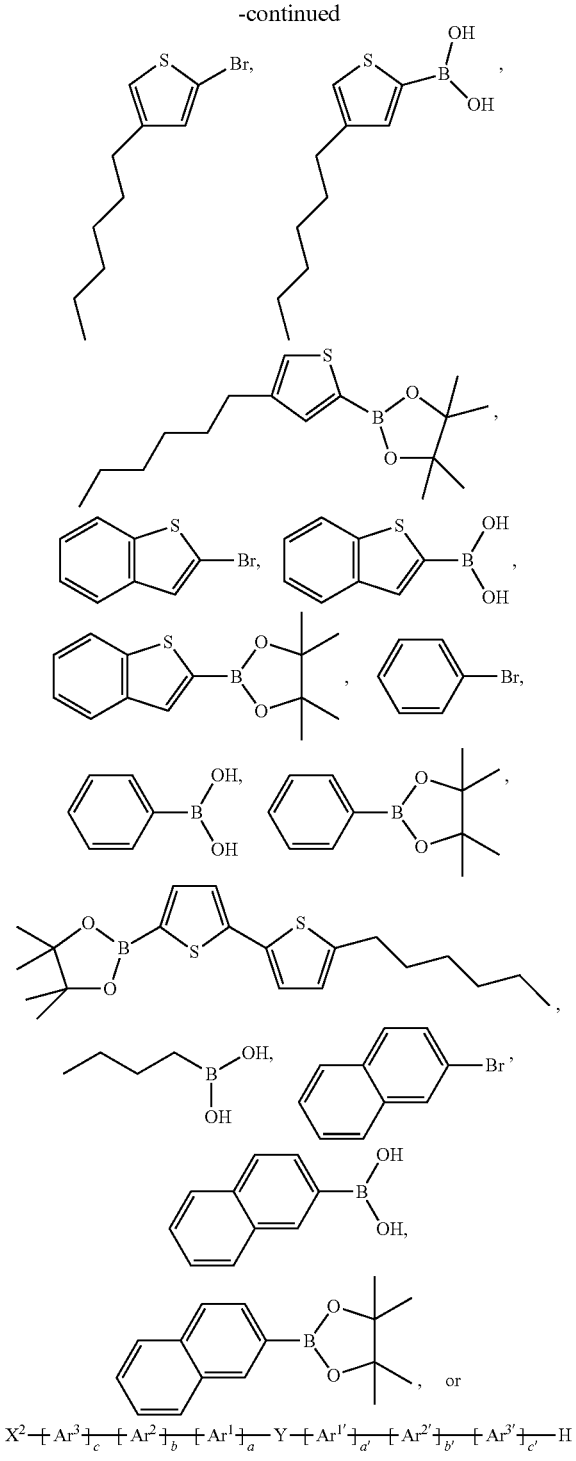

$X^2-[Ar^3]_c-[Ar^2]_b-[Ar^1]_a-Y-[Ar^{1'}]_{a'}-[Ar^{2'}]_{b'}-[Ar^{3'}]_{c'}-H$ ($X^2$ is Br, —B(OH)$_2$, —B(OY$^1$)$_2$,

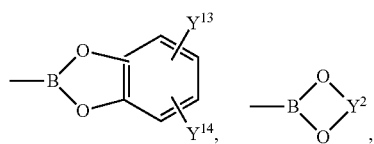

—BF$_4$Na, or —BF$_4$K) may be used as a chain-terminator in such reactions, which will result in the formation of a terminal aryl group.

It is possible to control the sequencing of the monomeric units in the resulting copolymer by controlling the order and composition of monomer feeds in the Suzuki reaction.

The polymers of the present invention can also be synthesized by the Stille coupling (see, for example, Babudri et al, J. Mater. Chem., 2004, 14, 11-34; J. K. Stille, Angew. Chemie Int. Ed. Engl. 1986, 25, 508). To prepare polymers corresponding to formula VII a dihalogenide of formula $X^{10}$-A-$X^{10}$ is reacted with a compound of formula $X^{11'}$-COM$^1$-$X^{11'}$ or a dihalogenide of formula $X^{10}$-COM$^1$-$X^{10}$ is reacted with a compound of formula $X^{11'}$-A-$X^{11'}$, wherein $X^{11'}$ is a group —SnR$^{207}$R$^{208}$R$^{209}$ and $X^{10}$ is as defined above, in an inert solvent at a temperature in range from 0° C. to 200° C. in the presence of a palladium-containing catalyst, wherein R$^{207}$, R$^{208}$ and R$^{209}$ are identical or different and are H or C$_1$-C$_6$alkyl, wherein two radicals optionally form a common ring and these radicals are optionally branched or unbranched. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

Alternatively, the polymers of the present invention can also be synthesized by the Negishi reaction using a zinc reagent A-(ZnX$^{12}$)$_2$, wherein X$^{12}$ is halogen and halides, and COM$^1$-(X$^{23}$)$_2$, wherein X$^{23}$ is halogen or triflate, or using A-(X$^{23}$)$_2$ and COM$^1$-(ZnX$^{23}$)$_2$. Reference is, for example, made to E. Negishi et al., Heterocycles 18 (1982) 117-22.

Alternatively, the polymers of the present invention can also be synthesized by the Hiyama reaction using a organosilicon reagent A-(SiR$^{210}$R$^{211}$R$^{212}$)$_2$, wherein R$^{210}$, R$^{211}$ and R$^{212}$ are identical or different and are halogen, or C$_1$-C$_6$alkyl, and COM$^1$-(X$^{23}$)$_2$, wherein X$^{23}$ is halogen or triflate, or using A-(X$^{23}$)$_2$ and COM$^1$-(SiR$^{210}$R$^{211}$R$^{212}$)$_2$. Reference is, for example, made to T. Hiyama et al., Pure Appl. Chem. 66 (1994) 1471-1478 and T. Hiyama et al., Synlett (1991) 845-853.

Homopolymers of the type (A)$_n$ can be obtained via Yamamoto coupling of dihalides $X^{10}$-A-$X^{10}$, where $X^{10}$ is halogen, preferably bromide. Alternatively homopolymers of the type $(A)_n$ can be obtained via oxidative polymerization of units $X^{10}$-A-$X^{10}$, where $X^{10}$ is hydrogen, e.g. with $FeCl_3$ as oxidizing agent.

The compounds of the formula

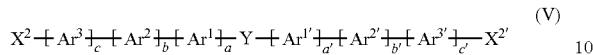
(V)

are intermediates in the production of the polymers of the present invention and are described in PCT/EP2012/075762 and EP13157961.7 (U.S. 61/773,166), which are incorporated herein by reference, and Daniel T. Gryko et al. Org. Lett., 14 (2012) 2670. a, a', b, b', c, c', Y, $Ar^1$, $Ar^{1'}$, $Ar^2$, $Ar^{2'}$, $Ar^3$ and $Ar^{3'}$ are as defined above, and $X^2$ and $X^{2'}$ are independently of each other halogen, especially Br, or J, $ZnX^{12}$, $-SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched; $-SiR^{210}R^{211}R^{212}$, wherein $R^{210}$, $R^{211}$ and $R^{212}$ are identical or different and are halogen, or $C_1$-$C_6$alkyl; $X^{12}$ is a halogen atom, very especially I, or Br; $-OS(O)_2CF_3$, $-OS(O)_2$-aryl, especially

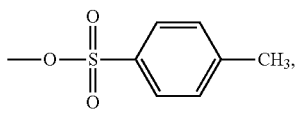

$-OS(O)_2CH_3$, $-B(OH)_2$, $-B(OY^1)_2$,

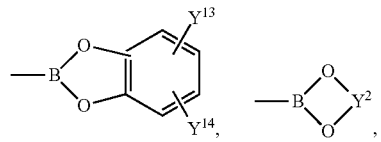

$-BF_4Na$, or $-BF_4K$, wherein $Y^1$ is independently in each occurrence a $C_1$-$C_{10}$alkyl group and $Y^2$ is independently in each occurrence a $C_2$-$C_{10}$alkylene group, such as $-CY^3Y^4-CY^5Y^6-$, or $-CY^7Y^8-CY^9Y^{10}-CY^{11}Y^{12}-$ wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially $-C(CH_3)_2C(CH_3)_2-$, $-C(CH_3)_2CH_2C(CH_3)_2-$, or $-CH_2C(CH_3)_2CH_2-$, and $Y^{13}$ and $Y^{14}$ are independently of each other hydrogen, or a $C_1$-$C_{10}$alkyl group. The compounds of the formula (V) can be used in the production of polymers.

$X^2$ and $X^{2'}$ are preferably the same.

For a, a', b, b', c, c', Y, $Ar^1$, $Ar^{1'}$, $Ar^2$, $Ar^{2'}$, $Ar^3$ and $Ar^{3'}$ the same preferences apply as described above for the repeating units of formula (I).

Compounds of formula

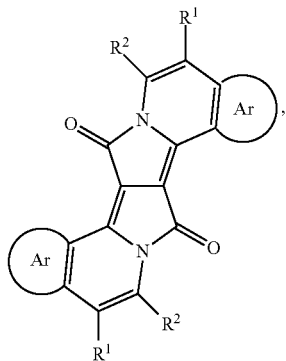

where $R^1$, $R^2$ and Ar are as defined above, can be obtained by reacting a diketopyrrolopyrrole of formula

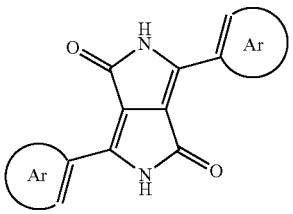

reacted with a compound of formula

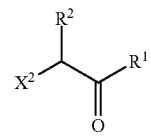

in the presence of a base, wherein $X^2$ is Cl, Br, or I; and then submitting the obtained N-alkylated derivative of formula

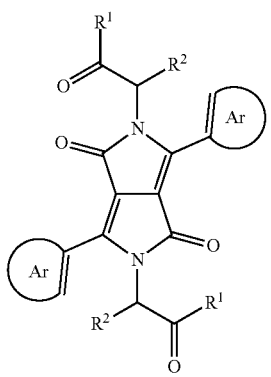

in the presence of acid to intramolecular condensation.

The alkylation reaction is preferably carried out in the presence of tetrabutylammonium hydrogen sulfate, or $K_2CO_3$ in dimethylformamide (DMF).

The cyclization reaction is preferably carried out in methylene chloride in the presence of trifluoromethanesulphonic acid.

Compound (5) can, for example, be prepared starting from the DPP derivative (2) as shown in the reaction scheme below:

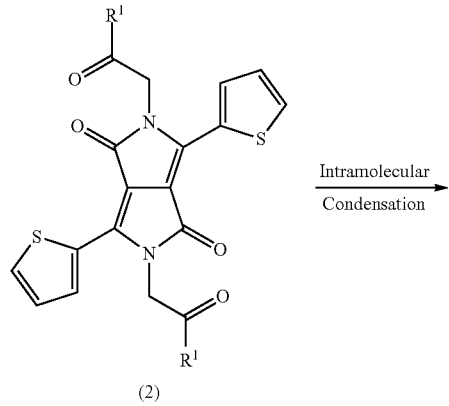

(2)

Intramolecular Condensation →

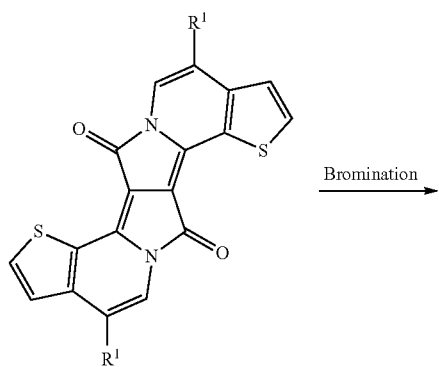

Bromination →

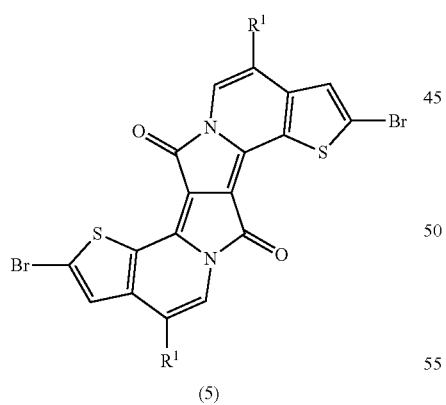

(5)

The bromination is carried out in a suitable solvent, like chloroform, using two equivalents of N-bromo-succinimide at a temperature between −30° C. and +50° C., preferably between −10° C. and room temperature, e.g. at 0° C.

Alternatively compounds of formula

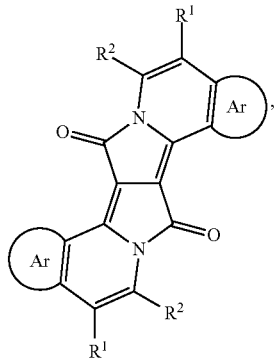

where $R^1$, $R^2$ and Ar are as defined above, can be obtained by reacting a diketopyrrolopyrrole of formula

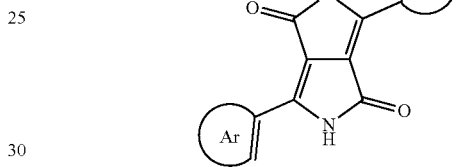

with a compound of formula

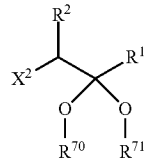

in the presence of a base, wherein $X^2$ is Cl, Br, or I; and then submitting the obtained N-alkylated derivative of formula

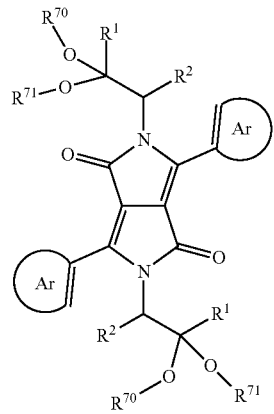

in the presence of acid to intramolecular condensation. In the acetals and ketals, oxygen can be replaced optionally by sulphur atoms.

$R^{70}$ and $R^{71}$ are independently of each other a $C_1$-$C_{25}$alkyl group which can optionally be substituted one or more times with $C_1$-$C_8$alkyl, $C_1$-$C_8$alkoxy and/or can optionally be interrupted by —O—, —S—, —NR$^{39}$—. Preferably, $R^{70}$ and $R^{71}$ are independently of each other a $C_1$-$C_{25}$alkyl group, especially a $C_1$-$C_4$alkyl group. Optionally $R^{70}$ and $R^{71}$ can form a five, or six membered ring.

The alkylation reaction is preferably carried out in the presence of tetrabutylammonium hydrogen sulfate, or $K_2CO_3$ in dimethylformamide (DMF). The cyclization reaction is preferably carried out in methylene chloride in the presence of trifluoromethanesulphonic acid.

Compounds of formula

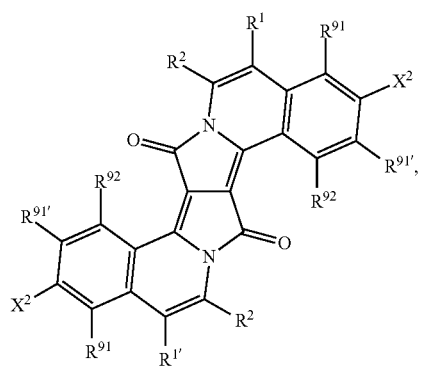
(Va)

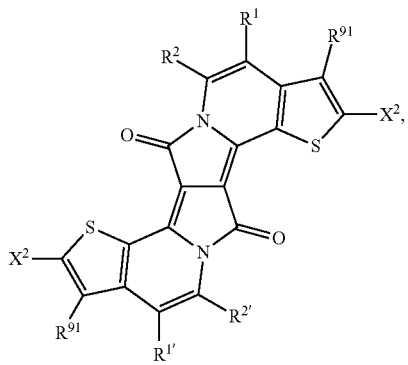
(Vb)

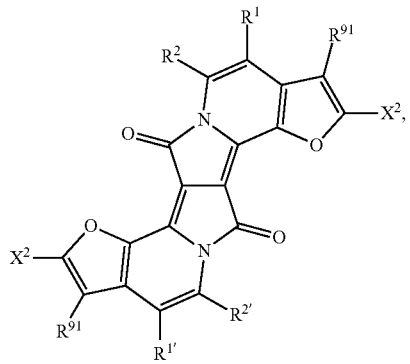
(Vc)

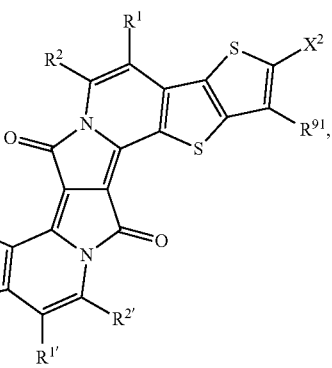
(Vd)

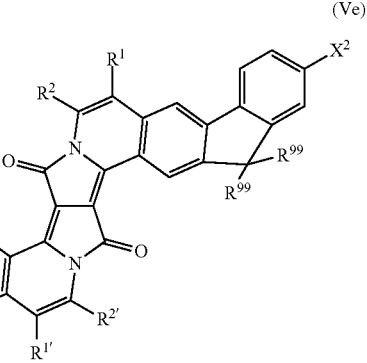
(Ve)
and are preferred, wherein $X^2$ is as defined above.

Compounds of formula (Ve)

(Vf)
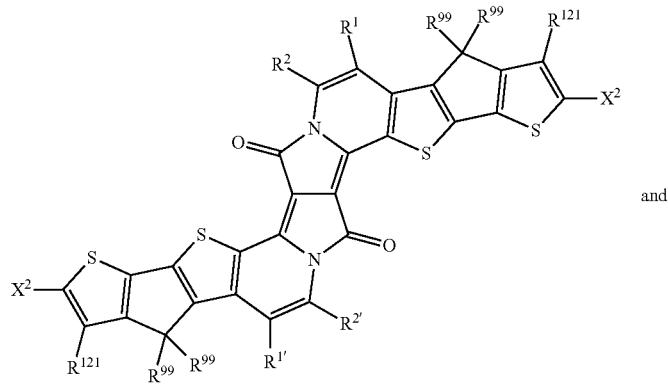
and
(Vg)
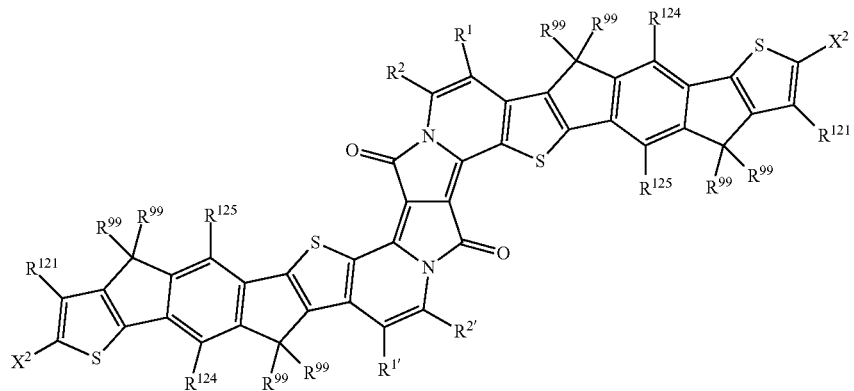
are also preferred, wherein $X^2$ is as defined above. For $R^1$, $R^{1'}$, $R^2$, $R^{2'}$, $R^{91}$, $R^{91'}$, $R^{92}$, $R^{99}$ and $R^{121}$ to $R^{125}$ the same preferences apply as described above for the repeating units of formula (I).
Examples of preferred compounds of formula V are shown below:
(I-1)
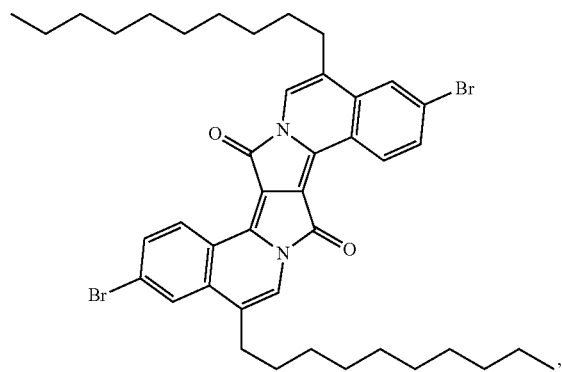
(I-2)
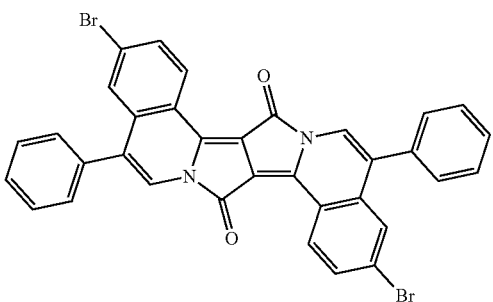

-continued
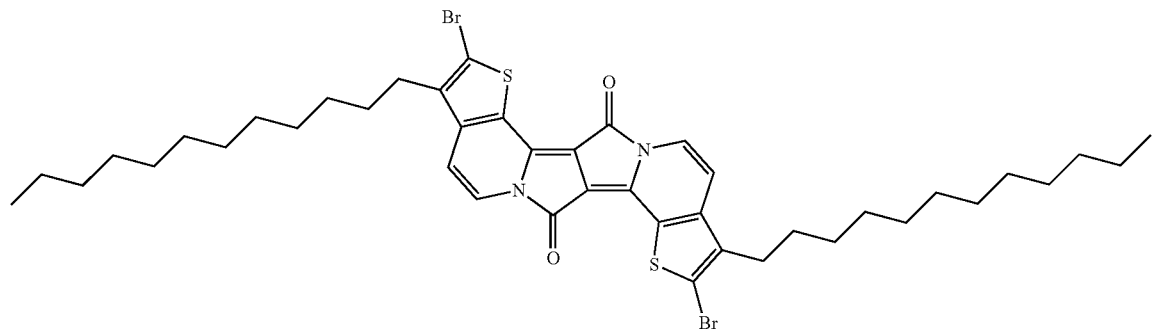
(I-3)
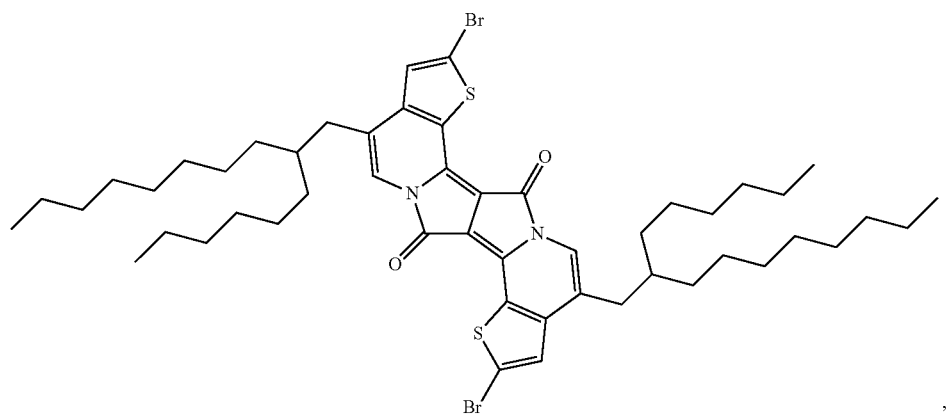
(I-4)
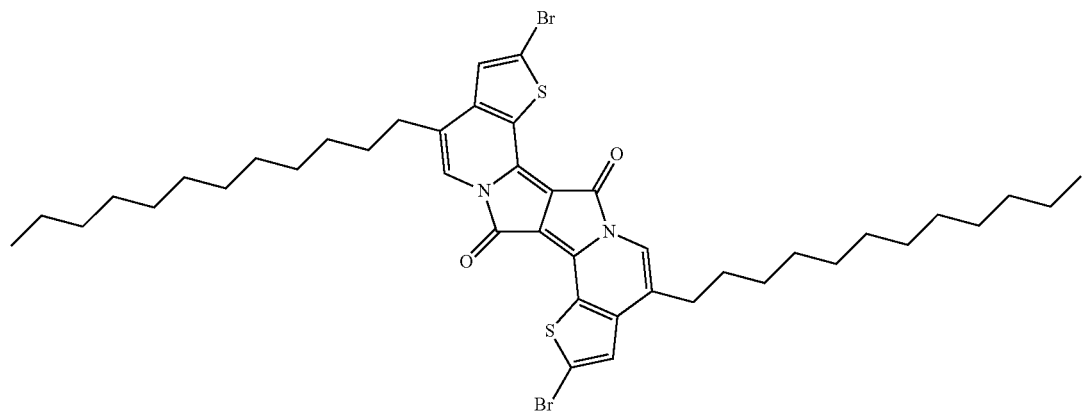
(I-5)
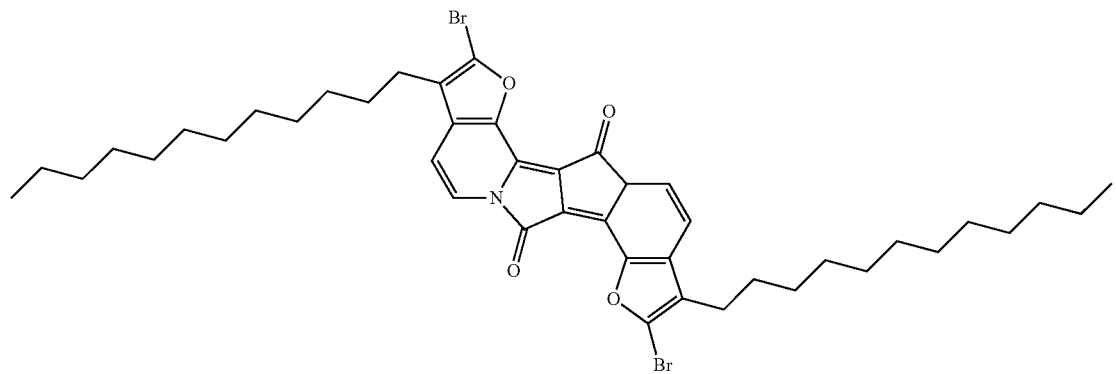
(I-6)

(I-7)
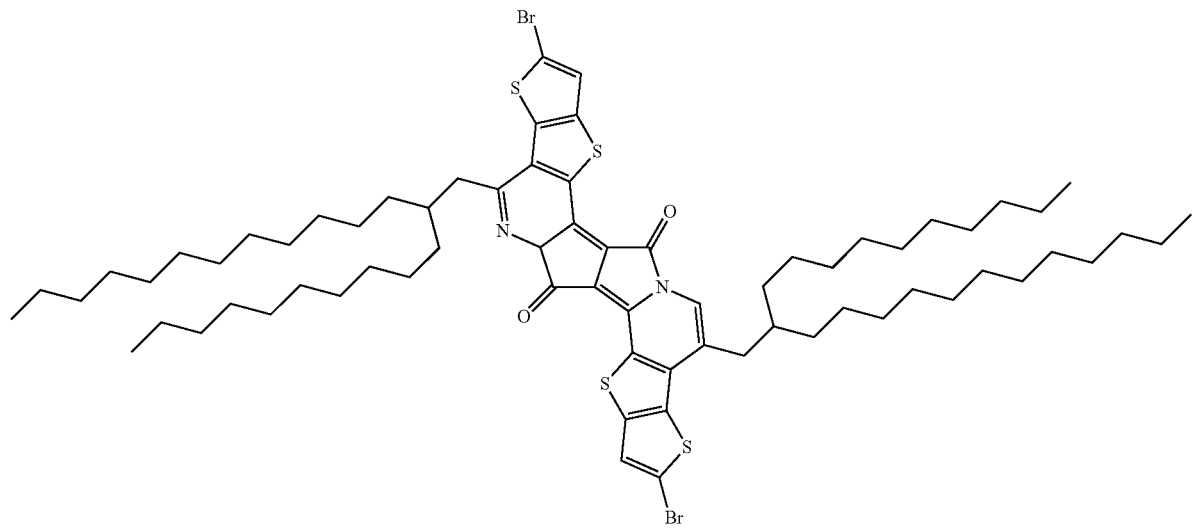
(I-8)
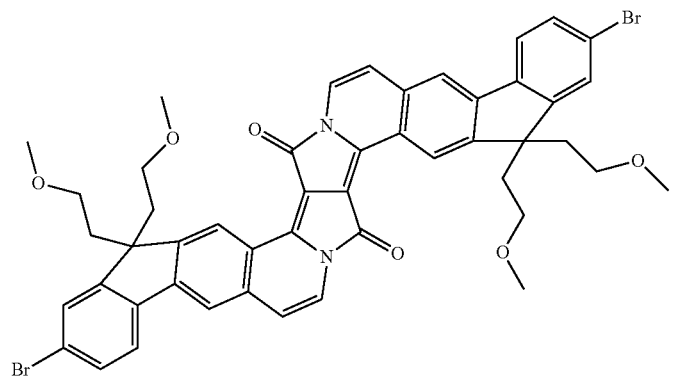
,
(I-9)
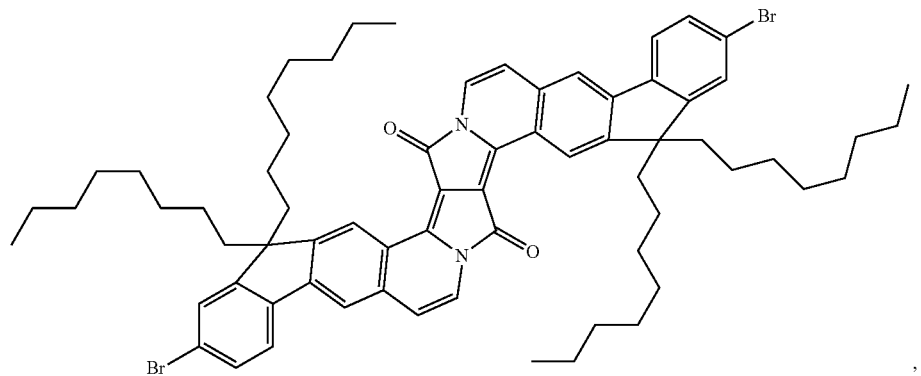
,

-continued
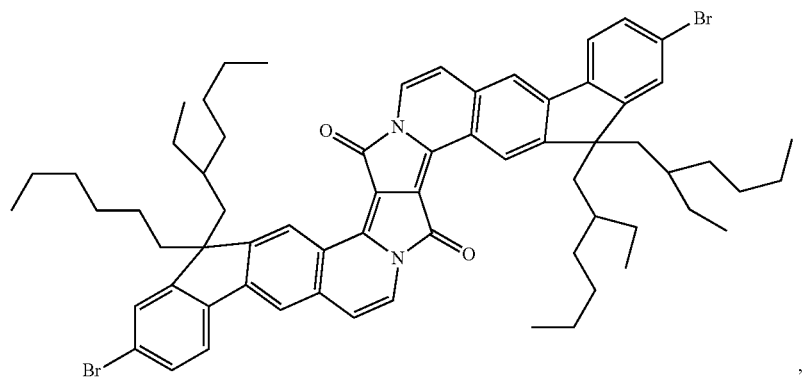
(I-10)
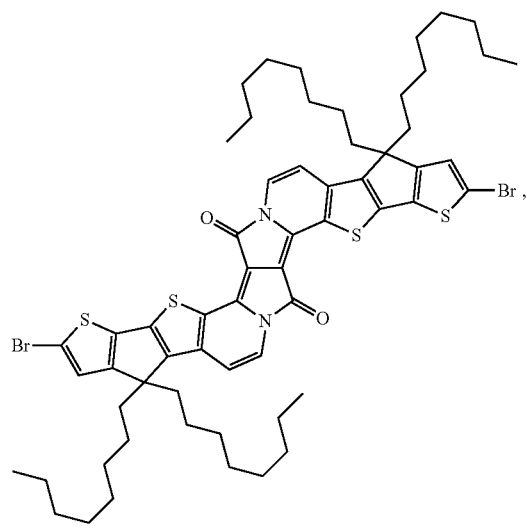
(I-11)
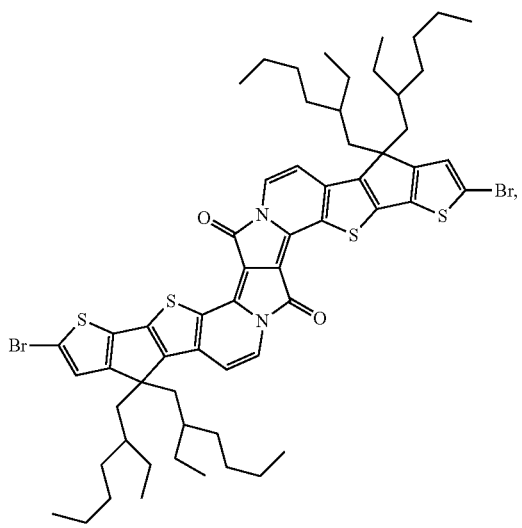
(I-12)
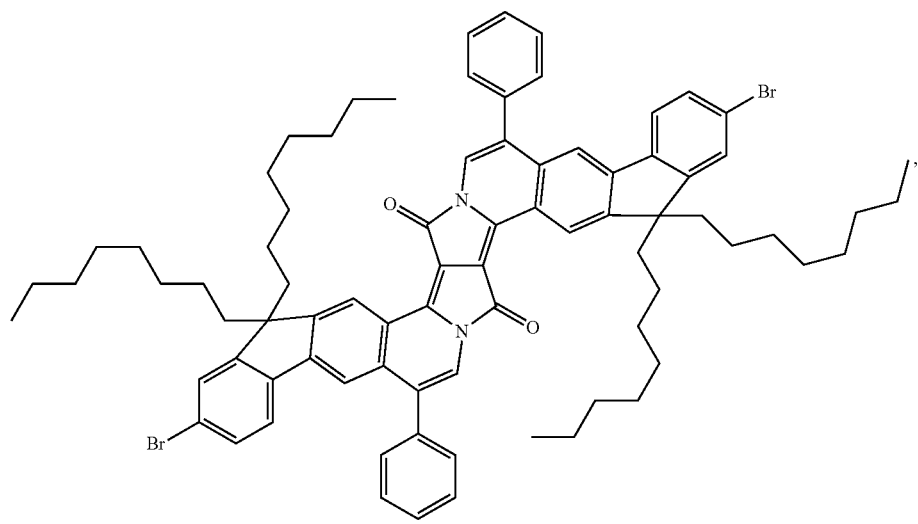
(I-13)

-continued
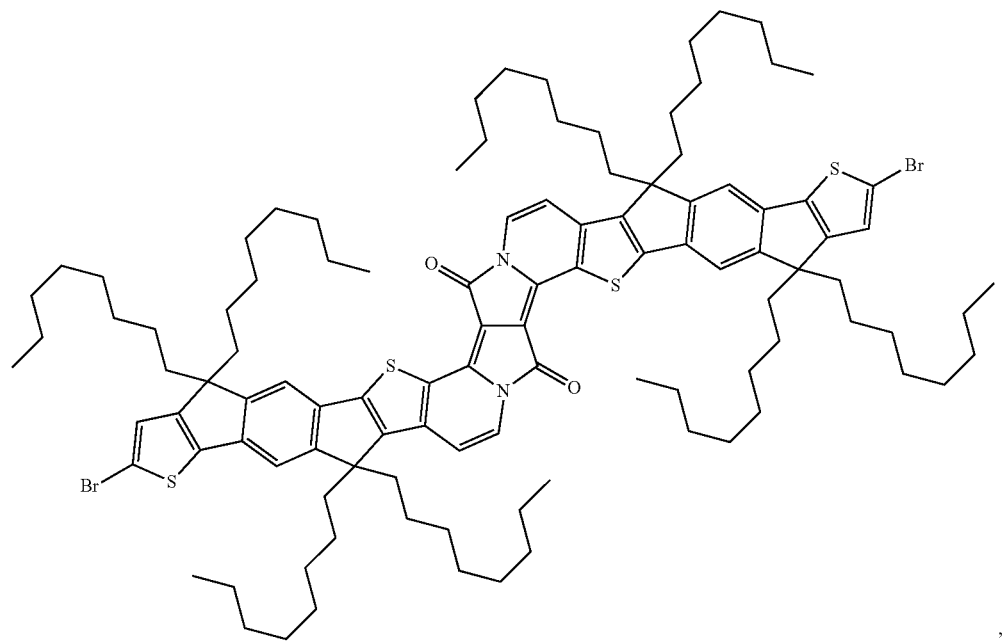
(I-14)
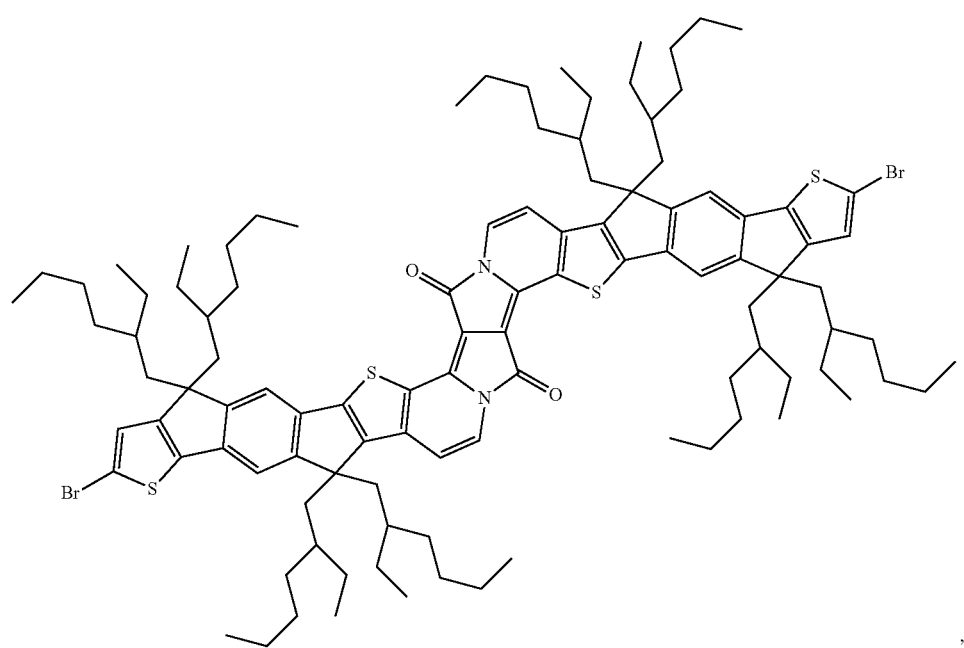
(I-15)
, and

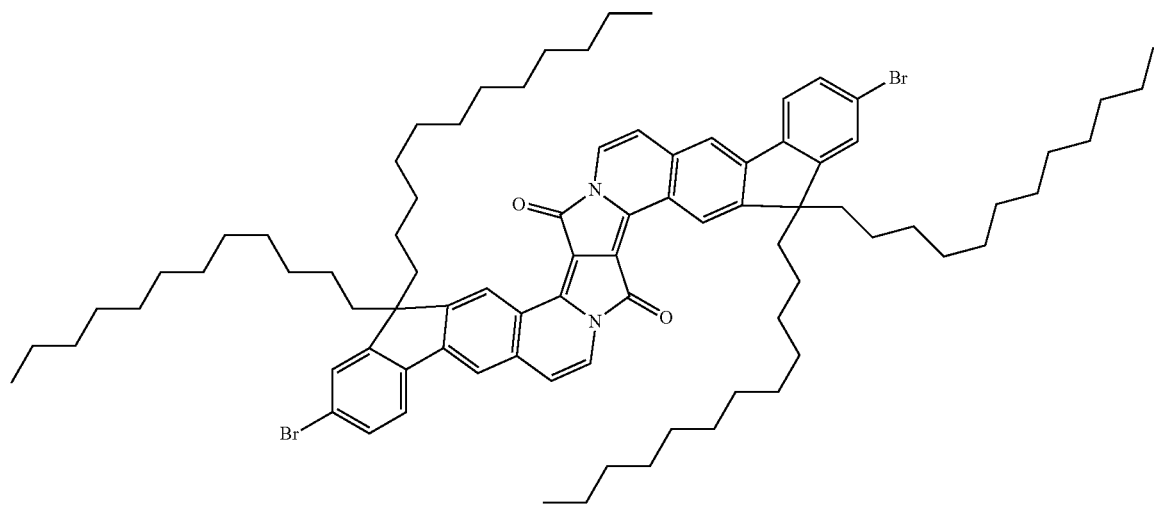
(I-16)
The following compounds of formula (IN-1) to (IN-17) are intermediates in the production of the compounds of formula
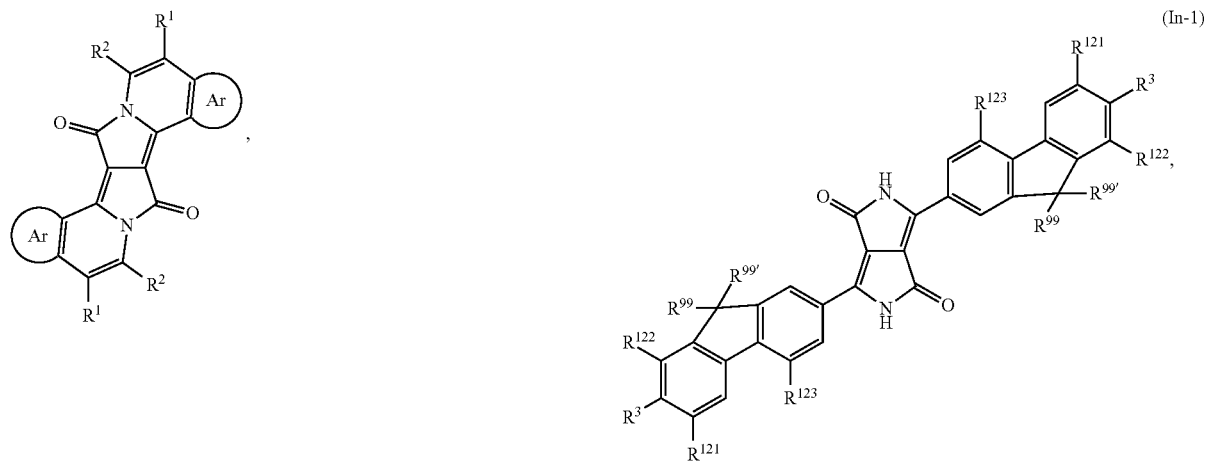
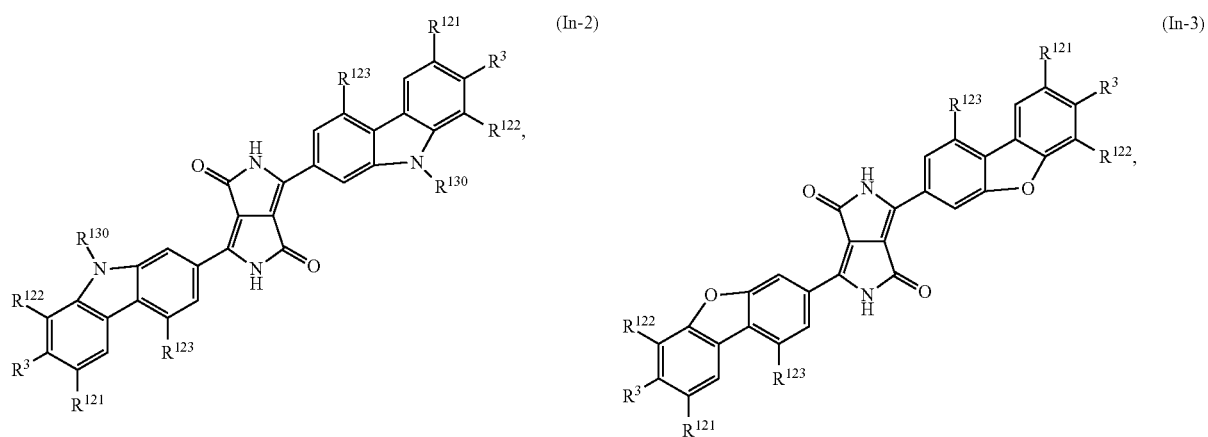

-continued
(In-4)
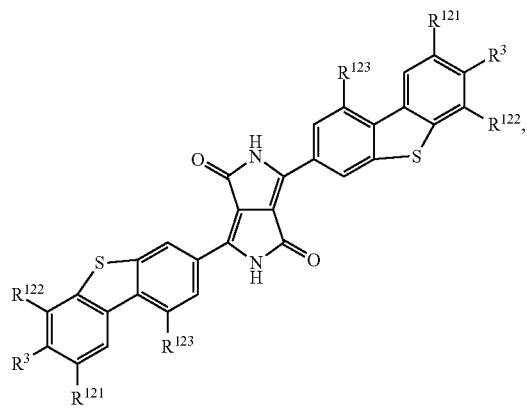
(In-5)
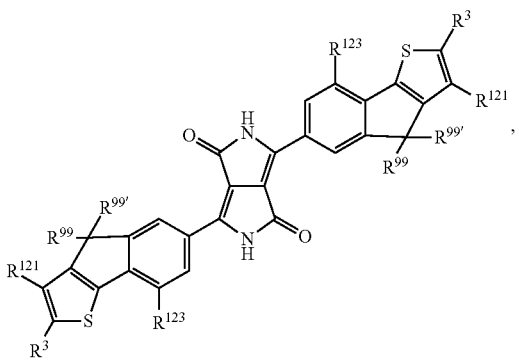
(IN-6)
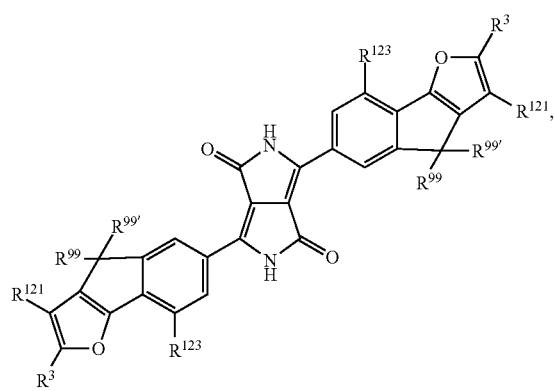
(IN-7)
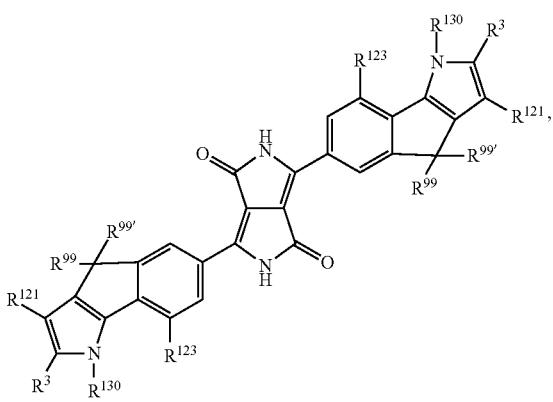
(IN-8)
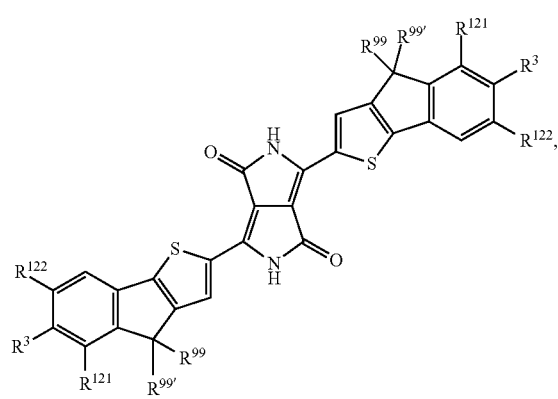
(IN-9)
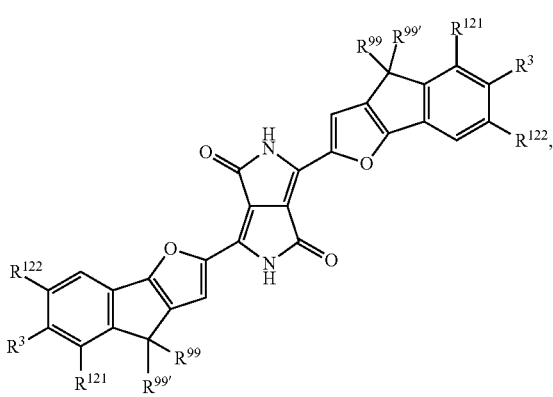
(IN-10)
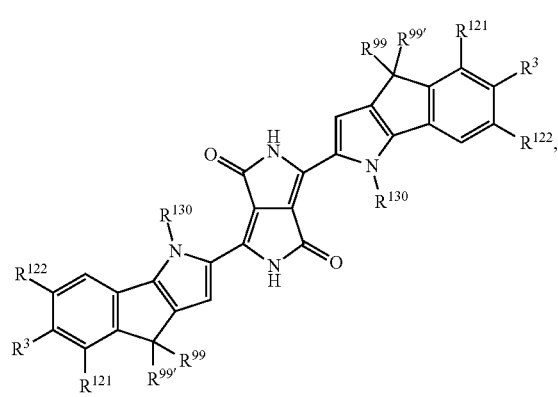
(IN-11)
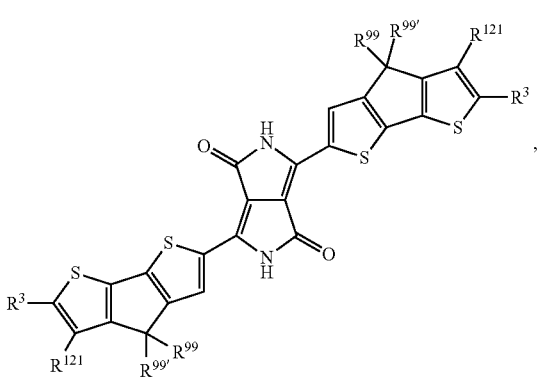

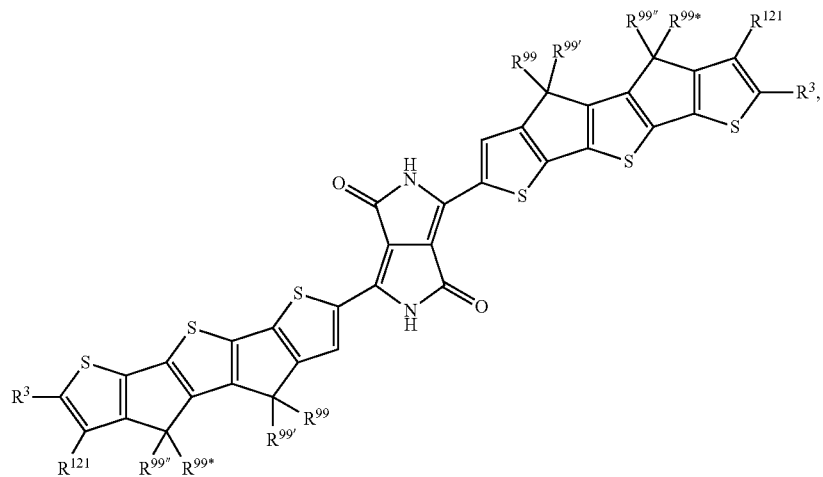
(IN-12)
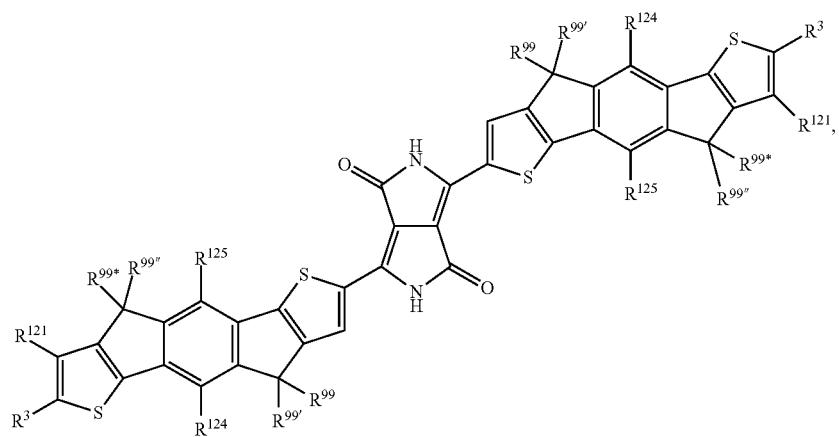
(IN-13)
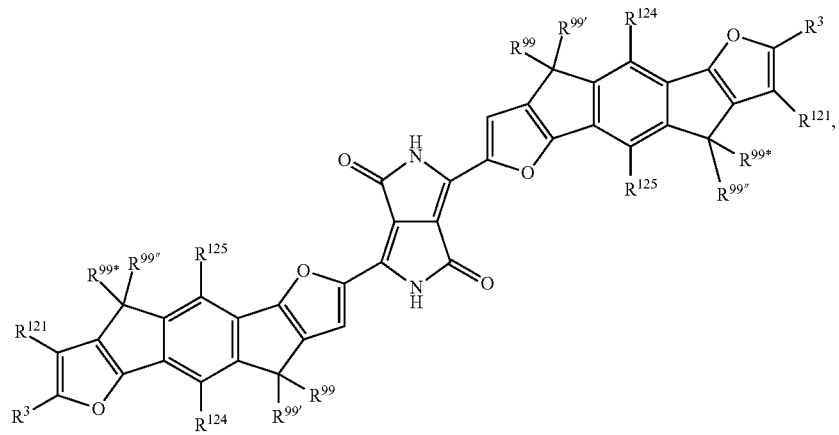
(IN-14)

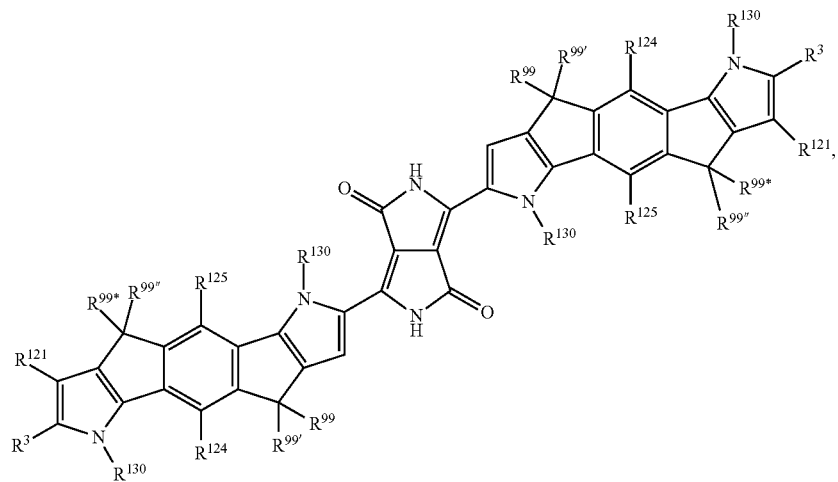
(IN-15)
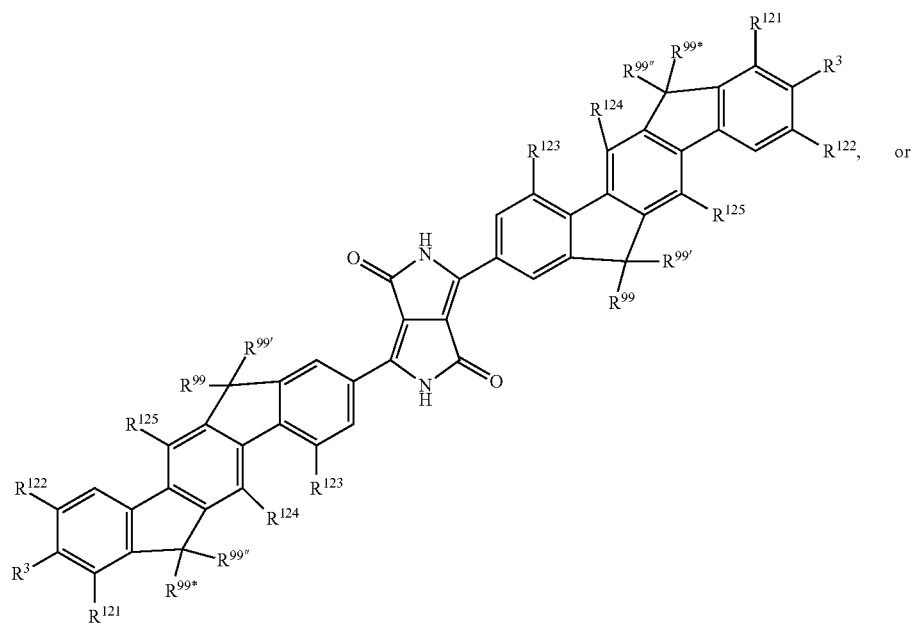
(IN-16) or (IN-17)

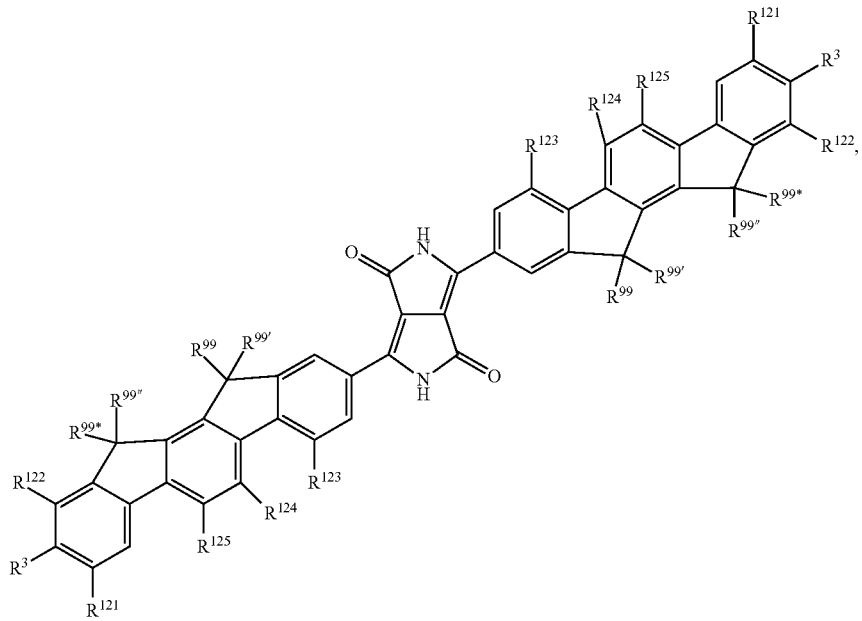

wherein R³ is hydrogen, halogen, especially F; cyano, $C_1$-$C_{25}$alkoxy, $C_1$-$C_{25}$alkyl substituted with one or more halogen atoms, especially F; $C_1$-$C_{25}$alkyl,

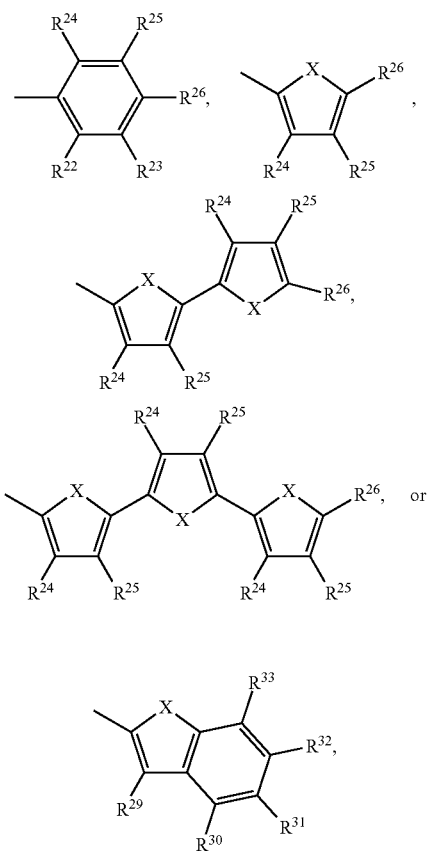

wherein
$R^{22}$ to $R^{25}$ and $R^{29}$ to $R^{33}$ represent independently of each other H, F, cyano, $C_1$-$C_{25}$alkoxy, $C_1$-$C_{25}$alkyl substituted with one or more halogen atoms, especially F; or $C_1$-$C_{25}$alkyl, and $R^{26}$ is H, F, cyano, phenyl, $C_1$-$C_{25}$alkoxy, $C_1$-$C_{25}$alkyl substituted with one or more halogen atoms, or $C_1$-$C_{25}$alkyl;

$R^{99}$, $R^{99'}$, $R^{99''}$ and $R^{99*}$ are independently of each other hydrogen, $C_1$-$C_{25}$alkyl, or $C_1$-$C_{25}$alkyl interrupted by one or more oxygen atoms; preferably $C_3$-$C_{25}$alkyl, or $C_3$-$C_{25}$alkyl which is interrupted by one or more oxygen atoms;

$R^{121}$, $R^{122}$, $R^{123}$, $R^{124}$ and $R^{125}$ are independently of each other hydrogen, halogen, $C_1$-$C_{18}$alkoxy or $C_1$-$C_{25}$alkyl; preferably hydrogen; and $R^{130}$ is hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl. Reference is made to PCT/EP2014/054060.

In the context of the present invention, the terms halogen, $C_1$-$C_{25}$alkyl $C_2$-$C_{25}$alkenyl ($C_2$-$C_{18}$alkenyl), $C_{2\text{-}25}$alkynyl ($C_{2\text{-}18}$alkynyl), aliphatic groups, aliphatic hydrocarbon groups, alkylene, alkenylene, cycloaliphatic hydrocarbon groups, cycloalkyl, cycloalkenyl groups, $C_1$-$C_{25}$alkoxy ($C_1$-$C_{18}$alkoxy), $C_1$-$C_{18}$perfluoroalkyl, carbamoyl groups, $C_6$-$C_{24}$aryl ($C_6$-$C_{18}$aryl), $C_7$-$C_{25}$aralkyl and heteroaryl are each defined as follows—unless stated otherwise:

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_2$-$C_{25}$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-25}$ alkynyl ($C_{2-18}$ alkynyl) is straight-chain or branched and preferably $C_{2-8}$ alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

An aliphatic hydrocarbon group having up to 25 carbon atoms is a linear or branched alkyl, alkenyl or alkynyl (also spelled alkinyl) group having up to 25 carbon atoms as exemplified above.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —$CH_2$—CH=CH—$CH_2$—.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

A cycloaliphatic hydrocarbon group is a cycloalkyl or cycloalkenyl group which may be substituted by one or more aliphatic and/or cycloaliphatic hydrocarbon groups.

A cycloaliphatic-aliphatic group is an aliphatic group substituted by a cycloaliphatic group, wherein the terms "cycloaliphatic" and "aliphatic" have the meanings given herein and wherein the free valency extends from the aliphatic moiety. Hence, a cycloaliphatic-aliphatic group is for example a cycloalkyl-alkyl group.

A cycloalkyl-alkyl group is an alkyl group substituted by a cycloalkyl group, e.g. cyclohexyl-methyl.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

For example, a cycloalkyl or cycloalkenyl group, in particular a cyclohexyl group, can be condensed one or two times with phenyl which can be substituted one to three times with $C_1$-$C_4$-alkyl. Examples of such condensed cyclohexyl groups are groups of the formulae:

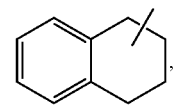
(XXIa)

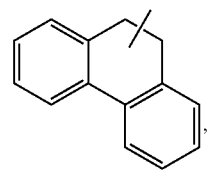
(XXIb)

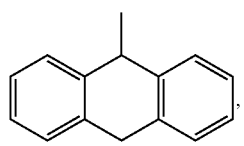
(XXII)

in particular

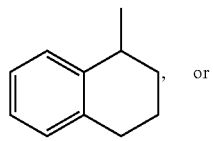
(XXIII)
, or

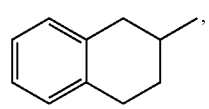
(XXIV)

which can be substituted in the phenyl moieties one to three times with $C_1$-$C_4$-alkyl.

A bivalent group of the formula XII wherein $R^{28}$ and $R^{27}$ together represent alkylene or alkenylene which may be both bonded via oxygen and/or sulfur to the thienyl residue and which may both have up to 25 carbon atoms, is e.g. a group of the formula

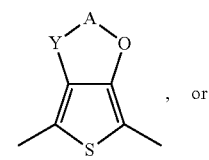
(XXIX)
, or

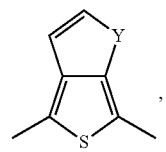
(XXX)

wherein A represents linear or branched alkylene having up to 25 carbon atoms, preferably ethylene or propylene which may be substituted by one or more alkyl groups, and Y represents oxygen or sulphur. For example, the bivalent group of the formula —Y-A-O— represents —O—CH$_2$—CH$_2$—O— or —O—CH$_2$—CH$_2$—CH$_2$—O—.

A group of the formula XI wherein two groups R$^{22}$ to R$^{26}$ which are in the neighborhood of each other, together represent alkylene or alkenylene having up to 8 carbon atoms, thereby forming a ring, is e.g. a group of the formula

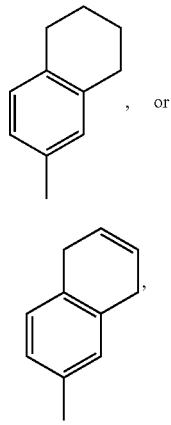

wherein in the group of the formula XXXII R$^{23}$ and R$^{24}$ together represent 1,4-butylene and in the group of the formula XXXIII R$^{23}$ and R$^{24}$ together represent 1,4-but-2-en-ylene.

C$_1$-C$_{25}$alkoxy groups (C$_1$-C$_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of C$_1$-C$_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably C$_1$-C$_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

C$_1$-C$_{18}$perfluoroalkyl, especially C$_1$-C$_4$perfluoroalkyl, is a branched or unbranched radical such as for example —CF$_3$, —CF$_2$CF$_3$, —CF$_2$CF$_2$CF$_3$, —CF(CF$_3$)$_2$, —(CF$_2$)$_3$CF$_3$, and —C(CF$_3$)$_3$.

The term "carbamoyl group" is typically a C$_{1-18}$carbamoyl radical, preferably C$_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

A cycloalkyl group is typically C$_3$-C$_{12}$cycloalkyl, such as, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, in particular a cyclohexyl group, can be condensed one or two times by phenyl which can be substituted one to three times with C$_1$-C$_4$-alkyl, halogen and cyano. Examples of such condensed cyclohexyl groups are:

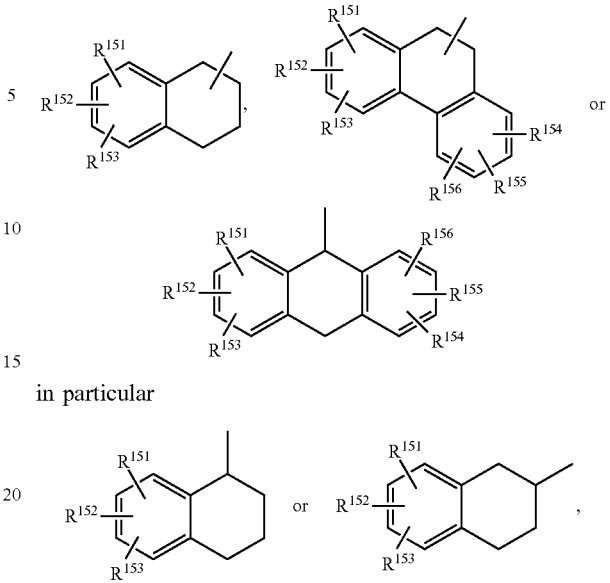

in particular wherein R$^{151}$, R$^{152}$, R$^{153}$, R$^{154}$, R$^{155}$ and R$^{156}$ are independently of each other C$_1$-C$_8$-alkyl, C$_1$-C$_8$-alkoxy, halogen and cyano, in particular hydrogen.

C$_6$-C$_{24}$aryl (C$_6$-C$_{18}$aryl) is typically phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of C$_6$-C$_{12}$aryl are phenyl, 1-naphthyl, 2-naphthyl, 3- or 4-biphenyl, 2- or 9-fluorenyl or 9-phenanthryl, which may be unsubstituted or substituted.

C$_7$-C$_{25}$aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably C$_7$-C$_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred C$_7$-C$_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

Heteroaryl is typically C$_2$-C$_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, thienothienyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a carbamoyl group, a nitro group or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{18}$alkyl interrupted by one or more O is, for example, $(CH_2CH_2O)_{1-9}$—$R^x$, where $R^x$ is H or $C_1$-$C_{10}$alkyl, $CH_2$—$CH(OR^{y'})$—$CH_2$—O—$R^y$, where $R^y$ is $C_1$-$C_{18}$alkyl, and $R^{y'}$ embraces the same definitions as $R^y$ or is H.

If a substituent, such as, for example $R^3$, occurs more than one time in a group, it can be different in each occurrence.

A mixture containing a polymer of the present invention results in a semi-conducting layer comprising a polymer of the present invention (typically 5% to 99.9999% by weight, especially 20 to 85% by weight) and at least another material. The other material can be, but is not restricted to a fraction of the same polymer of the present invention with different molecular weight, another polymer of the present invention, a semi-conducting polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.). The polymers of the present invention can be blended with small molecules described, for example, in WO2009/047104, WO2010108873 (PCT/EP2010/053655), WO09/047104, U.S. Pat. No. 6,690,029, WO2007082584, and WO2008107089:

WO2007082584:

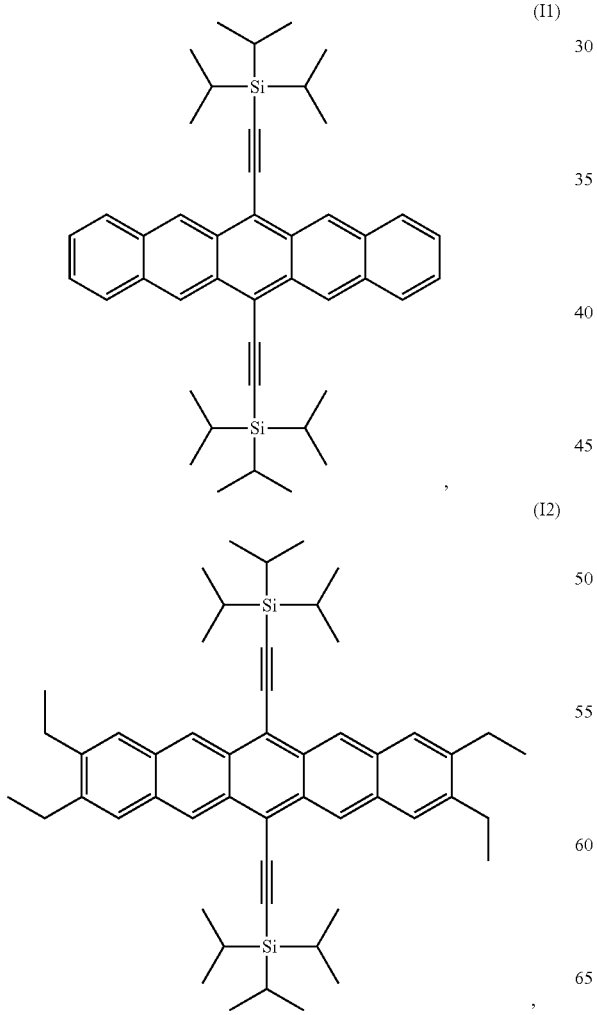

(I1)

(I2)

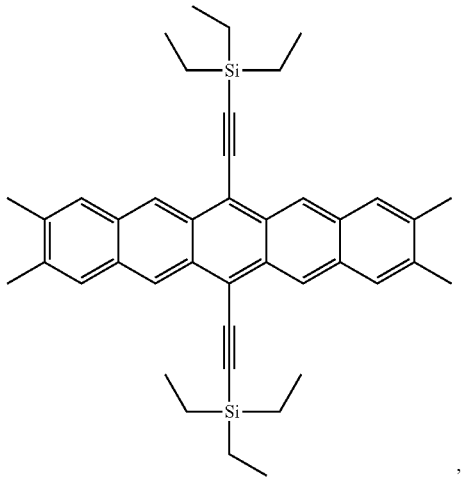

(I3)

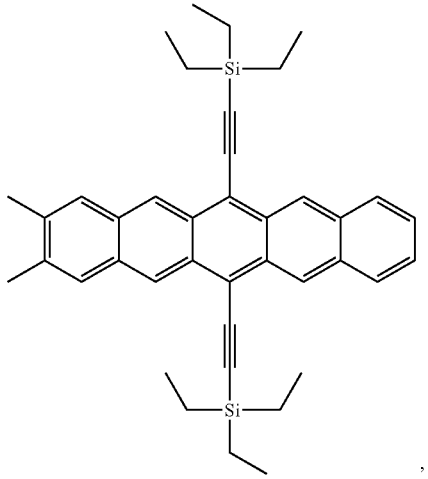

(I4)

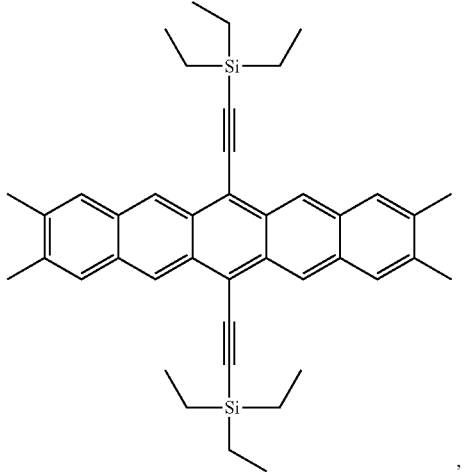

(I5)

(I6) 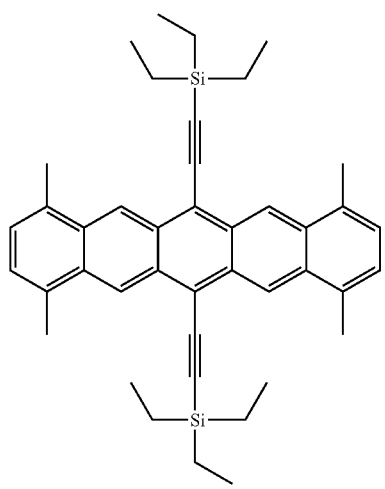

(I7) 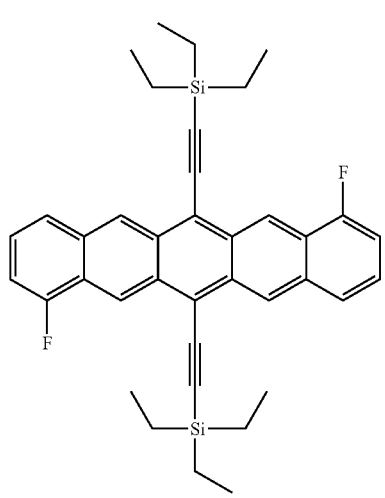

(I8) 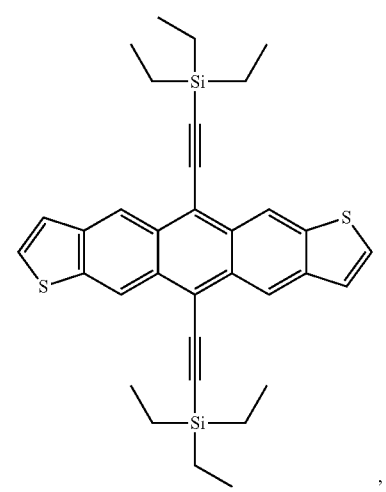

(I9) 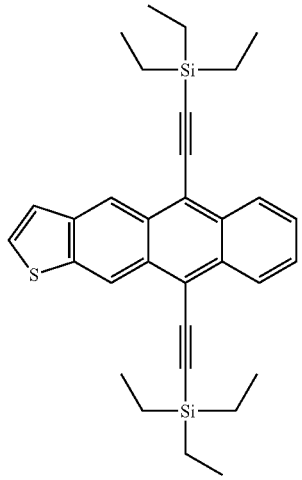

WO2008107089:

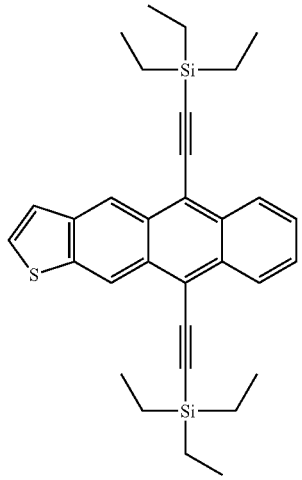

wherein one of $Y^{1'}$ and $Y^{2'}$ denotes —CH= or =CH— and the other denotes —X*—, one of $Y^{3'}$ and $Y^{4'}$ denotes —CH= or =CH— and the other denotes —X*—, X* is —O—, —S—, —Se— or NR'''—, R* is cyclic, straight-chain or branched alkyl or alkoxy having 1 to 20 C-atoms, or aryl having 2-30 C-atoms, all of which are optionally fluorinated or perfluorinated, R' is H, F, Cl, Br, I, CN, straight-chain or branched alkyl or alkoxy having 1 to 20 C-atoms and optionally being fluorinated or perfluorinated, optionally fluorinated or perfluorinated aryl having 6 to 30 C-atoms, or CO₂R'', with R'' being H, optionally fluorinated alkyl having 1 to 20 C-atoms, or optionally fluorinated aryl having 2 to 30 C-atoms, R''' is H or cyclic, straight-chain or branched alkyl with 1 to 10 C-atoms, y is 0, or 1, x is 0, or 1.

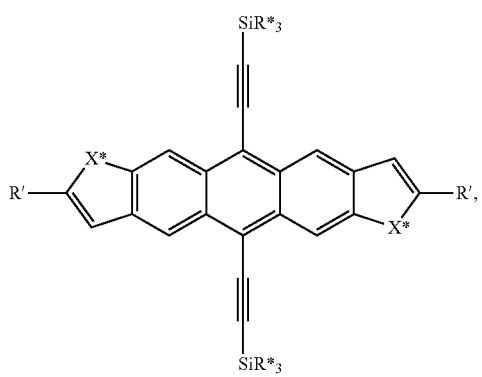

A1

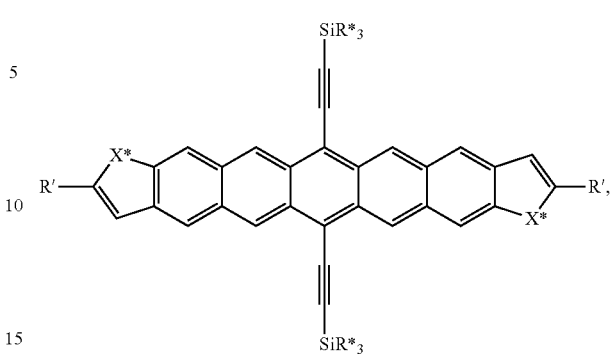

C1

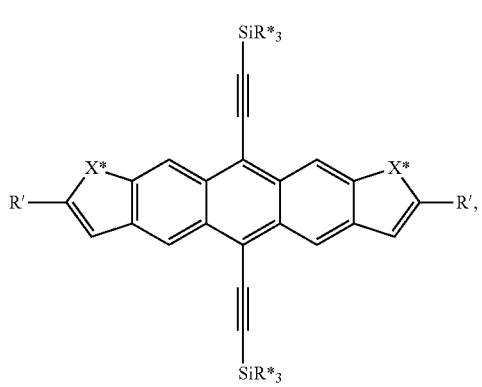

A2

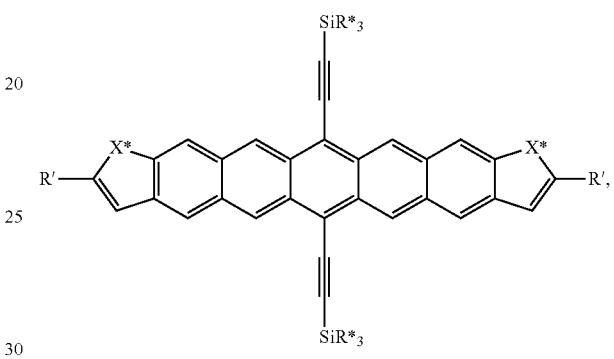

C2

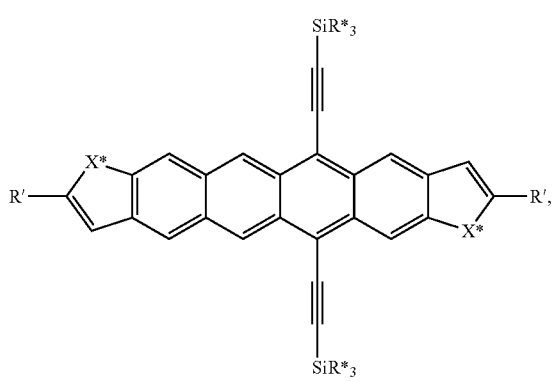

B1

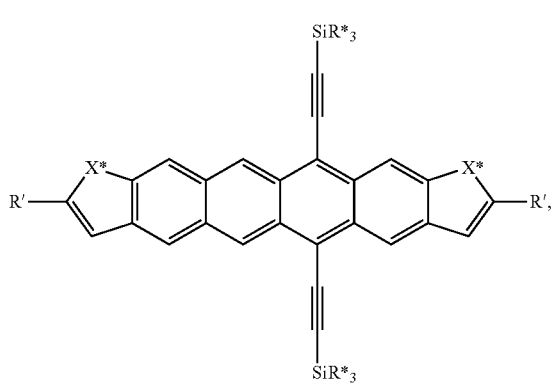

B2

The polymer can contain a small molecule, or a mixture of two, or more small molecule compounds.

Accordingly, the present invention also relates to an organic semiconductor material, layer or component, comprising a polymer according to the present invention.

The polymers of the invention can be used as the semiconductor layer in semiconductor devices. Accordingly, the present invention also relates to semiconductor devices, comprising a polymer of the present invention, or an organic semiconductor material, layer or component. The semiconductor device is especially an organic photovoltaic (PV) device (solar cell), a photodiode, or an organic field effect transistor.

The polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, slot die coating, ink jet printing, gravure printing, flexo printing, offset printing, screen printing, microcontact (wave)-printing, drop or zone casting, or other known techniques).

The polymers of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like.

A further aspect of the present invention is an organic semiconductor material, layer or component comprising one or more polymers, or compounds of the present invention. A further aspect is the use of the polymers or materials of the present invention in an organic photovoltaic (PV) device (solar cell), a photodiode, or an organic field effect transistor (OFET). A further aspect is an organic photovoltaic (PV) device (solar cell), a photodiode, or an organic field effect transistor (OFET) comprising a polymer or material of the present invention.

The polymers of the present invention are typically used as organic semiconductors in form of thin organic layers or films, preferably less than 30 microns thick. Typically the semiconducting layer of the present invention is at most 1 micron (=1 µm) thick, although it may be thicker if required. For various electronic device applications, the thickness may also be less than about 1 micron thick. For example, for use in an OFET the layer thickness may typically be 100 nm or less. The exact thickness of the layer will depend, for example, upon the requirements of the electronic device in which the layer is used.

For example, the active semiconductor channel between the drain and source in an OFET may comprise a layer of the present invention.

An OFET device according to the present invention preferably comprises:
a source electrode,
a drain electrode,
a gate electrode,
a semiconducting layer,
one or more gate insulator layers, and
optionally a substrate, wherein the semiconductor layer comprises one or more polymers of the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a polymer of the present invention located on the second side of the insulator, and a drain electrode and a source electrode located on the polymer layer.

The OFET device can be a top gate device or a bottom gate device.

Suitable structures and manufacturing methods of an OFET device are known to the person skilled in the art and are described in the literature, for example in WO03/052841.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43® (Acros, No. 12377).

The semiconducting layer comprising a polymer of the present invention may additionally comprise at least another material. The other material can be, but is not restricted to another polymer of the present invention, a semi-conducting polymer, a polymeric binder, organic small molecules different from a polymer of the present invention, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more polymers of the present invention and a polymeric binder. The ratio of the polymers of the present invention to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO2008/001123A1).

The polymers of the present invention are advantageously used in organic photovoltaic (PV) devices (solar cells). Accordingly, the invention provides PV devices comprising a polymer according to the present invention. A device of this construction will also have rectifying properties so may also be termed a photodiode. Photoresponsive devices have application as solar cells which generate electricity from light and as photodetectors which measure or detect light.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor. As stated above, the photoactive layer may also contain a polymeric binder. The ratio of the polymers of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

For heterojunction solar cells the active layer comprises preferably a mixture of a polymer of the present invention and a fullerene, such as [60]PCBM (=6,6-phenyl-$C_{61}$-butyric acid methyl ester), or [70]PCBM, in a weight ratio of 1:1 to 1:3. The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of any semi-conducting polymer, such as, for example, a polymer of the present invention, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a polymer of the present invention as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the polymers of the present invention can also be used alone or together with other materials in or as alignment layers in LCD or OLED devices, as described for example in US2003/0021913.

It is another object of the present invention to provide compounds, which show high efficiency of energy conversion, excellent field-effect mobility, good on/off current ratios and/or excellent stability, when used in organic field effect transistors, organic photovoltaics (solar cells) and photodiodes.

In addition, the polymers of the present invention may be used as IR absorbers.

Accordingly, the polymers of the present invention can be used inter alia for security printing, invisible and/or IR readable bar codes, the laser-welding of plastics, the curing of surface-coatings using IR radiators, the drying and curing of print, the fixing of toners on paper or plastics, optical filters for plasma display panels, laser marking of paper or plastics, the heating of plastics preforms, and for heat shielding applications.

In a further aspect, the invention provides a printing ink formulation for security printing, comprising at least one polymer of the present invention, such as, for example, a polymer selected from P-1 to P-14 and P-16 to P-25.

In a further aspect, the invention provides a security document, comprising a substrate and at least at least one polymer, or compound of the present invention. The security document may be a bank note, a passport, a check, a voucher, an ID- or transaction card, a stamp and a tax label.

In a further aspect, the invention provides a security document, obtainable by a printing process, wherein a printing ink formulation is employed that comprises at least one polymer, or compound of the present invention.

Advantageously, the polymers, or compounds of the present invention, such as, for example, a polymer selected from P-1 to P-14 and P-16 to P-25, may be used in a printing ink formulation for security printing.

In security printing, the polymers, or compounds of the present invention are added to a printing ink formulation. Suitable printing inks are water-based, oil-based or solvent-based printing inks, based on pigment or dye, for inkjet printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing and letterpress printing are usually formulated as high-viscosity paste printing inks, whereas printing inks for flexographic printing and intaglio printing are usually formulated as liquid printing inks with comparatively low viscosity.

The printing ink formulation, especially for security printing, according to the invention preferably comprises
a) at least one polymer, or compound of the present invention, such as, for example, a polymer selected from polymers P-1 to P-14 and P-16 to P-25,
b) a polymeric binder,
c) a solvent,
d) optionally at least one colorant, and
e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"—Ullmann's Encyclopedia of Industrial Chemistry, Sixth Edition, 1999 Electronic Release. A formulation of an IR-absorbing intaglio ink formulation is described in US 20080241492 A1. The disclosure of the afore-mentioned documents is incorporated herein by reference.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, antimony trioxide, lithopones (zinc sulfide+barium sulfate), or coloured pigments, examples being iron oxides, carbon black, graphite, zinc yellow, zinc green, ultramarine, manganese black, antimony black, manganese violet, Paris blue or Schweinfurt green. Besides the inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also dioxazine, quinacridone, phthalocyanine, isoindolinone, and metal complex pigments. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
   a) 0.0001 to 25% by weight of at least one polymer, or compound of the present invention, such as, for example, a polymer selected from polymers P-1 to P-14 and P-16 to P-25,
   b) 5 to 74% by weight of at least one polymeric binder,
   c) 1 to 94.9999% by weight of at least one a solvent,
   d) 0 to 25% by weight of at least one colorant, and
   e) 0 to 25% by weight of at least one further additive,
   wherein the sum of components a) to e) adds up to 100%.

The printing ink formulations according to the invention are advantageously prepared in a conventional manner, for example by mixing the individual components.

Primers can be applied prior to the printing ink formulation according to the invention. By way of example, the primers are applied in order to improve adhesion to the substrate. It is also possible to apply additional printing lacquers, e.g. in the form of a covering to protect the printed image.

The following examples are included for illustrative purposes only and do not limit the scope of the claims. Unless otherwise stated, all parts and percentages are by weight. Weight-average molecular weight (Mw) and polydispersity (Mw/Mn=PD) are determined by Heat Temperature Gel Permeation Chromatography (HT-GPC) [Apparatus: GPC PL 220 from Polymer laboratories (Church Stretton, UK; now Varian) yielding the responses from refractive index (RI), Chromatographic conditions: Column: 3 "PLgel Olexis" column from Polymer Laboratories (Church Stretton, UK); with an average particle size of 13 ím (dimensions 300×8 mm I.D.) Mobile phase: 1,2,4-trichlorobenzene purified by vacuum distillation and stabilised by butylhydroxytoluene (BHT, 200 mg/l), Chromatographic temperature: 150° C.; Mobile phase flow: 1 ml/min; Solute concentration: about 1 mg/ml; Injection volume: 200 íl; Detection: RI, Procedure of molecular weight calibration: Relative calibration is done by use of a set of 10 polystyrene calibration standards obtained from Polymer Laboratories (Church Stretton, UK) spanning the molecular weight range from 1'930'000 Da-5'050 Da, i.e., PS 1'930'000, PS 1'460'000, PS 1'075'000, PS 560'000, PS 330'000, PS 96'000, PS 52'000, PS 30'300, PS 10'100, PS 5'050 Da. A polynomic calibration is used to calculate the molecular weight.

All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1

Synthesis of Polymer P-11 a) 7-bromo-9,9-di(2-methoxyethyl)-9H-fluorene-2-carbonitrile 2: A mixture of 2,7-dibromo-9H-fluorene (11.34 g, 35 mmol), potassium iodide (100 mg, 0.60 mmol) and 150 ml of THF is stirred under argon at room temperature. Sodium hydride (7.00 g, 175 mmol, 60% in mineral oil) is carefully added in portions and the mixture is stirred for additional 15 min. Subsequently 1-chloro-2-methoxyethane (9.6 ml, 105 mmol) is added dropwise and the reaction mixture is stirred for 3 days at room temperature. The reaction is quenched by dropwise addition of 200 ml of water. The resulting black mixture is acidified with 6M HCl (color disappeared) and extracted three times with methylene chloride. Combined organic layers are washed twice with water and dried over sodium sulfate. Solvents are removed under reduced pressure and obtained solid residue is recrystallized from ethanol to give 13.40 g (87%) of 2,7-dibromo-9,9-di(2-methoxyethyl)-9H-fluorene 1 as a white powder. Mp: 138-140° C. $^1$H NMR (500 MHz, CDCl$_3$) δ 7.55 (d, J=1.4 Hz, 2H), 7.53 (d, J=8.1 Hz, 2H), 7.49 (dd, J=8.1, 1.7 Hz, 2H), 3.02 (s, 6H), 2.68 (dd, J=8.4, 6.7 Hz, 4H), 2.49-2.15 (m, 4H). $^{13}$C NMR (126 MHz, CDCl$_3$) δ 150.8, 138.4, 130.8, 126.5, 121.8, 121.3, 68.1, 58.4, 51.7, 39.4. HRMS (EI) calcd for C$_{19}$H$_{20}$Br$_2$O$_2$ (M$^+$): 437.9830. found: 437.9831.

b) 2,7-Dibromo-9,9-di(2-methoxyethyl)-9H-fluorene 1 (13.21 g, 30 mmol), copper(I) cyanide (2.78 g, 31 mmol) and 100 ml of DMF are stirred under argon at 160° C. in a tightly closed pressure vessel. After 40 h the reaction mixture is cooled down and a solution of 26 g of FeCl$_3$.6H$_2$O in 40 ml of concentrated hydrochloric acid and 10 ml of water is added. Resulting mixture is stirred for 20 min at 90° C., cooled down, diluted with water and extracted with 5 portions of methylene chloride. Organic layers are combined, washed twice with water and dried over MgSO$_4$. The product is purified by silica-gel chromatography (chloroform→chloroform:ethyl acetate 9:1) and recrystallized from ethanol. 5.20 g (45%) of 2 is obtained as off-white powder. Mp: 193-196° C. $^1$H NMR (500 MHz, CDCl$_3$) δ 7.75 (dd, J=7.9, 0.6 Hz, 1H), 7.70 (dd, J=1.4, 0.6 Hz, 1H), 7.66 (dd, J=7.9, 1.4 Hz, 1H), 7.64-7.59 (m, 2H), 7.55 (dd, J=8.1, 1.8 Hz, 1H), 2.99 (s, 6H), 2.78-2.70 (m, 2H), 2.70-2.62 (m, 2H), 2.41-2.27 (m, 4H). $^{13}$C NMR (126 MHz, CDCl$_3$) δ 151.9, 149.6, 143.8, 137.5, 131.9, 131.1, 127.0, 126.8, 123.4, 122.2, 120.5, 119.30, 110.7, 68.0, 58.4, 52.0, 39.2. HRMS (ESI) calcd for C$_{20}$H$_{20}$BrNO$_2$Na (M+Na$^+$): 408.0570. found: 408.0575.

DPP Synthesis

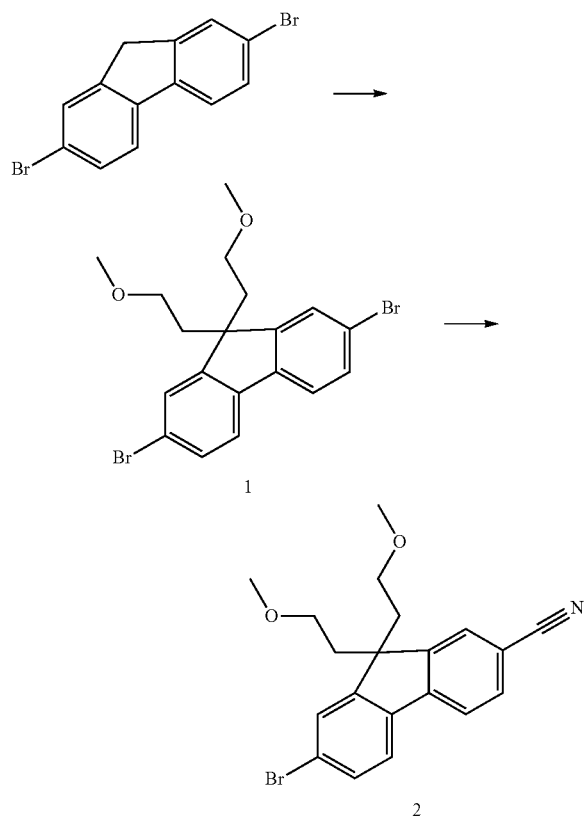

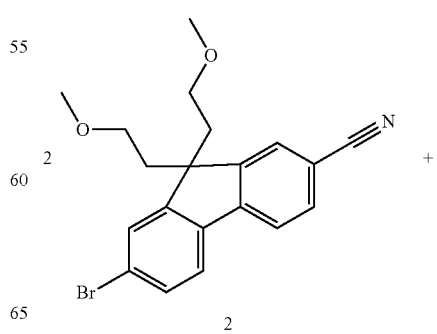

-continued

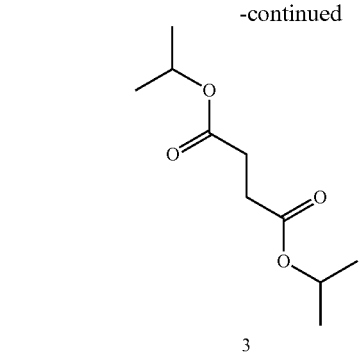

3

Synthesis of Diacetal

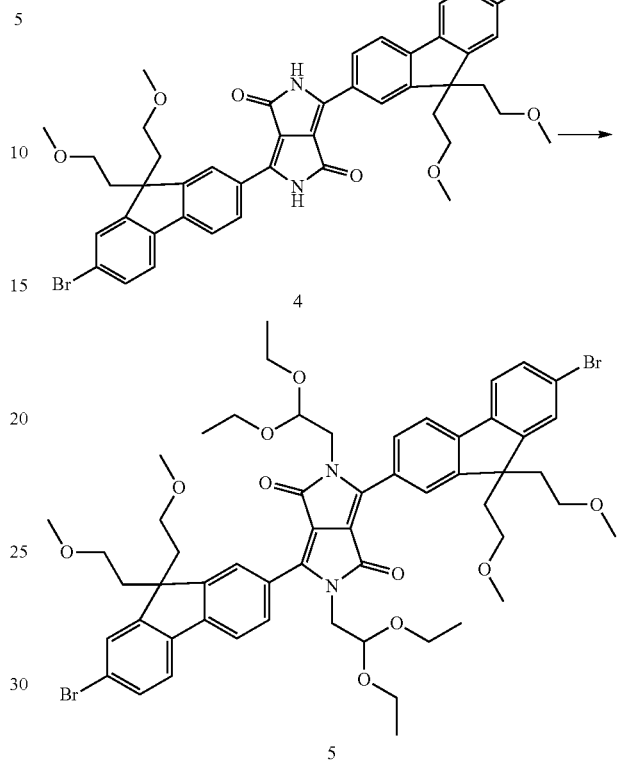

c) 3,6-Bis(7-bromo-9,9-di(2-methoxyethyl)-9H-fluoren-2-yl)-1,4-diketopyrrolo[3,4-c]pyrrole 4: Under an argon atmosphere, in a three-necked flask equipped with a reflux condenser and magnetic stirrer are placed 20 ml of tert-amyl alcohol, an catalytic amount of iron(III) chloride and sodium (0.690 g, 30 mmol). The mixture is heated under reflux until sodium is completely reacted. Then the reaction mixture is cooled to 90° C. and 7-bromo-9,9-di(2-methoxyethyl)-9H-fluorene-2-carbonitrile (2, 4.87 g, 12.6 mmol) is added. The mixture is then heated to 110° C. and 1.23 ml (6.0 mmol) of diisopropyl succinate 3 is added dropwise (30 min). After 16 h of reaction at 110° C., the mixture is cooled and 30 ml of water/acetic acid 1:1 is added. Resulting suspension is refluxed for a few minutes and cooled to 30° C. Precipitate of obtained pigment is then filtered out, washed several times with hot water and methanol and dried under vacuum. 1.66 g (32%) of 4 is obtained as dark brown powder. Mp: >400° C. $^1$H NMR (500 MHz, CDCl$_3$: TFA-d 4:1) δ 8.48 (br s, 2H), 8.22 (br s, 2H), 7.96 (br s, 2H), 7.72 (d, J=8.0 Hz, 2H), 7.69-7.62 (m, 4H), 3.17 (s, 6H), 3.11-2.95 (m, 8H), 2.59 (br s, 4H), 2.50 (br s, 4H). HRMS (ESI) calcd for C$_{44}$H$_{42}$Br$_2$N$_2$O$_6$Na (M+Na$^+$): 875.1301. found: 875.1307.

d) 2,5-Bis(2,2-diethoxyethyl)-3,6-bis(7-bromo-9,9-di(2-methoxyethyl)-9H-fluoren-2-yl)-1,4-diketopyrrolo[3,4-c]pyrrole 5: A mixture of 3,6-Bis(7-bromo-9,9-di(2-methoxyethyl)-9H-fluoren-2-yl)-1,4-diketopyrrolo[3,4-c]pyrrole (4, 684 mg, 0.80 mmol), tetrabutylammonium bisulfate (TBAHS, 14 mg, 0.04 mmol), potassium carbonate (1.66 g, 12 mmol) and 20 ml of DMF is heated to 130° C. under an argon atmosphere. Then bromoacetaldehyde diethyl acetal (1.20 ml, 8.0 mmol) is added dropwise by a syringe (30 min). The reaction mixture is stirred for 16 h at 130° C., cooled and diluted with water and methylene chloride. The aqueous layer is extracted with five portions of methylene chloride, combined organic layers are washed with water and brine and dried over sodium sulfate. Solvents are evaporated, the product is separated by the column chromatography (methylene chloride:acetone 19:1→9:1) and recrystallized from CHCl$_3$/MeOH. 440 mg (51%) of 5 is obtained as orange-yellow fluorescent powder. Mp: 197-199° C. $^1$H NMR (500 MHz, CDCl$_3$) δ 8.23 (d, J=1.1 Hz, 2H), 8.16 (dd, J=8.0, 1.5 Hz, 2H), 7.82 (d, J=8.0 Hz, 2H), 7.65-7.60 (m, 4H), 7.53 (dd, J=8.2, 1.7 Hz, 2H), 4.97 (t, J=5.6 Hz, 2H), 3.90 (d, J=5.6 Hz, 4H), 3.73 (dq, J=9.3, 7.0 Hz, 4H), 3.55 (dq, J=9.4, 7.0 Hz, 4H), 3.05 (s, 12H), 2.85-2.73 (m, 8H), 2.45 (ddd, J=15.0, 9.5, 5.7 Hz, 4H), 2.34 (ddd, J=13.5, 9.6, 5.4 Hz, 4H), 1.19 (t, J=7.0 Hz, 12H). $^{13}$C NMR (126 MHz, CDCl$_3$) δ 163.4, 152.1, 149.1 (2 signals), 142.3, 138.5, 130.9, 129.7, 127.1, 126.8, 124.3, 122.5, 121.8, 120.3, 109.6, 100.4, 68.3, 63.8, 58.4, 51.8, 45.8, 39.3, 15.5. HRMS (ESI) calcd for C$_{56}$H$_{66}$Br$_2$N$_2$O$_{10}$Na (M+Na$^+$): 1107.2982. found: 1107.3010.

Cyclization of Acetal

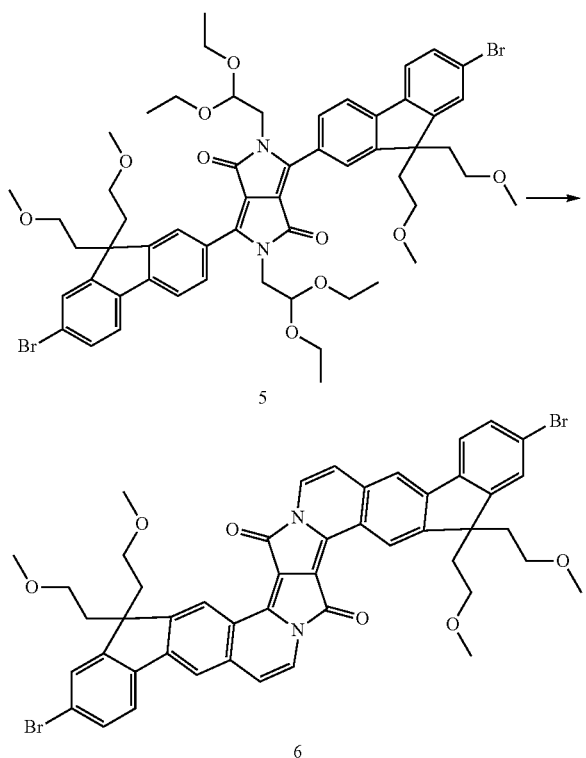

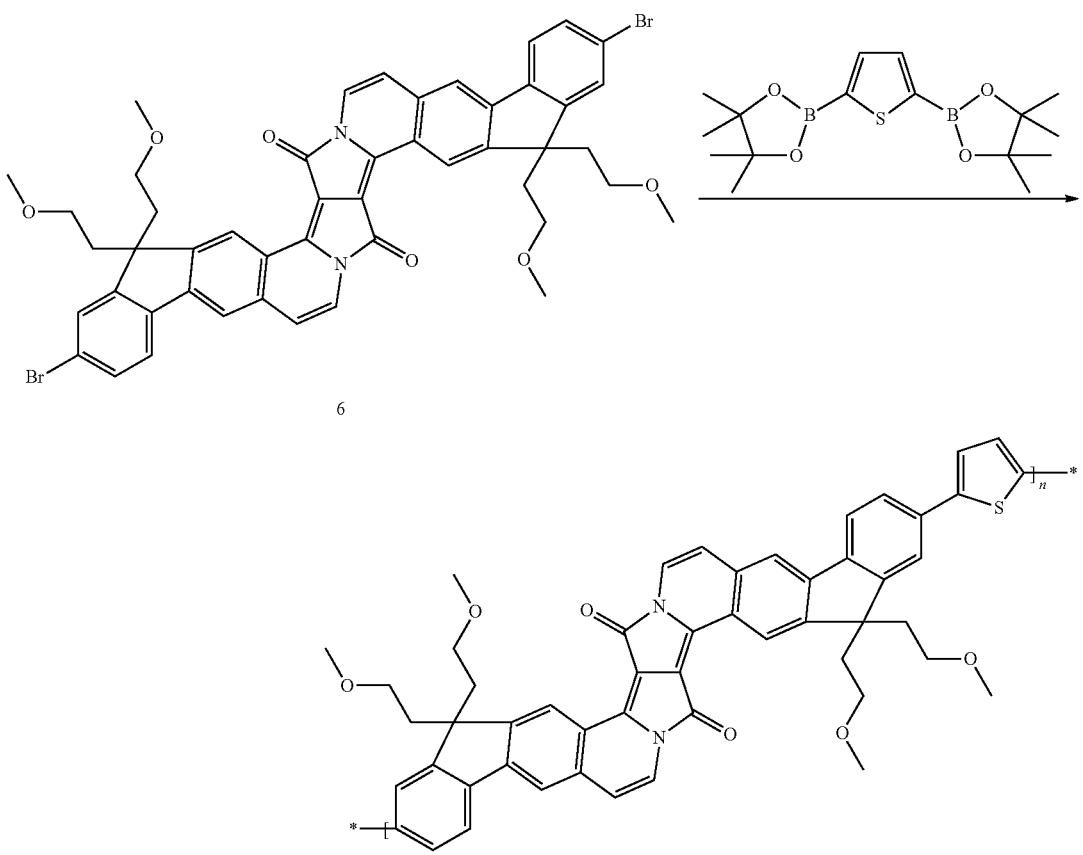

e) 2,5-Bis(2,2-diethoxyethyl)-3,6-bis(7-bromo-9,9-di(2-methoxyethyl)-9H-fluoren-2-yl)-1,4-diketopyrrolo[3,4-c]pyrrole (6=compound 1-8): (5, 435 mg, 0.40 mmol) is dissolved in 8 ml of chloroform. Subsequently trifluoromethanesulfonic acid (0.78 ml, 8.8 mmol) is slowly added and the reaction mixture is stirred at 60° C. for 1 h. Then the reaction mixture is cooled down and triethyl amine (1.4 ml, 10 mmol) is slowly added in order to neutralize acid. Obtained dark blue mixture is diluted with methylene chloride, washed 3 times with water and dried over sodium sulfate. Solvents are evaporated and the solid residue is recrystallized from $CHCl_3$/MeOH. 329 mg (91%) of 6 is obtained as dark violed crystals. Mp: 354-356° C. $^1$H NMR (500 MHz, $CDCl_3$) δ 9.26 (s, 2H), 7.91 (d, J=7.3 Hz, 2H), 7.84 (s, 2H), 7.70 (d, J=8.1 Hz, 2H), 7.67 (d, J=1.4 Hz, 2H), 7.57 (dd, J=8.1, 1.8 Hz, 2H), 6.88 (d, J=7.3 Hz, 2H), 3.01 (s, 12H), 2.92-2.78 (m, 8H), 2.61 (ddd, J=14.5, 8.9, 5.7 Hz, 4H), 2.40 (ddd, J=14.1, 9.0, 5.5 Hz, 4H). $^{13}$C NMR (126 MHz, $CDCl_3$) δ 155.8, 152.7, 150.0, 144.4, 141.4, 137.8, 134.6, 131.1, 127.2, 124.1, 123.6, 123.2, 122.7, 122.3, 117.4, 112.3, 101.5, 68.4, 58.3, 51.9, 39.5. HRMS (ESI) calcd for $C_{48}H_{42}Br_2N_2O_6$ (M+): 900.1410. found: 900.1396.

f) (compound 7=Polymer P-11) One equivalent of compound 6 and one equivalent of the thiophene-bis-boronicacidester [175361-81-6] are copolymerized under Suzuki reaction conditions to get the polymer P-11.

Example 2

Synthesis of Polymer P-2 a) The synthesis of the monomer 10 is made according to Org. Lett. 2012, p. 2670: the DPP pigment 8 [84632-54-2] is reacted with 2 equivalents of phenacyl bromide [70-11-1] and a base to get the alkylated DPP 9:

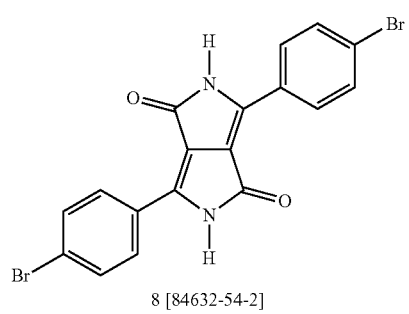

8 [84632-54-2]

+

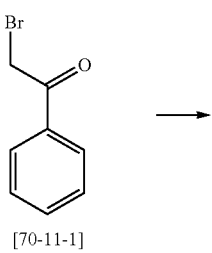

[70-11-1]

→

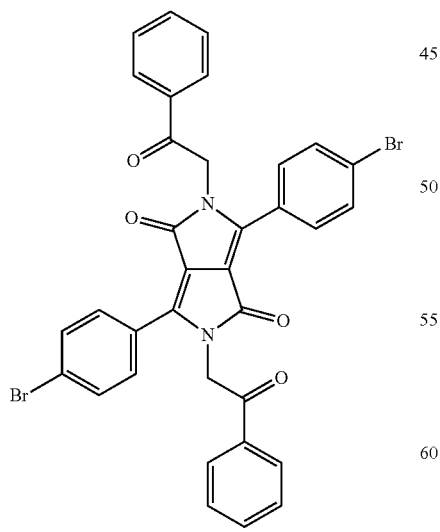

9 b) The ring closure to compound 10 is made under acidic conditions:

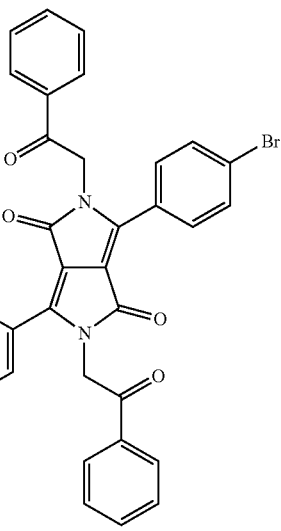

9

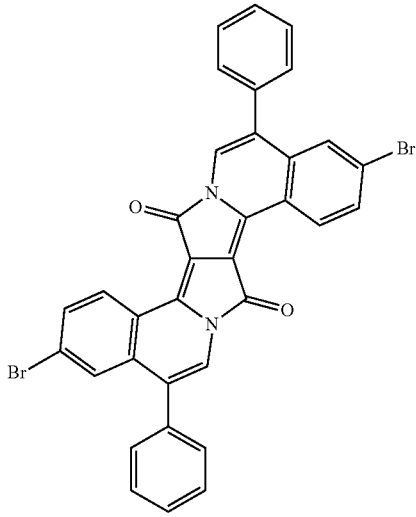

10 c) The polymer P-2 is then made by Suzuki co-polymerization of 1 equivalent of compound 10 and one equivalent of the diboronicacidester 11 using the polymerisation conditions of example 1f):

111 112
Example 3
Synthesis of Polymer P-12 (Compound 18)
a) Compound 14 is synthesized according to compound 2:
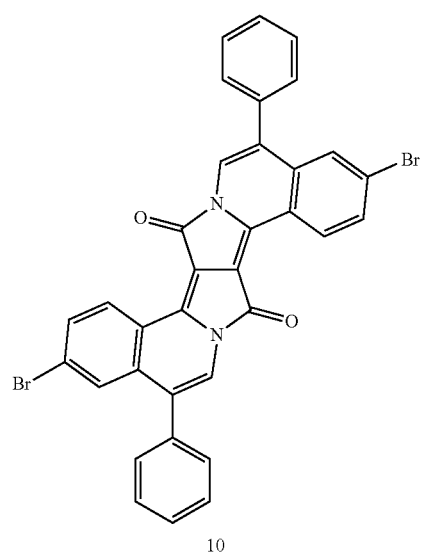
10
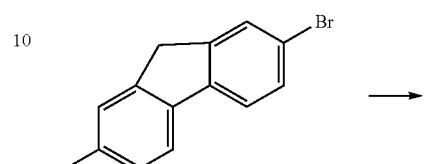
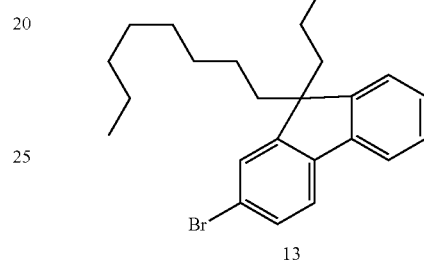
13
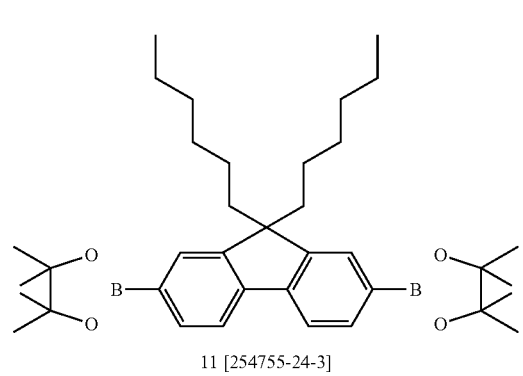
11 [254755-24-3]
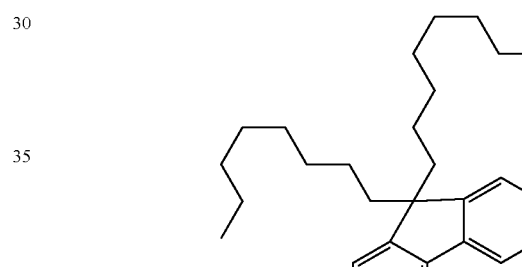
14
Compound 14 can be alternatively synthesized by the following route:
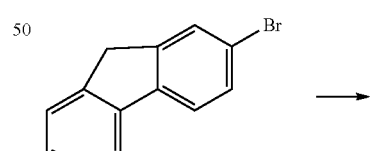
[1133-80-8]
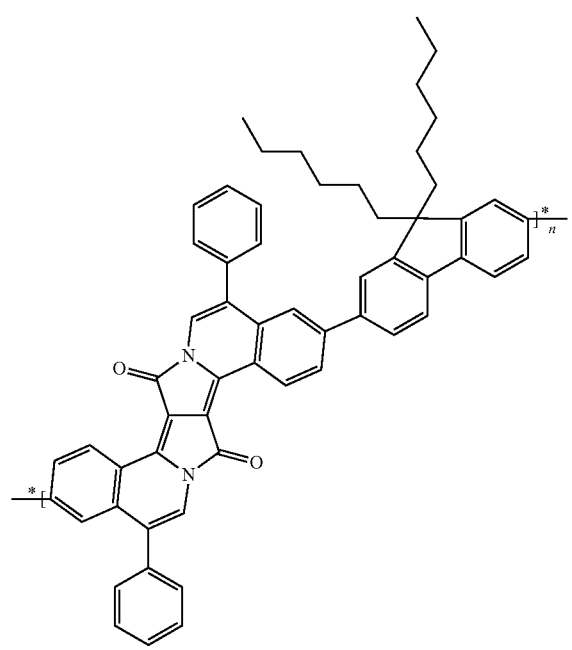
12 (= P-2)
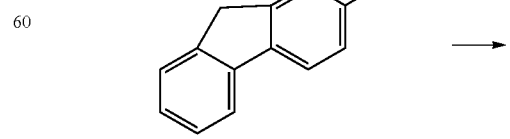
[2523-48-0]

-continued

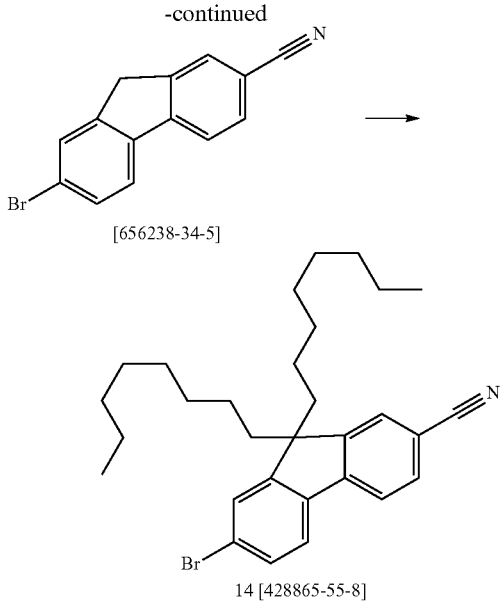

[656238-34-5]

14 [428865-55-8]

Synthesis of 9H-Fluorene-2-carbonitrile [2523-48-0]:

Under an argon atmosphere, in a three-necked flask (250 mL) are placed 2-bromo-9H-fluorene ([1133-80-8], 37.86 g, 0.15 mol), copper(I)cyanide (21.68 g, 0.242 mol) and dimethylformamide (190 mL). Resulting suspension is heated to reflux under argon. The reaction mixture is stirred at 152° C. (oil bath 165° C.) for 17 h under argon. The reaction mixture is cooled to room temperature and then poured into cold water with ammonium hydroxide (600 mL cold water with ice, 200 mL 25% $NH_4OH$ aq) and stirred for 2 h. The light brownish precipitate formed is collected by filtration. The solids are washed with dilute ammonium hydroxide (800 mL) and then with water (800 mL) to get the crude product. The wet product is washed from the funnel (6×100 mL) dichloromethane and the combined organic phases are washed with water (200 mL), NaCl sat. (50 mL) and dried over $Na_2SO_4$ (40.0 g). After that, the $Na_2SO_4$ is filtered off, washed with methylene chloride (2×50 mL). The solvent is evaporated. The raw product [2523-48-0] is dried under vacuum at 40° C. for 2 h. Yield 28.58 g (99.6%). M.p. 88-90° C. The crude product is used to the next step without purification.

Synthesis of 7-bromo-9H-fluorene-2-carbonitrile [656238-34-5]:

To a stirred solution of 9H-fluorene-2-carbonitrile (25.39 g, 0.132 mol) in $CH_2Cl_2$ (200 mL) is added $Br_2$ (27.2 mL, 0.53 mol, 4.0 eq). The HBr evolved from solution is guided through a trap to a scrubbing solution of NaOH. The mixture is stirred for 16 h. The yellow precipitate is filtered off, washed with 5% $NaHSO_3$ (500 mL), water (4×500 mL) and is dried on an evaporator at 50° C. for 1 h and overnight at room temperature in vacuum (oil pump). The crude grey solid is isolated. Yield 16.45 g 45.8%

The filter funnel is washed with 200 mL of dichloromethane and combined with the filtrate. After separation the water layer is extracted with dichloromethane (200 mL). The combined organic layers are washed with water (4×400 mL) brine (100 mL) and dried over $Na_2SO_4$. The drying agent is filtered off (wash 100 mL $CH_2C_{12}$) and after evaporation of solvent the residue is died under vacuum. Yield 17.46 g 48.6% Total yield 94.4% of product [656238-34-5]. M.p. 166-173° C., lit m.p. 172° C.

Synthesis of 7-bromo-9,9-dioctyl-9H-fluorene-2-carbonitrile [428865-55-8]:

27.2 g (0.1 mol) of 7-Bromo-9H-fluorene-2-carbonitrile and potassium iodide (0.9 g) are dissolved in 150 mL of dimethyl sulfoxide under argon. The solution is cooled to 10° C. and 1-bromooctane (44.6 g, 0.23 mol) is added dropwise and potassium hydroxide (34.0 g 0.6 mol) is added in small portions under argon. The temperature is monitored to be under 20° C. Afterwards the reaction mixture is stirred overnight at room temperature. The mixture is diluted with diethyl ether (250 mL), then filtered through celite (40.0 g) and washed with diethyl ether (150 mL, 50 mL). The filtrate is poured into de-ionized water with ice (500 mL).

The organic phases are collected and washed with water (3×100 mL), brine (50 mL) and dried over sodium sulphate (50 g). The solution is filtered through celite (50.0 g) and silica (80 g), washed with diethyl ether (3×100 mL) and concentrated to give the crude product as yellow oil (51.86 g). Product is isolated by recrystallization from a mixture of methanol (80 mL), isopropanol (10 mL) and diethyl ether (2 mL) to give product [428865-55-8]. Yield 33.89 g (68.1%), m.p.: 50.0-54.0° C. lit. mp. 48.3-52.2° C., $^1H$ NMR (500 MHz, $CDCl_3$) δ: 7.74 (dd, J=7.9, 0.5 Hz, 1H), 7.58-7.68 (m 3H), 7.49-7.53 (m, 2H), 1.95 (ddd, J=9.5, 6.3, 2.8 Hz, 4H, $CH_2CH_2(CH_2)_5CH_3$), 1.03-1.25 (m, 20H, $CH_2CH_2(CH_2)_5CH_3$), 0.83 (t, J=7.2 Hz, 6H, $CH_2CH_2(CH_2)_5CH_3$), 0.55 (m, 4H, $CH_2CH_2(CH_2)_5CH_3$).

DPP Synthesis

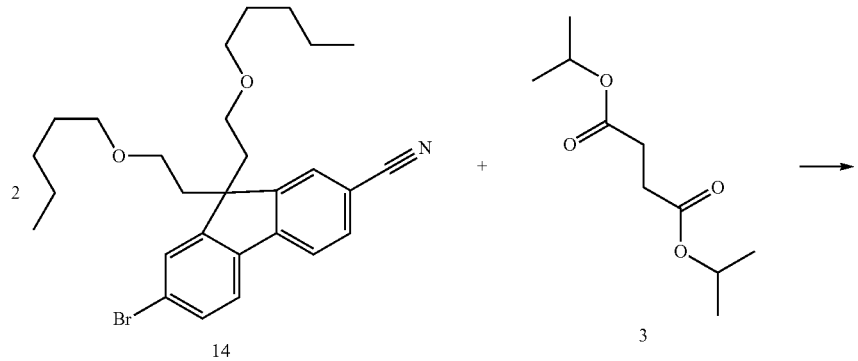

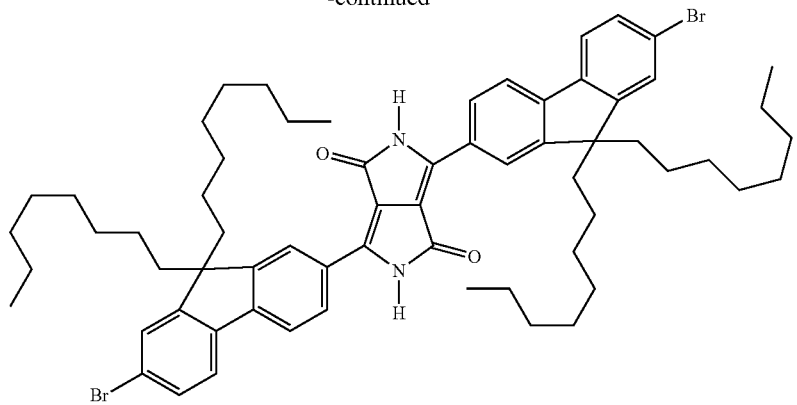

15 b) Reaction flask (250 mL) is charged with 40 ml 2-methyl-2-butanol, 2.0 g (86.9 mmol) sodium, and 30 mg iron(III) chloride under argon. The reaction mixture is heated to 100° C. under argon. The reaction mixture is stirred 1 h to the moment when all sodium is dissolved. Then the reaction mixture is cooled to 90° C. and 7-bromo-9,9-dioctyl-9H-fluorene-2-carbonitrile (10.14 g, 20.5 mmol) is added in one portion (wash with 20 ml of 2-methyl-2-butanol). The reaction is stirred for 10 minutes, warmed up to 110° C. and 1.98 g (9.79 mmol) diisopropyl succinate is added via syringe. The reaction mixture is stirred in an oil bath at 110° C. under argon overnight. Next day the reaction mixture is cooled to 60° C., quenched by addition of 25 mL AcOH, 25 mL water and 25 mL EtOH. After 1 h at 100° C. the stirring is continued overnight at RT. Next day 100 mL of water are added and the raw product is filtered on G3 filter. To the residue filter cake water (25 mL) and EtOH (600 mL) are added in small portions, then the product is isolated by filtration and dried at room temperature under vacuum (oil pump). Yield 2.49 g (23.7%) of a compound of formula 15. This compound is directly used in the next reaction to give compound 16.

Synthesis of Diacetal

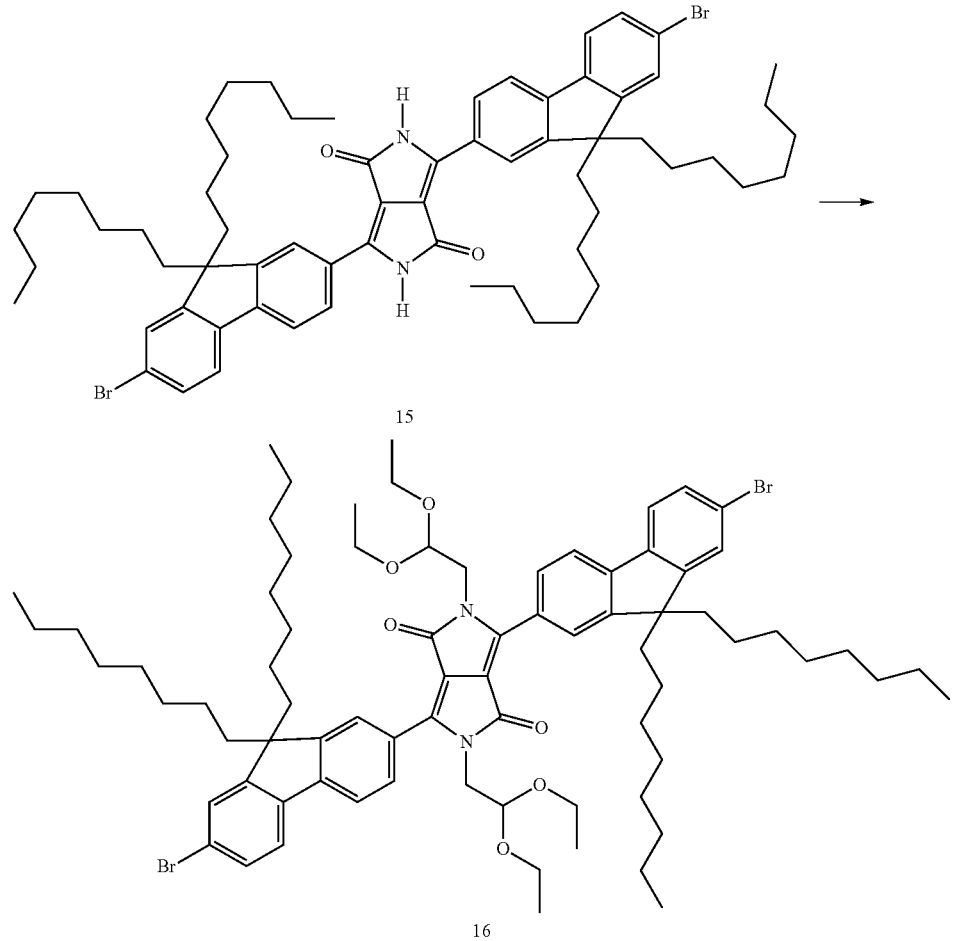

15

16 c) A mixture of 3,6-bis(7-bromo-9,9-dioctyl-9H-fluoren-2-yl)-1,4-diketopyrrolo[3,4-c]pyrrole (1.24 g, 1.16 mmol), potassium carbonate (2.40 g, 17.4 mmol) and 25 ml of NMP is heated to 120° C. under an argon atmosphere. Then bromoacetaldehyde diethyl acetal (1.70 ml, 10.0 mmol) is added by a syringe. The reaction mixture is stirred for 1 h at 120° C. then second portion of bromoacetaldehyde diethyl acetal (1.70 ml, 10.0 mmol) is added by a syringe and the reaction is continued over night at 130° C. Next day the reaction mixture is cooled and quenched with water. The product is extracted with three portions of hexane. The combined organic layers are washed twice with water and brine. Finally dried over sodium sulfate, solvents are evaporated and the product is purified by column chromatography (hexane:ethyl acetate 29:1→19:1). 0.723 g (48%) of a compound of formula 16 are obtained as red-orange fluorescent solid after drying overnight in vacuum (oil pump).

Cyclization of Acetal (Compound (I-9))

chloroform under an argon atmosphere. Subsequently trifluoromethanesulfonic acid (0.92 ml, 10.4 mmol) is slowly added and the reaction mixture is stirred at 60° C. for 1 h. Then the reaction mixture is cooled down and a solution of triethyl amine (1.75 ml, 12.6 mmol) in 5 ml of CHCl$_3$ is slowly added in order to neutralize the acid. The obtained dark blue mixture is placed in a 500 ml Erlenmeyer flask and 200 ml of EtOH are added. The resulting suspension is cooled down and the precipitate is filtered off and dried under vacuum to give a compound of formula 17 (=compound (I-9) as dark blue powder. Yield: 536 mg (92%).

$^1$H NMR (500 MHz, CDCl$_3$) δ 9.19 (s, 2H, 9-H and 20-H), 7.91 (d, J=7.3 Hz, 2H, 1-H and 12-H), 7.83 (s, 2H, 3-H and 14-H), 7.70 (d, J=7.9 Hz, 2H, 4-H and 15-H), 7.59-7.50 (m, 4H, 7-H and 18-H+, 5-H and 16-H), 6.88 (d, J=7.4 Hz, 2H, 2-H and 13-H), 2.29-2.15 (m, 4H, CH$_2$CH$_2$(CH$_2$)$_5$CH$_3$), 2.12-1.98 (m, 4H, CH$_2$CH$_2$(CH$_2$)$_5$CH$_3$), 1.32-

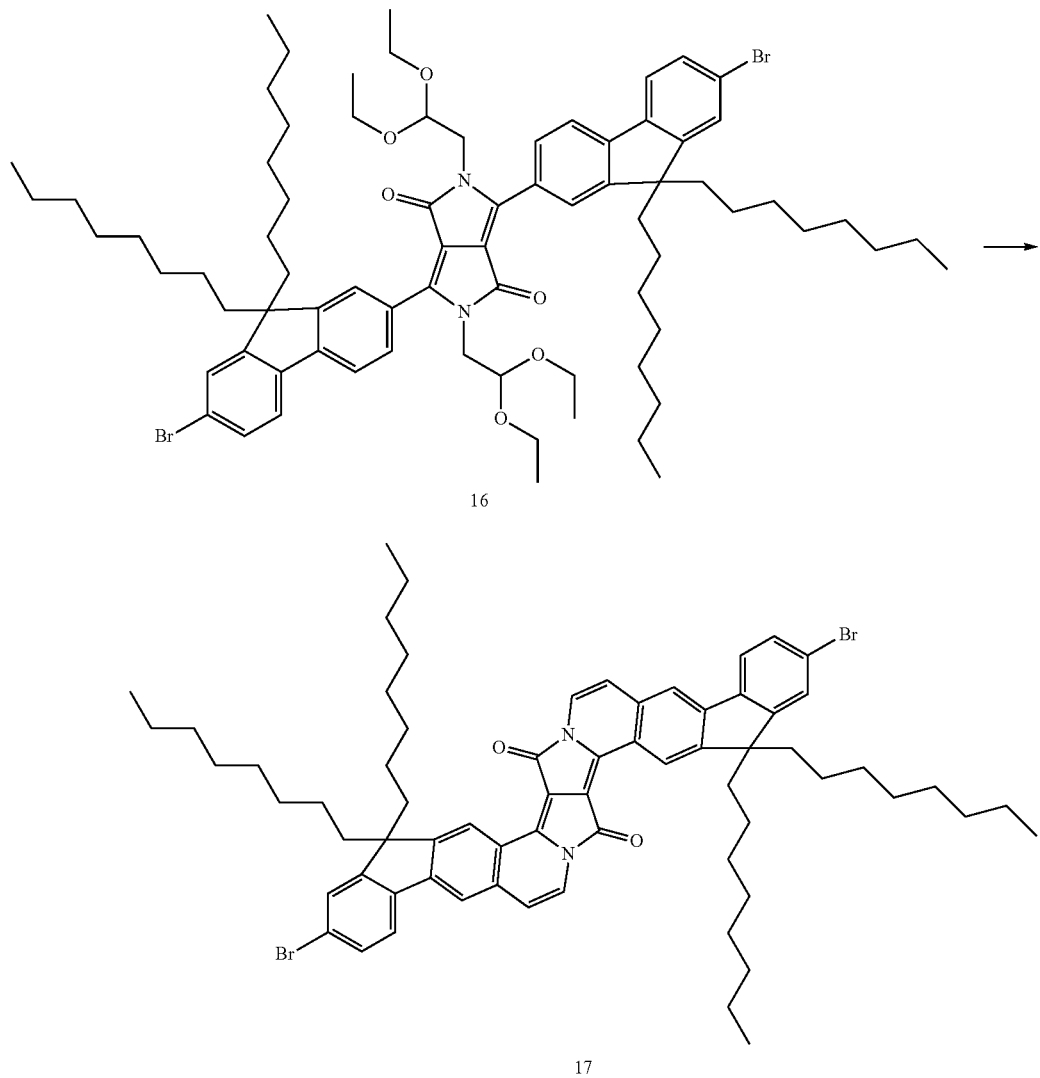

16

17 d) The diacetal, 3,6-bis(7-bromo-9,9-dioctyl-9H-fluoren-2-yl)-2,5-bis(2,2-diethoxyethyl)-1,4-diketopyrrolo-[3,4-c]pyrrole (677 mg, 0.519 mmol), is dissolved in 10 ml of 0.94 (m, 40H, CH$_2$CH$_2$(CH$_2$)$_5$CH$_3$), 0.78 (t, J=7.1 Hz, 12H, CH$_2$CH$_2$(CH$_2$)$_5$CH$_3$), 0.72-0.62 (m, 8H, CH$_2$CH$_2$(CH$_2$)$_5$CH$_3$).

Polymerization
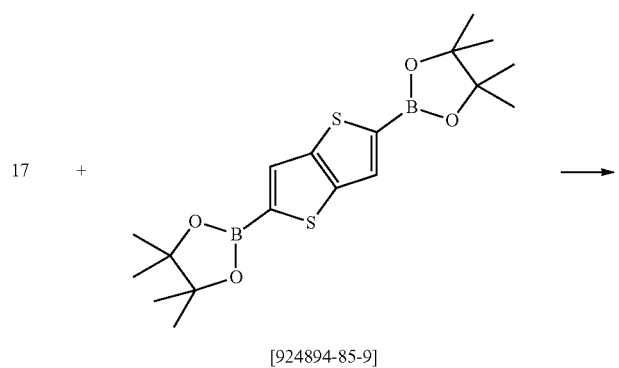
[924894-85-9]
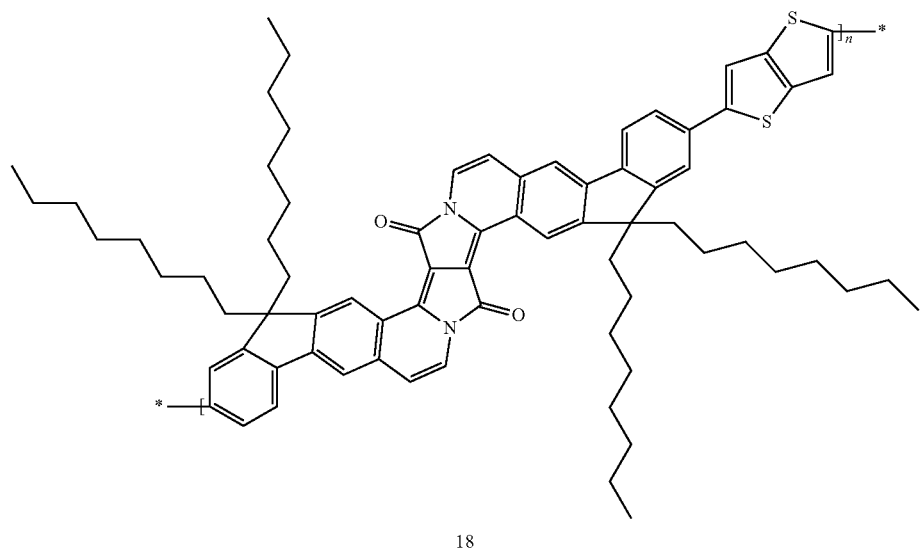
18
The polymer P-12 (compound 18) is obtained according to polymer P-11 via Suzuki-polymerization reaction of compound 17 and compound [924894-85-9].
Example 4
Synthesis of Polymer P-21 (Compound 19)
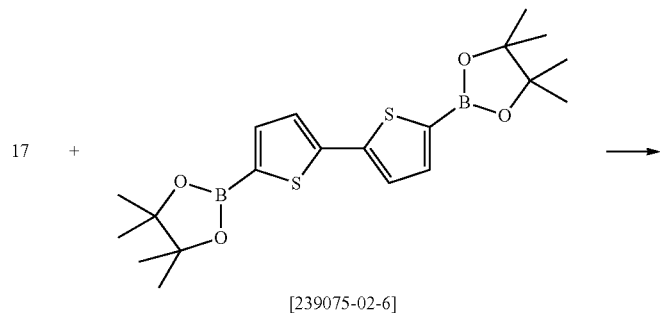
[239075-02-6]

-continued

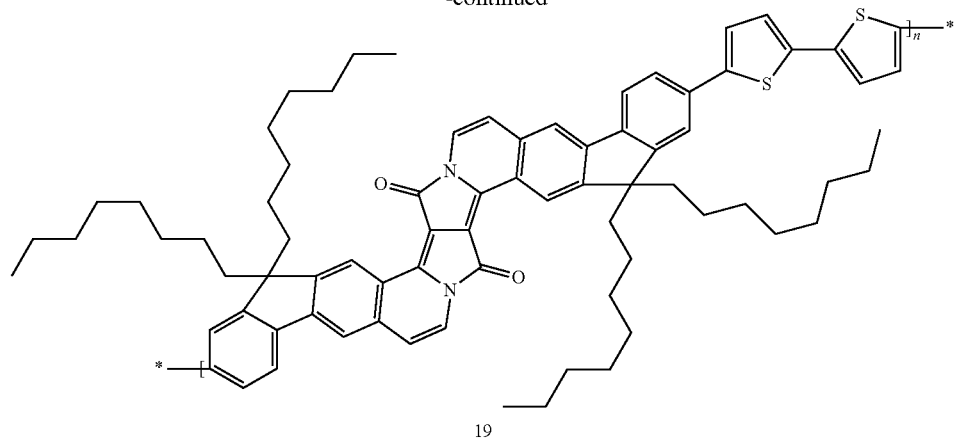

19

500 mg of compound 17 and 186.8 mg of compound [239075-02-6] are added under argon to 25 ml of tetrahydrofuran. Then 48.24 mg of the phosphine ligand [740815-37-6] are added together with 8 mg of palladium(II)acetate. Then the mixture is heated to reflux. Then 112.47 mg of LiOH monohydrate is added and the mixture is heated at reflux overnight. The mixture is cooled and poured into water. The precipitate is filtered and washed with water and methanol. The filter cake is then Soxhlet extracted with heptane, tetrahydrofuran and toluene. The tetrahydrofurane fraction contains a polymer 19 having a weight-average molecular weight ($M_w$) of 20'246 Da and a polydispersity (PDI) of 2.52. The toluene fraction contains a polymer 19 having $M_w$ of 28'825 Da and PDI of 1.72.

Example 5

Synthesis of Polymer P-22 (Compound 20)

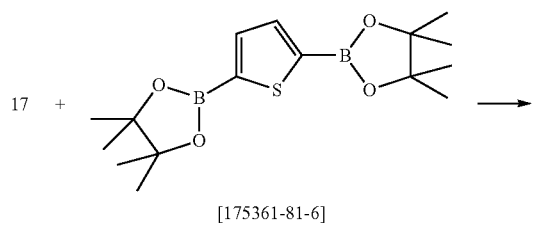

[175361-81-6]

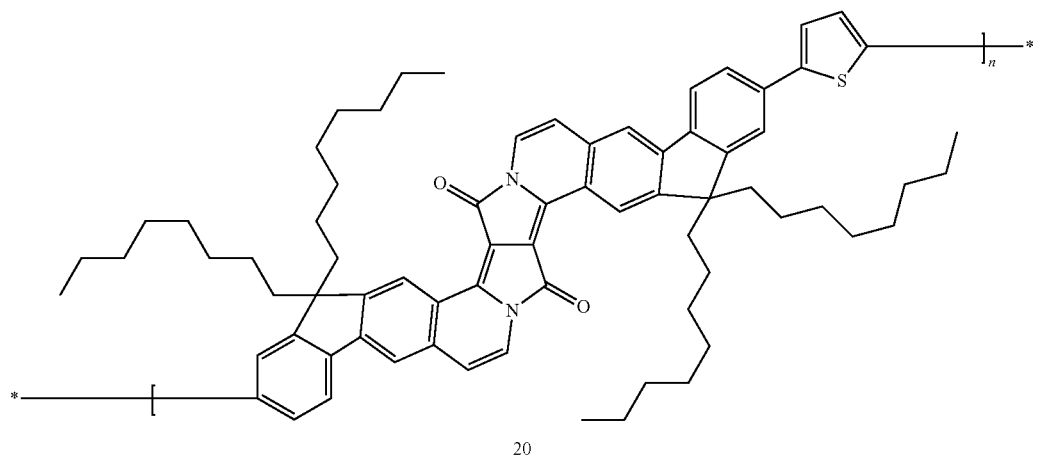

20

The polymer P-22 (compound 20) is obtained in analogy to polymer P-21 (compound 19) via Suzuki-polymerization reaction of compound 17 and compound [175361-81-6]. The tetrahydrofurane fraction contains a polymer 20 having a $M_w$ of 27'769 Da and a PDI of 2.04. The toluene fraction contains a polymer 20 having a $M_w$ of 54'561 Da and a PDI of 1.70.

Example 6

Synthesis of Compound 21 (P-23)

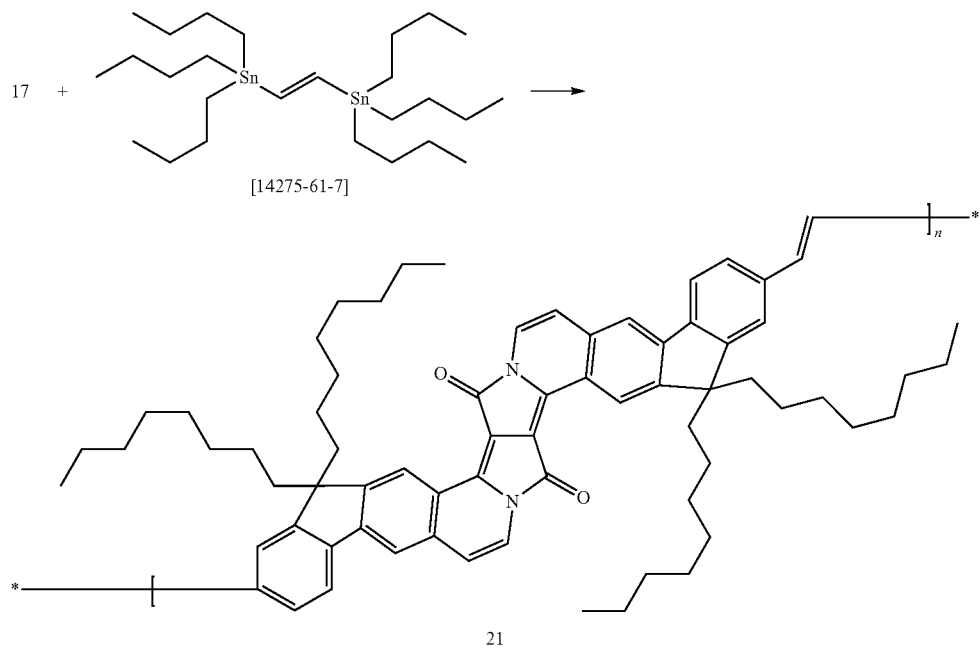

1000 mg of compound 17 and 520.76 mg of the tin compound [14275-61-7] are added to dry toluene under argon. Then 29.78 mg of tetrakis(triphenylphosphine)palladium are added and the mixture is heated to reflux overnight. The reaction mixture is cooled and poured into methanol. The precipitate is filtered and the filter cake is washed with methanol and acetone. The filter cake is then Soxhlet extracted with heptane, tetrahydrofuran and toluene. The tetrahydrofurane fraction contains a polymer 21 having a $M_w$ of 30'484 Da and a PDI of 3.14. The toluene fraction contains a polymer 21 having a $M_w$ of 65'063 Da and a PDI of 2.83.

Example 7

Synthesis of Compound 25 (I-16)

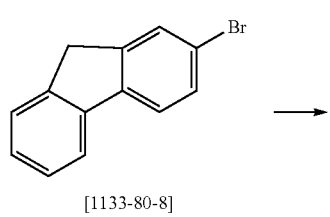

-continued

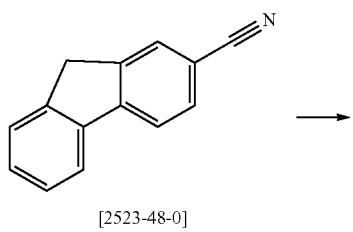

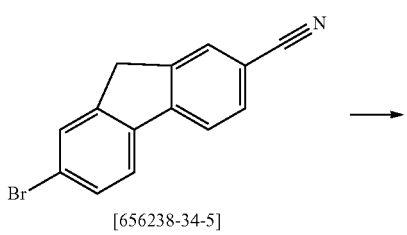

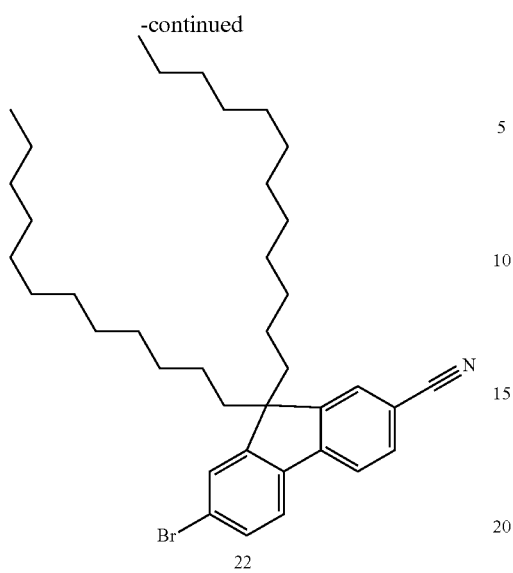
a) Synthesis of compound 22 is made in analogy to the synthesis of compound 14 by the alkylation of compound [656238-34-5] with 1-bromo-dodecane.
$^1$H NMR (500 MHz, CDCl$_3$) δ: 7.73 (d, J=7.8 Hz, 1H), 7.63 (dd, J=7.9, 1.2 Hz, 1H), 7.61-7.58 (m, 3H), 7.49-7.52 (m 2H), 1.95 (ddd, J=9.9, 6.4, 2.8 Hz, 4H, CH$_2$CH$_2$(CH$_2$)$_9$CH$_3$), 1.30-1.10 (m, 36H, CH$_2$CH$_2$(CH$_2$)$_9$CH$_3$), 0.83 (t, J=7.1 Hz, 6H, CH$_2$CH$_2$(CH$_2$)$_9$CH$_3$), 0.55 (m, 4H, CH$_2$CH$_2$(CH$_2$)$_9$CH$_3$).
Synthesis of Compound 23
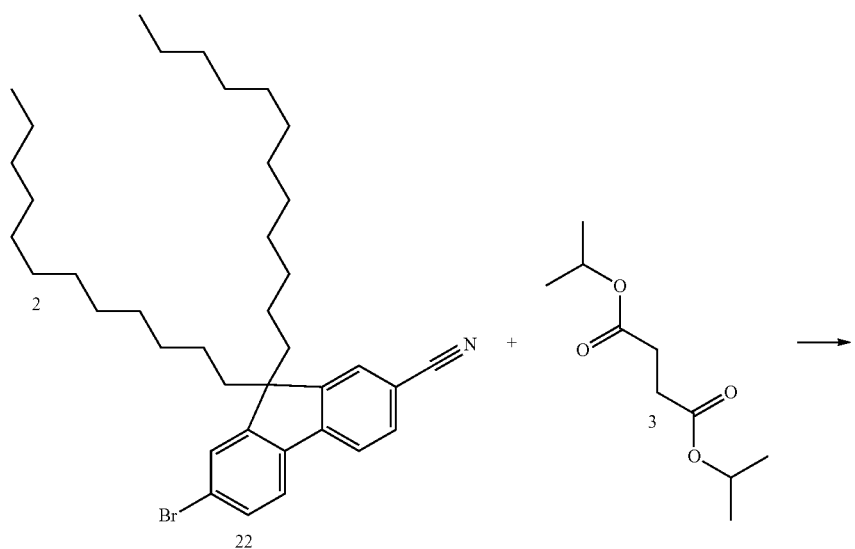

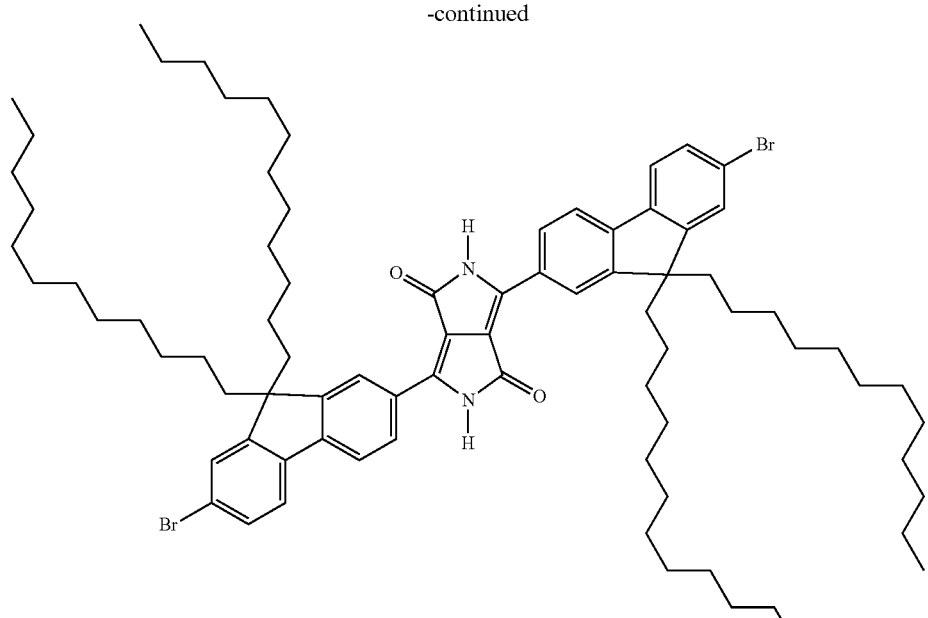

23 b) Synthesis of compound 23 is made in analogy to the synthesis of compound 15 by the condensation reaction of compound 22 and compound 3.

$^1$H NMR (500 MHz, CDCl$_3$: TFA-d 4:1) δ 8.41 (br s, 2H, 1-H at fluorenyl), 8.20 (br d, J=6.4 Hz, 2H, 3-H at fluorenyl), 7.90 (d, J=7.9 Hz, 2H, 4-H at fluorenyl), 7.72-7.56 (m, 6H, 5-H, 6-H and 8-H at fluorenyl), 2.19 (td, J=10.0, 3.8 Hz, 4H, CH$_2$CH$_2$(CH$_2$)$_9$CH$_3$), 2.08 (td, J=10.0, 3.8 Hz, 4H, CH$_2$CH$_2$(CH$_2$)$_9$CH$_3$), 1.38-0.96 (m, 72H, CH$_2$CH$_2$(CH$_2$)$_9$CH$_3$), 0.86 (t, J=6.2 Hz, 12H, CH$_3$), 0.82-0.64 (m, 8H, CH$_2$CH$_2$(CH$_2$)$_9$CH$_3$).

Synthesis of Compound 24

23 →

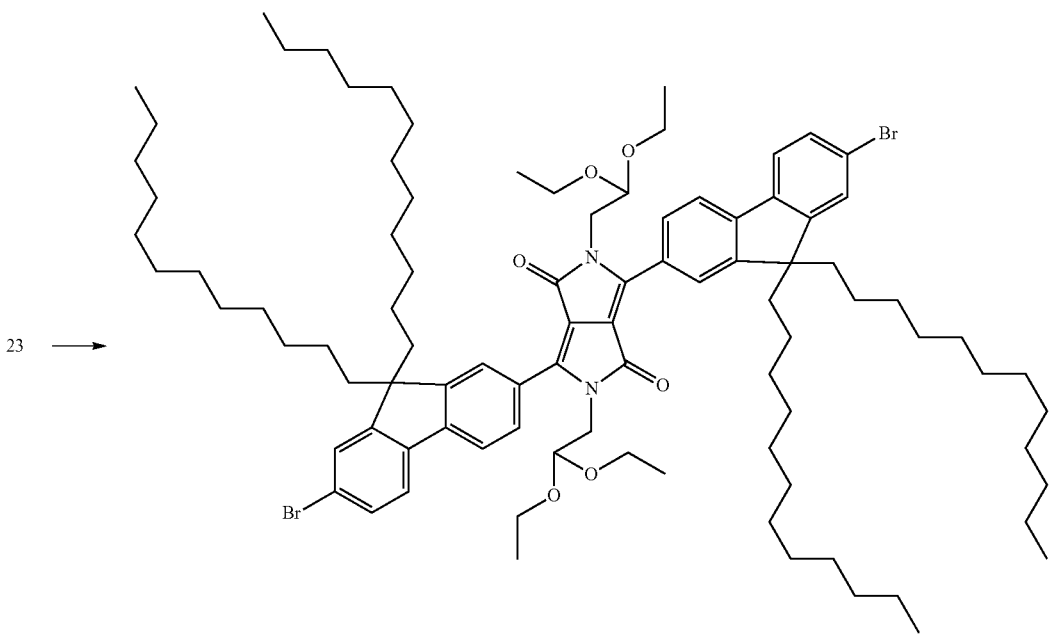

24 c) Synthesis of compound 24 is made in analogy to the synthesis of compound 16 by the alkylation of compound 23 with bromoacetaldehyde diethyl acetal.

$^1$H NMR (500 MHz, CDCl$_3$) δ: 8.16 (s, 2H), 8.15 (dd, J=7.9, 1.2 Hz, 1H,), 7.80 (d, J=7.9 Hz, 1H,), 7.61 (d, J=7.9 Hz, 1H), 7.47-7.60 (m 3H),). 4.99 (t, J=5.6 Hz, 2H, NCH$_2$CH(OEt)$_2$), 3.90 (d, J=5.8 Hz, 4H, NCH$_2$CH(OEt)$_2$), 3.73 (dq, J=9.5, 7.1 Hz, 4H, OCH$_2$CH$_3$), 3.55 (dq, J=9.2, 7.0 Hz, 4H, OCH$_2$CH$_3$), 2.05 (ddd, J=13.4, 10.1, 6.4 Hz, 4H, CH$_2$CH$_2$(CH$_2$)$_9$CH$_3$), 1.96 (ddd, J=13.4, 10.1, 6.4 Hz, 4H, CH$_2$CH$_2$(CH$_2$)$_9$CH$_3$), 1.00-1.30 (m, 96H, CH$_2$CH$_2$(CH$_2$)$_9$CH$_3$ and OCH$_2$CH$_3$), 0.85 (t, J=7.0 Hz, 12H, CH$_2$CH$_2$(CH$_2$)$_9$CH$_3$), 0.62-0.71 (m, 8H, CH$_2$CH$_2$(CH$_2$)$_9$CH$_3$).

Synthesis of Compound 25 (I-16)

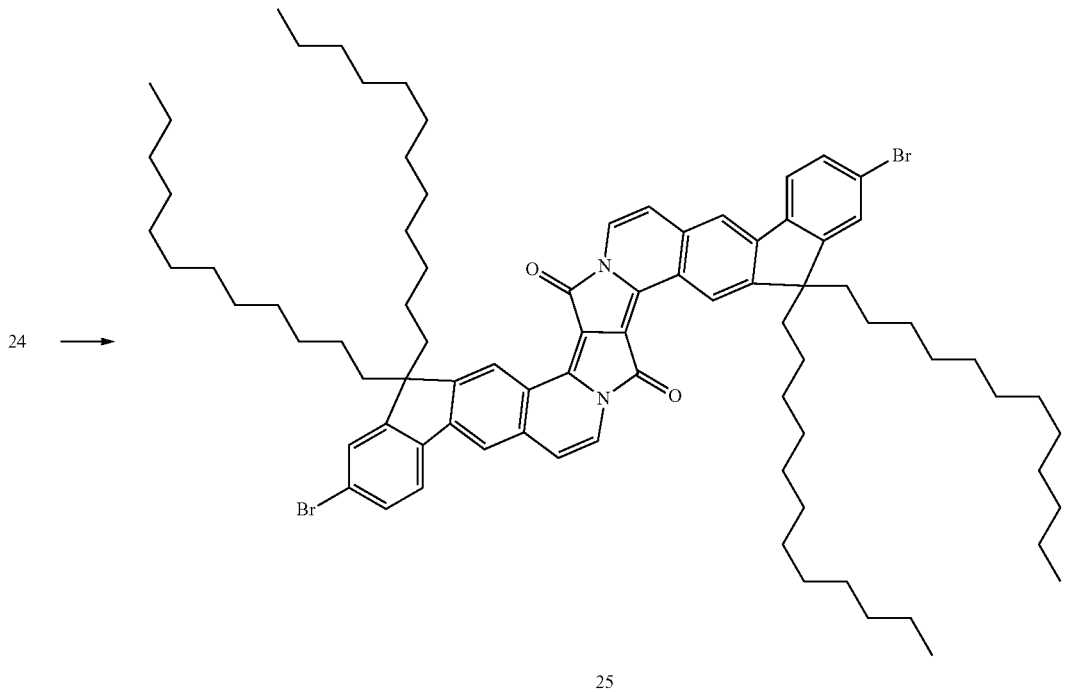 [SMILES: CCCCCCCCCCCCC1(CCCCCCCCCCCC)c2cc(Br)ccc2-c2cc3c(cc21)C1=C2C(=O)N4C=Cc5cc6c(cc5C4=C2C(=O)N1C=C3)C(CCCCCCCCCCCC)(CCCCCCCCCCCC)c1cc(Br)ccc1-6]

d) Synthesis of compound 25 is made in analogy to the synthesis of compound 17 by ring closing reaction of compound 24 under acidic conditions.

$^1$H NMR (500 MHz, CDCl$_3$) δ 9.19 (s, 2H, 9-H and 20-H), 7.91 (d, J=6.7 Hz, 2H, 1-H and 12-H), 7.83 (s, 2H, 3-H and 14-H), 7.69 (d, J=7.9 Hz, 2H, 4-H and 15-H), 7.60-7.50 (m, 4H, 7-H and 18-H+, 5-H and 16-H), 6.87 (d, J=7.3 Hz, 2H, 2-H and 13-H), 2.28-2.18 (m, 4H, CH$_2$CH$_2$(CH$_2$)$_9$CH$_3$), 2.09-1.98 (m, 4H, CH$_2$CH$_2$(CH$_2$)$_9$CH$_3$), 1.24-1.00 (m, 72H, CH$_2$CH$_2$(CH$_2$)$_9$CH$_3$), 0.82 (t, J=7.1 Hz, 12H, CH$_2$CH$_2$(CH$_2$)$_9$CH$_3$), 0.73-0.63 (m, 8H, CH$_2$CH$_2$(CH$_2$)$_9$CH$_3$).

Example 8

Synthesis of Compound 26 (P-24)

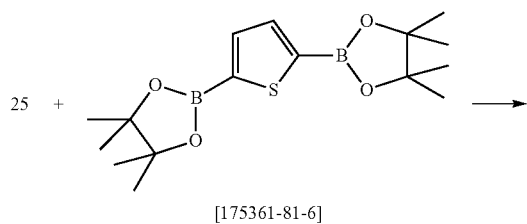

[175361-81-6]

-continued
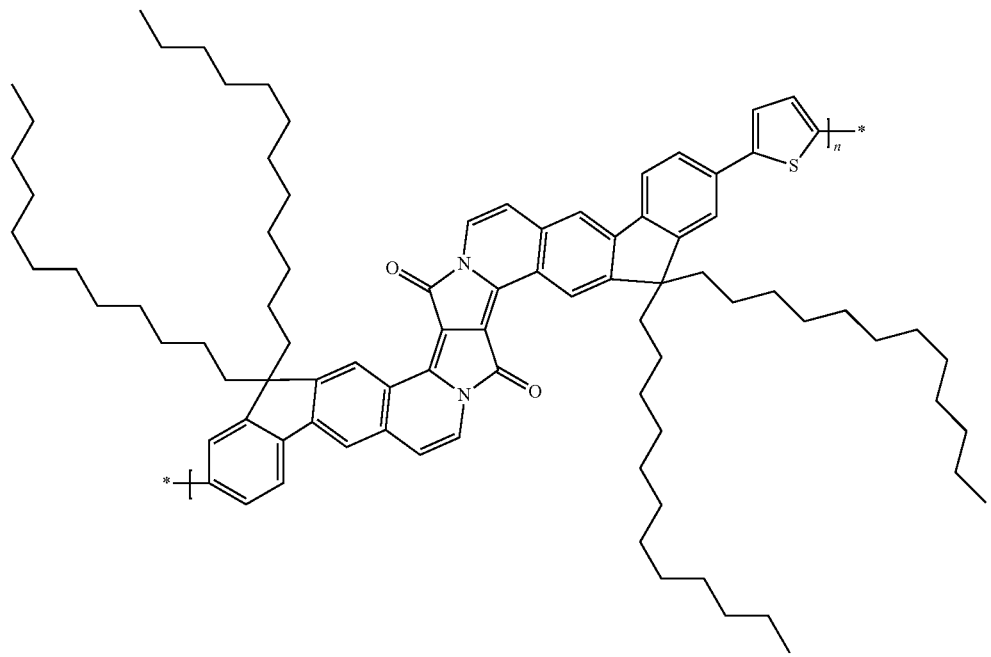
26
The polymer P-24 (compound 26) is obtained in analogy to polymer P-21 (compound 19) via Suzuki polymerization reaction of compound 25 and compound [175361-81-6]. The tetrahydrofuran fraction contains a polymer 26 having a $M_w$ of 44'416 Da and a PDI of 1.73.
Example 8
Synthesis of Compound 27 (P-25)
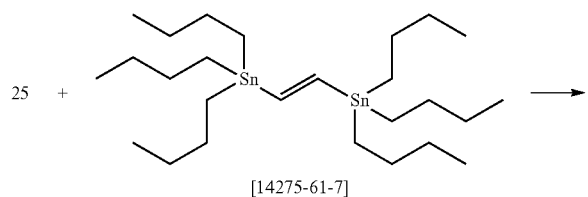
[14275-61-7]

-continued

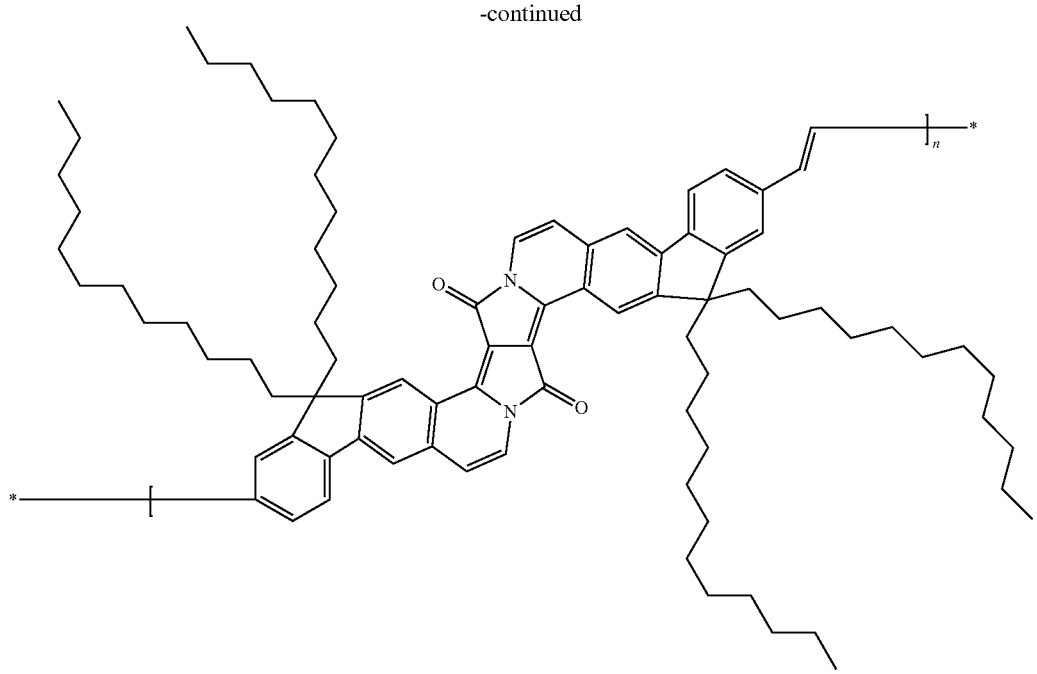

27

The polymer P-25 (compound 27) is obtained in analogy to polymer P-23 (compound 21) via Stille polymerization reaction of compound 25 and compound [14275-61-7]. The tetrahydrofuran fraction contains a polymer 27 having a $M_w$ of 124'676 Da and a PDI of 4.58.

Application Example 1

Fabrication and Electrical Characterization of an Organic Field-Effect Transistor (OFET) Based on Polymer P-22
Preparation of Bottom-Contact, Top-Gate FETs Polymer P-22 is dissolved at a concentration of 0.75 wt % in toluene and subsequently coated onto a PET-substrate with lithographically patterned gold contacts, serving as Source and Drain contact of the OFET. 100 µl of the formulation is coated by a standard blade coater at a coating speed of 20 mm/s, yielding a homogenous layer of the semiconductor over the entire substrate. After the coating is completed, the substrate is immediately transferred onto a preheated hotplate and heated for 30 s at 90° C. Next the gate dielectric layer consisting of Cytop CTL-809M is spin coated on top of the organic semiconductor (1200 rpm, 30 s). After spin coating, the substrate is again transferred to the hotplate and annealed for another 5 Min at 100° C. Finally 50 nm thick shadow-mask patterned gold gate electrodes are deposited by vacuum evaporation to complete FETs in the BGTC-configuration.

With the channel length L=10 µm and the channel width W=250 µm, the hole mobility is calculated to $\mu \sim 1 \times 10^{-4}$ cm$^2$/Vs for this representative device. The threshold voltage is −6.5V, for the ON/OFF ratio is $1.06 \times 10^2$.

Application Example 2

Fabrication and Electrical Characterization of an Organic Field-Effect Transistor (OFET) Based on Polymer P-25

The sample preparation and electrical characterization is identical to the description in Application Example 1.

With the channel length L=10 µm and the channel width W=250 µm, the hole mobility is calculated to $\mu \sim 4 \times 10^{-5}$ cm$^2$/Vs for this representative device. The threshold voltage is −8V, for the ON/OFF ratio is $1.1 \times 10^1$.

Application Example A3

A solution of polymer P-21 in toluene is bladed on a top gate bottom contact transistor (gold contacts, channel length 100 µm and 200 µm, channel width 10000 µm). Cytop is used as dielectric. A hole mobility of 0.001 cm$^2$/Vs is measured for both channel lengths.

The invention claimed is:

1. A polymer, comprising one or more (repeating) unit(s) of formula

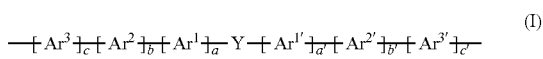

(I)

wherein Y is of formula

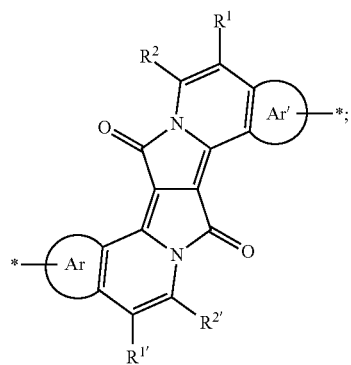

a is 0, 1, 2, or 3, a' is 0, 1, 2, or 3; b is 0, 1, 2, or 3; b' is 0, 1, 2, or 3; c is 0, 1, 2, or 3; and c' is 0, 1, 2, or 3;

Ar and Ar' denote a homo- or heteroaromatic system, which may be substituted, or unsubstituted;

$R^1$, $R^{1'}$, $R^2$ and $R^{2'}$ may be the same or different, and are selected from hydrogen, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —NR$^{39}$—, CONR$^{39}$—, NR$^{39}$CO—, —COO—, —CO— or —OCO—, a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —NR$^{39}$—, CONR$^{39}$—, NR$^{39}$CO—, —COO—, —CO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —NR$^{39}$—, CONR$^{39}$—, NR$^{39}$CO—, —COO—, —CO— or —OCO—, a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —NR$^{39}$—, CONR$^{39}$—, NR$^{39}$CO—, —COO—, —CO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group;

a C2-C20heteroaryl group which can optionally be substituted one or more times with C1-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group;

a —CO—$C_1$-$C_{18}$alkyl group, a —CO—$C_5$-$C_{12}$cycloalkyl group, or —COO—$C_1$-$C_{18}$alkyl group; $R^{39}$ is hydrogen, $C_1$-$C_{18}$alkyl, $C_1$-$C_{18}$haloalkyl, $C_7$-$C_{25}$arylalkyl, or $C_1$-$C_{18}$alkanoyl, $Ar^1$, $Ar^{1'}$, $Ar^2$, $Ar^{2'}$, $Ar^3$ and $Ar^{3'}$ are independently of each other

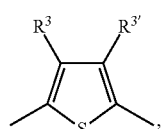

(XIa)

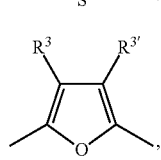

(XIb)

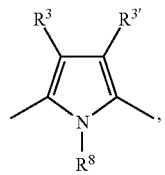

(XIc)

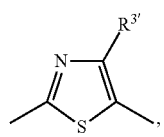

(XId)

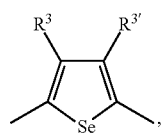

(XIe)

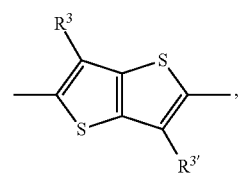

(XIf)

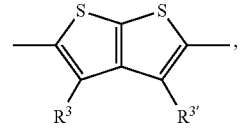

(XIg)

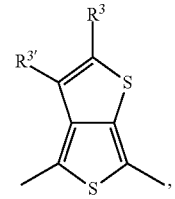

(XIh)

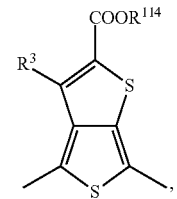

(XIi)

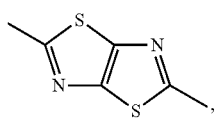

(XIj)

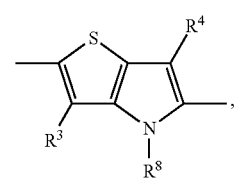

(XIk)

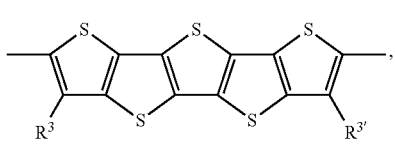 (XIl)
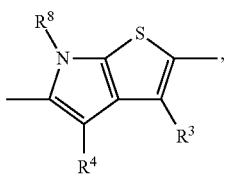 (XIm)
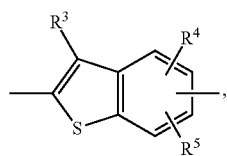 (XIn)
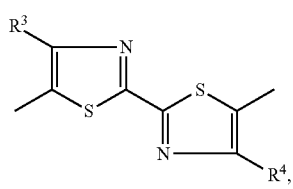 (XIo)
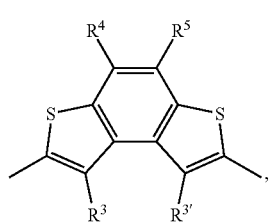 (XIp)
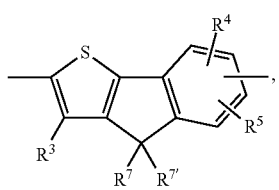 (XIq)
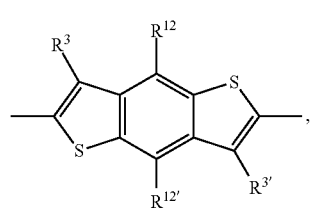 (XIr)
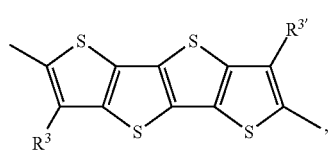 (XIs)
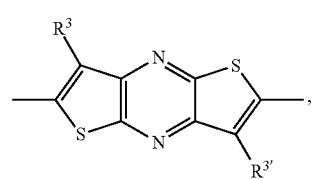 (XIt)
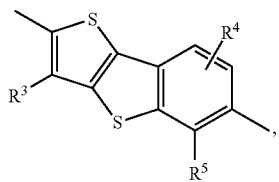 (XIu)
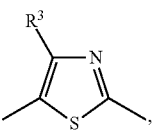 (XIv)
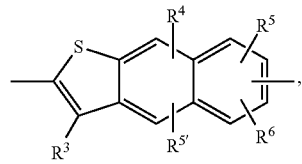 (XIw)
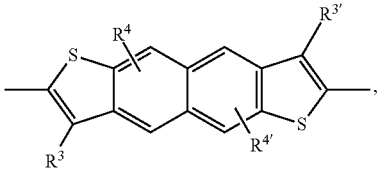 (XIx)
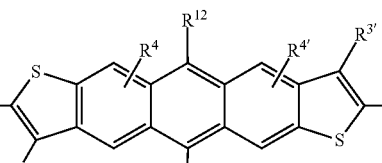 (XIy)
 (XIz)
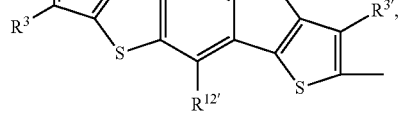 (XIIa)
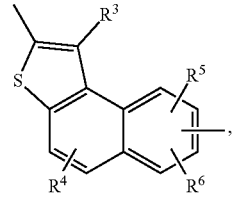 (XIIb)
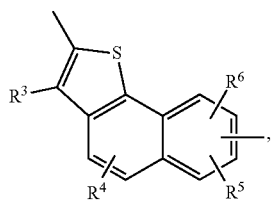 (XIIc)

-continued
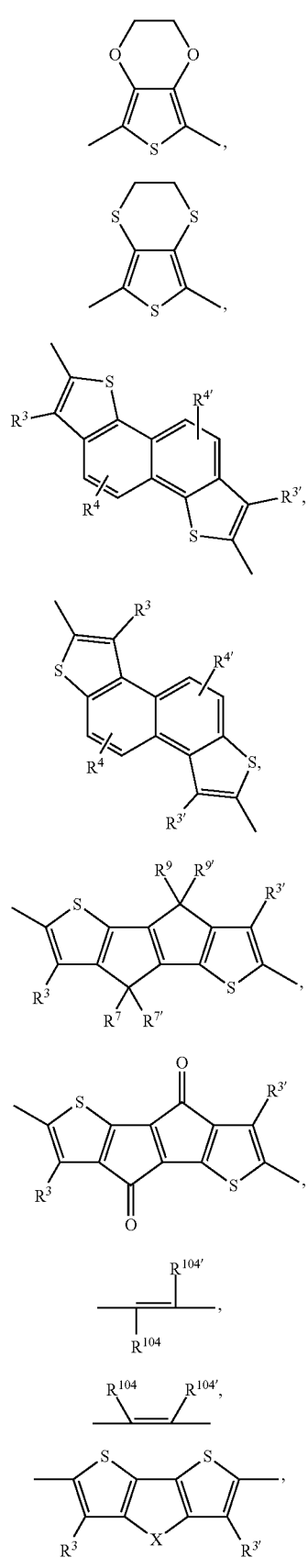
such as, for example,
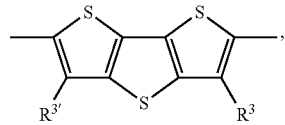 (XIIIa)
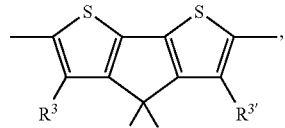 (XIIIb)
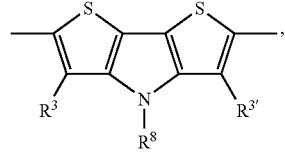 (XIIIc)
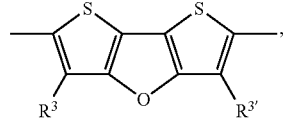 (XIIId)
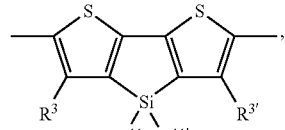 (XIIIe)
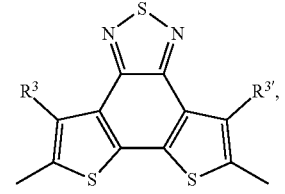 (XIIIf)
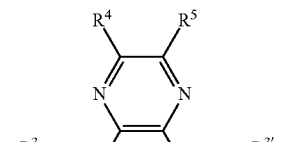 (XIIIg)
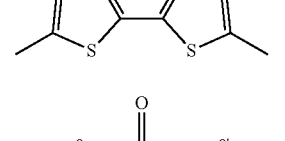 (XIIIh)
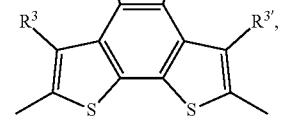

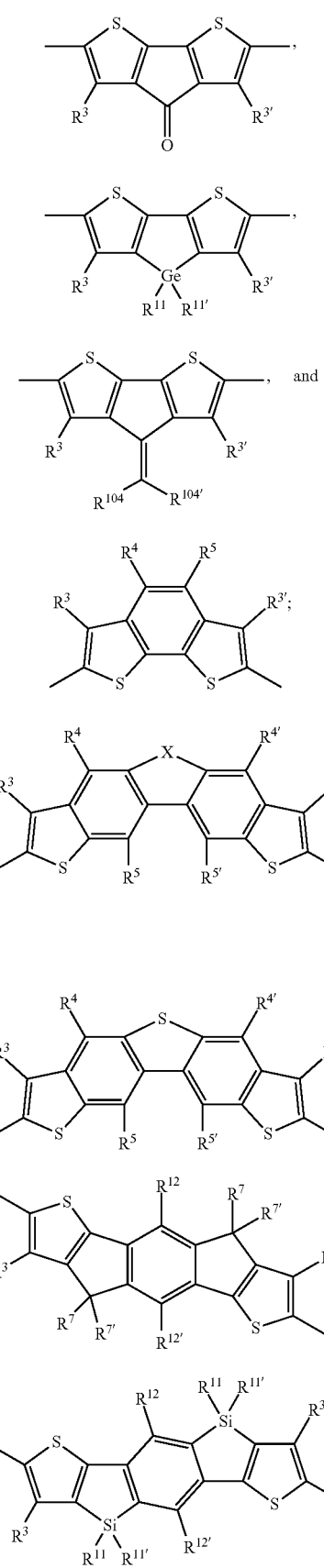
wherein
X is —O—, —S—, —NR⁸—, —Si(R¹¹)(R¹¹')—, —Ge(R¹¹)(R¹¹')—, —C(R⁷)(R⁷')—, —C(=O)—,

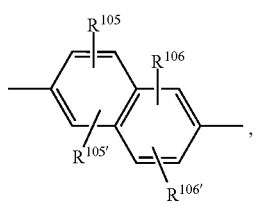
(XVb)
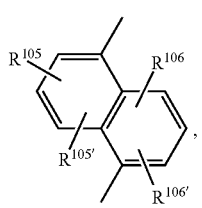
(XVc)
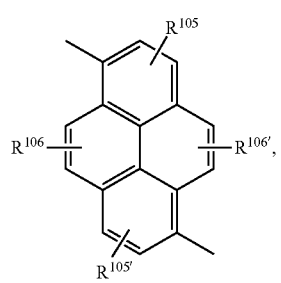
(XVd)
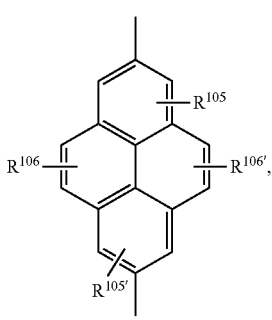
(XVe)
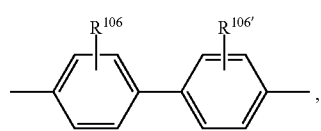
(XVf)
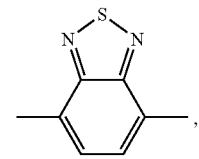
(XVg)
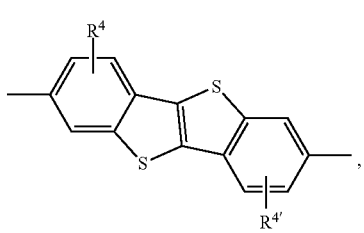
(XVh)
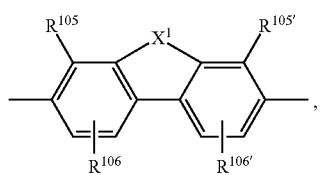
(XVI)
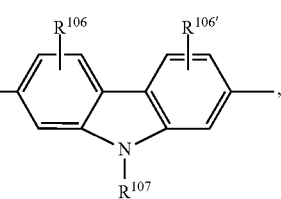
(XVIa)
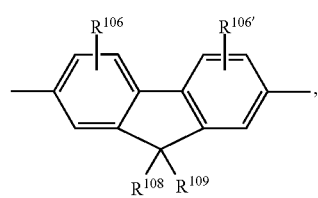
(XVIb)
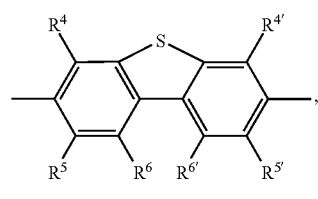
(XVIc)
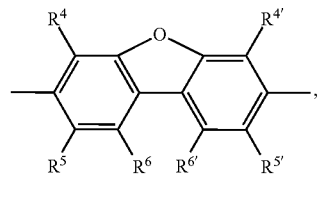
(XVId)
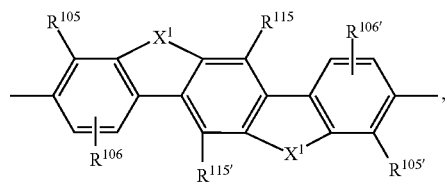
(XVII)
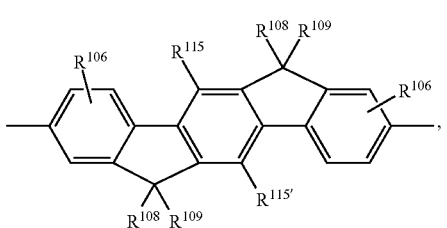
(XVIIa)

-continued

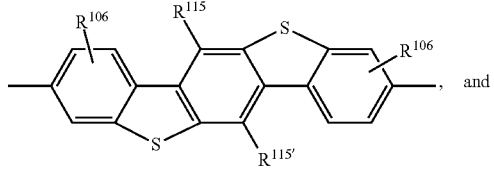
(XVIIb)

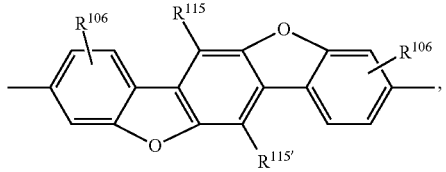
(XVIIc)

wherein
X¹ is S, O, NR$^{107}$—, —Si(R$^{117}$)(R$^{117'}$)—, —Ge(R$^{117}$)(R$^{117'}$)—C(R$^{108}$)(R$^{109}$)—, —C(=O)—,

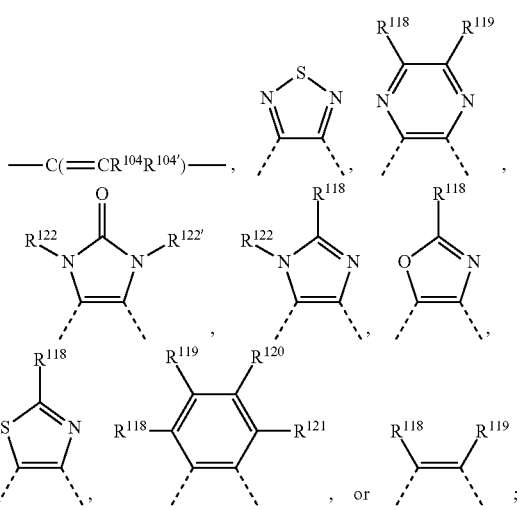

R³ and R$^{3'}$ are independently of each other hydrogen, halogen, halogenated C$_1$-C$_{25}$alkyl, CF$_3$, cyano, C$_1$-C$_{25}$alkyl, C$_3$-C$_{25}$alkyl, which is optionally interrupted by one or more oxygen or sulphur atoms; C$_7$-C$_{25}$arylalkyl, or C$_1$-C$_{25}$alkoxy;

R⁴, R$^{4'}$, R⁵, R$^{5'}$, R⁶ and R$^{6'}$ are independently of each other hydrogen, halogen, halogenated C$_1$-C$_{25}$alkyl, especially CF$_3$, cyano, C$_1$-C$_{25}$alkyl, especially C$_3$-C$_{25}$alkyl, which is optionally interrupted by one or more oxygen or sulphur atoms; C$_7$-C$_{25}$arylalkyl, or C$_1$-C$_{25}$alkoxy;

R⁷, R$^{7'}$, R⁹ and R$^{9'}$ are independently of each other hydrogen, C$_1$-C$_{25}$alkyl, C$_3$-C$_{25}$alkyl, which is optionally interrupted by one, or more oxygen, or sulphur atoms; or C$_7$-C$_{25}$arylalkyl, R⁸ and R$^{8'}$ are independently of each other hydrogen, C$_6$-C$_{18}$aryl; C$_6$-C$_{18}$aryl which is substituted by C$_1$-C$_{18}$alkyl, or C$_1$-C$_{18}$alkoxy; or C$_1$-C$_{25}$alkyl, especially C$_3$-C$_{25}$alkyl, which is optionally interrupted by one or more oxygen or sulphur atoms; or C$_7$-C$_{25}$arylalkyl, R¹¹ and R$^{11'}$ are independently of each other C$_1$-C$_{25}$alkyl group, especially a C$_1$-C$_8$alkyl group, C$_7$-C$_{25}$arylalkyl, or a phenyl group, which can be substituted one to three times with C$_1$-C$_8$alkyl and/or C$_1$-C$_8$alkoxy;

R¹² and R$^{12'}$ are independently of each other hydrogen, halogen, cyano, C$_1$-C$_{25}$alkyl, especially C$_3$-C$_{25}$alkyl, which is optionally interrupted by one or more oxygen, or sulphur atoms, C$_1$-C$_{25}$alkoxy, C$_7$-C$_{25}$arylalkyl, or —≡—R$^{13}$, wherein R$^{13}$ is a C$_1$-C$_{10}$alkyl group, or a tri(C$_1$-C$_8$alkyl)silyl group;

R$^{104}$ and R$^{104'}$ are independently of each other hydrogen, C$_1$-C$_{18}$alkyl, cyano, COOR$^{103}$, C$_6$-C$_{10}$aryl, which may optionally be substituted by G, or C$_2$-C$_8$heteroaryl, which is optionally substituted by G, R$^{103}$ and R$^{103'}$ are independently of each other C$_1$-C$_{100}$alkyl, especially C$_3$-C$_{25}$alkyl, C$_1$-C$_{25}$alkyl substituted by E and/or interrupted by D, C$_7$-C$_{25}$arylalkyl, C$_6$-C$_{24}$aryl, C$_6$-C$_{24}$aryl which is substituted by G, C$_2$-C$_{20}$heteroaryl, or C$_2$-C$_{20}$heteroaryl which is substituted by G, R$^{105}$, R$^{105'}$, R$^{106}$, and R$^{106'}$ are independently of each other hydrogen, halogen, cyano, C$_1$-C$_{25}$alkyl, which is optionally interrupted by one or more oxygen or sulphur atoms; C$_7$-C$_{25}$arylalkyl, or C$_1$-C$_{18}$alkoxy, R$^{107}$ is hydrogen, C$_7$-C$_{25}$arylalkyl, C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$perfluoroalkyl; C$_1$-C$_{25}$alkyl; C$_3$-C$_{25}$alkyl, which may be interrupted by —O—, or —S—; or —COOR$^{103}$; R$^{103}$ is as defined above;

R$^{108}$ and R$^{109}$ are independently of each other H, C$_1$-C$_{25}$alkyl, C$_1$-C$_{25}$alkyl which is substituted by E and/or interrupted by D, C$_7$-C$_{25}$arylalkyl, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, or R$^{108}$ and R$^{109}$ together form a group of formula =CR$^{110}$R$^{111}$, wherein R$^{110}$ and R$^{111}$ are independently of each other H, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, or C$_2$-C$_{20}$heteroaryl, or C$_2$-C$_{20}$heteroaryl which is substituted by G, or R$^{108}$ and R$^{109}$ together form a five or six membered ring, which optionally is substituted by C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, D is —CO—, —COO—, —S—, —O—, or —NR$^{112}$—,
E is C$_1$-C$_8$thioalkoxy, C$_1$-C$_8$alkoxy, CN, —NR$^{112}$R$^{113}$, —CONR$^{112}$R$^{113}$ or halogen,
G is E, or C1-C18alkyl, and
R$^{112}$ and R$^{113}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—,
R$^{114}$ is C$_1$-C$_{25}$alkyl, especially C$_3$-C$_{25}$alkyl, which is optionally interrupted by one, or more oxygen, or sulphur atoms,
R$^{115}$ and R$^{115'}$ are independently of each other hydrogen, halogen, cyano, C$_1$-C$_{25}$alkyl, especially C$_3$-C$_{25}$alkyl, which is optionally interrupted by one, or more oxygen, or sulphur atoms, C$_1$-C$_{25}$alkoxy, C$_7$-C$_{25}$arylalkyl, or —≡—R$^{116}$, wherein R$^{116}$ is a C$_1$-C$_{10}$alkyl group, or a tri(C$_1$-C$_8$alkyl)silyl group;
R$^{117}$ and R$^{117'}$ are independently of each other C$_1$-C$_{25}$alkyl group, a C$_1$-C$_8$alkyl group, C$_7$-C$_{25}$arylalkyl, or a phenyl group, which can be substituted one to three times with C$_1$-C$_8$alkyl and/or C$_1$-C$_8$alkoxy;
R$^{118}$, R$^{119}$, R$^{120}$ and R$^{121}$ are independently of each other hydrogen, halogen, halogenated C$_1$-C$_{25}$alkyl, especially CF$_3$, cyano, C$_1$-C$_{25}$alkyl, especially C$_3$-C$_{25}$alkyl, which may optionally be interrupted by one or more oxygen or sulphur atoms; $C_7$-$C_{25}$arylalkyl, or $C_1$-$C_{25}$alkoxy;

$R^{122}$ and $R^{122'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_3$-$C_{25}$alkyl, which is optionally interrupted by one or more oxygen or sulphur atoms; or $C_7$-$C_{25}$arylalkyl.

2. The polymer according to claim 1, comprising one or more units of formula

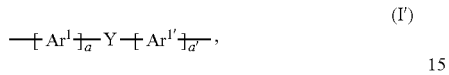
(I')

wherein Y is of formula

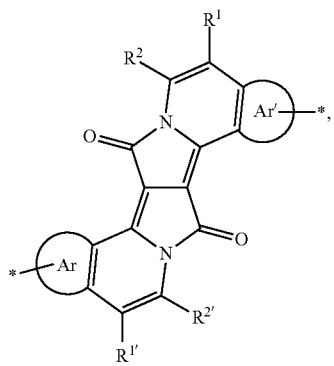

wherein
a is 0, 1, 2, or 3, a' is 0, 1, 2, or 3.

3. The polymer according to claim 1, comprising one or more units of formula (Ya)
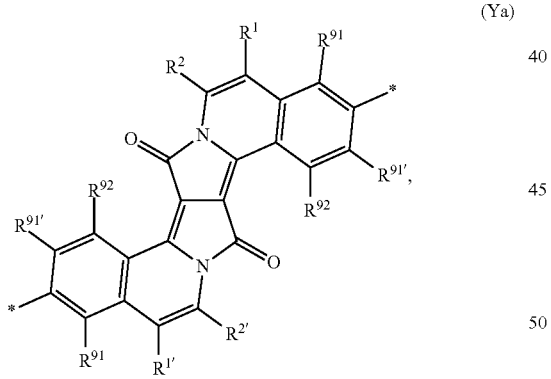

(Yb)
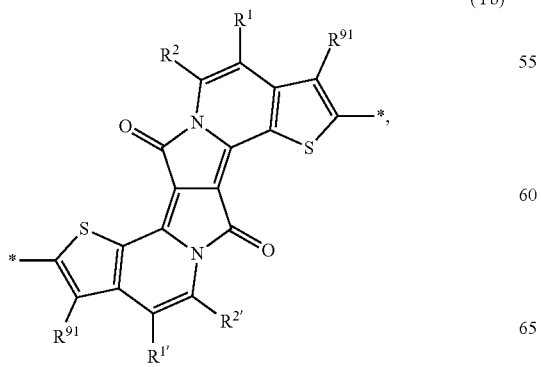

(Yc)
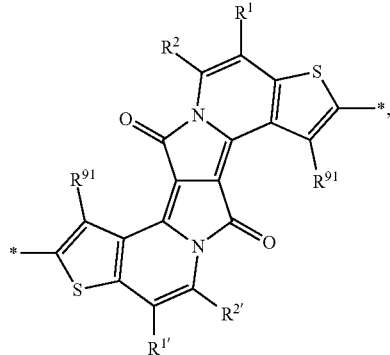

(Yd)
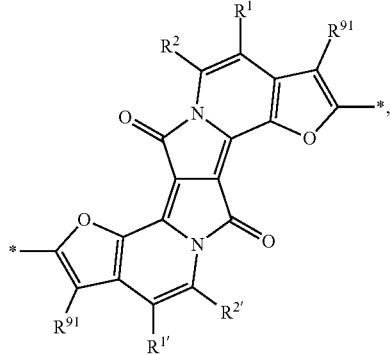

(Ye)
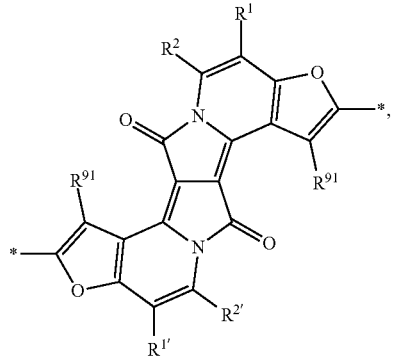

(Yf)
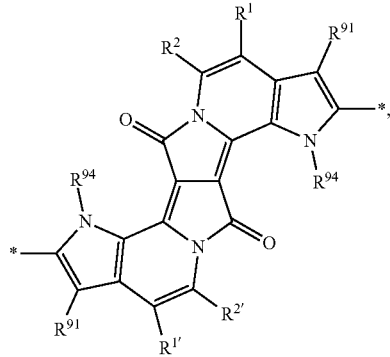

-continued
(Yg)
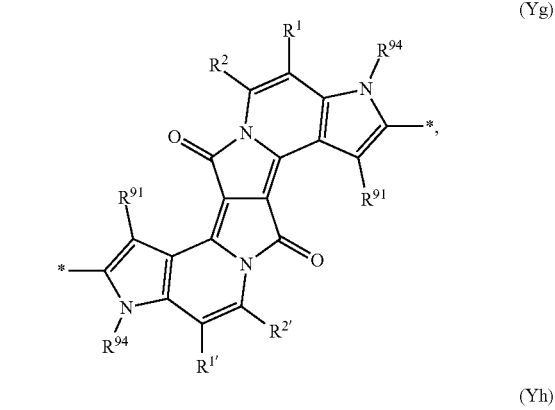
(Yh)
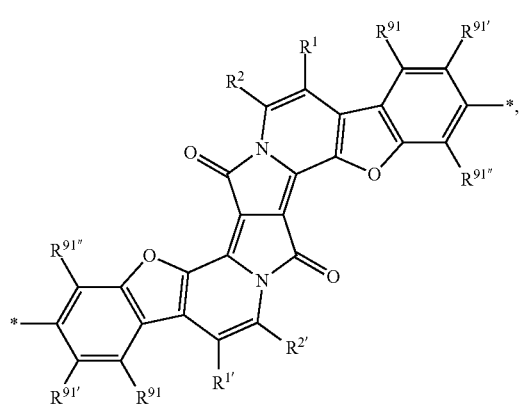
(Yi)
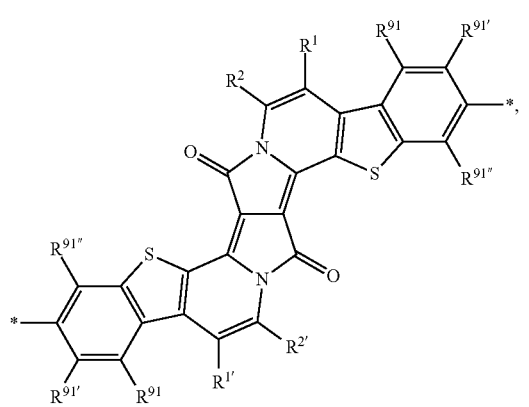
(Yj)
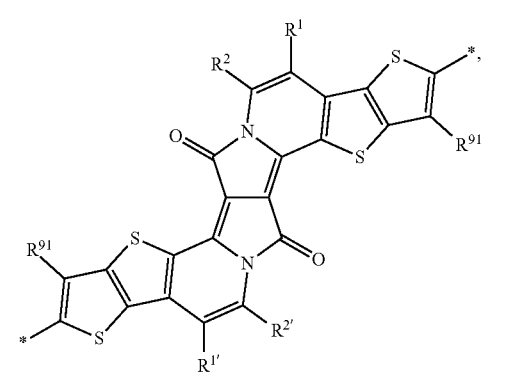
(Yk)
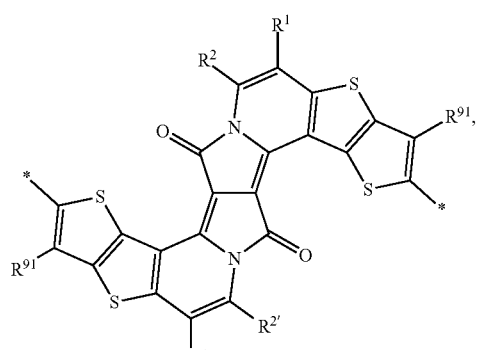
(Yl)
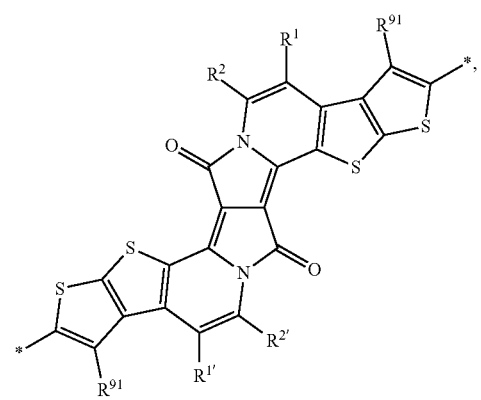
(Ym)
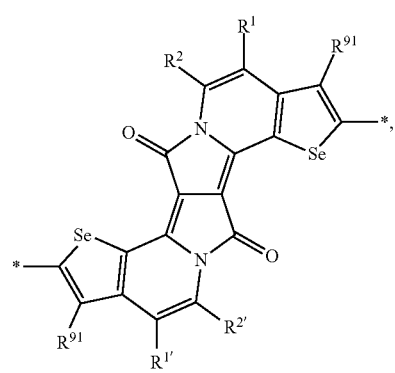
(Yn)
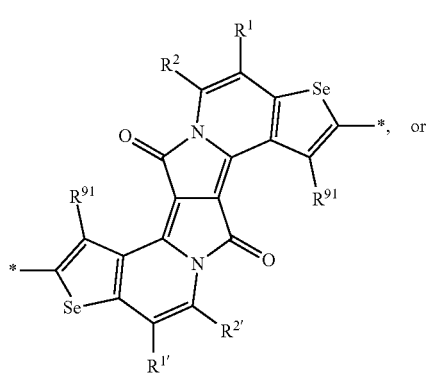
or

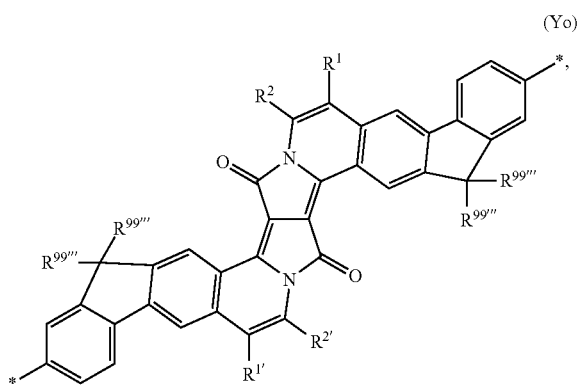
(Yo)

wherein
R¹, R¹', R² and R²' may be the same or different and are selected from hydrogen or a $C_1$-$C_{38}$alkyl group;

$R^{91}$, $R^{91'}$ and $R^{91''}$ are independently of each other H, halogen, especially F; cyano, $C_1$-$C_{25}$alkoxy, $C_1$-$C_{25}$alkyl substituted with one or more halogen atoms, especially F; or $C_1$-$C_{25}$alkyl, $R^{92}$ is H, halogen, especially F; cyano, $C_1$-$C_{25}$alkoxy, or $C_1$-$C_{25}$alkyl, $R^{94}$ is hydrogen, $C_6$-$C_{18}$aryl; $C_6$-$C_{18}$aryl which is substituted by $C_1$-$C_{18}$alkyl, halogen, F; or $C_1$-$C_{18}$alkoxy; $C_1$-$C_{25}$alkyl, which may optionally be interrupted by one or more oxygen or sulphur atoms and/or is optionally substituted by one or more halogen atoms, F; or $C_7$-$C_{25}$arylalkyl; and $R^{99''}$ is hydrogen, $C_1$-$C_{25}$alkyl, or $C_1$-$C_{25}$alkyl substituted with one or more halogen atoms and/or interrupted by one or more oxygen atoms, or two groups $R^{99}$ can form a 5 or 6 membered alkyl ring; or is one or more units of formula

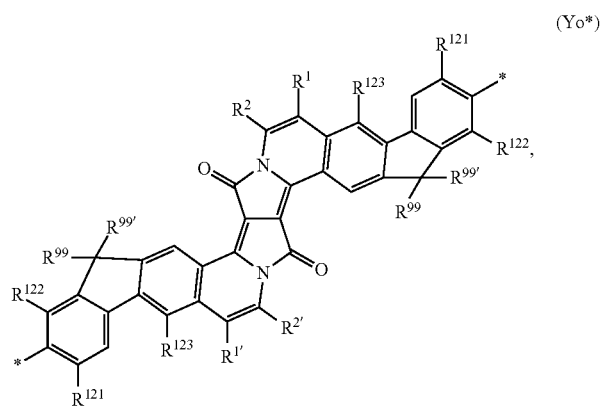
(Yo*)

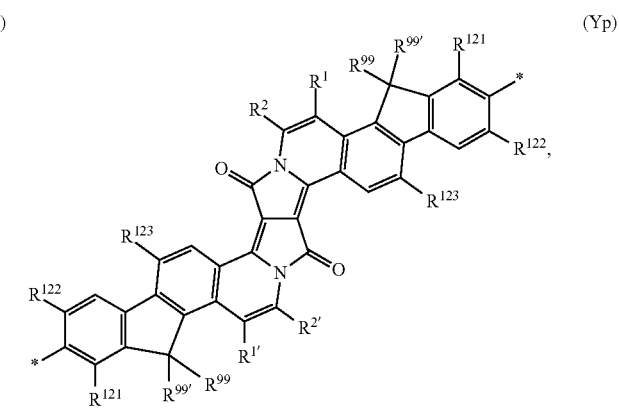
(Yp)

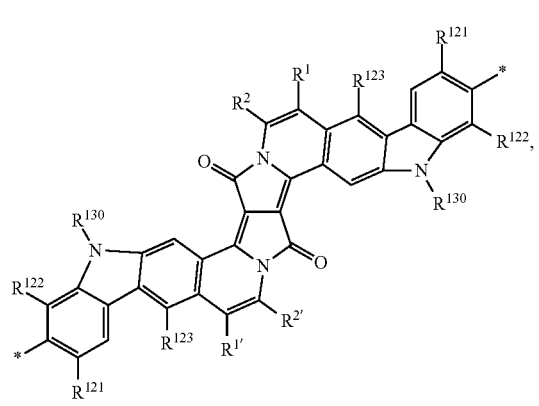
(Yq)

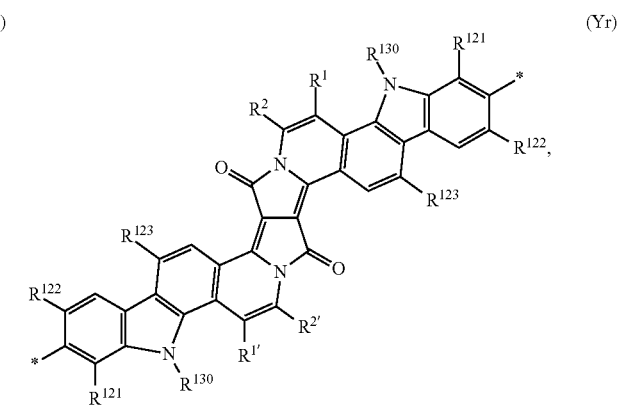
(Yr)

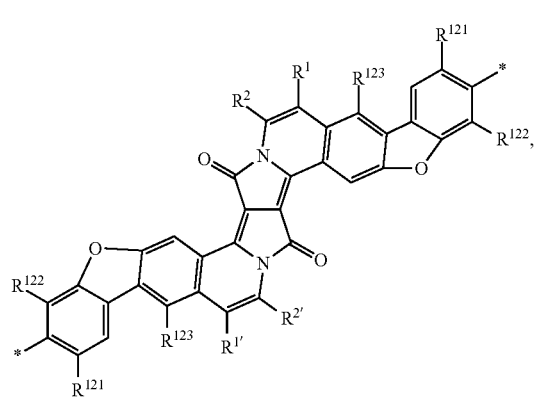
(Ys)

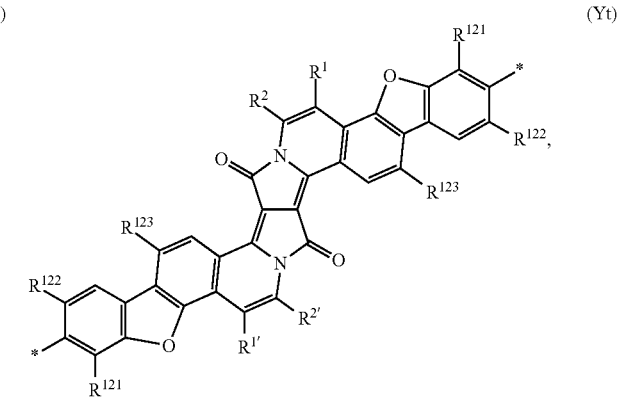
(Yt)

-continued
(Yu)
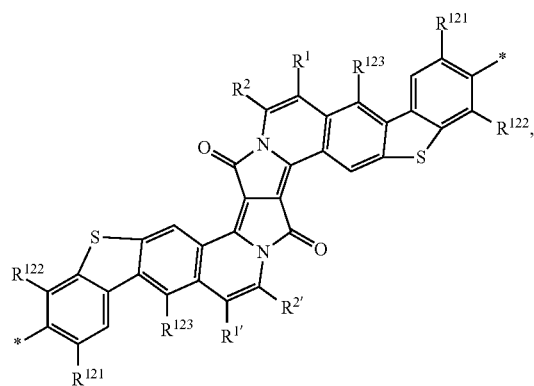
(Yv)
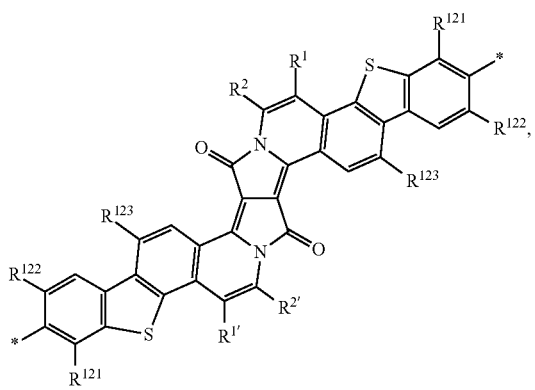
(Yw)
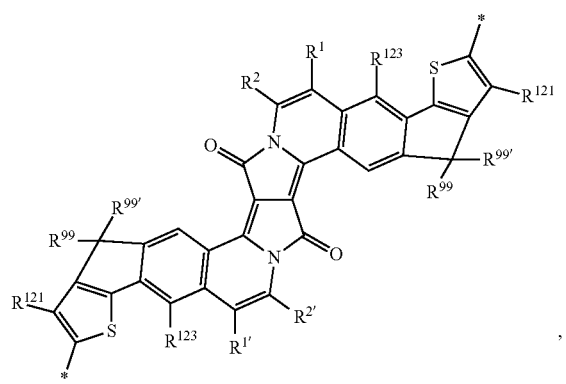
(Yx)
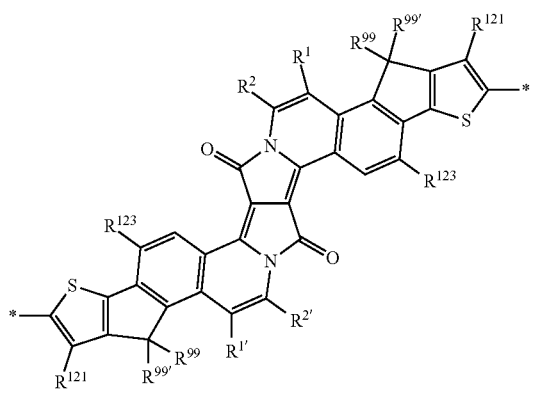
(Yy)
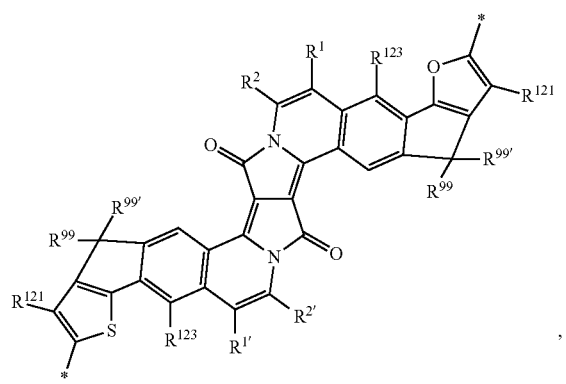
(Yz)
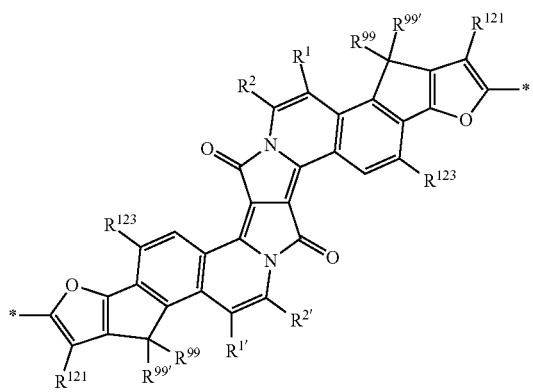
(Yaa)
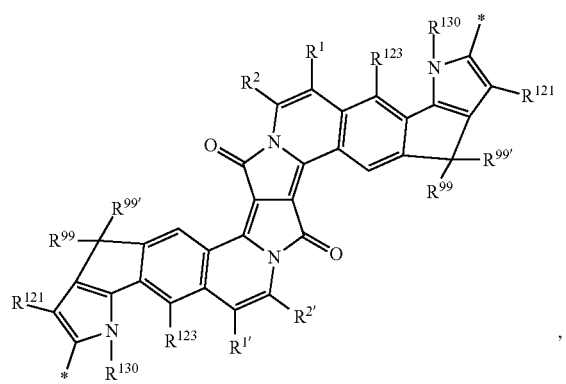
(Yab)
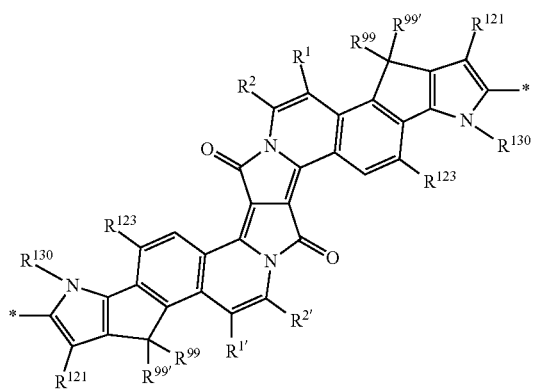

(Yac)
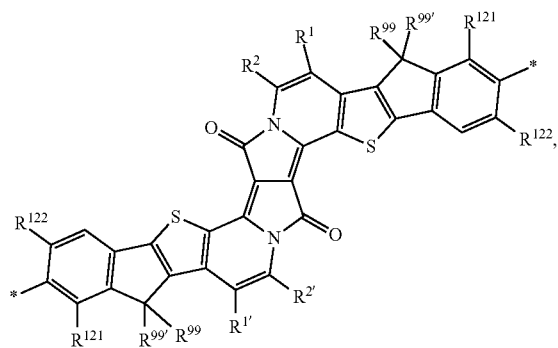
(Yad)
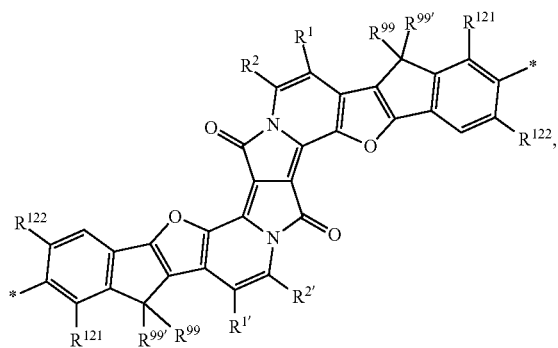
(Yae)
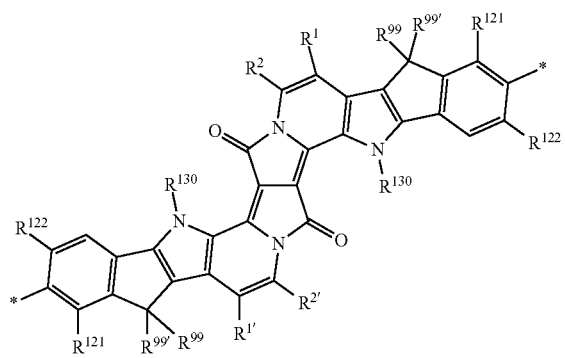
(Yaf)
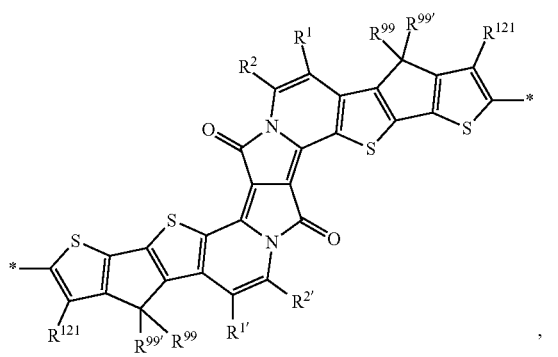
(Yag)
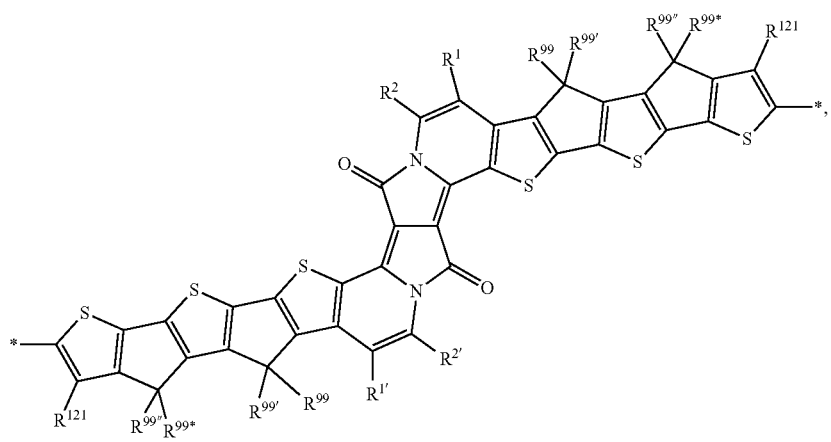
(Yah)
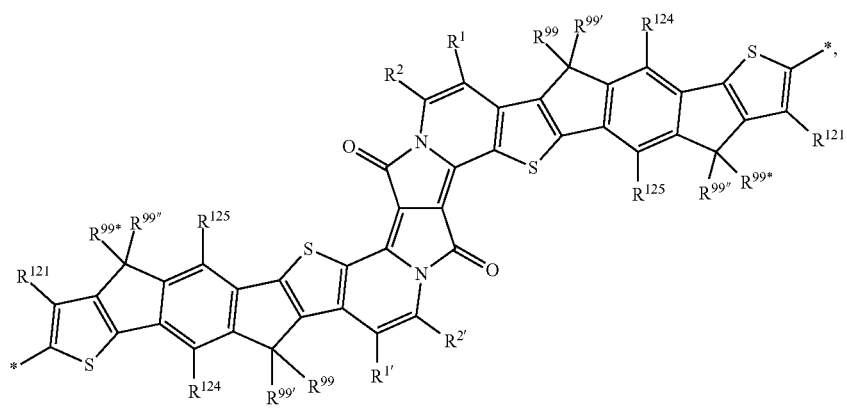

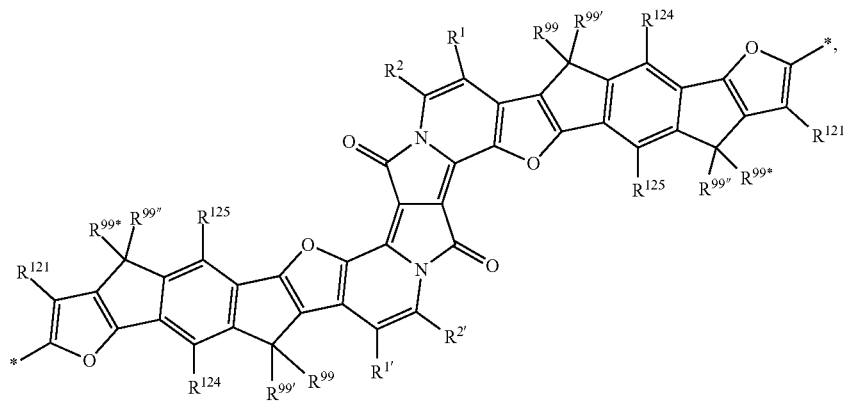
(Yai)
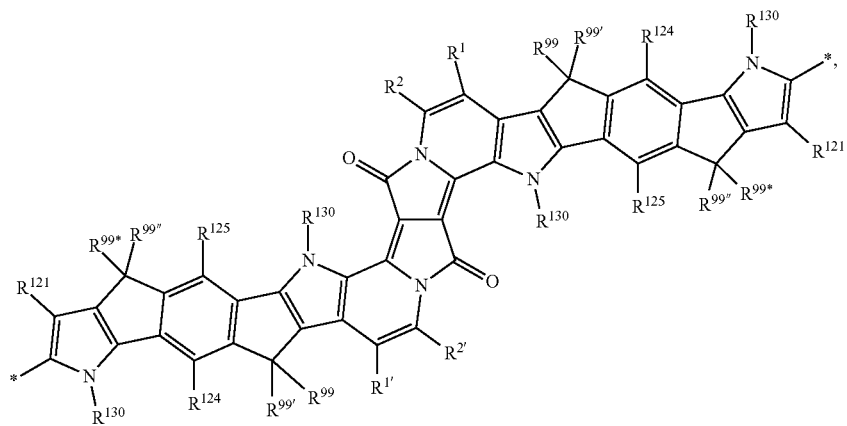
(Yaj)
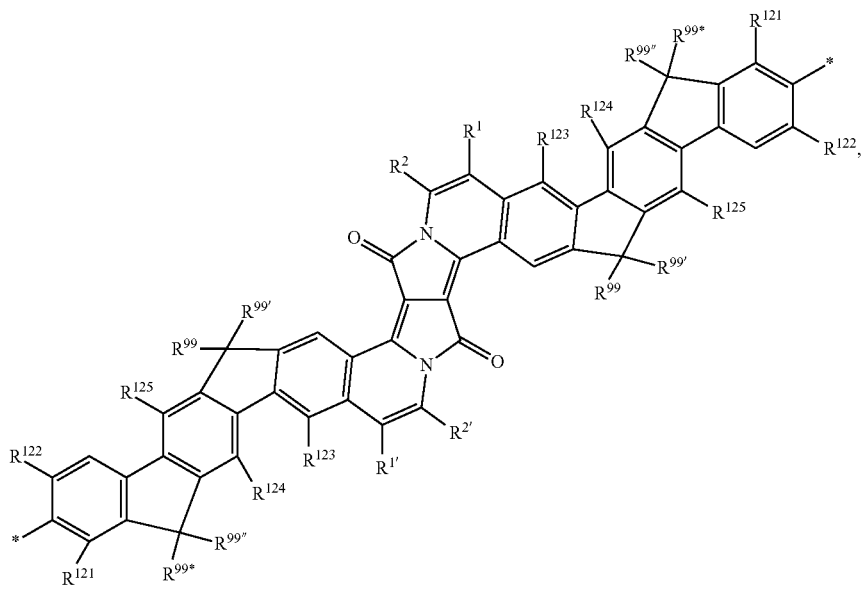
(Yak)

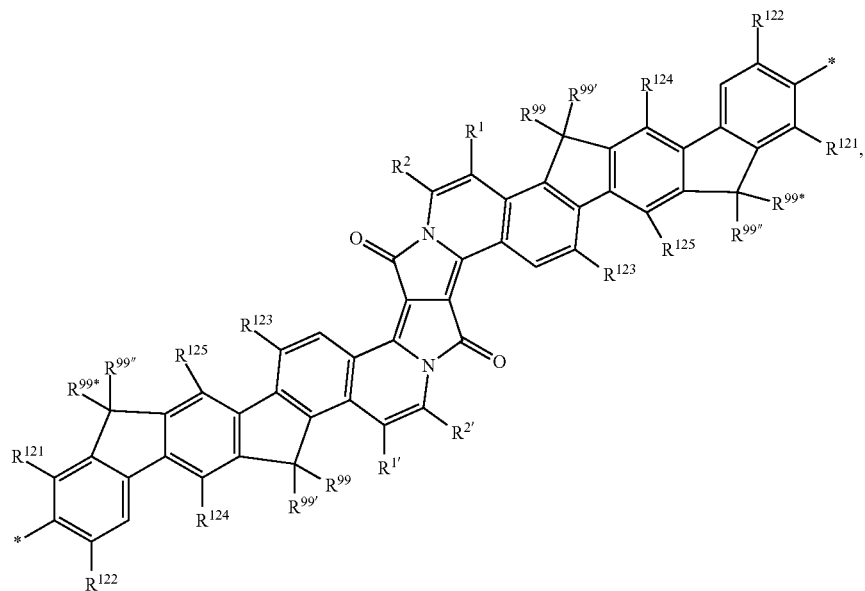
(Yal)
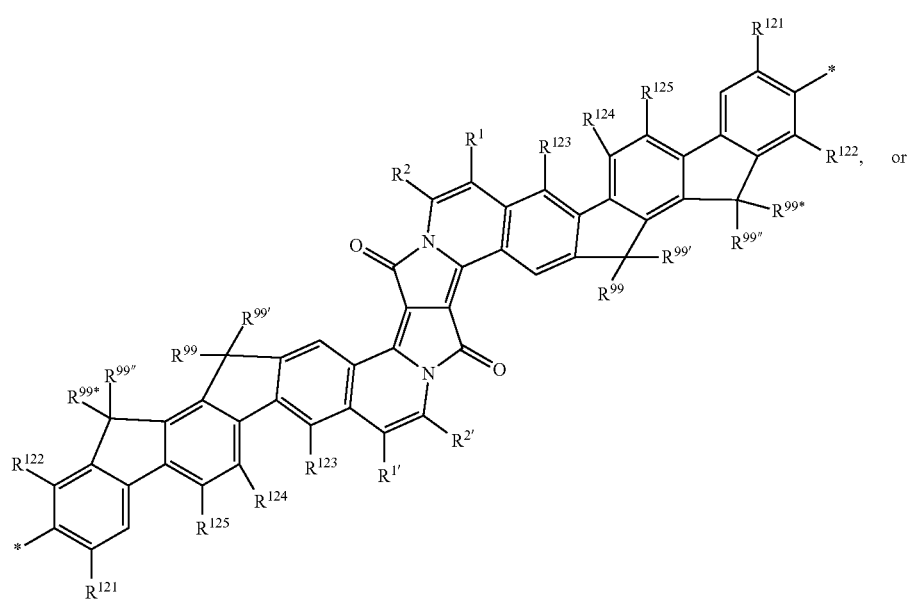
(Yam) or

-continued

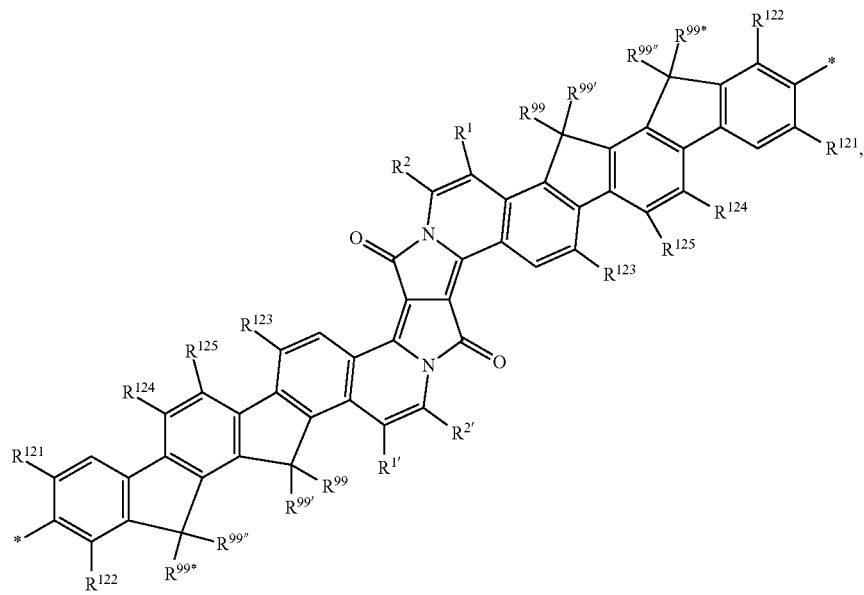
(Yan)

wherein
$R^1$, $R^{1'}$, $R^2$ and $R^{2'}$ may be the same or different and are selected from hydrogen or a $C_1$-$C_{38}$alkyl group;
$R^{99}$, $R^{99'}$, $R^{99''}$ and $R^{99*}$ are independently of each other hydrogen, $C_1$-$C_{25}$alkyl, or $C_1$-$C_{25}$alkyl interrupted by one or more oxygen atoms; $C_3$-$C_{25}$alkyl, or $C_3$-$C_{25}$alkyl which is interrupted by one or more oxygen atoms;
$R^{121}$, $R^{122}$, $R^{123}$, $R^{124}$ and $R^{125}$ are independently of each other hydrogen, halogen, $C_1$-$C_{18}$alkoxy or $C_1$-$C_{25}$alkyl; and $R^{130}$ is hydrogen, $C_6$-$C_{18}$aryl; $C_6$-$C_{18}$aryl which is substituted by $C_1$-$C_{18}$alkyl, halogen, F; or $C_1$-$C_{18}$alkoxy; $C_1$-$C_{25}$alkyl, which is optionally interrupted by one or more oxygen or sulphur atoms and/or is optionally substituted by one or more halogen atoms, F; or $C_7$-$C_{25}$arylalkyl.

4. The polymer according to claim 3, comprising one or more units of formula

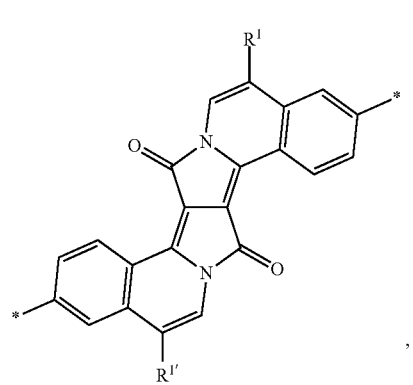
(Ya')

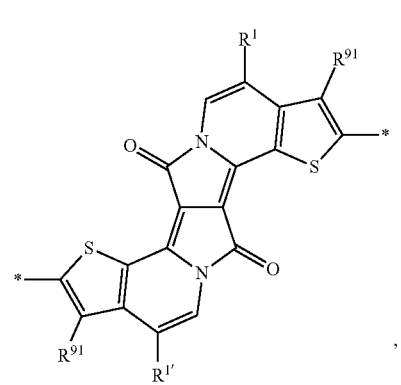
(Yb')

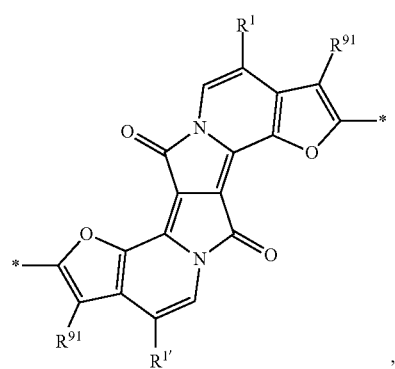
(Yd')

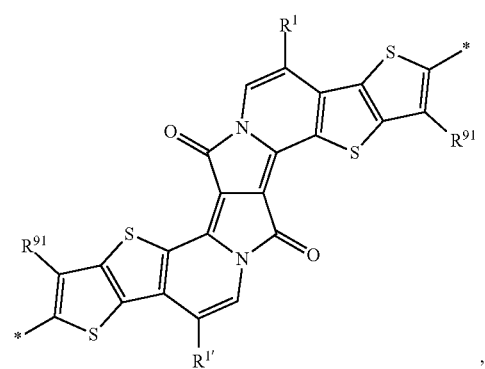
(Yj')

, or

-continued (Yo') 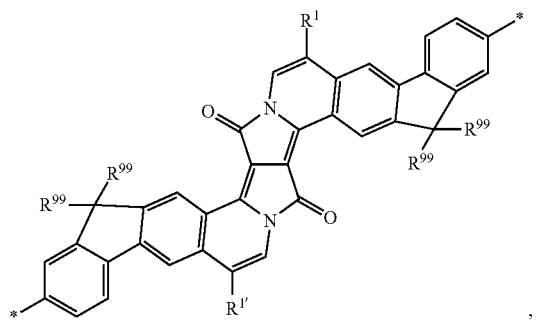 (Yaf') 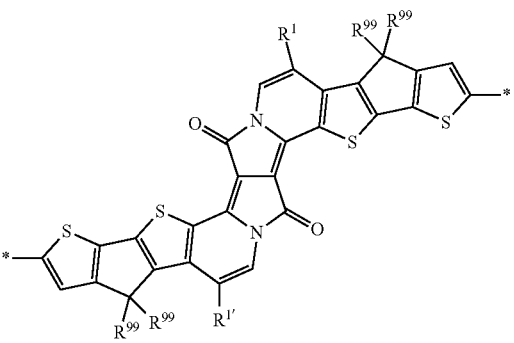

, or (Yah') 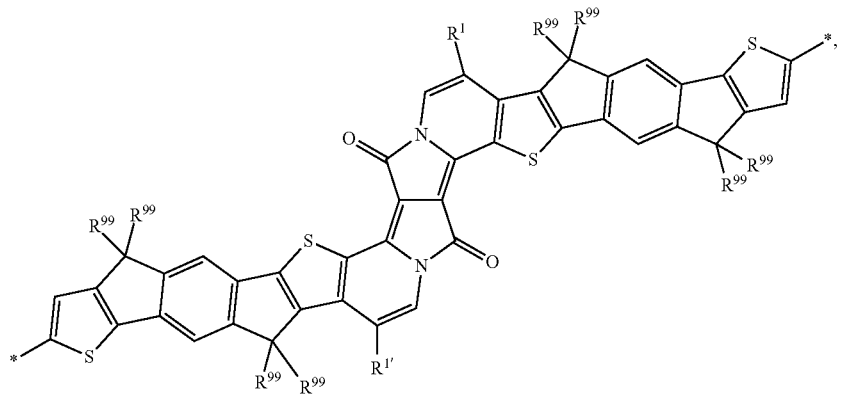

, wherein
R[1] and R[1'] may be the same or different and are selected from hydrogen, or a $C_1$-$C_{38}$alkyl group; R[91] is H, F; cyano, $C_1$-$C_{25}$alkoxy, $C_1$-$C_{25}$alkyl substituted with one or more F; or $C_1$-$C_{25}$alkyl, R[99] is hydrogen, $C_1$-$C_{25}$alkyl, or $C_1$-$C_{25}$alkyl substituted with one or more halogen atoms and/or interrupted by one or more oxygen atoms, or two groups R[99] form a 5 or 6 membered alkyl ring.

5. The polymer according to claim 1, comprising units of formula

 and *―COM[1]―*, wherein
A is a repeating unit of formula (I), and
-COM[1]- is a repeating unit, which has the meaning of Ar[1], wherein Ar[1] is as defined in claim 1, or is of formula

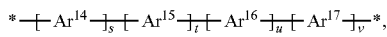

s is 1, t is 1, u is 0, or 1, v is 0, or 1, and
Ar[14], Ar[15], Ar[16] and Ar[17] are independently of each other a group of formula

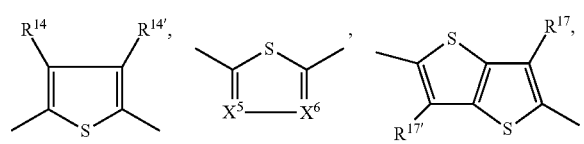

-continued

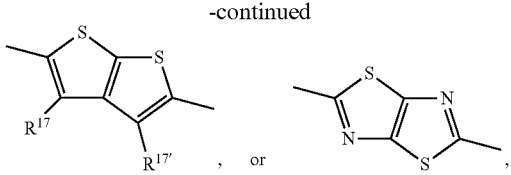

wherein one of X[5] and X[6] is N and the other is CR[14], and
R[14], R[14'], R[17] and R[17'] are independently of each other H, or a $C_1$-$C_{25}$alkyl group.

6. The polymer according to claim 5, which is a polymer of formula (VII')

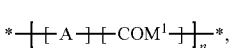

wherein A and COM[1] are as defined in claim 5; and n is 4 to 1000.

7. The polymer according to claim 5, wherein A is a repeating unit of formula (Ya), (Yb), (Yd), (Yj), (Yo), (Yo*), (Yaf), (Yah), (Ya'), (Yb'), (Yd'), (Yj'), (Yo'), (Yaf'), or (Yah')

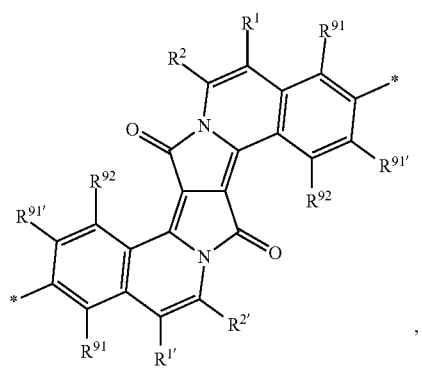
(Ya)
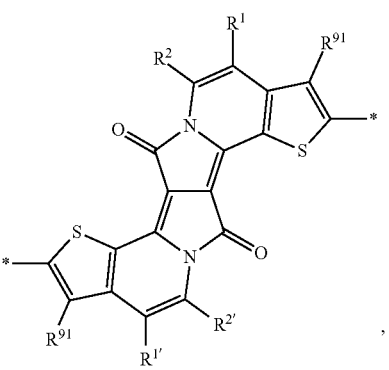
(Yb)
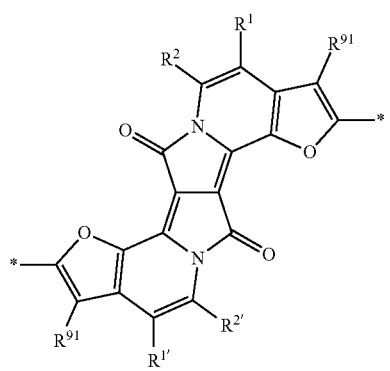
(Yd)
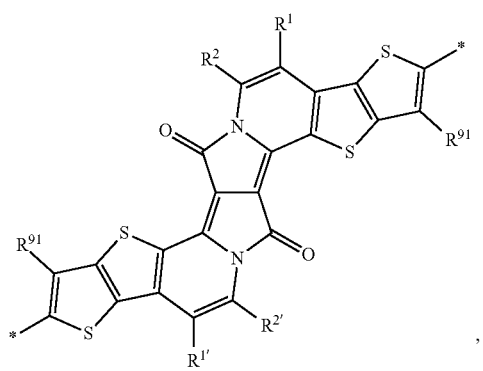
(Yj)
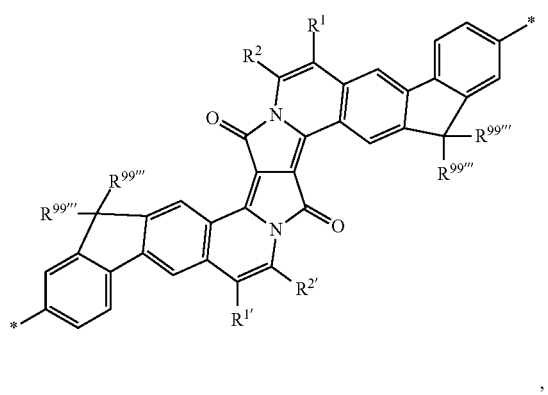
(Yo)
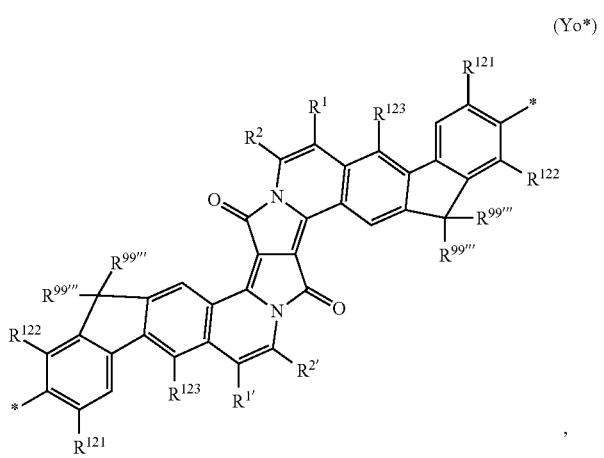
(Yo*)
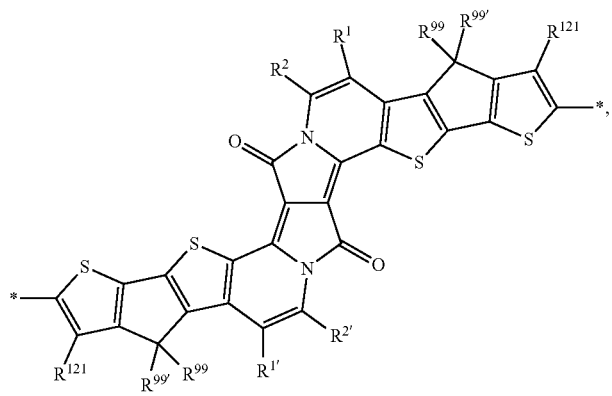
(Yaf)

-continued
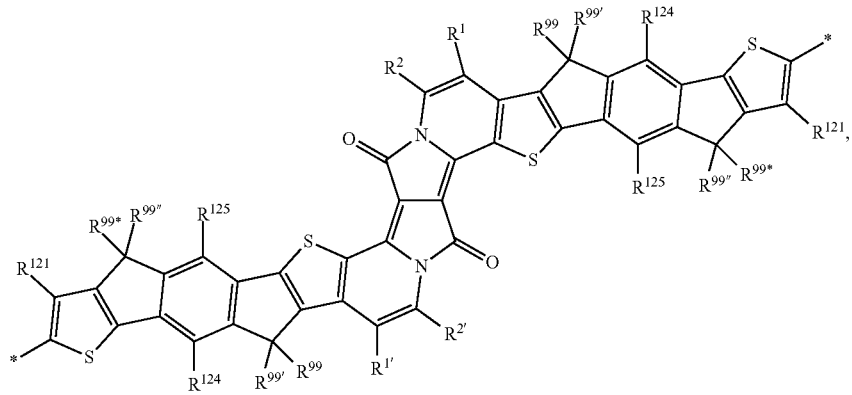
(Yah)
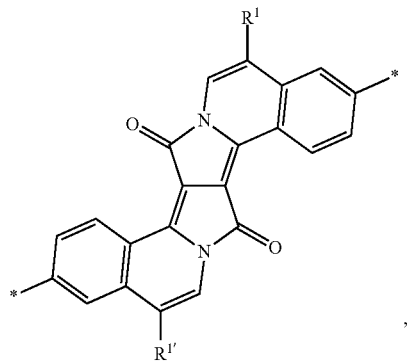
(Ya')
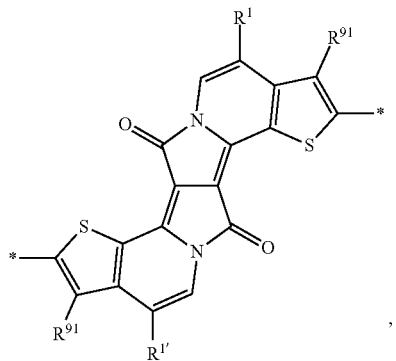
(Yb')
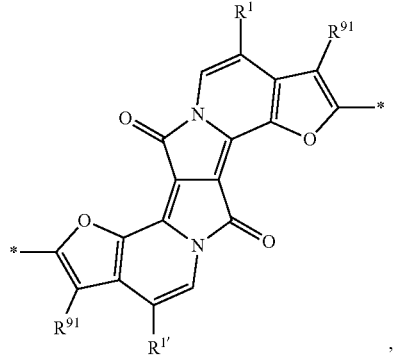
(Yd')
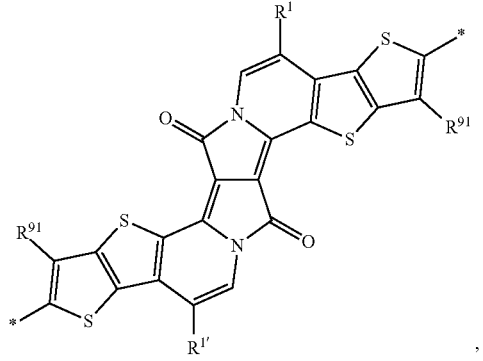
(Yj')
, or
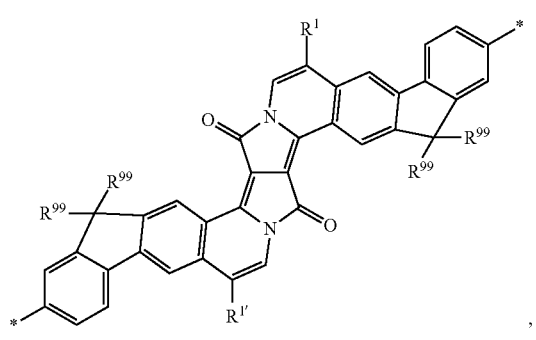
(Yo')
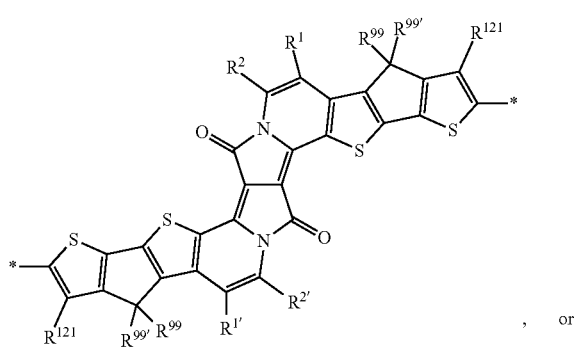
(Yaf')
, or -continued

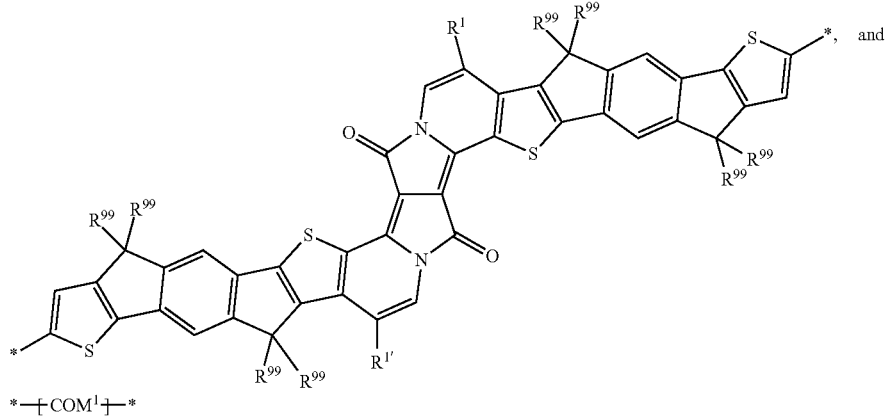

*―[COM¹]―* is of formula

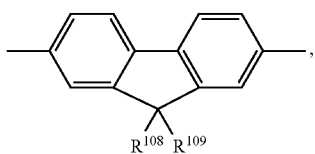

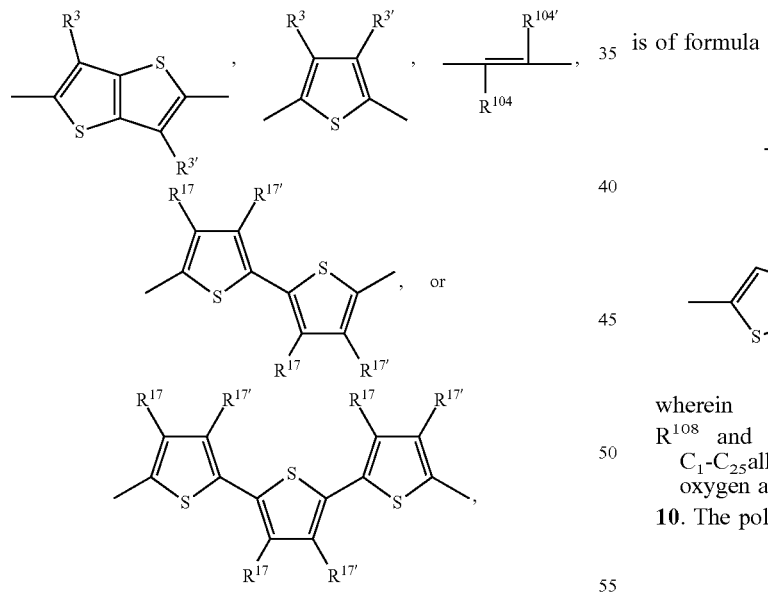

where $R^3$, $R^{3'}$, $R^{17}$ and $R^{17'}$ are independently of each other hydrogen, or $C_1$-$C_{25}$alkyl, and $R^{104}$ and $R^{104'}$ are independently of each other hydrogen, cyano or a $C_1$-$C_{25}$alkyl group, and $R^{108}$ and $R^{109}$ are independently of each other a $C_1$-$C_{25}$alkyl, which may be interrupted by one or more oxygen atoms.

8. The polymer according to claim 7 including a repeat unit of formula $$*\!-\!\!\left[\!\left[\text{A}\right]\!-\!\!\left[\text{COM}^1\right]\!\right]_n\!-\!*,$$ (VII')

and n is 4 to 1000.

9. The polymer according to claim 5, wherein

*―[COM¹]―* is of formula

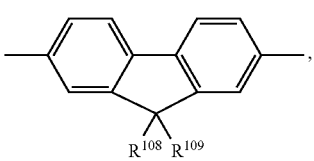

wherein $R^{108}$ and $R^{109}$ are independently of each other a $C_1$-$C_{25}$alkyl, which may be interrupted by one or more oxygen atoms.

10. The polymer according to claim 8, wherein

*―[COM¹]―* is of formula

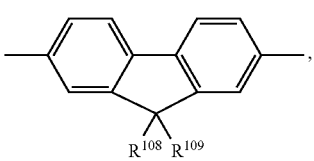

-continued
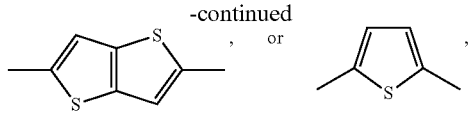
wherein
R[108] and R[109] are independently of each other a C$_1$-C$_{25}$alkyl, which may be interrupted by one or more oxygen atoms.
11. The polymer according to claim 5, which is of formula
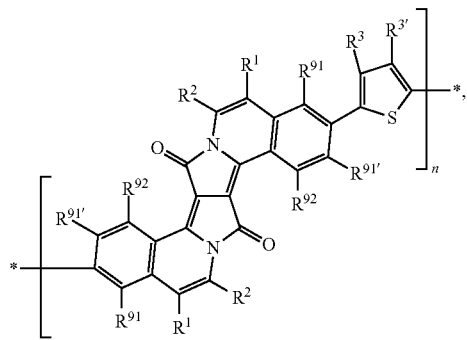
(Ia-1)
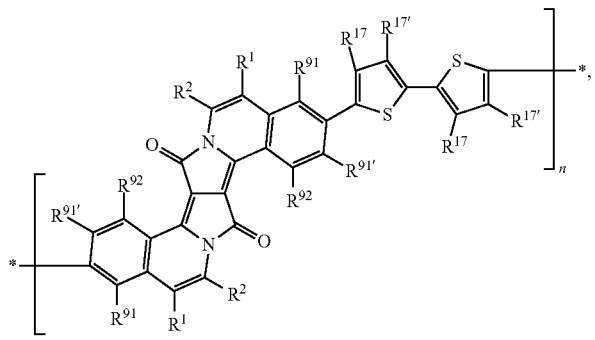
(Ia-2)
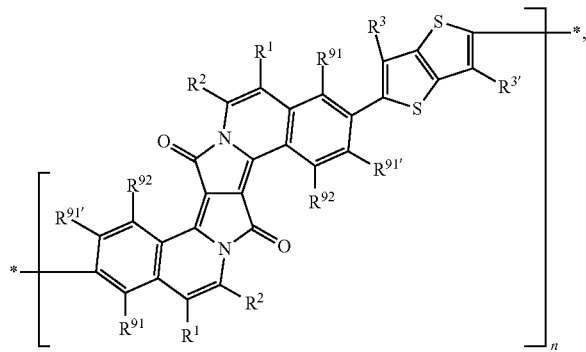
(Ia-3)
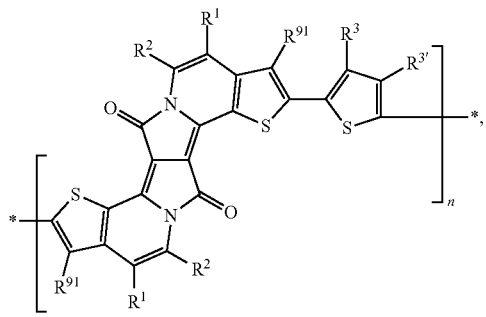
(Ia-4)
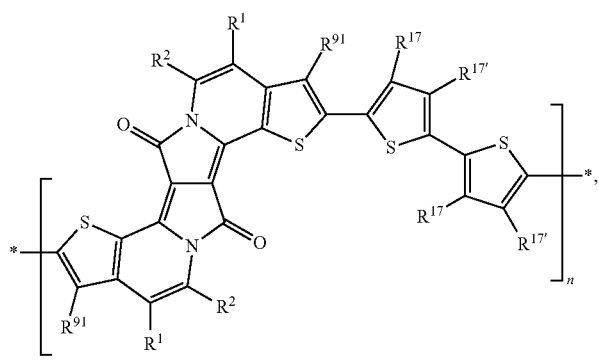
(Ia-5)
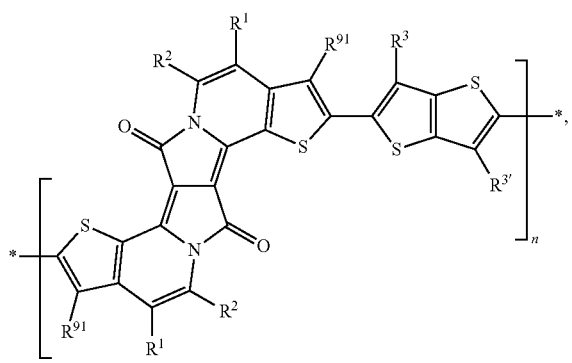
(Ia-6)

-continued
(Ia-7)
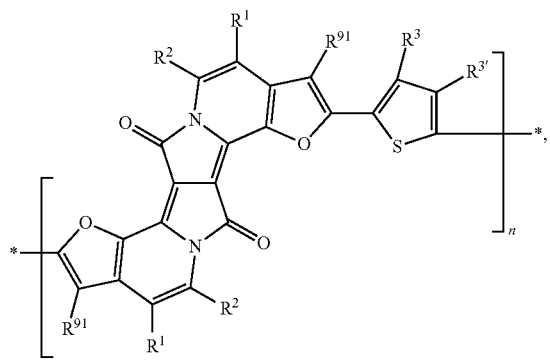
(Ia-8)
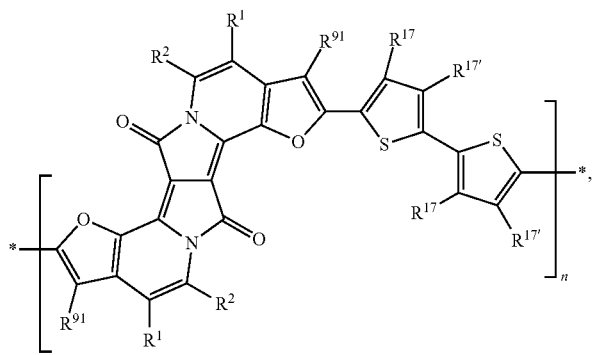
(Ia-9)
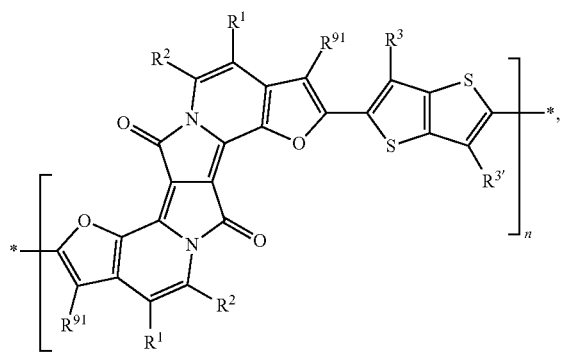
(Ia-10)
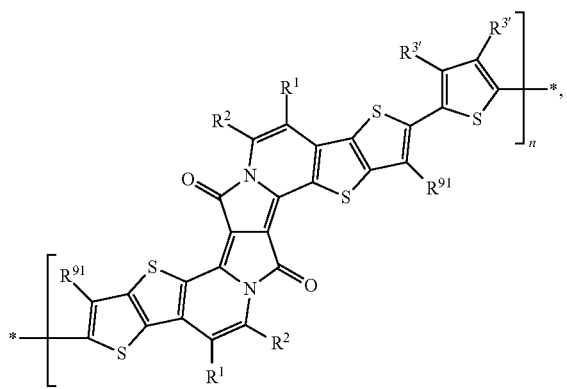
(Ia-11)
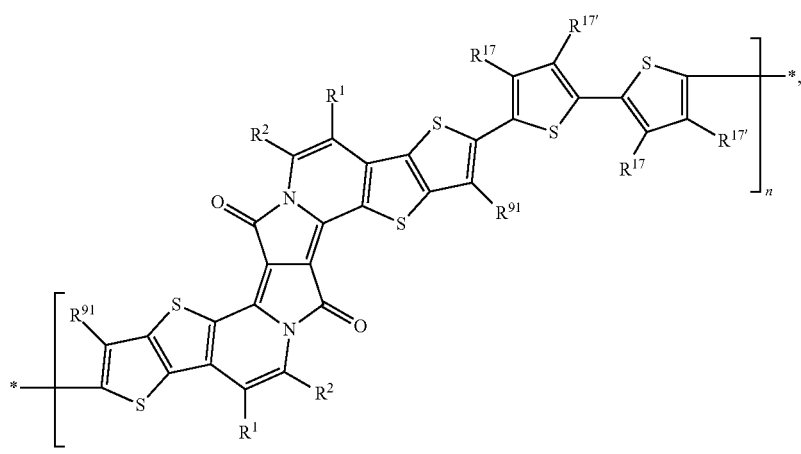
(Ia-12)
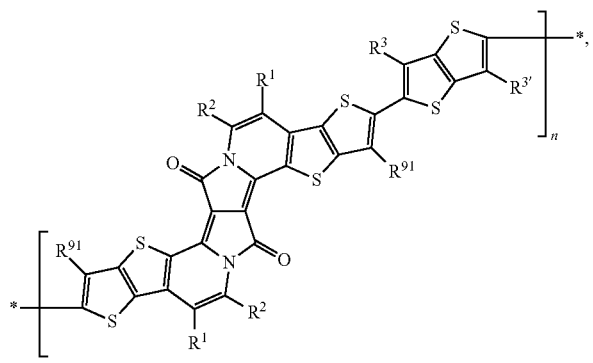
(Ia-13)
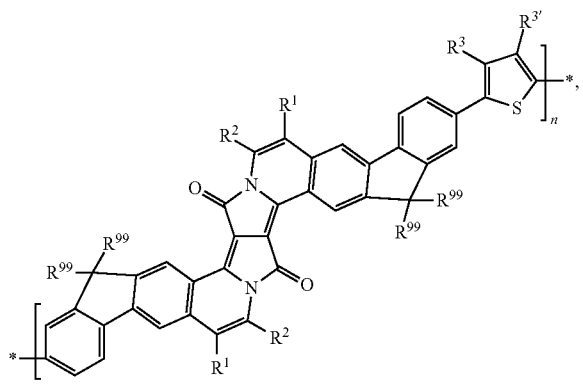

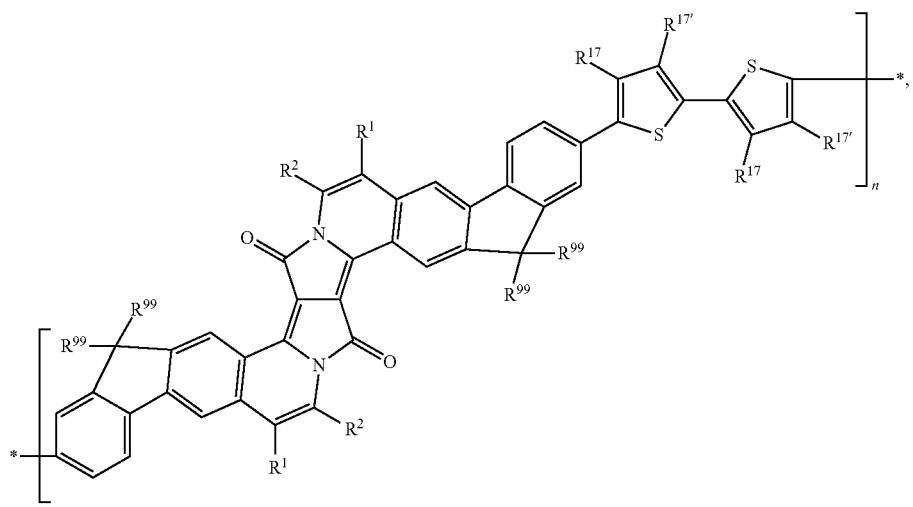
(Ia-14)
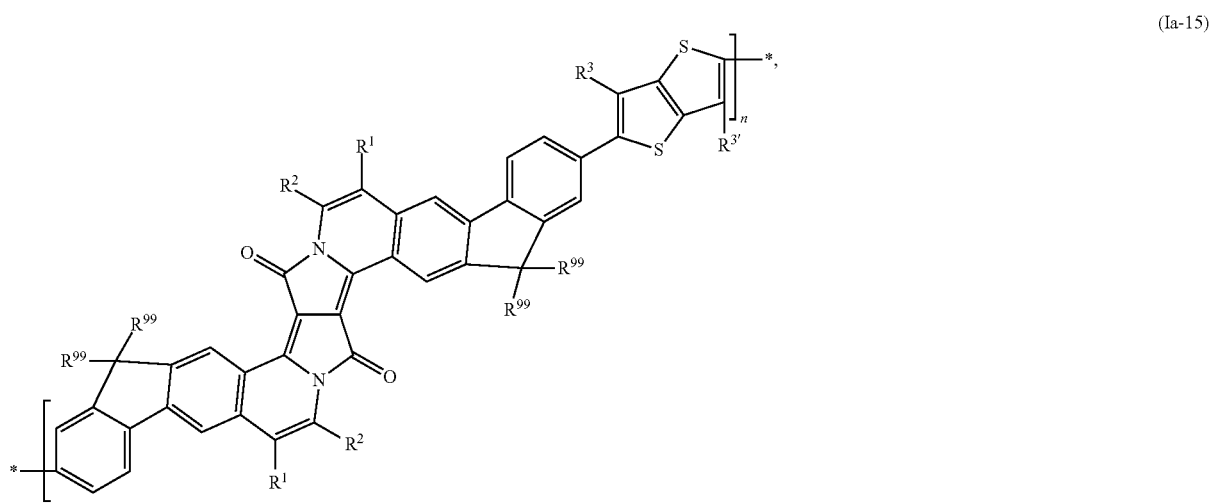
(Ia-15)
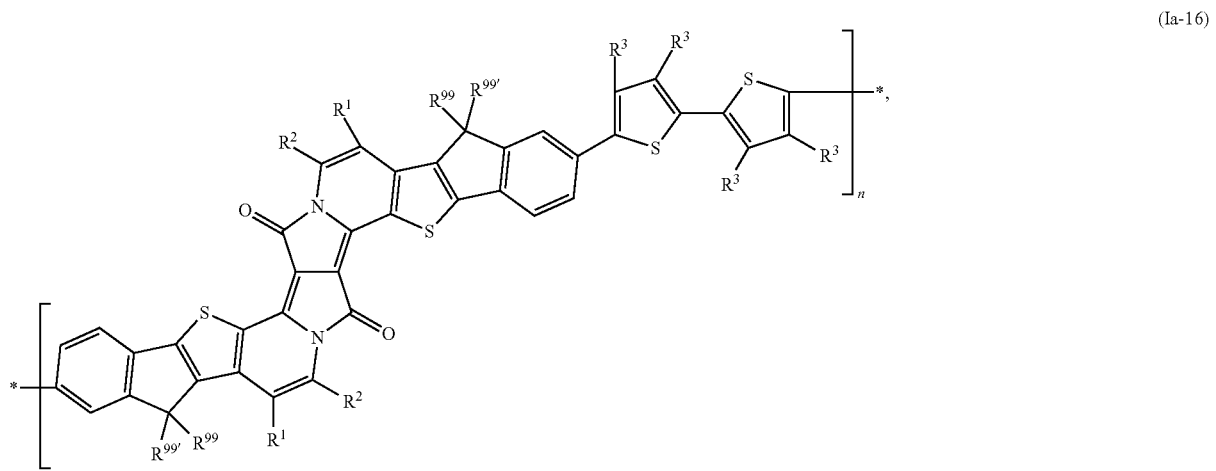
(Ia-16)

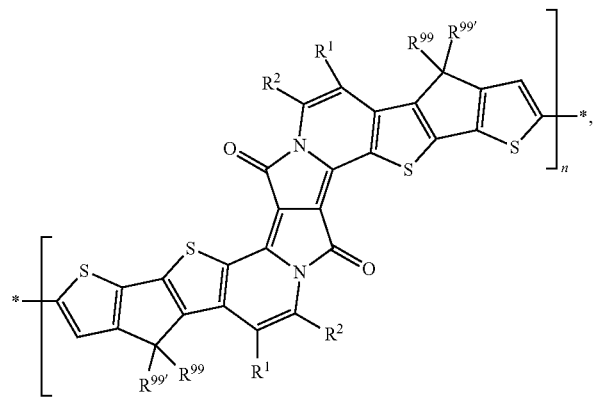
(Ia-17)
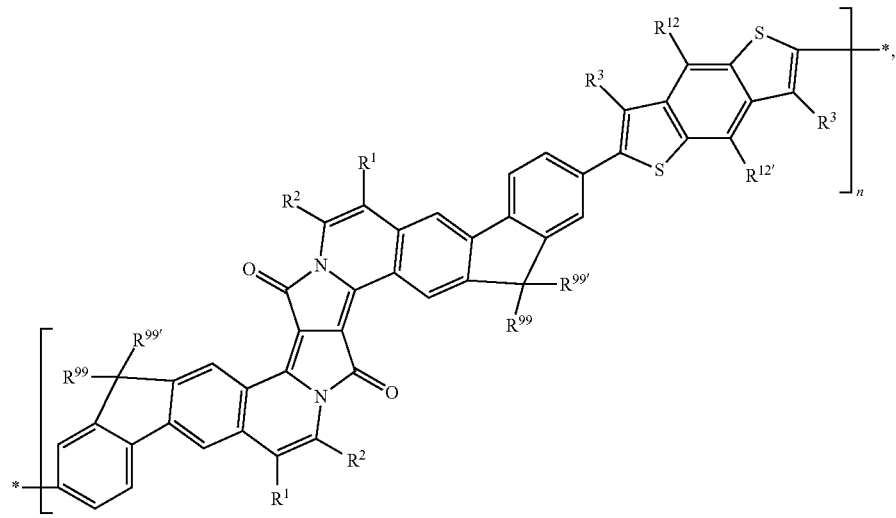
(Ia-18)
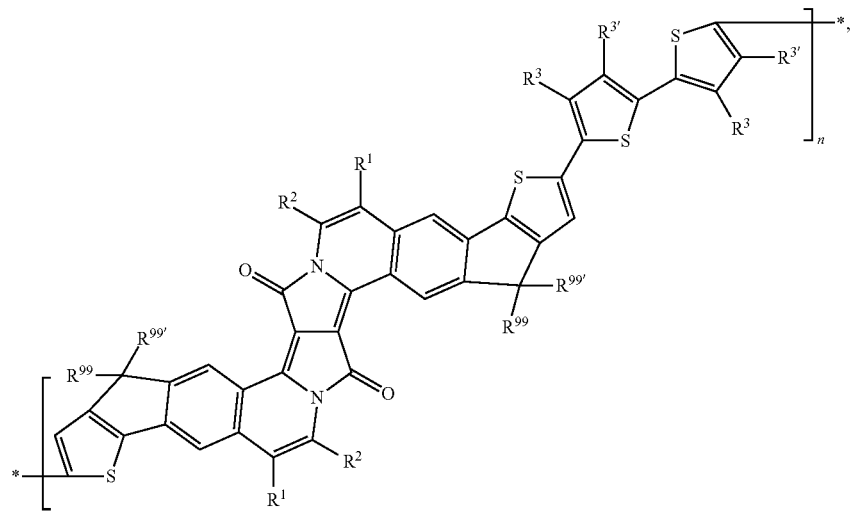
(Ia-19)

-continued
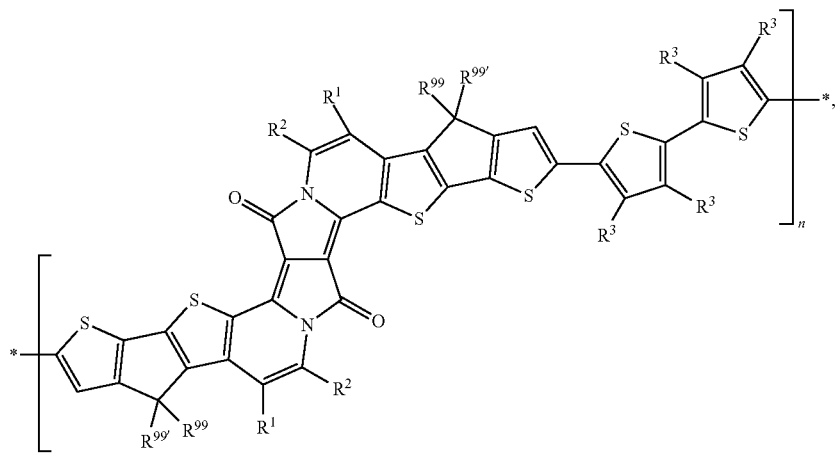
(Ia-20)
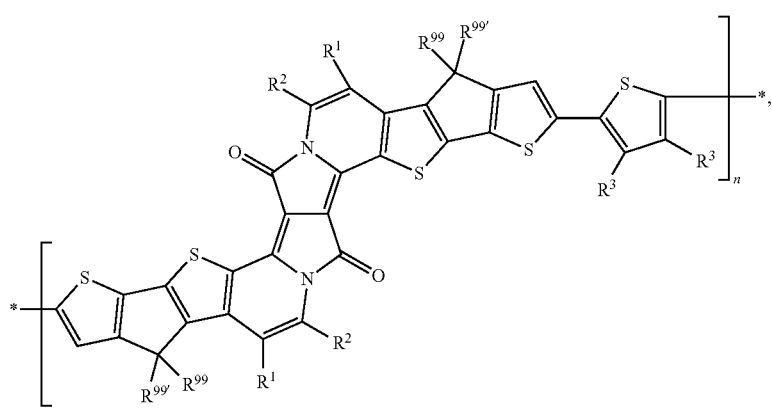
(Ia-21)
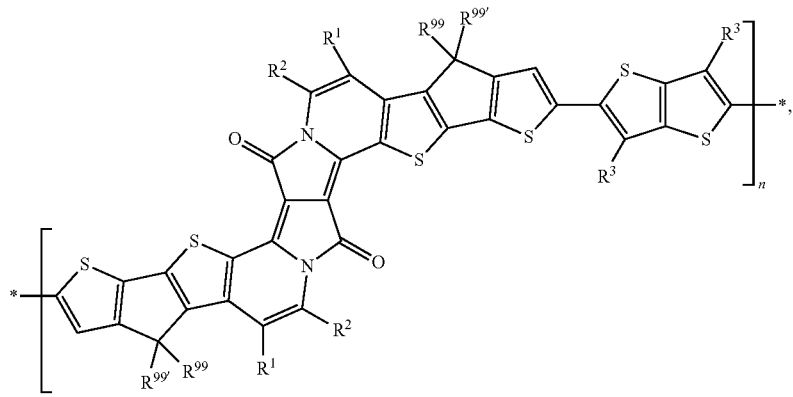
(Ia-22)
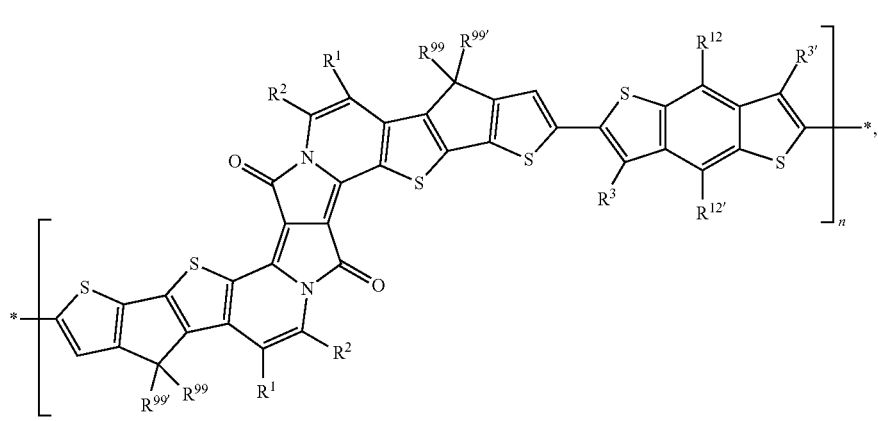
(Ia-23)

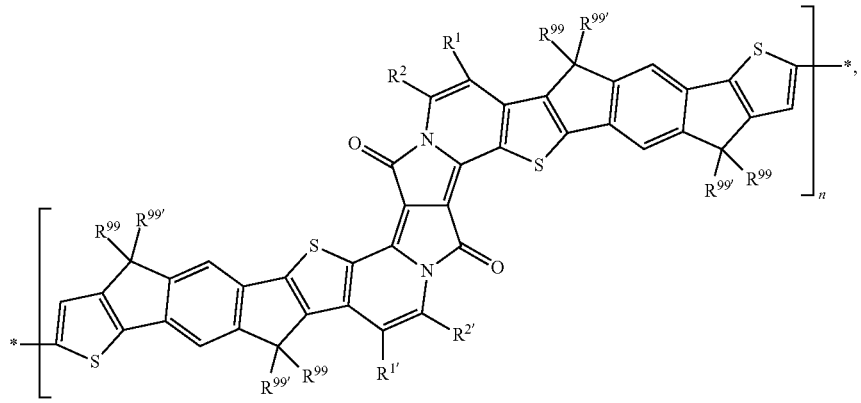
(Ia-24)
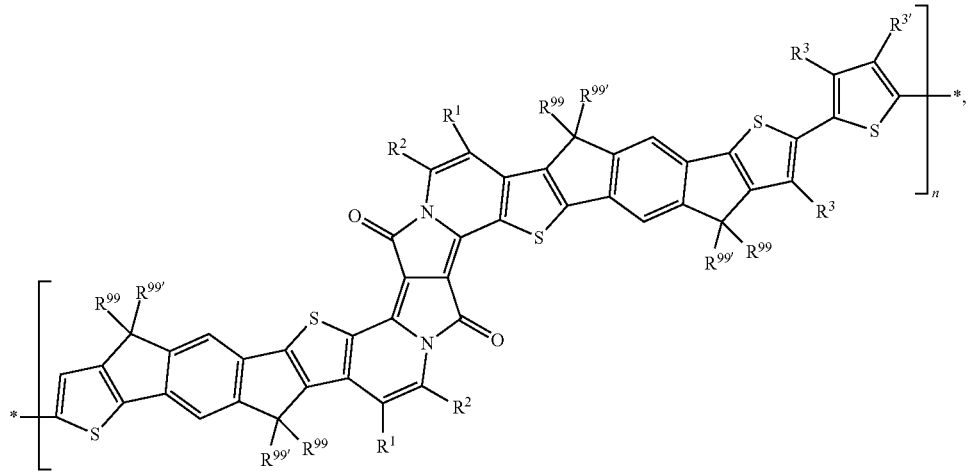
(Ia-24)
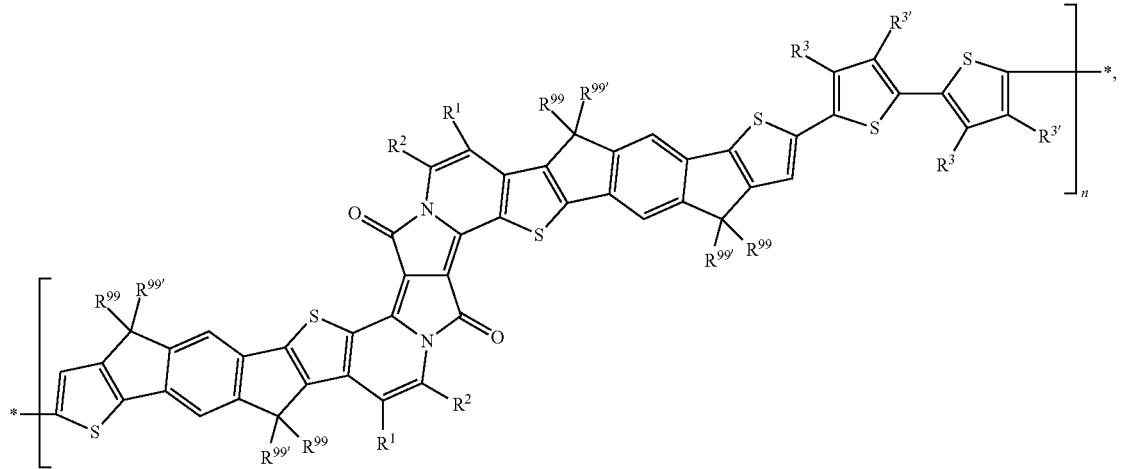
(Ia-25)

-continued
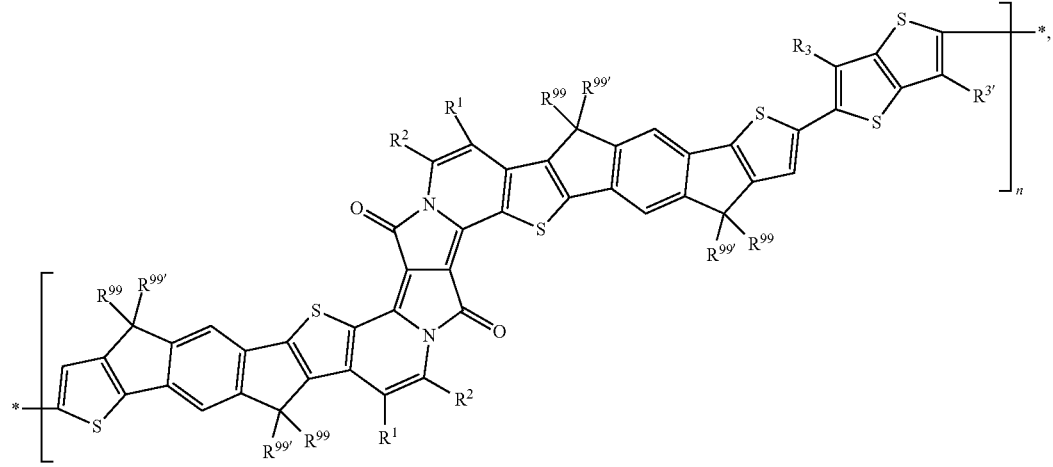
(Ia-26)
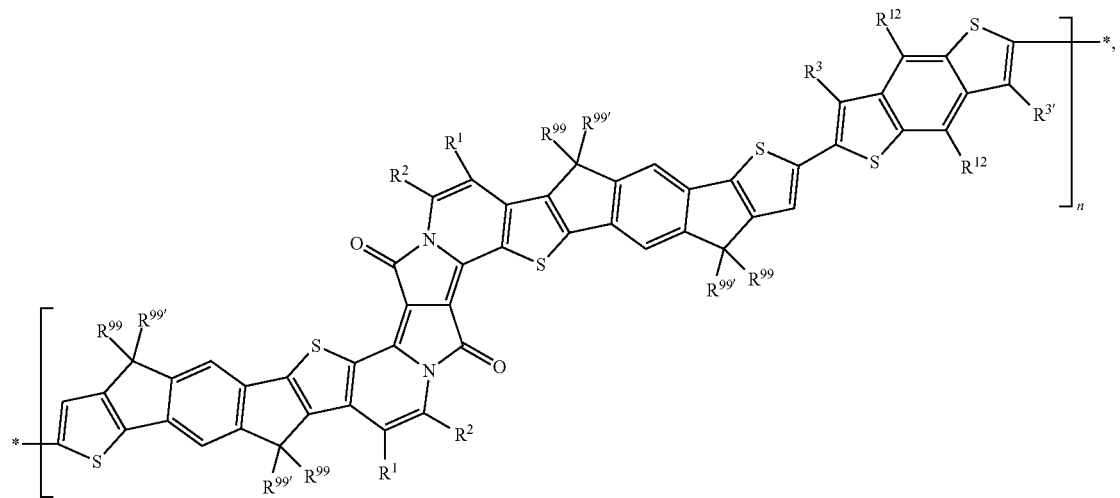
(Ia-27)
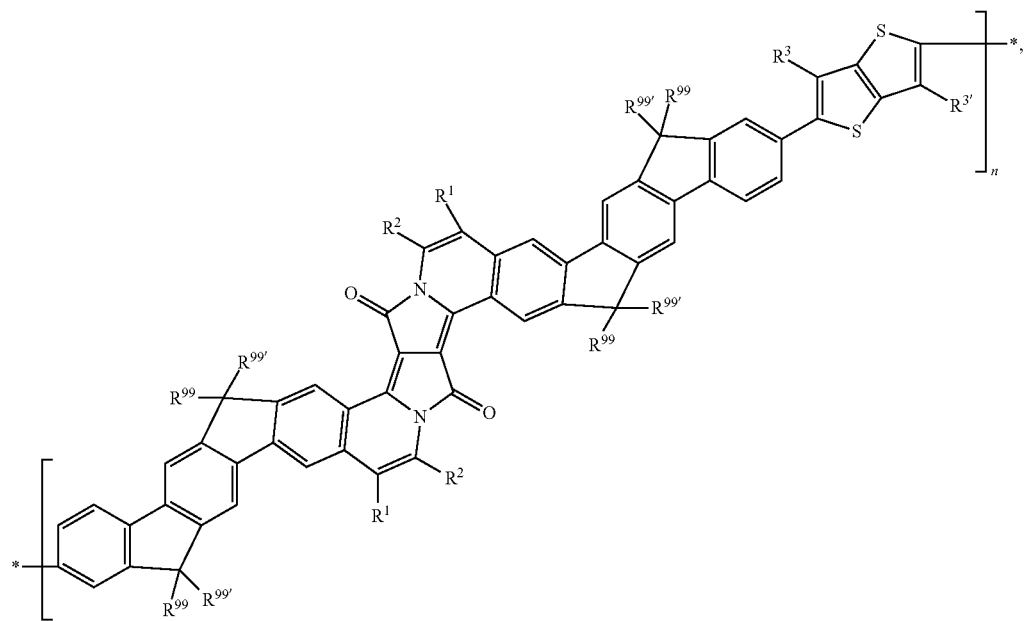
(Ia-28)

(Ia-29)

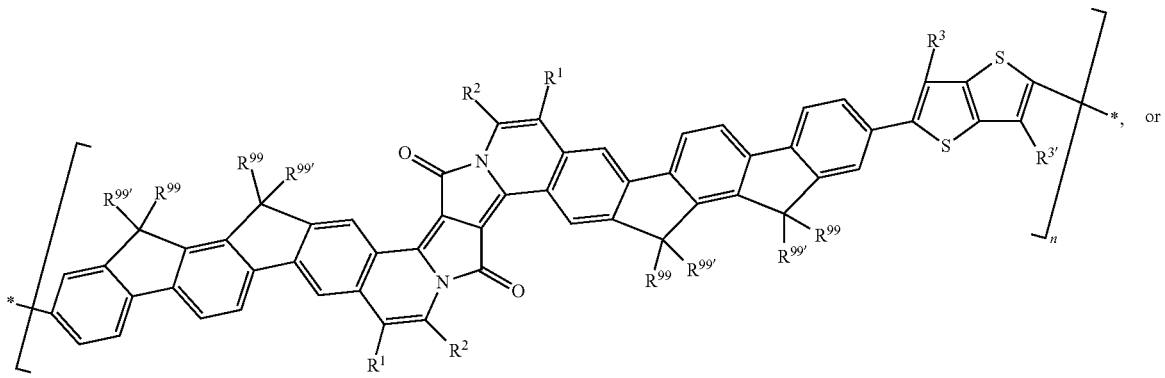

(Ia-30)

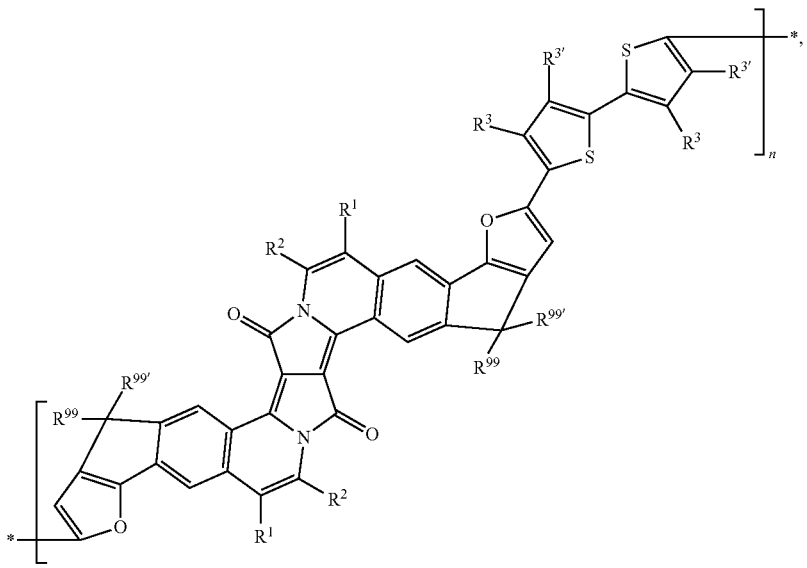

wherein n is 4 to 1000, $R^1$ and $R^2$ are independently of each other hydrogen, a phenyl group, which is optionally substituted by one, or more $C_1$-$C_{18}$alkyl groups, or a $C_1$-$C_{38}$alkyl group, $R^3$ and $R^{3'}$ are independently of each other hydrogen, or $C_1$-$C_{25}$alkyl;

$R^{12}$ and $R^{12'}$ are independently of each other hydrogen, F, cyano, $C_1$-$C_{25}$alkyl, or =$R^{13}$, and $R^{13}$ is a $C_1$-$C_{10}$alkyl group, or a tri($C_1$-$C_8$alkyl)silyl group;

$R^{17}$ and $R^{17'}$ are independently of each other H, or a $C_1$-$C_{25}$alkyl group;

$R^{91}$, $R^{91'}$ and $R^{91''}$ are independently of each other H, halogen, F; cyano, $C_1$-$C_{25}$alkoxy, $C_1$-$C_{25}$alkyl substituted with one or more halogen atoms or $C_1$-$C_{25}$alkyl, $R^{92}$ is H, halogen, F, cyano, $C_1$-$C_{25}$alkoxy, or $C_1$-$C_{25}$alkyl, and $R^{99}$ and $R^{99'}$ are independently of each other hydrogen, $C_1$-$C_{25}$alkyl, or $C_1$-$C_{25}$alkyl substituted with one or more halogen atoms and/or interrupted by one or more oxygen atoms, or two moieties $R^{99}$ form a 5 or 6 membered alkyl ring.

12. The polymer according to claim 11 which is of formula 187 188
(P-1)
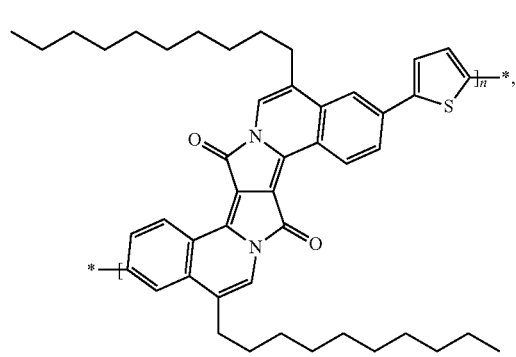
(P-2)
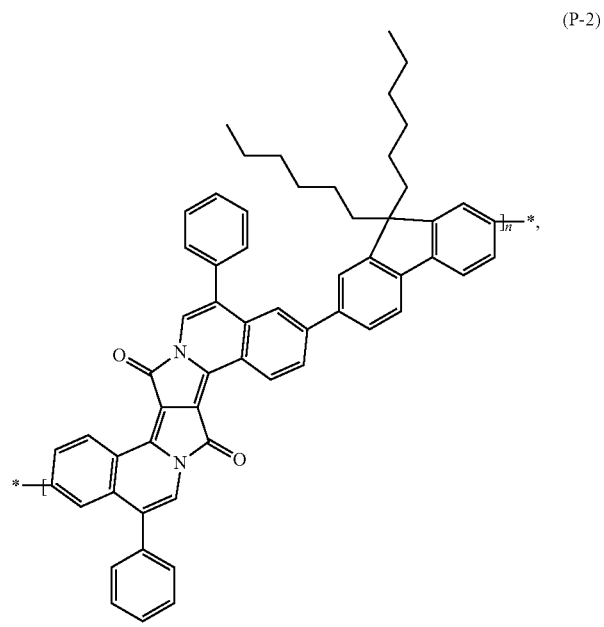
(P-3)
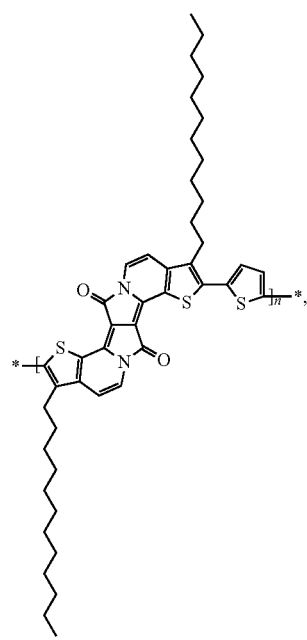
(P-4)
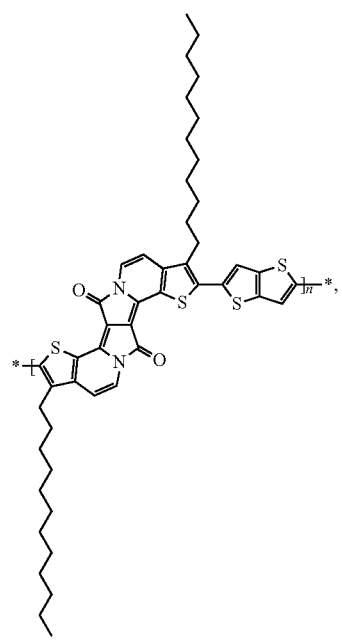

-continued
(P-5)
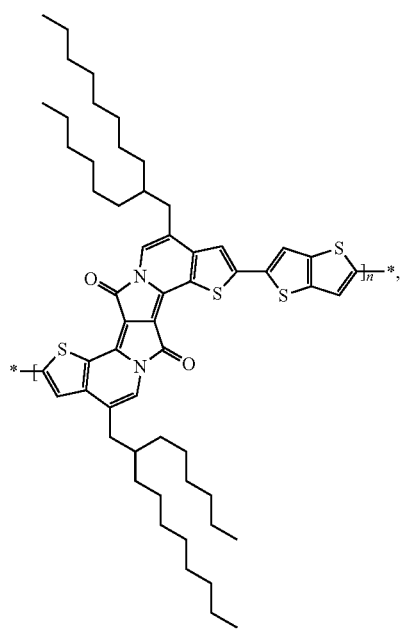
(P-6)
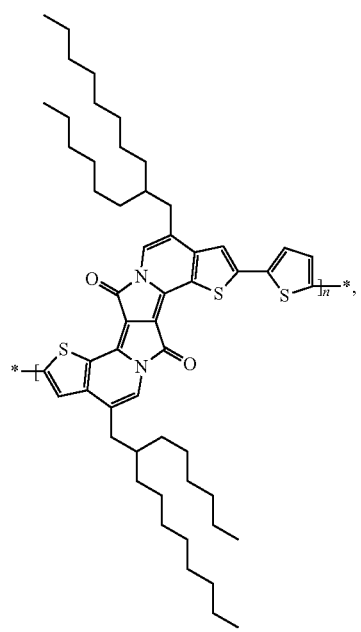
(P-7)
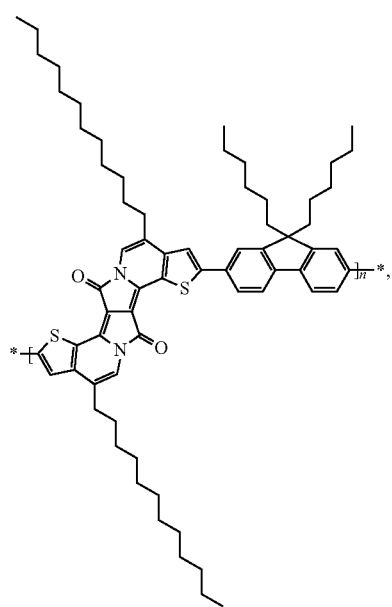
(P-8)
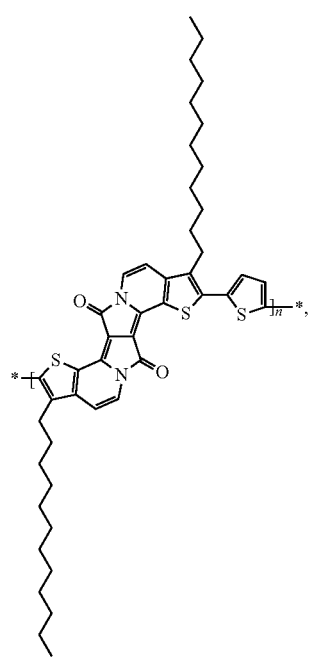

-continued
(P-9)
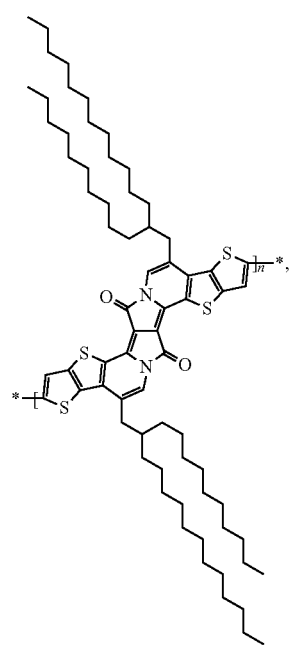
(P-10)
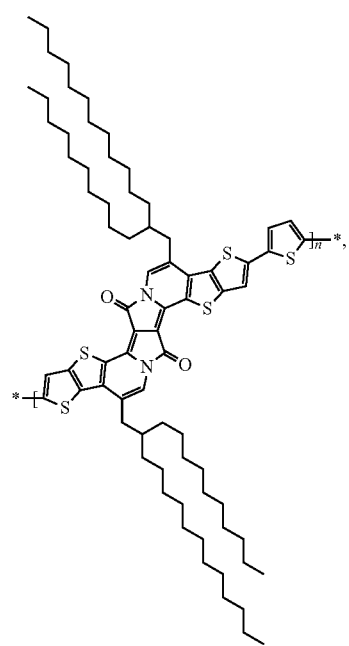
(P-11)
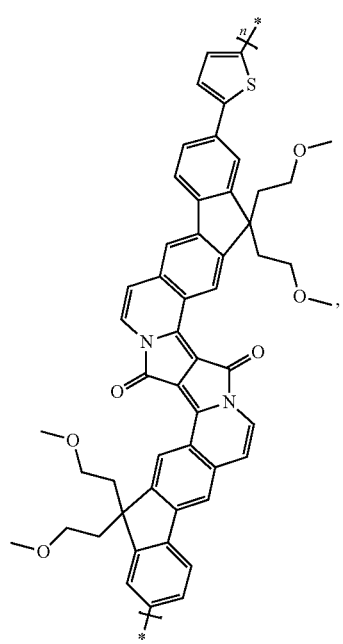

(P-12)
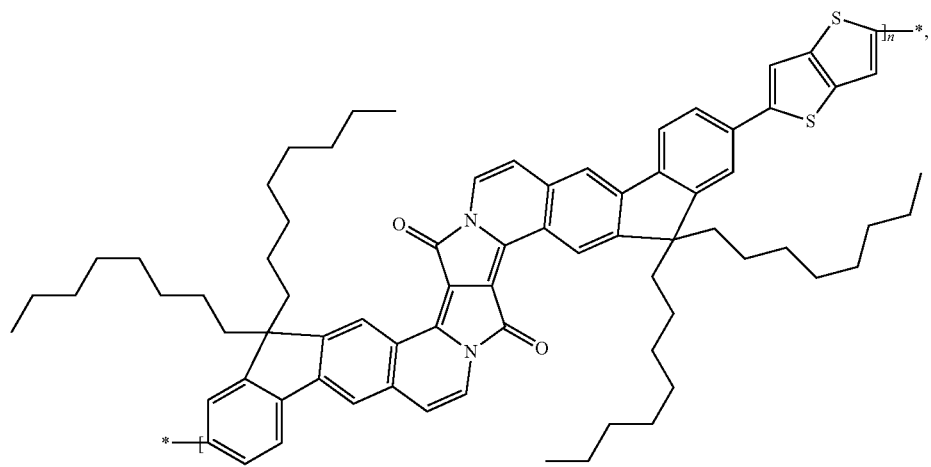
(P-13)
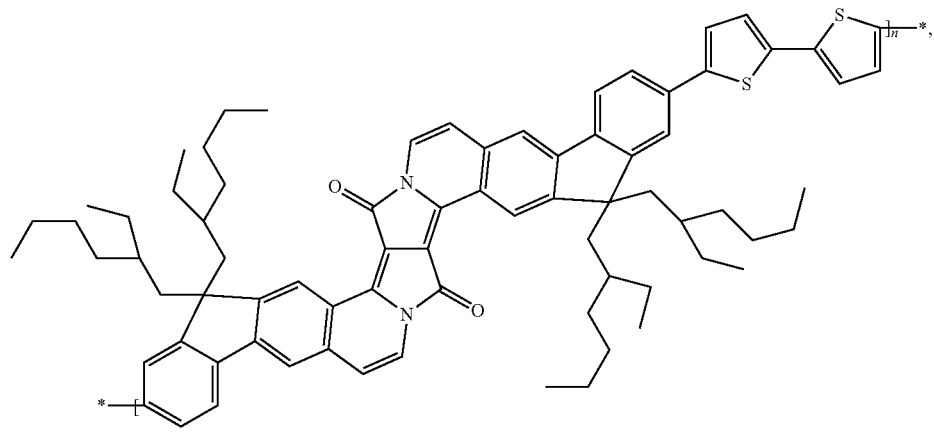
(P-14)
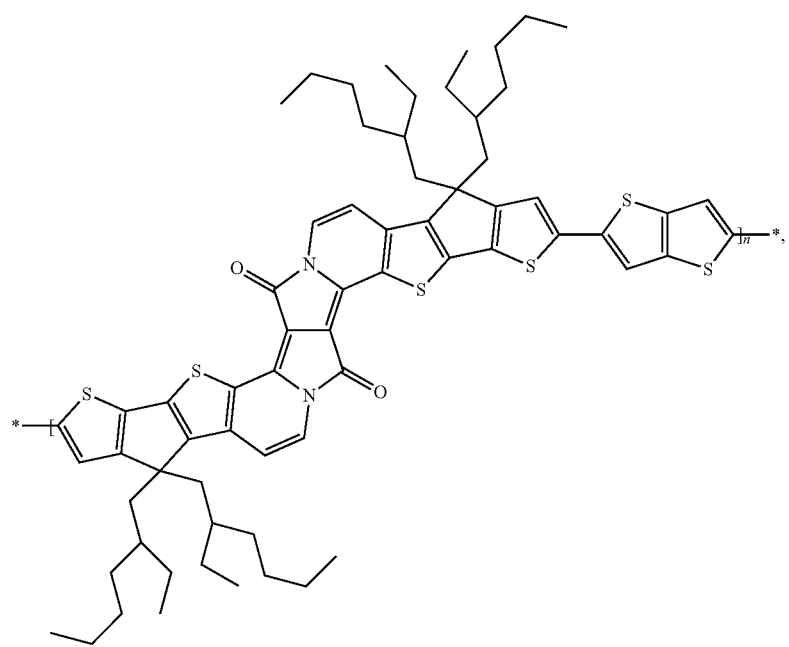

-continued
(P-15)
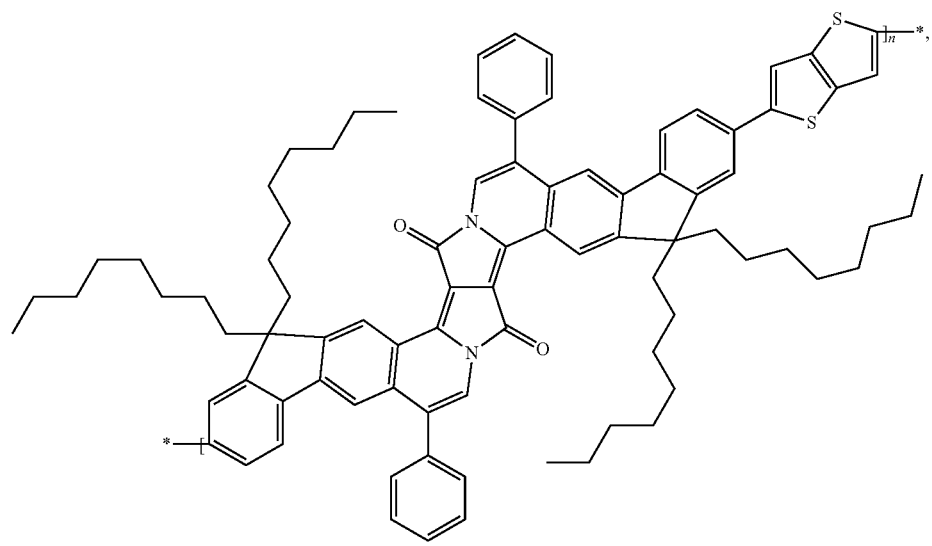
(P-16)
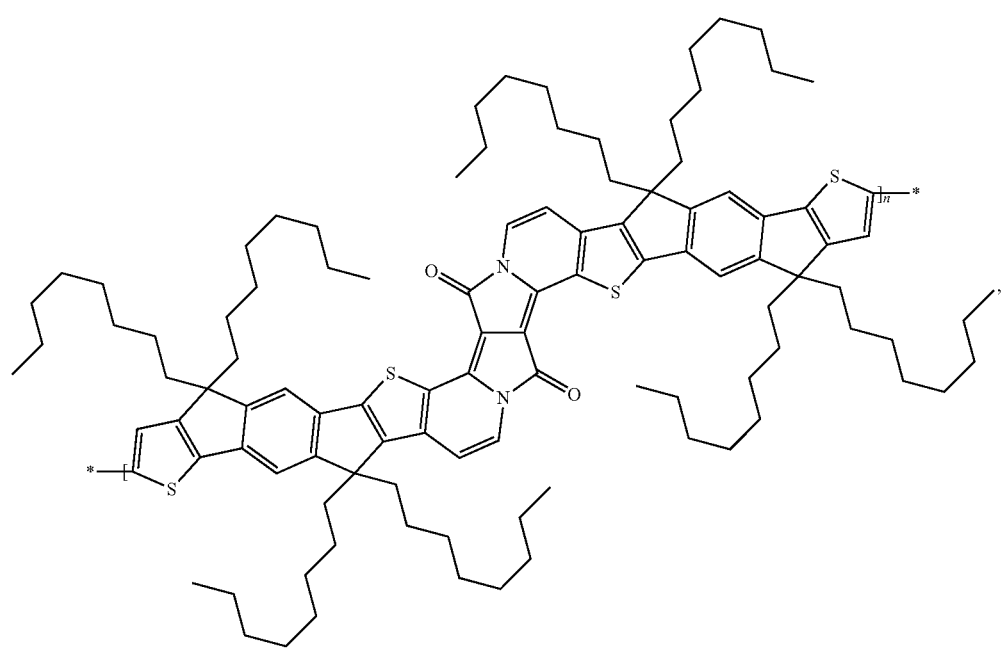

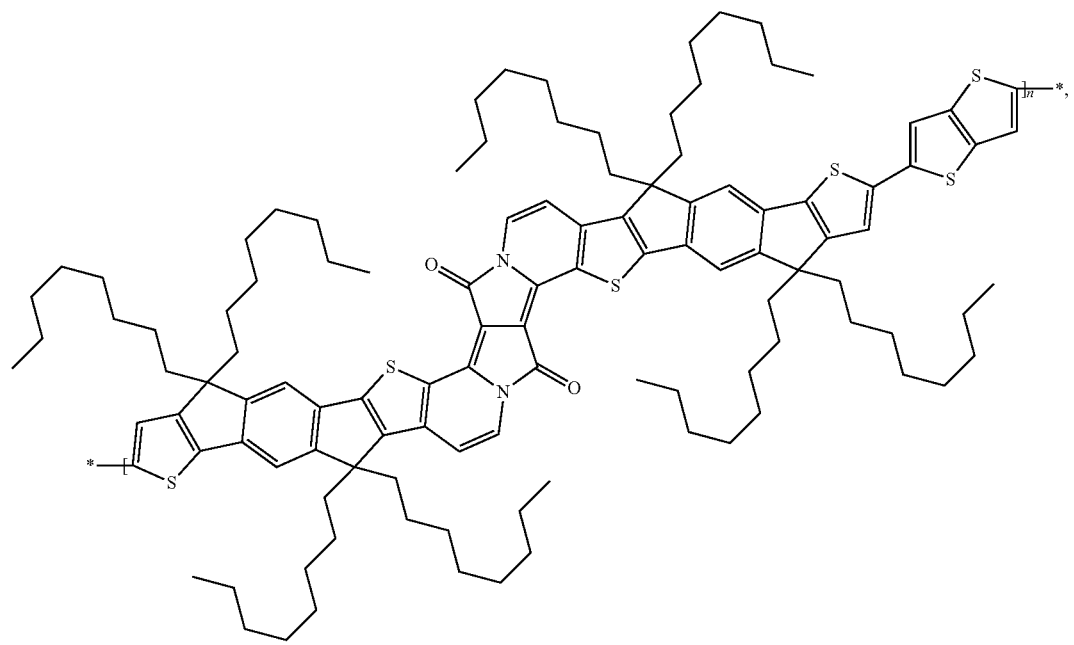
(P-17)
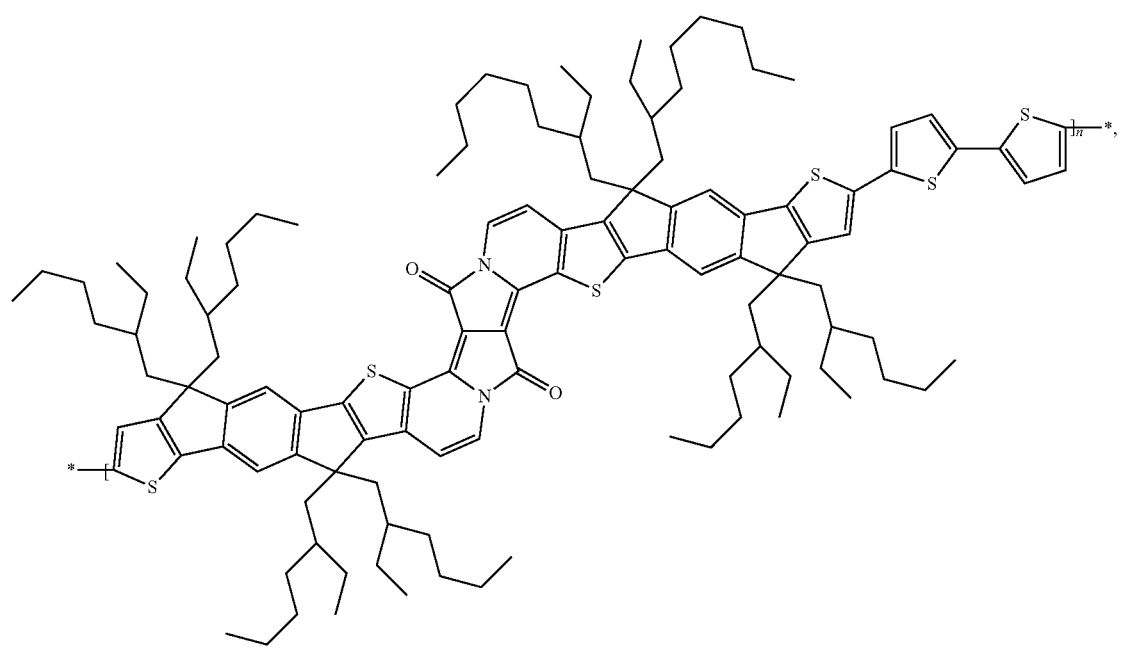
(P-18)

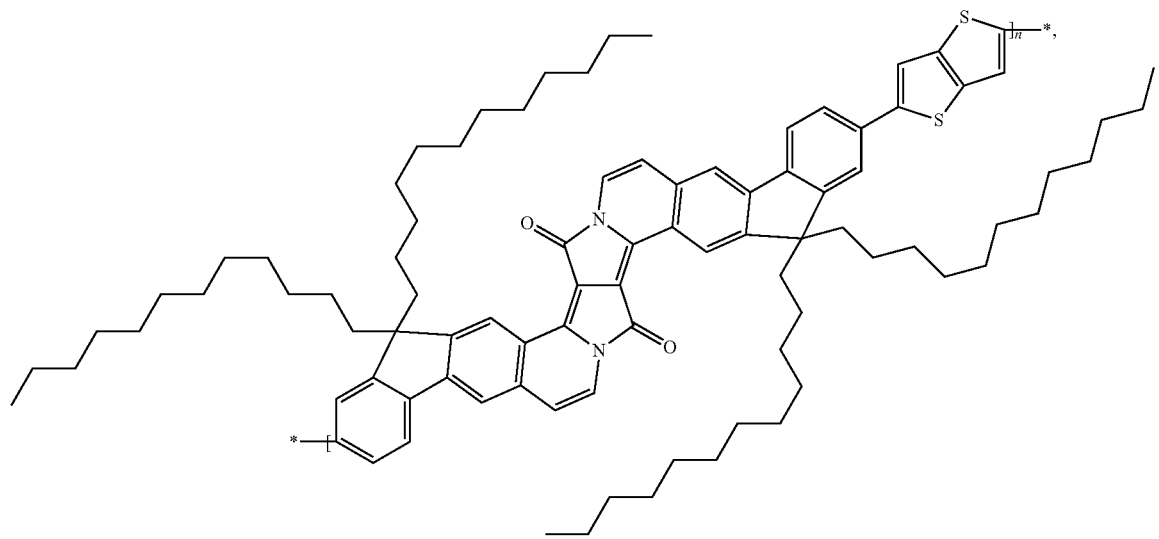
(P-19)
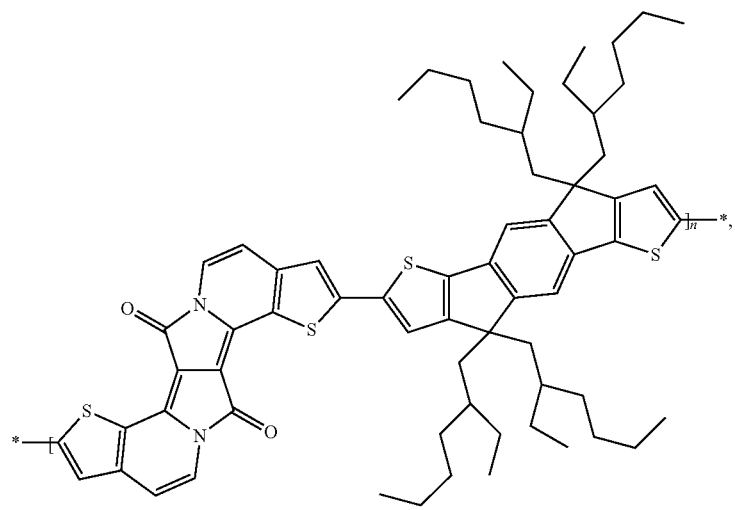
(P-20)
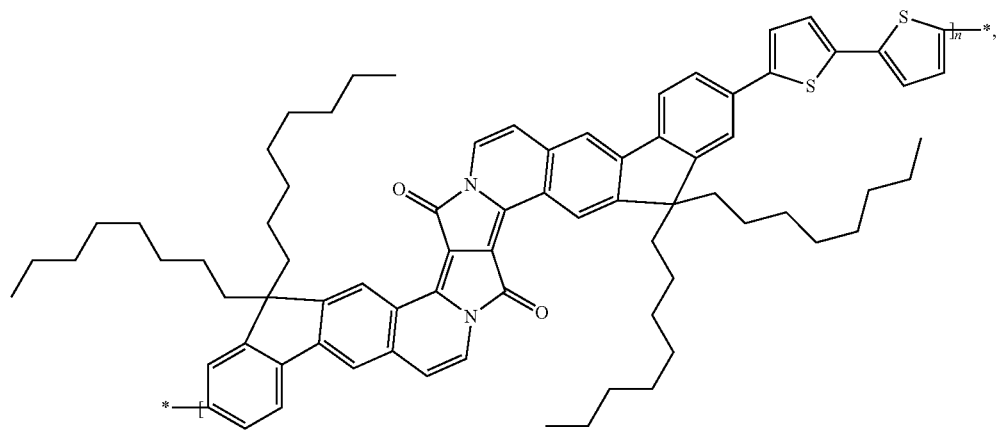
(P-21)

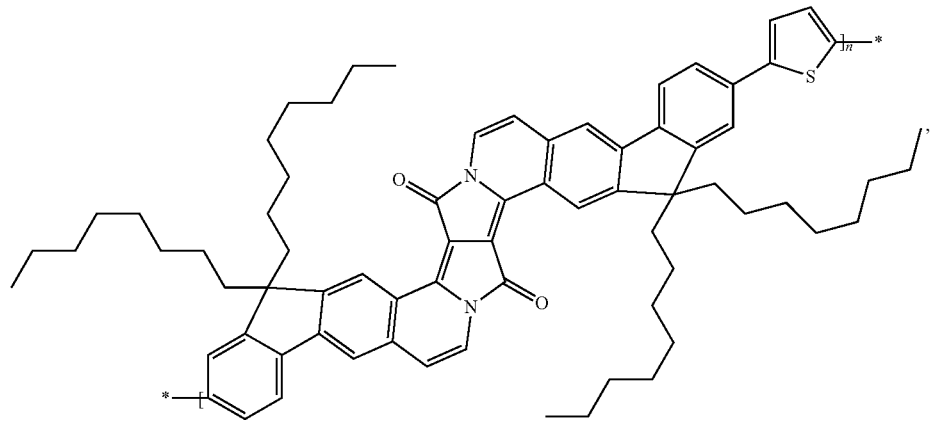
(P-22)
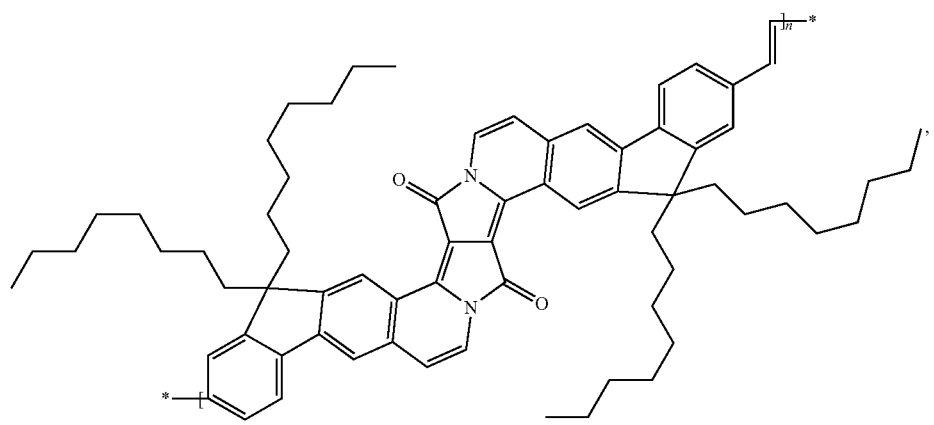
(P-23)
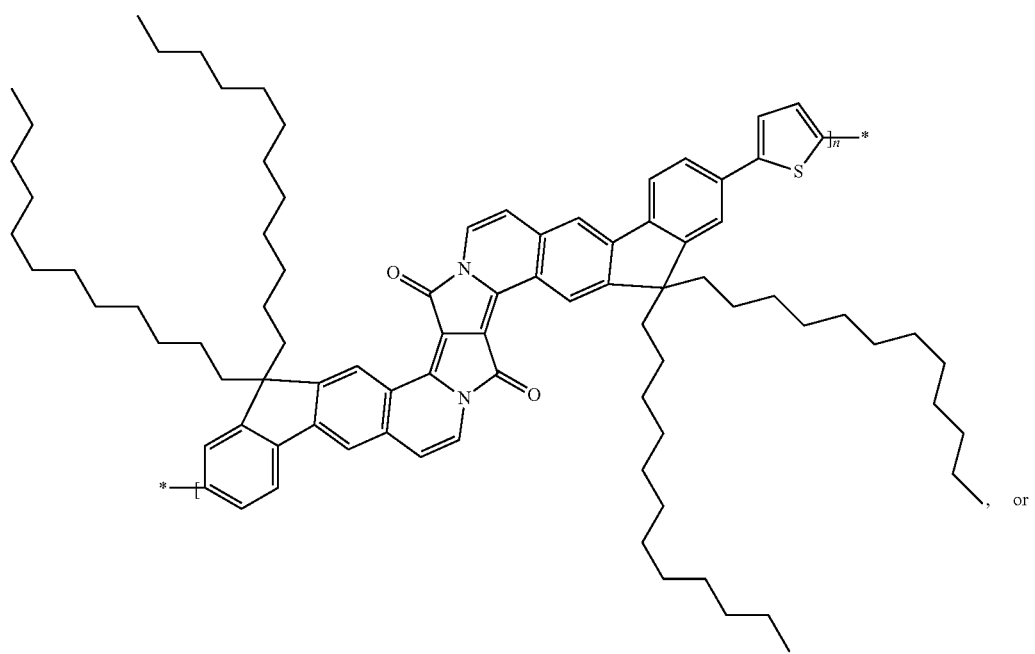
(P-24)
, or (P-25)

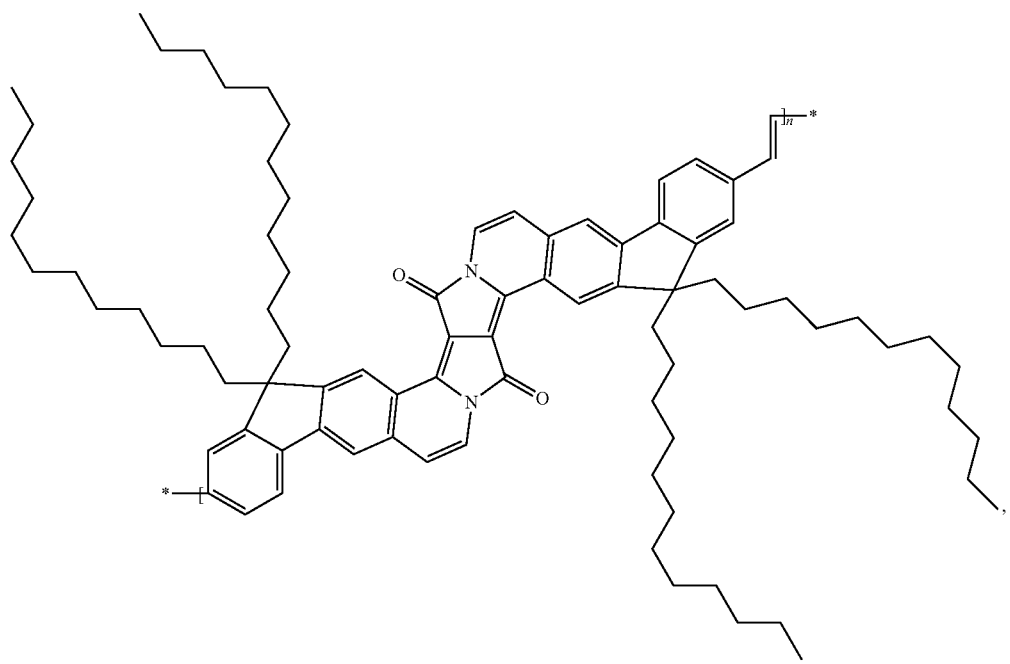

wherein n is 4 to 1000.

13. An organic semiconductor material, layer or component, comprising a polymer according to claim 1.

14. A semiconductor device comprising a polymer according to claim 1.

15. A semiconductor device comprising an organic semiconductor material layer or component according to claim 13.

16. The semiconductor device according to claim 14, which is an organic photovoltaic device, a photodiode, or an organic field effect transistor.

17. Process for the preparation of an organic semiconductor device, the process comprising providing a solution and/or dispersion of a polymer according to claim 1 in an organic solvent, applying the solution and/or dispersion to a suitable substrate, and removing the solvent.

18. A compound of formula (V)

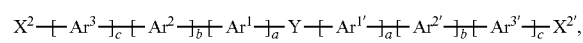

wherein $X^2$ and $X^{2'}$ are independently of each other F, Cl, Br, or I, $ZnX^{12}$, $-SnR^{207}R^{208}R^{209}$, and $R^{207}$, $R^{208}$ and $R^{209}$ are identical or different, and are H or $C_1$-$C_6$alkyl, wherein two radicals optionally form a common ring and these radicals are optionally branched or unbranched, $-SiR^{210}R^{211}R^{212}$, and $R^{210}$, $R^{211}$ and $R^{212}$ are identical or different, and are halogen or $C_1$-$C_6$alkyl;

$X^{12}$ is a halogen atom, I, or Br; $-OS(O)_2CF_3$, $-OS(O)_2$-aryl, $-B(OH)_2$, $-B(OY^1)_2$, $-OS(O)_2CH_3$,

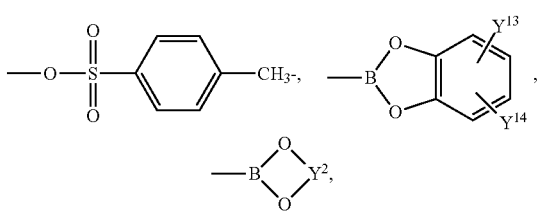

$-BF_4Na$, or $-BF_4K$, wherein $Y^1$ is independently in each occurrence a $C_1$-$C_{10}$alkyl group and $Y^2$ is independently in each occurrence a $C_2$-$C_{10}$alkylene group, $-CY^3Y^4-CY^5Y^6-$, or $-CY^7Y^8-CY^9Y^{10}-CY^{11}Y^{12}-$, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, $-C(CH_3)_2C(CH_3)_2-$, $-C(CH_3)_2CH_2C(CH_3)_2-$, or $-CH_2C(CH_3)_2CH_2-$, and $Y^{13}$ and $Y^{14}$ are independently of each other hydrogen, or a $C_1$-$C_{10}$alkyl group;

Y is a group of formula

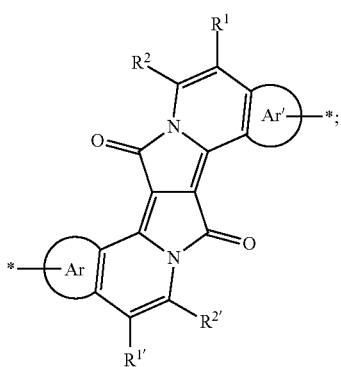

a is 0, 1, 2, or 3; a' is 0, 1, 2, or 3; b is 0, 1, 2, or 3; b' is 0, 1, 2, or 3; c is 0, 1, 2, or 3; c' is 0, 1, 2, or 3;
Ar and Ar' are independently of each other
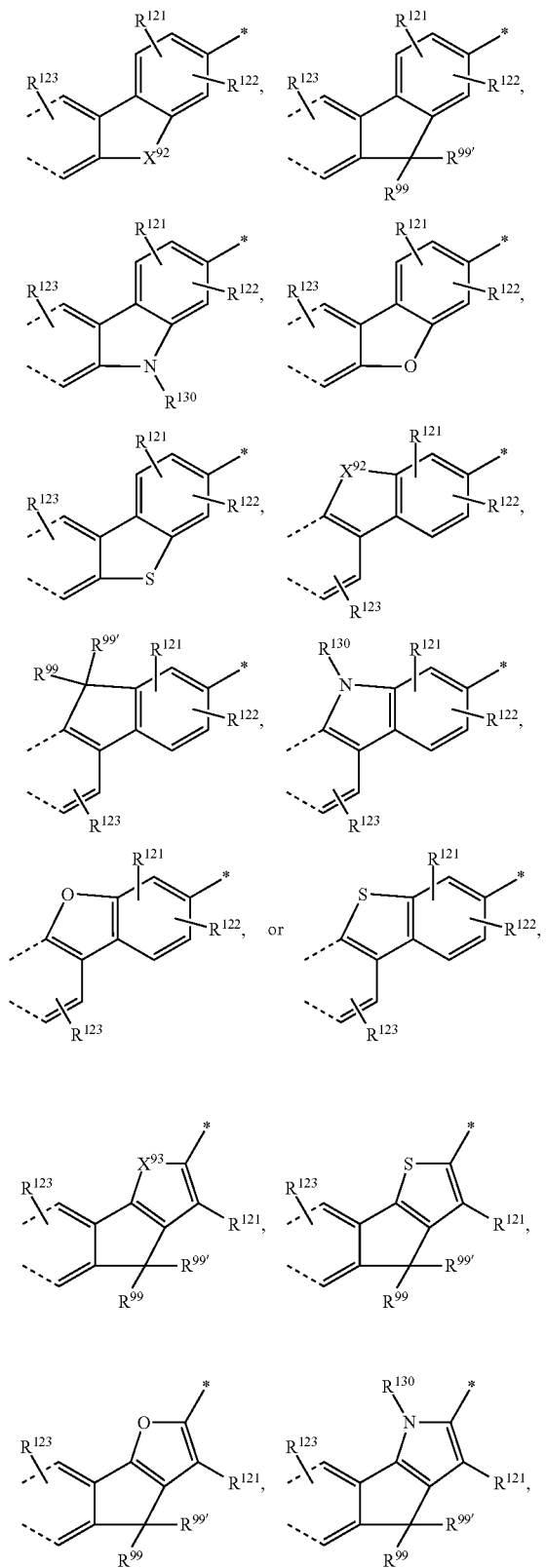
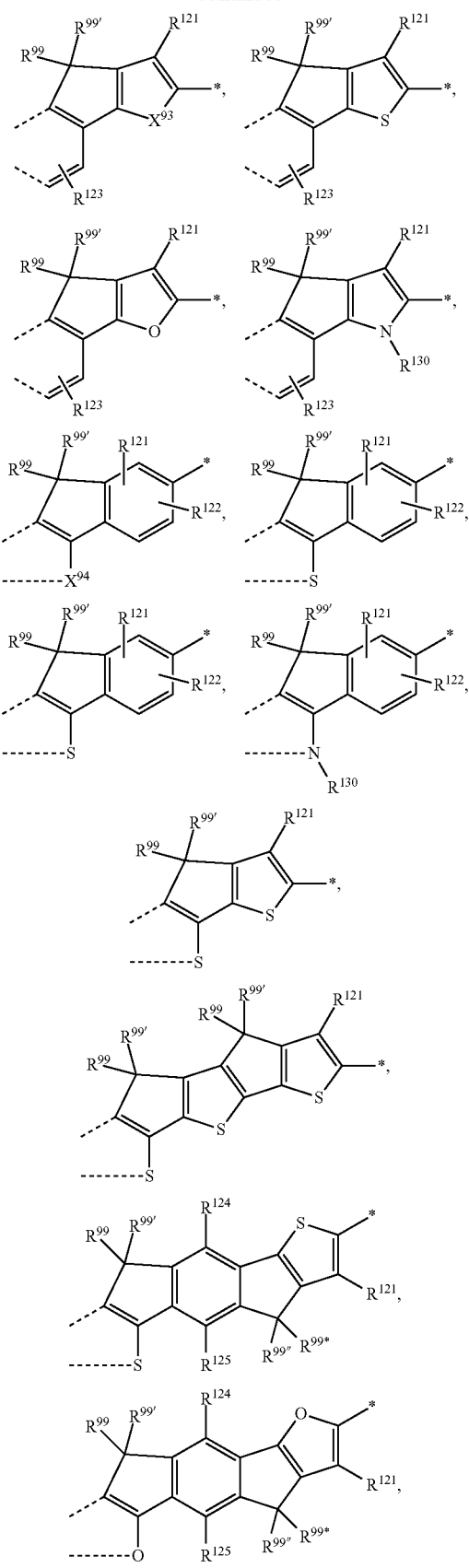

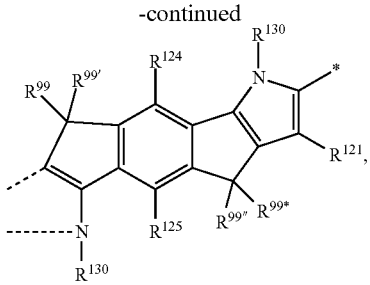

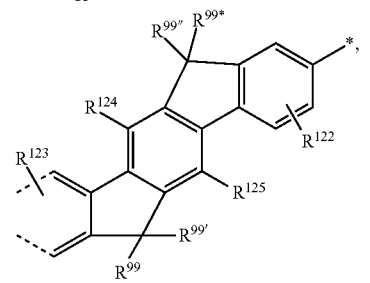

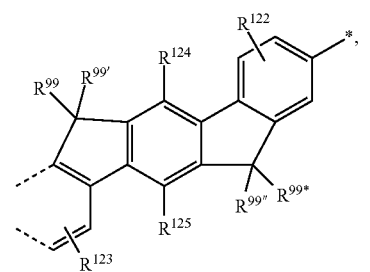

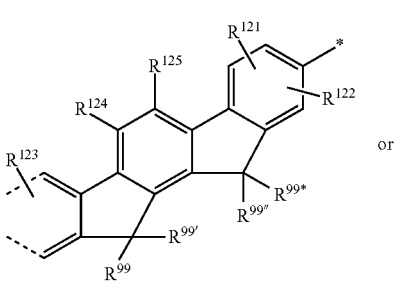

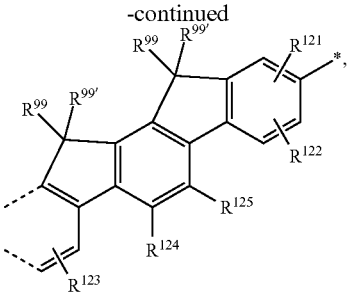

wherein
$R^1$, $R^{1'}$, $R^2$ and $R^{2'}$ may be the same or different and are selected from hydrogen or a $C_1$-$C_{38}$alkyl group, $X^{92}$ is O, S, $CR^{99}R^{99'}$, or $NR^{130}$, $X^{93}$ is O, S, or $NR^{130}$, $X^{94}$ is O, S, or $NR^{130}$, $R^{99}$, $R^{99'}$, $R^{99''}$ and $R^{99*}$ are independently of each other hydrogen, $C_1$-$C_{25}$alkyl, or $C_1$-$C_{25}$alkyl substituted with one or more halogen atoms and/or interrupted by one or more oxygen atoms, or two moieties $R^{99}$ and $R^{99'}$ or $R^{99''}$ and $R^{99*}$ can form a 5 or 6 membered alkyl ring, which is optionally substituted with one or more halogen atoms and/or interrupted by one or more oxygen atoms;

$R^{121}$, $R^{122}$, $R^{123}$, $R^{124}$ and $R^{125}$ are independently of each other hydrogen, halogen, $C_6$-$C_{18}$aryl; $C_6$-$C_{18}$aryl which is substituted by $C_1$-$C_{18}$alkyl, halogen; or $C_1$-$C_{18}$alkoxy; $C_1$-$C_{25}$alkyl, which is optionally interrupted by one or more oxygen or sulphur atoms or is optionally substituted by one or more halogen atoms, F or $C_7$-$C_{25}$arylalkyl;

$R^{130}$ is hydrogen, $C_6$-$C_{18}$aryl; $C_6$-$C_{18}$aryl which is substituted by $C_1$-$C_{18}$alkyl, halogen, especially F; or $C_1$-$C_{18}$alkoxy; $C_1$-$C_{25}$alkyl, which is optionally interrupted by one or more oxygen or sulphur atoms or is optionally substituted by one or more halogen atoms; or $C_7$-$C_{25}$arylalkyl; and Ar1, Ar1', Ar2, Ar2', Ar3 and Ar3' are as defined in claim 7.

19. The compound according to claim 18 of formula

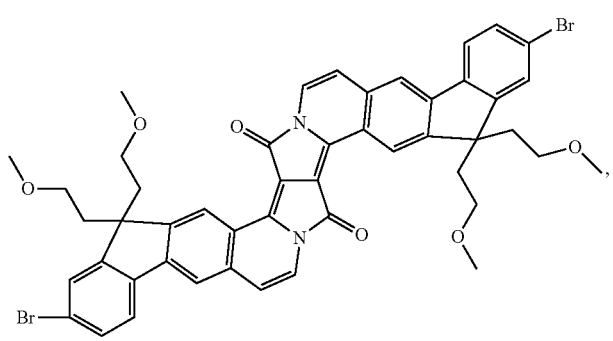

(I-8)

(I-9)
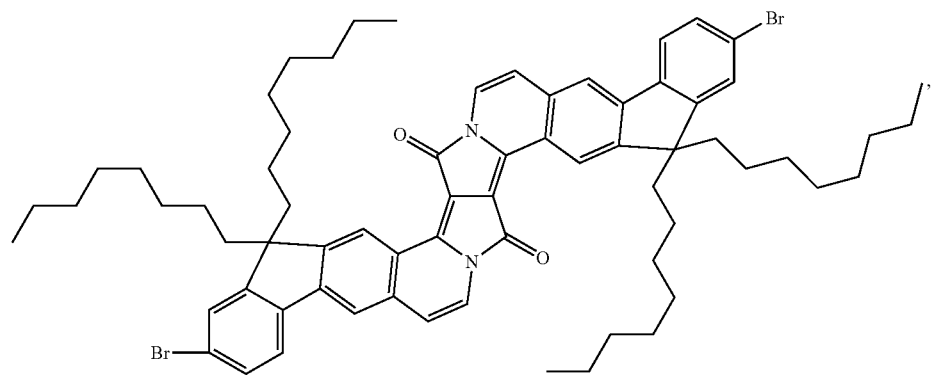
(I-10)
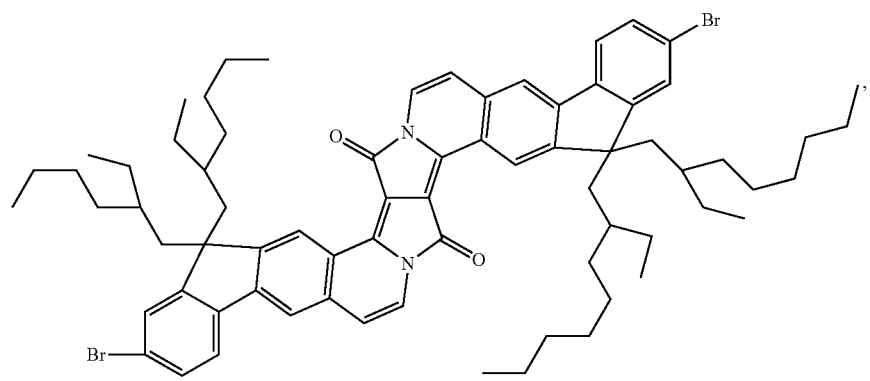
(I-11) (I-12)
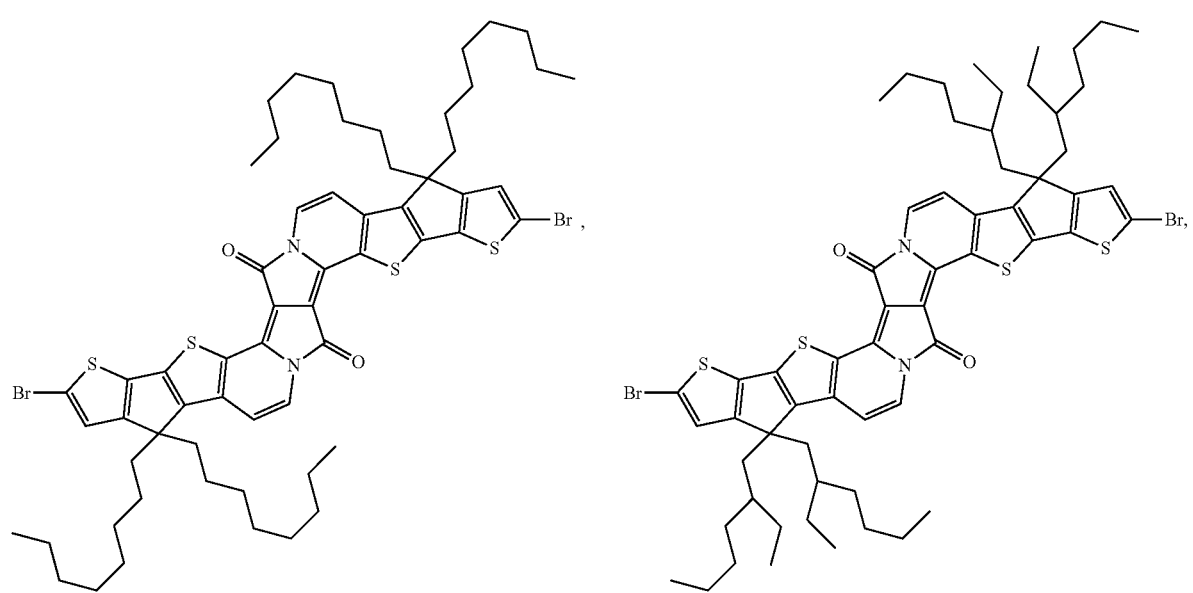

(I-13)
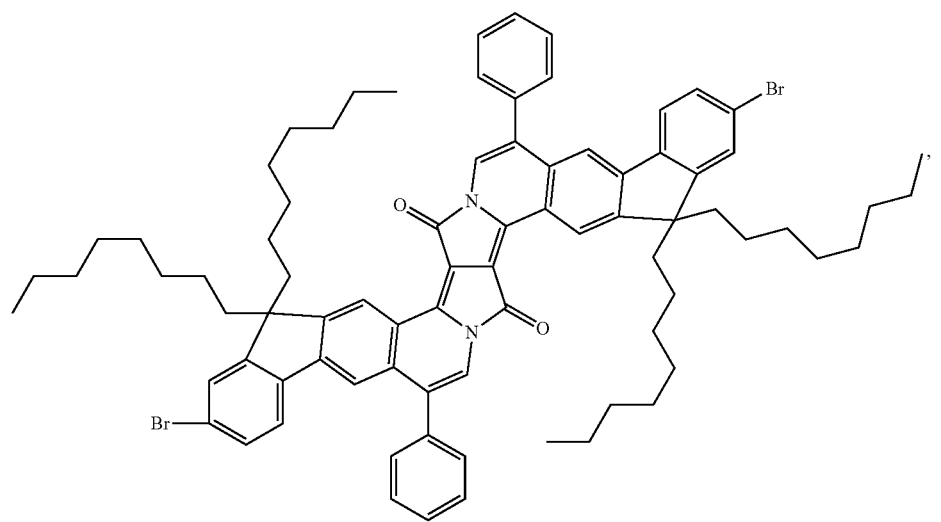
(I-14)
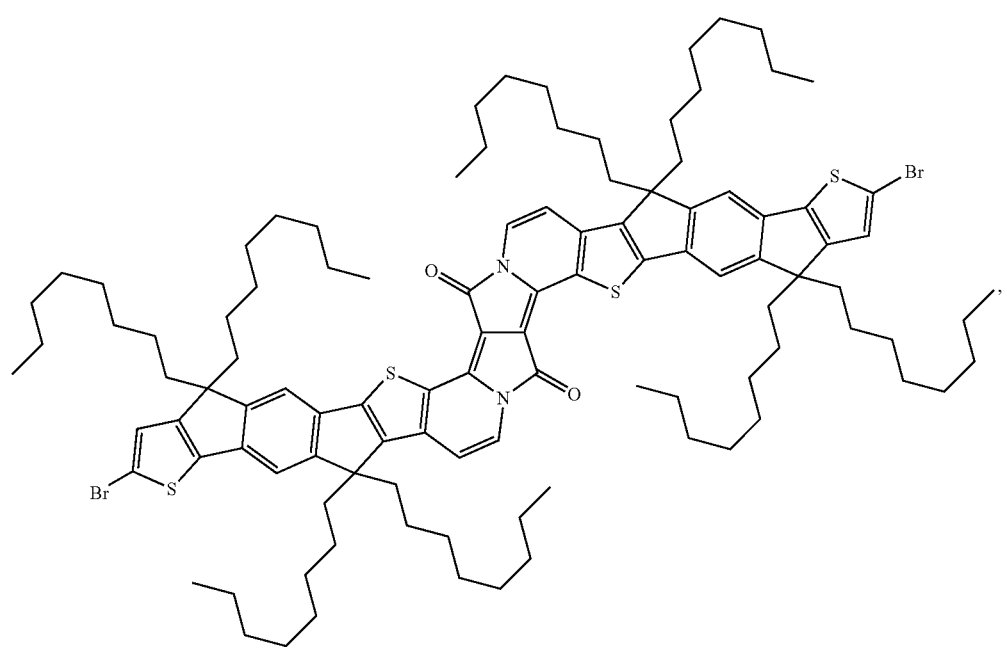

-continued
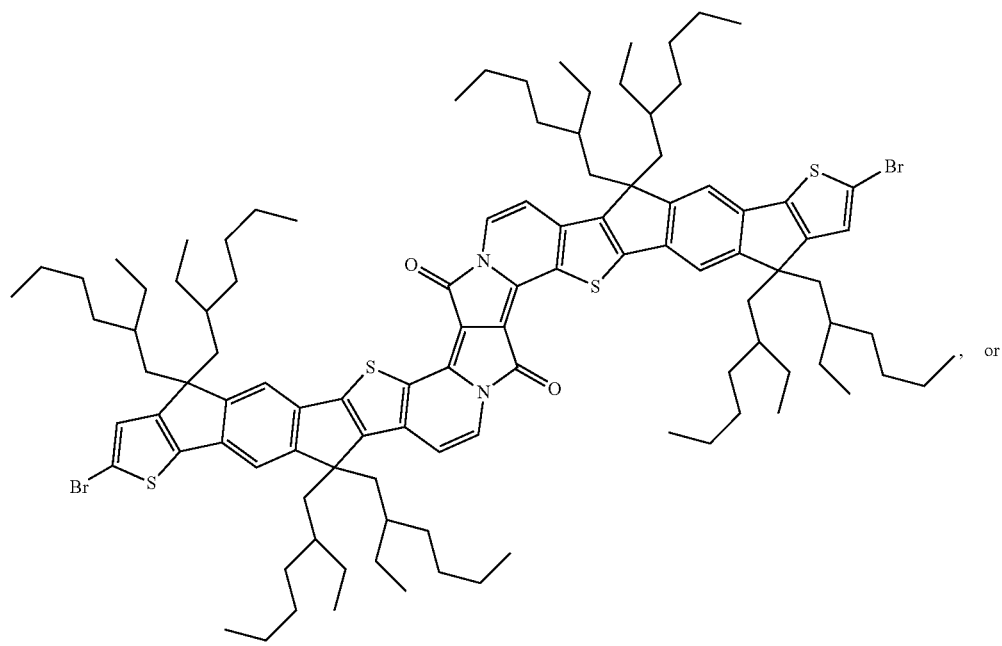
(I-15)
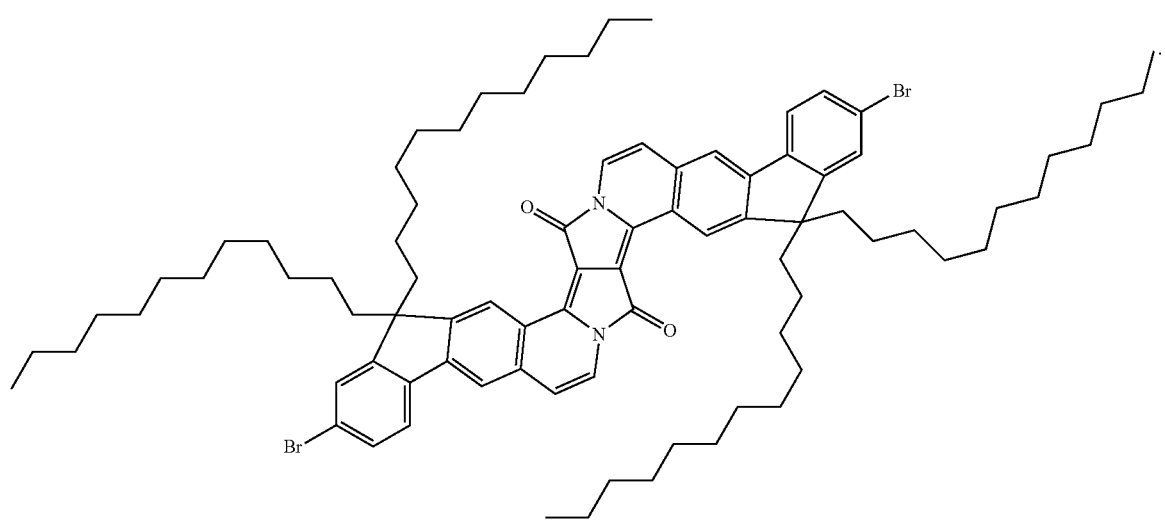
(I-16)
20. The compound according to claim 18 of formula $X^2$ and $X^{2'}$ are independently selected from Br or I.